(12) United States Patent
Boebel et al.

(10) Patent No.: US 9,955,691 B2
(45) Date of Patent: *May 1, 2018

(54) MACROCYCLIC PICOLINAMIDES AS FUNGICIDES

(71) Applicant: DOW AGROSCIENCES LLC, Indianapolis, IN (US)

(72) Inventors: Timothy A. Boebel, Indianapolis, IN (US); Yu Lu, Indianapolis, IN (US); Kevin G. Meyer, Zionsville, IN (US); Chenglin Yao, Westfield, IN (US); John F. Daeuble, Sr., Carmel, IN (US); Karla Bravo-Altamirano, Carmel, IN (US); Benjamin M. Nugent, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/793,311

(22) Filed: Jul. 7, 2015

(65) Prior Publication Data

US 2016/0007601 A1 Jan. 14, 2016

Related U.S. Application Data

(60) Provisional application No. 62/021,863, filed on Jul. 8, 2014.

(51) Int. Cl.
| | |
|---|---|
| C07D 405/12 | (2006.01) |
| A01N 43/40 | (2006.01) |
| A01N 43/24 | (2006.01) |
| C07D 321/00 | (2006.01) |
| A01N 47/18 | (2006.01) |

(52) U.S. Cl.
CPC .............. *A01N 43/40* (2013.01); *A01N 43/24* (2013.01); *A01N 47/18* (2013.01); *C07D 321/00* (2013.01); *C07D 405/12* (2013.01)

(58) Field of Classification Search
CPC .................................................. C07D 405/12
USPC ........................................ 546/281.7; 514/336
See application file for complete search history.

(56) References Cited

U.S. PATENT DOCUMENTS

| 4,051,173 A | 9/1977 | Schact et al. |
|---|---|---|
| 5,401,871 A | 3/1995 | Feldman-Krane et al. |
| 6,355,660 B1 | 3/2002 | Ricks |
| 6,436,421 B1 | 4/2002 | Schindler et al. |
| 6,410,572 B1 | 6/2002 | Schelberger et al. |
| 6,521,622 B1 | 2/2003 | Ricks |
| 6,706,740 B2 | 3/2004 | Ricks |
| 6,861,390 B2 | 3/2005 | Meyer |
| 6,916,932 B2 | 7/2005 | Meyer et al. |
| 6,927,225 B2 | 8/2005 | Ricks |
| 7,034,035 B2 | 4/2006 | Ricks |
| 7,183,278 B1 | 2/2007 | Imamura |
| 7,250,389 B1 | 7/2007 | Sakanaka |
| RE39,991 E | 1/2008 | Ricks et al. |
| 7,442,672 B2 | 10/2008 | Muller et al. |
| 8,008,231 B2 | 8/2011 | Leatherman |
| 8,470,840 B2 | 6/2013 | Klittich et al. |
| 8,476,193 B2 | 7/2013 | Kenney et al. |
| 8,604,215 B2 | 12/2013 | Phiasivongsa et al. |
| 8,785,479 B2 | 7/2014 | Meyer |
| 8,835,462 B2 | 9/2014 | Meyer |
| 8,883,811 B2 | 11/2014 | Owen |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,271,496 B2 | 3/2016 | Kemmitt |
| 9,439,422 B2 | 9/2016 | Martin et al. |
| 9,549,555 B2 | 1/2017 | DeLorbe et al. |
| 9,549,556 B2 | 1/2017 | DeKorver et al. |

(Continued)

FOREIGN PATENT DOCUMENTS

| CN | 102638989 | 8/2012 |
|---|---|---|
| EP | 1054011 | 11/2000 |

(Continued)

OTHER PUBLICATIONS

Koyanagi et al., "Bioisoterism, etc.," Synthesis and Chemistry of Agrochemicals IV; Baker ,D et al., 1995, 15-24.*
International Searching Authority, International Search Report for PCT/US15/39407, dated Sep. 30, 2015, 5 pages.
International Searching Authority, Written Opinion for PCT/US15/39407, dated Sep. 30, 2015, 4 pages.
Anonymous, Synergistic Fungicidal Composition of Heterocyclic Aromatic Amides and Triazoles, IP.com, Electronic Publication, 2004, 11 pages.
Anonymous, Synergistic Fungicidal Composition of Heterocyclic Aromatic Amides and Triazoles, IP.com Journal, IP.com, Inc., West Henrietta, NY, US, Dated Jul. 2004, 10 pages.

(Continued)

*Primary Examiner* — Patricia L Morris
(74) *Attorney, Agent, or Firm* — Charles W. Arnett; Faegre Baker Daniels LLP

(57) ABSTRACT

This disclosure relates to macrocyclic picolinamides of Formula I and their use as fungicides.

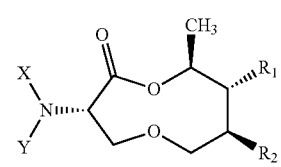

7 Claims, No Drawings

(56) References Cited

U.S. PATENT DOCUMENTS

| | | |
|---|---|---|
| 9,629,365 B2 | 4/2017 | Li et al. |
| 9,681,664 B2 | 6/2017 | LaLonde et al. |
| 9,750,248 B2 | 9/2017 | Ouimette et al. |
| 2002/0119979 A1 | 8/2002 | Degenhardt et al. |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2003/0022903 A1 | 1/2003 | Ricks et al. |
| 2004/0034025 A1 | 2/2004 | Ricks |
| 2004/0048864 A1 | 3/2004 | Ricks |
| 2004/0171838 A1 | 9/2004 | Owen |
| 2004/0186296 A1 | 9/2004 | Nyaz |
| 2004/0192924 A1 | 9/2004 | Meyer et al. |
| 2005/0239873 A1 | 10/2005 | Hockenbery |
| 2006/0040995 A1 | 2/2006 | Bacque et al. |
| 2007/0010401 A1 | 1/2007 | Noon |
| 2007/0060579 A1 | 3/2007 | Wachendorff-Neumann |
| 2007/0066629 A1 | 3/2007 | Tormo I Blasco |
| 2008/0070985 A1 | 3/2008 | Derrer et al. |
| 2008/0293798 A1 | 11/2008 | Dietz |
| 2008/0318785 A1 | 12/2008 | Koltzenburg |
| 2009/0203770 A1 | 8/2009 | Hockenberry et al. |
| 2009/0306142 A1 | 12/2009 | Carson |
| 2010/0016163 A1 | 1/2010 | Keiper et al. |
| 2011/0034493 A1 | 2/2011 | Boebel et al. |
| 2011/0053891 A1 | 3/2011 | Boebel et al. |
| 2011/0053966 A1 | 3/2011 | Klittich et al. |
| 2011/0070278 A1 | 3/2011 | Lopez |
| 2011/0082039 A1 | 4/2011 | Keeney et al. |
| 2011/0082160 A1 | 4/2011 | Owen |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |
| 2013/0296371 A1 | 11/2013 | Meyer |
| 2013/0296372 A1 | 11/2013 | Owen et al. |
| 2013/0296373 A1 | 11/2013 | Meyer et al. |
| 2013/0296374 A1 | 11/2013 | Owen et al. |
| 2013/0296375 A1 | 11/2013 | Meyer et al. |
| 2014/0128411 A1 | 5/2014 | Ogawa et al. |
| 2014/0187587 A1 | 7/2014 | Ouimette |
| 2014/0187588 A1 | 7/2014 | Lalonde |
| 2014/0187590 A1 | 7/2014 | Ouimette et al. |
| 2014/0275171 A1 | 9/2014 | Meyer |
| 2014/0357713 A1 | 12/2014 | Damaj et al. |
| 2015/0065529 A1 | 3/2015 | Owen |
| 2015/0094341 A1 | 4/2015 | Li et al. |
| 2015/0181868 A1 | 7/2015 | DeKorver et al. |
| 2015/0183759 A1 | 7/2015 | DeLorbe et al. |
| 2015/0289508 A1 | 10/2015 | Meyer et al. |
| 2015/0322051 A1 | 11/2015 | Lu et al. |
| 2017/0183324 A1 | 6/2017 | Li et al. |
| 2017/0273306 A1 | 9/2017 | LaLonde et al. |

FOREIGN PATENT DOCUMENTS

| | | |
|---|---|---|
| EP | 1516874 | 3/2005 |
| WO | 1999011127 | 11/1999 |
| WO | 2001/14339 | 3/2001 |
| WO | WO 2001/014365 | 3/2001 |
| WO | WO 03/011857 | 2/2003 |
| WO | WO 03/035617 | 5/2003 |
| WO | WO 2007017416 | 2/2007 |
| WO | 2009040397 | 9/2008 |
| WO | WO 2009040397 | 9/2008 |
| WO | WO 2011028657 | 3/2011 |
| WO | WO 2011044213 | 4/2011 |
| WO | WO 2011069893 | 6/2011 |
| WO | 2012020777 | 2/2012 |
| WO | WO 2012/016972 | 2/2012 |
| WO | WO 2012016989 | 2/2012 |
| WO | 2012/070015 | 5/2012 |
| WO | WO 2013/110002 | 7/2013 |
| WO | WO 2013/116251 | 8/2013 |
| WO | WO 2015/103161 | 7/2015 |

OTHER PUBLICATIONS

K. Tani, et al., Journal of Antibiotics, vol. 55, No. 3, Mar. 2002, pp. 315-321.

Z. Hu, et al, Synthesis of Novel Analogues of Antimycin A3, Tetrahedron Letters 49 (2008) pp. 5192-5195.

Y.Usuki, et al. Journal of Antibiotics, vol. 55, No. 6, Jun. 2002, pp. 607-610.

Kissling, Crop Protection pipeline value jumps to €2.4 billion. BASF. Mar. 11, 2010, pp. 1-4, [retrieved on Feb. 4, 2014] Retrieved from the Internet: <URL: http://www.agro.basf.com/agr/AP-Internet/en/content/news_room/news/basf-crop-protection-pipeline-value>.

BASF new fungicide Xemium got full approval in EU. AgroNews. Jul. 18, 2012 [retrieved on 1-20 Feb. 4, 2014). Retrieved from the Internet: <URL: http://news.agropages.com/News/NewsDetail-7386.htm>.

Gisi, U. The American Phytopathological Society, vol. 86, No. 11, 1996, p. 1273-79.

Koyanagi et al., "Bioisoterism, etc.," Synthesis and Chemistry of Agrochemicals IV; Baker, D, et al., 1995, 15-24.

Masashi Ueki et al., "UK-2A, B, C, and D, Novel Antifungal Antibiotics from Streptomyces sp. 517-02 I. Fermentation, Isolation, and Biological Properties," The Journal of Antibiotics, vol. 49, No. 7, Jul. 1996, pp. 639-634.

Usuki, et al., "Semi-synthesis and biological evaluation of analogues of UK-2A, a novel antifungal antibiotic from Steptomyces sp. 517-02," Bioorganic & Medicinal Chemistry Letters, Pergamon, Amsterdam, KL, vol. 15, No. 8, Apr. 15, 2005, pp. 2011-2014, XP027801790.

Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.

Huang, et al., Synergistic Interactions between Chitinase ChiCW and Fungicides Against Plant Fungal Pathogens, J. Microbiol. Biotechnol., 2008, 18(4) 784-787.

Backman, P., Fungicide Formulation: Relationship to Biological Activity, 1978, 16, 211-237.

Latin, et al, Re-Examining Fungicide Synergism for Dollar Spot Control, GCM, 2008, 84-87.

O'Sullivan, et al., Fungicide Resistance—an Increasing Problem, Proceedings of National Tillage Conference 2007, Published by Crop Research Centre Oak Park Carlow, date Jan. 31, 2007, 14 pages.

Bolton, Md et al., Wheat leaf rust caused by Puccinia triticina. Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf; p. 564, col. 1, paragraph 4.

Davari, M. et al. ""Quantum Chemical Investigation of Intramolecular Thione-Thiol Tautomerism of 1, 2, 4-triazole-3-thione and its disubstituted derivatives,"" Journal of Molecular Modeling, Sep. 2009, 16(5), pp. 841-55.

FRAC Code List: Fungicides Sorted by Mode of Action (including FRAC Code numbering), Dec. 2008, pp. 1-10.

Fungicidal Mixtures, IP.com Prior Art Database Technical Disclosure, (Jul. 5, 2005), pp. 1-10, XP055073888, DOI: http://ip.com/pdf/ipcompad/IPCOM000126160D.pdf.

Parker, J.E., et al., ""Mechanism of Binding of Prothioconazole to Mycosphaerella graminicola CYP51 Differes from That of Other Azole Antifungals,"" Applied and Environmental Microbiology, Feb. 2011, pp. 1460-1465.

Science for a Better Life, Bayer Cropscience, Jun. 2008, p. 22.

Sulfonate (http://www.hichem.com/product/showproduct.php?id=334639) Mar. 28, 2013, p. 1-4.

(56) References Cited

OTHER PUBLICATIONS

The Merck Index, Twelfth Edition, S. Budavari, Ed. Merck and Co., Whitehouse Station, NJ, 1996, pp. 2220, 3666, 7937 and 7946.
Webster's New World Dictionary, 2nd college edition, The World Publishing Co., New York, p. 1127 (1972).
Wilson, C.L. et al. "Fruit Volatiles Inhibitory to Monilinia Fruiticola and Botrytis cinerea," 1987, Plant Disease 71: 316-319.

* cited by examiner

MACROCYCLIC PICOLINAMIDES AS FUNGICIDES

CROSS REFERENCE TO RELATED APPLICATIONS

This application claims the benefit of U.S. Provisional Patent Application Ser. No. 62/021,863 filed Jul. 8, 2014, which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

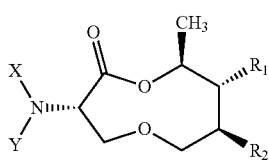

I

X is hydrogen or $C(O)R_3$;
Y is hydrogen, $C(O)R_3$, or Q;
Q is

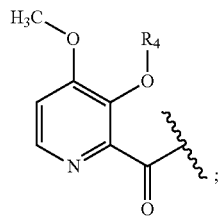

;

wherein $R_1$ and $R_2$ are independently selected from the group consisting of alkyl, alkenyl, and aryl, each optionally substituted with 0, 1 or multiple $R_6$;
$R_3$ is alkoxy or benzyloxy, each optionally substituted with 0, 1, or multiple $R_6$;
$R_4$ is hydrogen, —$C(O)R_5$, or —$CH_2O\,C(O)R_5$;
$R_5$ is alkyl, alkoxy, or aryl, each optionally substituted with 0, 1, or multiple $R_6$;
$R_6$ is hydrogen, alkyl, aryl, halo, acyloxy, alkenyl, alkoxy, heteroaryl, heterocyclyl, or thioalkyl, each optionally substituted with 0, 1, or multiple $R_7$;
$R_7$ is hydrogen, alkyl, haloalkyl, alkoxy, haloalkoxy, aryl, or halo.

In some embodiments X and Y in Formula I, are hydrogen. In some embodiments X is $C(O)R_3$ and Y is hydrogen. In some embodiments X is hydrogen and Y is Q; in some of these embodiments $R_4$ is hydrogen and other of these embodiments $R_4$ is —$C(O)R_5$ or —$CH_2OC(O)R_5$; in still other of these embodiments. In some embodiment when $R_4$ is —$C(O)R_5$ or —$CH_2O\,C(O)R_5$, $R_5$ may be one of the following: alkyl or alkoxy, each optionally substituted with 0, 1, or multiple $R_6$ in some of these embodiments R5 is chosen from: $CH_3$, —$CH(CH_3)_2$, —$CH_2OCH_2CH_3$, or —$CH_2CH_2OCH_3$.

Additional embodiments of the present disclosure may include a fungicidal composition for the control or prevention of fungal attack comprising the compounds described above (of Formula I) and a phytologically acceptable carrier material. In some embodiments the compostions of Formula I may be mixed with other pesticides including pesticides selected from the group consisting of fungicides, insecticides, nematocides, miticides, arthropodicides, bactericides, and combinations thereof. In some embodiments these compounds and mixtures may be used to control at least one pathogen selected from the group consisting of: Leaf Blotch of Wheat (*Mycosphaerella graminicola*; anamorph: *Septoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley Scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*). In some embodiments the fungal pathogen is at least one of the following pathogens: Leaf Blotch of Wheat (*Septoria tritici*), Wheat Brown Rust (*Puccinia triticina*), and Rust of Soybean (*Phakopsora pachyrhizi*).

Yet other embodiments of the present disclosure may include a method for the control or prevention of fungal attack on a plant, these methods including the steps of applying a fungicidally effective amount of one or more of the compounds (of Formula I) described above or mixtures including at least one of these compound to at least one fungus, and/or at least one portion of a plant, an area adjacent to the plant, a portion of soil adapted to support growth of the plant, a root of the plant, and foliage of the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocycle" refers to any aromatic or non-aromatic ring, mono- or bi-cyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —N(R)$_2$ substituent.
The term "arylalkoxy" refers to —O(CH$_2$)$_n$Ar where n is an integer selected from the list 1, 2, 3, 4, 5, or 6.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halogen" or "halo" refers to one or more halogen atoms, defined as F, Cl, Br, and I.

The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzovindiflupyr benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; anamorph: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f sp. *tritici*), powdery mildew of barley (*Blumeria graminis* f sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.10, where $R_1$ and $R_3$ are as originally defined, can be prepared according to the methods outlined in Scheme 1, steps a-i. Compounds of Formula 1.1, where $R_1$ is as originally defined, can be obtained by reacting a chiral oxazolidinone, for example the compound of Formula 1.0, with n-butyllithium (n-BuLi) followed by treating the resulting anion with an acyl halide, such as $R_1CH_2C(O)Cl$ where $R_1$ is as originally defined, in a solvent such as tetrahydrofuran (THF) at cryogenic temperatures of about −78° C., as shown in a. Compounds of Formula 1.2 where $R_1$ is as originally defined, can be obtained by using the methodology reported by Kise, N.; et al. *J. Org. Chem.* 2000, 65, 464-468, wherein compounds of Formula 1.1, can be treated with lithium diisopropylamide (LDA), generated in situ from n-BuLi and diisopropylamine (i-Pr$_2$NH) at about −78 to about 0° C., followed by reacting with bis(acetoxy)iodobenzene in a polar, aprotic solvent like THF from about −78° C. to about 22° C., as shown in b. Compounds of Formula 1.3, where R$_1$ is as originally defined can be obtained from compounds of Formula 1.2, by treating with a nucleophile such as lithium hydroperoxide, generated in situ from hydrogen peroxide and lithium hydroxide (LiOH), in a mixed solvent system, such as aqueous THF at about 22° C., as depicted in c. Diols of Formula 1.4, where R$_1$ is as originally defined can obtained from compounds of Formula 1.3, by treating with a reducing agent such as lithium aluminum hydride (LiAlH$_4$ or LAH), in a polar, aprotic solvent like THF from about 0° C. to about 22° C., as depicted in d. Compounds of Formula 1.6, where R$_1$ and R$_3$ are as originally defined can obtained from compounds of Formula 1.4, by treating with a protected aziridine of Formula 1.5, wherein R$_3$ is as originally defined, for example (S)-1-tert-butyl 2-methyl aziridine-1,2-dicarboxylate, followed by treatment with a Lewis acid such as borontrifluoride diethyletherate (BF$_3$.OEt$_2$) in a halogenated solvent such as dichloromethane (CH$_2$Cl$_2$) at reduced temperatures between about −78 and 0° C., as is depicted in e. Compounds of Formula 1.7, where R$_1$ and R$_3$ are as originally defined can obtained from compounds of Formula 1.6, by reacting with an oxidant such as sulfurtrioxide pyridine complex (SO$_3$.pyr) and a base such as triethylamine (NEt$_3$) in a mixed solvent system, such as CH$_2$Cl$_2$ and dimethylsulfoxide (DMSO), at a temperature of about 0° C. to about 22° C., as depicted in f. Compounds of Formula 1.8, where R$_1$ and R$_3$ are as originally defined can obtained from compounds of Formula 1.7, by treatment with an organometallic reagent, for example methyl-magnesium bromide (MeMgBr), in a halogenated solvent such as CH$_2$Cl$_2$ at reduced temperatures between about −78 and −13° C., as depicted in g. Compounds of Formula 1.9, where R$_1$ and R$_3$ are as originally defined can obtained from compounds of Formula 1.8, by reacting with an oxidant, such as SO$_3$.pyr, and a base, such as NEt$_3$, in a mixed solvent system like CH$_2$Cl$_2$ and DMSO at a temperature between about 0° C. and about 22° C., as depicted in h. Compounds of Formula 1.10, where R$_1$ and R$_3$ are as originally defined can obtained from compounds of Formula 1.9, by addition into a mixture of a chiral catalyst such as (R)-1-methyl-3,3-diphenylhexahydropyrrolo[1,2-c][1,3,2]oxazaborole and a reductant such as borane dimethylsulfide complex (BH$_3$.SMe$_2$) in an aromatic solvent like toluene (PhCH$_3$) between about 0° C. and about 22° C., as depicted in i.

Scheme 1

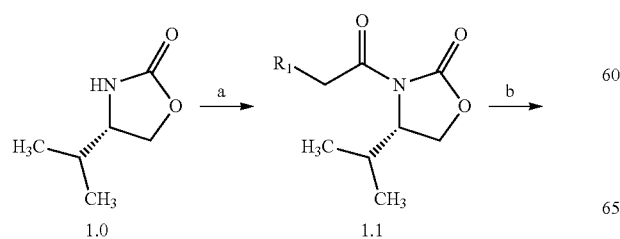

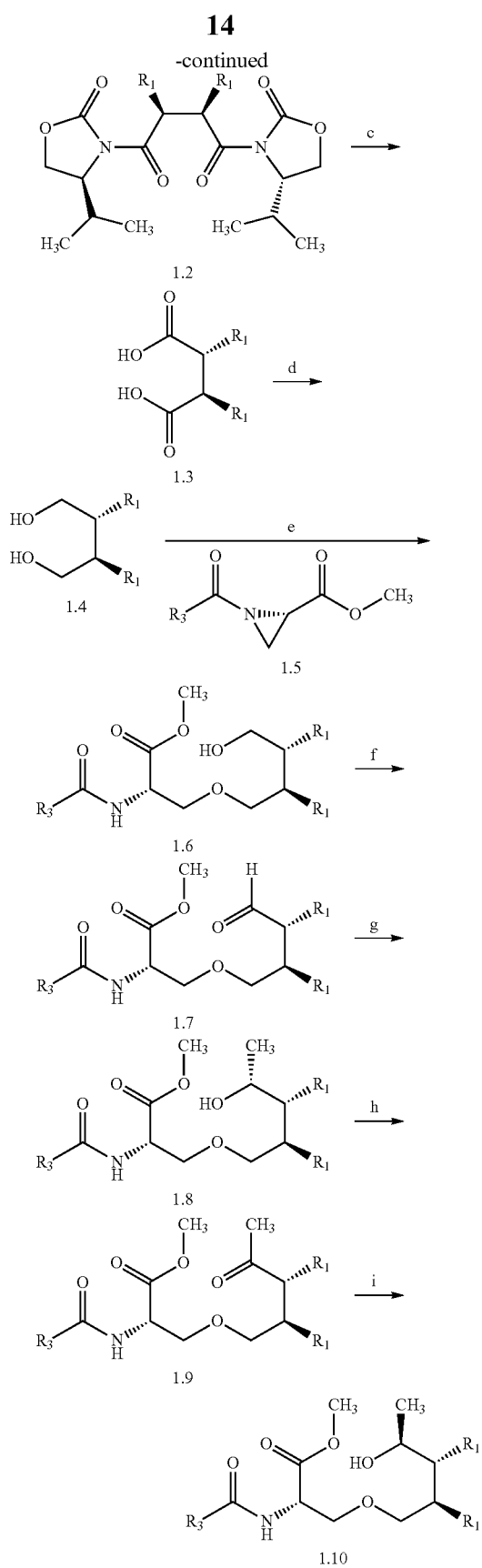

Compounds of Formula 2.5, where R$_1$, R$_2$, and R$_3$ are as originally defined, can be prepared according to the methods outlined in Scheme 2, steps a-d. Compounds of Formula 2.1, where $R_1$ is as originally defined, can be obtained by reaction of (S)-5-methylfuran-2(5H)-one (Formula 2.0; prepared as reported in Kobayashi et al. *Tetrahedron* 2003, 59, 9743-9758) with a Grignard reagent, such as $R_1MgX$, where $R_1$ is as originally defined and X is a halide, for example bromide or chloride, and copper (I) iodide (CuI) in a polar, aprotic solvent such as THF at cryogenic temperatures of about −78° C., as shown in a. Compounds of Formula 2.2, where $R_1$ and $R_2$ are as originally defined, can be obtained by treating compounds of Formula 2.1, where $R_1$ is as originally defined, with LDA, generated in situ from n-BuLi and i-$Pr_2NH$ at about −20° C., followed by reacting with alkyl or benzyl bromide, such as $R_2Br$, where $R_2$ is as originally defined, in a solvent such as THF from about −78° C. to about 22° C., as depicted in b. Diols of Formula 2.3 where $R_1$ and $R_2$ are as originally defined can be prepared from compounds of Formula 2.2, by treatment with a reducing agent such as LAH in a polar, aprotic solvent such as THF, at a reduced temperature of about 0° C. as depicted in c. Compounds of Formula 2.5, where $R_1$ and $R_2$ are as originally defined and $R_3$ is as originally defined, for example tert-butoxy or benzyloxy, can be obtained from compounds of Formula 2.3 by treating with a protected aziridine of Formula 2.4, wherein $R_3$ is as originally defined, for example (S)-1-tert-butyl 2-methyl aziridine-1,2-dicarboxylate or (S)-1-benzyl 2-methyl aziridine-1,2-dicarboxylate, followed by treatment with a Lewis acid such as $BF_3.OEt_2$ in a halogenated solvent such as $CH_2Cl_2$ at reduced temperatures from about −78° C. to about 0° C., as is depicted in d.

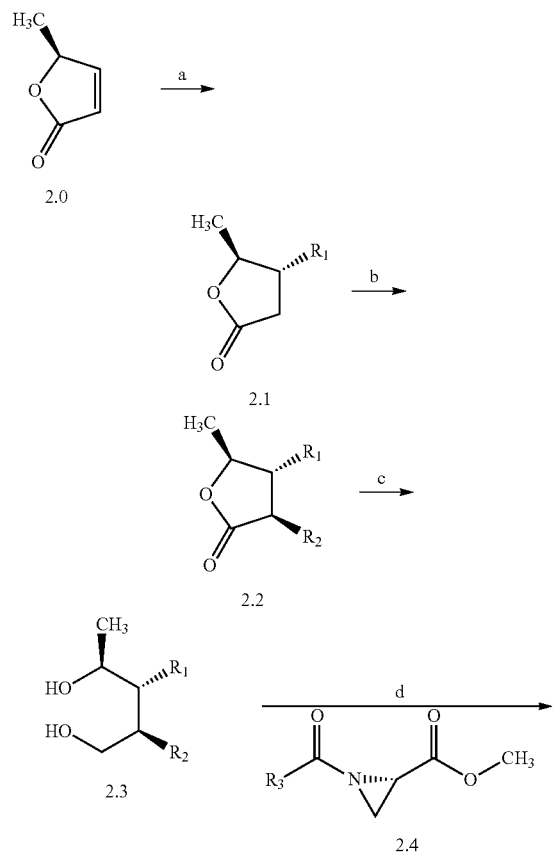

Scheme 2

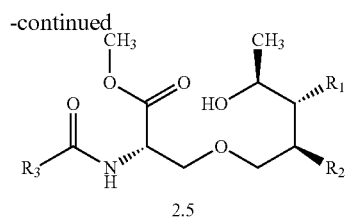

2.5

Compounds of Formulae 3.10 and 3.11, wherein $R_2$ and $R_3$ are as originally defined and n is an integer between 0 and 5, can be prepared according to the methods outlined in Scheme 3, steps a-i. The alcohol of Formula 3.1 can be obtained by reacting prop-1-yn-1-ylmagnesium bromide (Formula 3.0) with an aldehyde, for example acetaldehyde, in a polar, aprotic solvent like THF at a reduced temperature of about 0° C., as depicted in a. The compound of formula 3.2 can be obtained by reacting the alcohol of Formula 3.1 with hydrogen gas ($H_2$) in the presence of a palladium (Pd) catalyst, such as the Lindlar catalyst, in a hydrocarbon solvent such as pentane at about 22° C., as depicted in b. Compounds of Formula 3.4 can be prepared by reacting a compound of Formula 3.2 with a propionic acid of Formula 3.3, wherein $R_2$ is as originally defined and n is an integer between 0 and 5, in the presence of a coupling reagent such as 3-(((ethylimino)methylene)-amino)-N,N-dimethylpropan-l-aminium chloride (EDC), and a nucleophilic catalyst such as N,N-dimethylaminopyridine (DMAP) in a halogenated solvent like $CH_2Cl_2$ at about 22° C., as depicted in c. Compounds of Formula 3.5, wherein $R_2$ and n are as previously defined, can be synthesized from compounds of Formula 3.4 using an Alder-ene reaction as described in He et al. *Tetrahedron Lett.* 2005, 46, 1823-1826. This methodology utilizes a rhodium catalyst, such as chloro(1,5-cyclooctadiene)rhodium(I) dimer ([Rh(cod) Cl]$_2$), a chiral phosphine ligand, such as (R)-(+)-(1,1'-binaphthalene-2,2'-diyl)bis(diphenylphosphine) ((R)-BINAP), and a silver salt, such as silver hexafluorostibate (AgSbF$_6$), in a halogenated solvent like 1,2-dichloroethane (DCE) at about 22° C. to give the appropriately substituted butyrolactone, as depicted in d. Compounds of Formula 3.6, wherein $R_2$ and n are as previously defined, can be prepared from compounds of Formula 3.5, using the methodology referenced above, by treatment with a reducing agent, such as lithium tri-sec-butylhydroborate, in a polar, aprotic solvent like THF at cryogenic temperatures of about −78° C., as depicted in e. The hydroxymethyl intermediates of Formula 3.7, wherein $R_2$ and n are as previously defined, can be prepared by reacting compounds of Formula 3.6 with an oxidant, such as ozone ($O_3$), in a mixture of a halogenated hydrocarbon and an alcohol, for example $CH_2Cl_2$ and methanol (MeOH), at cryogenic temperatures of about −78° C., followed by treatment with a reductant such as sodium borohydride ($NaBH_4$) from about −78° C. to about 22° C., as depicted in f. Allylated compounds of Formula 3.8, wherein $R_2$ and n are as previously defined, can be prepared by treating compounds of Formula 3.7 with either a symmetric or mixed carbonate, for example bis-2methallyl carbonate or tert-butyl(2-methallyl) carbonate respectively, in the presence of a palladium catalyst, such as tris(dibenzylidineacetone)dipalladium(0) chloroform adduct (($Pd_2(dba)_3.CHCl_3$), in a polar, aprotic solvent like THF at elevated temperatures of about 60° C., as depicted in g. Compounds of Formula 3.9, wherein $R_2$ and n are as previously defined, in which the alcohol is capped with a protecting group (PG), for example a trialkylsilane such as triisopropylsilane (TIPS), can be prepared by treating compounds of Formula 3.7 with a silylating reagent, such as triisopropylsilyl trifluoromethanesulfonate (TIPSOTf), in the presence of an organic base, such as 2,6-dimethylpyridine, in a halogenated solvent like $CH_2Cl_2$ from about 0° C. to about 22° C., as depicted in h. Compounds of Formulae 3.10 and 3.11, wherein $R_2$ and $R_3$ are as originally defined and n is an integer between 0 and 5, can be prepared as depicted in i, which represents the methodology previously disclosed in Scheme 2, step c and step d.

Compounds of Formula 4.2, wherein $R_1$, $R_2$, and $R_3$ are as originally defined, can be prepared according to the methods outlined in Scheme 4, steps a-b. Compounds of Formula 4.1, wherein $R_1$, $R_2$, and $R_3$ are as originally defined, can be prepared from compounds of Formula 4.0, by treating with a hydroxide base, such as lithium hydroxide (LiOH), in an aqueous solvent system, such as THF/water, at about 22° C., as depicted in a. Compounds of formula 4.2, wherein $R_1$, $R_2$, and $R_3$ are as originally defined, can be prepared by adding a solution of the compound of Formula 4.1 in a halogenated solvent such as $CH_2Cl_2$ or an aromatic solvent such as $PhCH_3$ to a mixture of a base, such as DMAP, and a mixed anhydride, such as 2-methyl-6-nitrobenzoic anhydride (MNBA), in either a halogenated solvent such as $CH_2Cl_2$ or an aromatic solvent such as $PhCH_3$ at a temperature between about 21° C. and about 60° C. over a period of 4-12 hours (h), as shown in b.

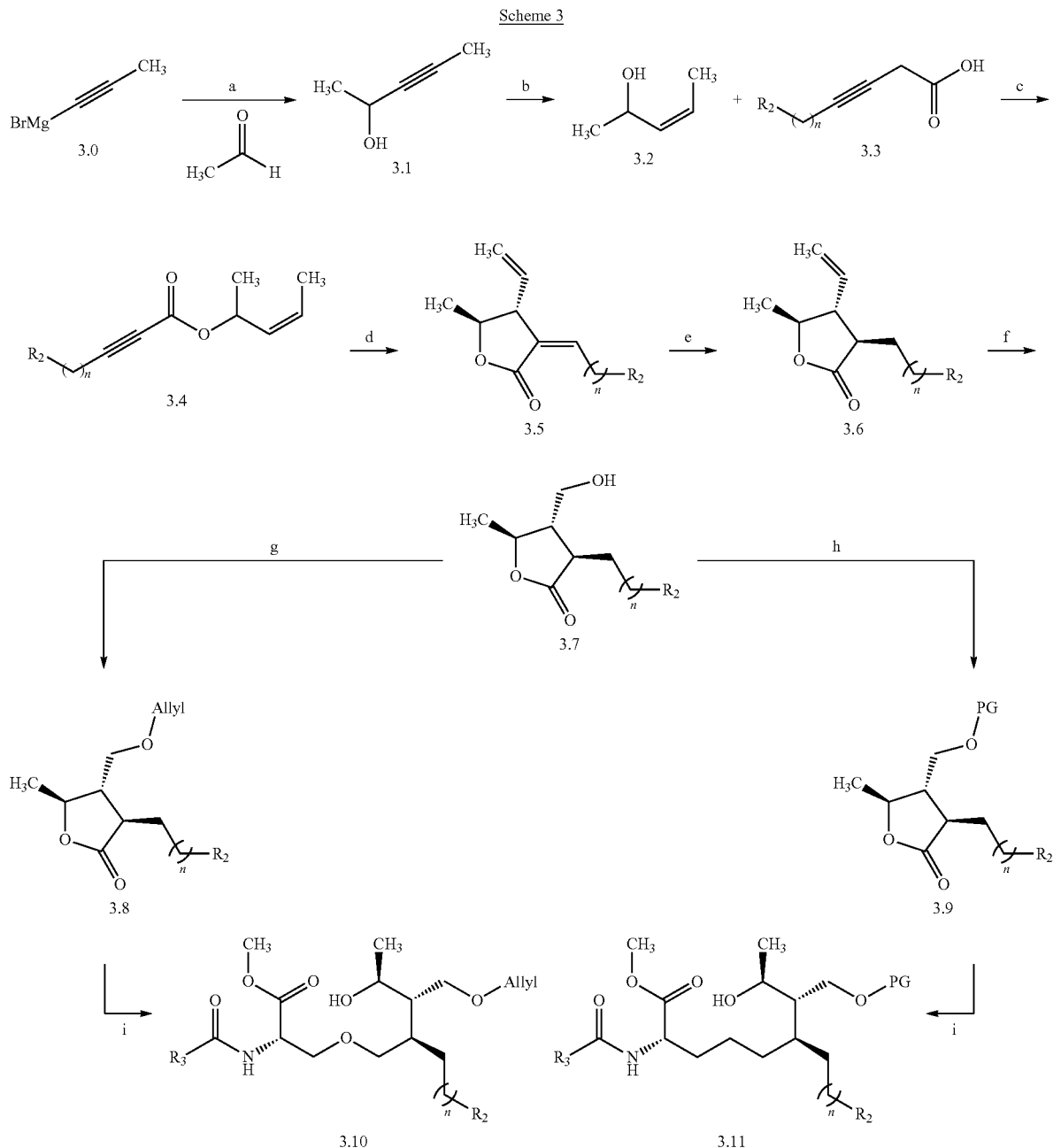

Scheme 3

Scheme 4

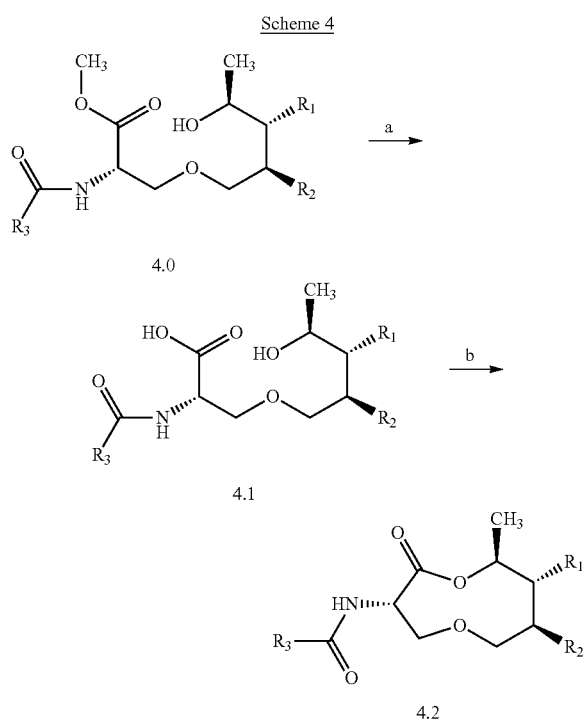

Compounds of Formula 5.1, wherein $R_2$ is as originally defined and is inert to hydrogenation conditions, can be prepared according to the method outlined in Scheme 5. Compounds of Formula 5.1 can be prepared by reacting compounds of Formula 5.0 with $H_2$ in the presence of a catalyst like Pd/C (10%) in a polar solvent like EtOAc at about 22° C., as depicted in a.

Scheme 5

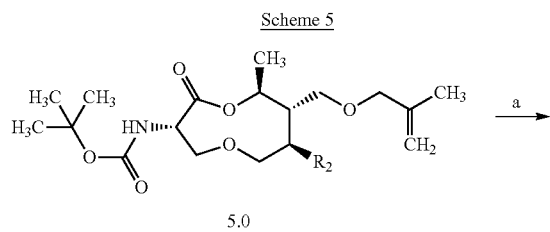

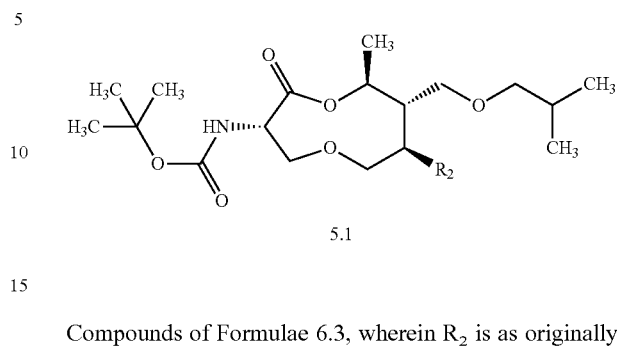

Compounds of Formulae 6.3, wherein $R_2$ is as originally defined and $R_3$ is tert-butoxy, and 6.4, wherein $R_2$ and $R_3$ are as originally defined, can be prepared according to the methods outlined in Scheme 6, steps a-d. Compounds of Formula 6.1, wherein $R_2$ and $R_3$ are as originally defined, can be prepared from compounds of Formula 6.0 by reacting with a fluoride source such as tetrabutylammonium fluoride (TBAF) in a polar, aprotic solvent like THF at a reduced temperature of about 0° C., as depicted in a. Compounds of Formula 6.2, wherein $R_2$ is as originally defined and $R_3$ is tert-butoxy can be prepared from compounds of Formula 6.1, wherein $R_2$ is as originally defined and $R_3$ is tert-butoxy, using the allylation methodology described in Scheme 3, step g, as shown in b. Compounds of Formula 6.3, wherein $R_2$ is as originally defined and $R_3$ is tert-butoxy, can be prepared from compounds of Formula 6.2 using the hydrogenation conditions described in Scheme 5, step a, as shown in c. Aryl ethers of Formula 6.4, wherein $R_2$ and $R_3$ are as originally defined, can be prepared using Mitsunobu conditions, namely by reacting a compound of Formula 6.1, wherein $R_2$ and $R_3$ are as originally defined, with an alcohol, for example phenol, a nucleophilic phosphine such as triphenylphosphine (PPh$_3$), and an azidodicarboxylate such as (E)-diisopropyl diazene-1,2-dicarboxylate (DIAD) in a polar, aprotic solvent like THF at a temperature of about about 0° C. to about 22° C., as depicted in d.

Scheme 6

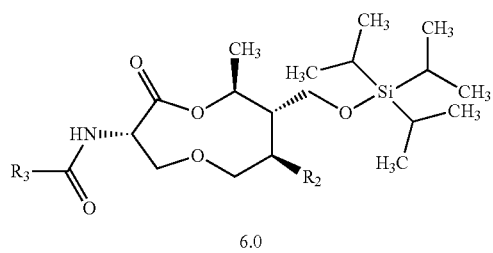

a ↓

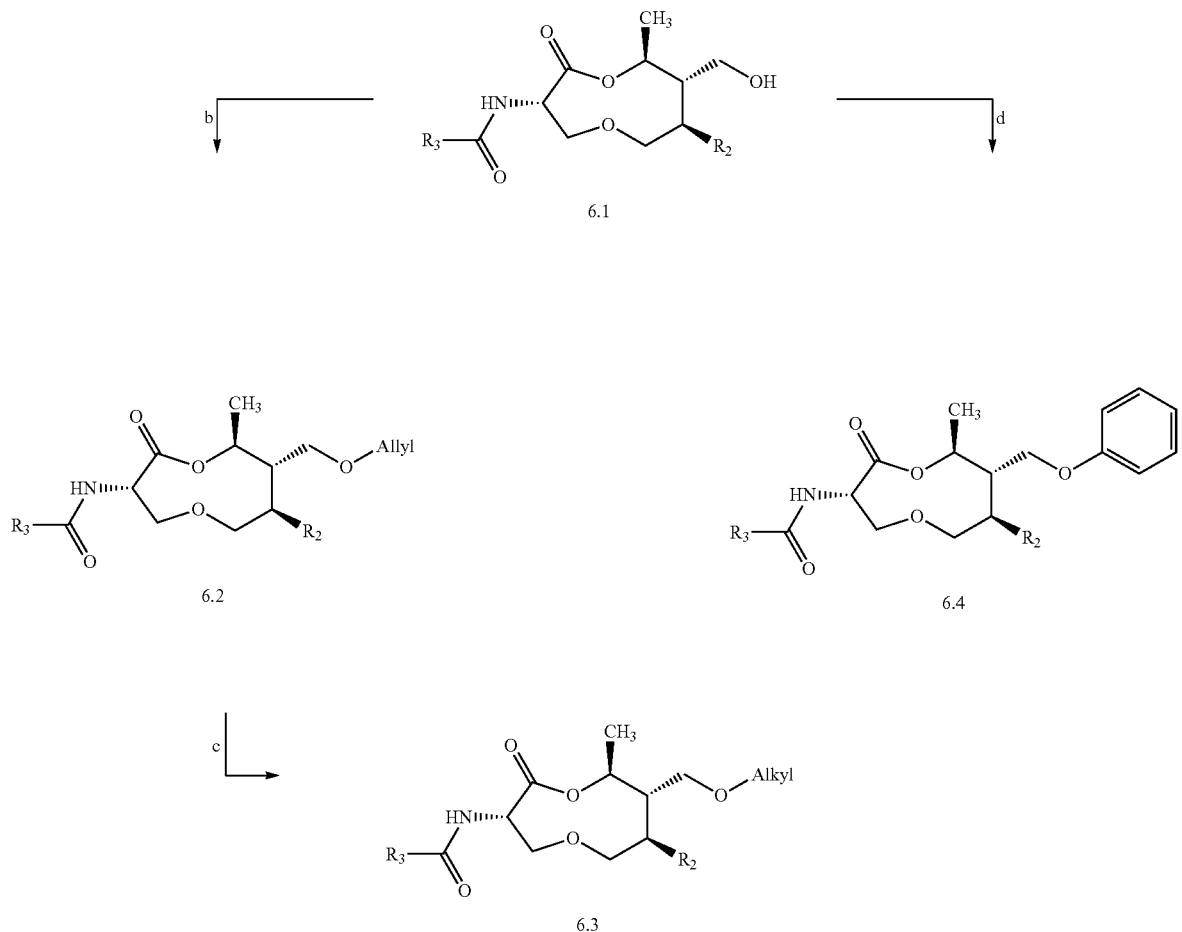

Compounds of Formula 7.4, wherein $R_1$ and $R_2$ are as originally defined, can be prepared through the methods shown in Scheme 7, steps a-e. Compounds of Formula 7.1, wherein $R_1$ and $R_2$ are as originally defined, can be obtained from compounds of Formula 7.0, wherein $R_1$ and $R_2$ are as orginally defined, X is tert-butoxycarbonyl (BOC) and Y is hydrogen, by treating with an acid, such as a solution of 4.0 Molar (M) hydrogen chloride (HCl) in dioxane, in an an aprotic solvent like $CH_2Cl_2$ at about 22° C., as shown in a. Compounds of Formula 7.2, wherein $R_1$ and $R_2$ are as orginally defined, can be prepared from compounds of Formula 7.0, wherein $R_1$ and $R_2$ are as orginally defined, X is carboxybenzyl (Cbz), and Y is hydrogen, by treating with $H_2$ in the presence of a palladium catalyst, for example palladium on carbon (Pd/C, 5 or 10 weight %), in a polar solvent like ethyl acetate (EtOAc) at about 22° C., as shown in b. Compounds of Formula 7.3, wherein $R_1$ and $R_2$ are as orginally defined, can be prepared from compounds of Formula 7.0, wherein $R_1$ and $R_2$ are as orginally defined, X is Cbz, and Y is hydrogen, by treating with an acid, for example aqueous hydrogen bromide (HBr, 33%), in a solvent like glacial acetic acid (HOAc) from about 0° C. to about 22° C., as shown in c. Compounds of Formula 7.4, wherein $R_1$ and $R_2$ are as originally defined, can be prepared from compounds of Formula 7.2 by treating with 3-hydroxy-4-methoxypicolinic acid in the presence of a base, such as 4-methylmorpholine, and a peptide coupling reagent, such as O-(7-azabenzotriazol-1-yl)-N,N,N',N'-tetramethyluronium hexafluoro-phosphate (HATU) or benzotriazol-1-yloxytripyrrolidino-phosphonium hexafluorophosphate (PyBOP), in an aprotic solvent such as $CH_2Cl_2$, as shown in e. Additionally, compounds of Formula 7.4, wherein $R_1$ and $R_2$ are as originally defined, can be prepared from compounds of Formulae 7.1 and 7.3 using the methodology previously described in step e, wherein the the hydrogen chloride and hydrogen bromide salts are neutralized in situ. Alternatively, the the salts of Formulae 7.1 and 7.3, may be neutralized with a weak base, for example saturated aqueous sodium bicarbonate ($NaHCO_3$), and isolated as the free base to give compounds of Formula 7.2, as shown in step d, which are converted to compounds of Formula 7.4 in step e, as described above.

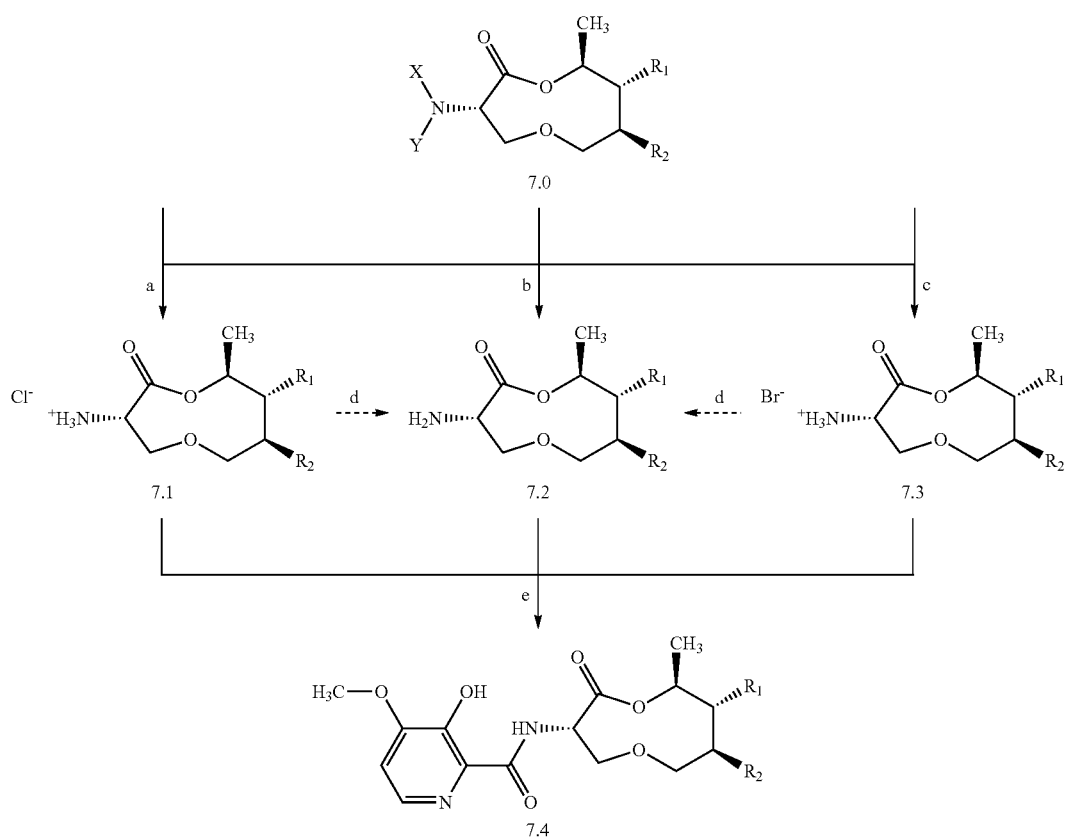

Compounds of Formula 8.0, wherein $R_1$, $R_2$ and $R_4$ are as originally defined, can be prepared by the method shown in Scheme 8. Compounds of Formula 8.0 can be prepared from compounds of Formula 7.4, wherein $R_1$ and $R_2$ are as originally defined, by treatment with an appropriate alkyl halide, an alkali carbonate base, for example sodium carbonate ($Na_2CO_3$) or potassium carbonate ($K_2CO_3$), and with or without a reagent such as sodium iodide (NaI) in a solvent such as acetone or by treatment with an acyl halide in the presence of an amine base, such as pyridine, $Et_3N$, DMAP, or mixtures thereof, in an aprotic solvent such as $CH_2Cl_2$, as shown in step a.

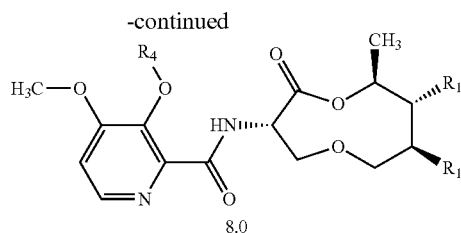

EXAMPLES

Example 1, Step 1

Preparation of (S)-4-isopropyl-3-(3-phenylpropanoyl)oxazolidin-2-one

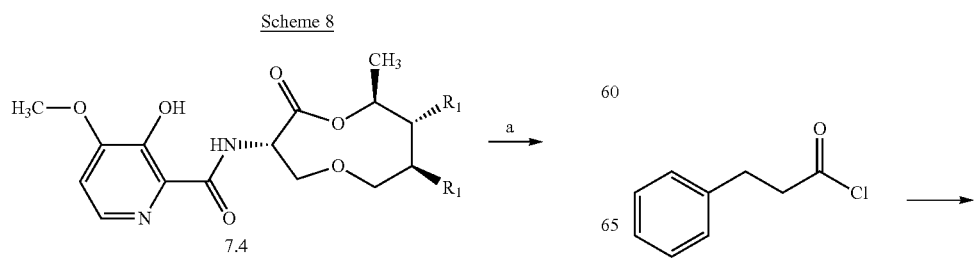

-continued

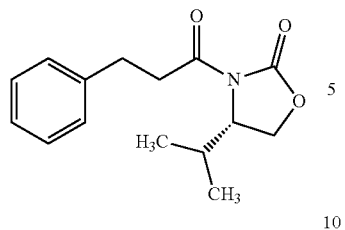

An oven-dried 500 milliliter (mL) Schlenk flask was cooled under nitrogen gas (N$_2$) and then charged with (S)-4-isopropyloxazolidin-2-one (7.05 grams (g), 54.6 millimoles (mmol)) and anhydrous THF (300 mL). After sealing with a rubber septum, the resulting colorless solution was cooled to −78° C. in a dry ice/acetone bath and treated with a solution of n-BuLi (2.5 Molar (M) in hexanes, 24.0 mL, 60.0 mmol). The reaction mixture was stirred at −78° C. for 30 minutes (min) and treated with via syringe with 3-phenylpropanyl chloride (8.80 mL, 59.2 mmol). The resulting yellow solution was stirred for 2.5 hours (h) at −78° C., the cold bath was removed, a solution of saturated aqueous ammonium chloride (NH$_4$Cl, 100 mL) was added, and the resulting white suspension was allowed to stir at room temperature for 10 min. The crude reaction mixture was extracted with ethyl acetate (EtOAc, 3×100 mL), and the combined organic extracts were washed with saturated aqueous sodium chloride solution (NaCl, brine, 100 mL), dried over anhydrous sodium sulfate (Na$_2$SO$_4$), filtered, and concentrated by rotary evaporation. The crude concentrate was purified via column chromatography (silica gel (SiO2), 1→30% acetone in hexanes) to give the title compound (11.4 g, 80%) as a white solid: mp 59-62° C.; $^1$H NMR (400 MHz, CDCl$_3$) δ 7.33-7.16 (m, 5H), 4.44-4.39 (m, 1H), 4.24 (dd, J=9.1, 8.1 Hz, 1H), 4.19 (dd, J=9.1, 3.2 Hz, 1H), 3.32 (ddd, J=16.9, 8.6, 6.7 Hz, 1H), 3.22 (ddd, J=16.9, 8.0, 7.2 Hz, 1H), 3.06-2.92 (m, 2H), 2.35 (pd, J=7.0, 3.9 Hz, 1H), 0.90 (d, J=7.0 Hz, 2H), 0.84 (d, J=7.0 Hz, 2H); $^{13}$C NMR (101 MHz, CDCl$_3$) δ 172.40, 154.06, 140.49, 128.56, 128.46, 126.24, 63.40, 58.45, 37.07, 30.45, 28.39, 17.97, 14.64; ESIMS m/z 262 ([M+H]$^+$).

Example 1, Step 2

Preparation of (2R,3R)-2,3-dibenzyl-1,4-bis((S)-4-isopropyl-2-oxooxazolidin-3-yl)butane-1,4-dione

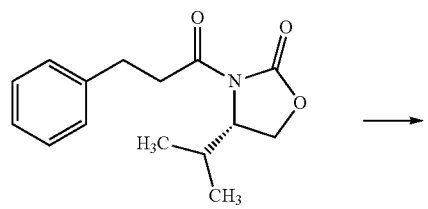

-continued

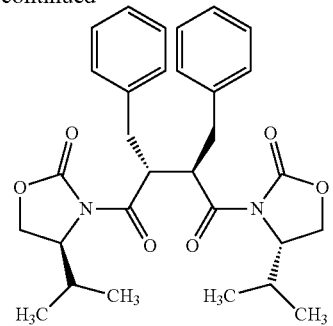

An oven-dried 500 mL Schlenk flask was cooled under N$_2$, charged with anhydrous THF (200 mL) and N,N-diisopropylamine (6.66 mL, 47.5 mmol), and sealed with a rubber septum. The resulting colorless solution was cooled to −78° C. in a dry ice/acetone bath and treated with a solution of n-BuLi (2.5 M in hexanes, 19.0 mL, 47.5 mmol). The reaction mixture was stirred at −78° C. for 15 min, warmed to 0° C. and stirred for 15 min, cooled to −78° C., and treated with a solution of (S)-4-isopropyl-3-(3-phenyl-propanoyl)oxazolidin-2-one (10.4 g, 39.6 mmol) in anhydrous THF (100 mL) via a canula over a 20 min period. The resulting solution was stirred at −78° C. for 20 min, whereupon bis(acetoxy)iodobenzene (15.3 g, 47.5 mmol) was added. The cold bath was removed and the reaction was stirred at room temperature. After 21 h, the reaction mixture was diluted with 1.0 M aqueous hydrogen chloride (HCl, 100 mL) and extracted with diethyl ether (Et$_2$O, 1×200 mL and 2×100 mL). The combined organic extracts were washed with a 1:1 mixture of brine and water (200 mL), dried over anhydrous magnesium sulfate (MgSO$_4$), filtered, and concentrated by rotary evaporation. The crude concentrate was purified via column chromatography (SiO$_2$, 10→100% dichloromethane (CH$_2$Cl$_2$) in hexanes) to give the title compound (4.54 g, 44%) as a cream colored solid: mp 193-196° C.; $^1$H NMR (400 MHz, CDCl$_3$) δ 7.31-7.25 (m, 2H), 7.25-7.18 (m, 3H), 4.82-4.74 (m, 1H), 4.00-3.91 (m, 2H), 3.65-3.52 (m, 1H), 3.11 (dd, J=13.0, 5.3 Hz, 1H), 2.93-2.85 (m, 1H), 2.23-2.10 (m, 1H), 0.81 (d, J=4.1 Hz, 3H), 0.79 (d, J=4.0 Hz, 3H); $^{13}$C NMR (101 MHz, CDCl$_3$) δ 175.43, 153.06, 137.78, 129.32, 128.31, 126.78, 62.86, 58.81, 46.51, 37.77, 28.45, 17.93, 14.56; ESIMS m/z 543 ([M+Na]$^+$).

Example 1, Step 3

Preparation of (2R,3R)-2,3-dibenzylsuccinic acid

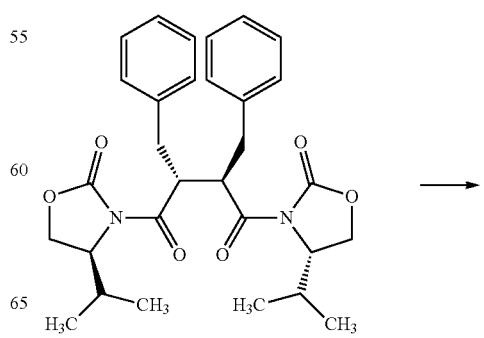

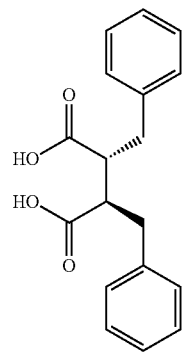

A 250 mL round bottom flask was charged with (2R,3R)-2,3-dibenzyl-1,4-bis((S)-4-isopropyl-2-oxooxazolidin-3-yl)butane-1,4-dione (4.5 g, 8.64 mmol), THF (50 mL) and water (30 mL). The resulting mixture was cooled to 0° C. in an ice bath and treated with 30% hydrogen peroxide (H$_2$O$_2$, 9.00 mL, 88.0 mmol) followed by lithium hydroxide (LiOH, 832 milligrams (mg), 34.7 mmol). After stirring at room temperature for 44 h, the reaction was cooled to 0° C. in an ice bath and treated with 1.5 M aqueous sodium sulfite (Na$_2$SO$_3$, 75 mL). After stirring for 10 min, the crude reaction mixture was diluted with brine (25 mL) and washed with CH$_2$Cl$_2$ (3×50 mL). The aqueous phase was acidified with 12.0 M HCl (25 mL), extracted with EtOAc (3×50 mL), and the combined organic extracts were washed with brine (50 mL), dried over anhydrous MgSO$_4$, filtered and concentrated to provide the title compound (2.58 g, 100%) as a colorless oil: $^1$H NMR (400 MHz, CDCl$_3$) δ 10.61 (s, 2H), 7.32-7.15 (m, 6H), 7.05-6.91 (m, 4H), 3.14 (dd, J=14.0, 6.2 Hz, 2H), 3.04 (dd, J=14.0, 7.7 Hz, 2H), 2.93-2.84 (m, 2H); $^{13}$C NMR (101 MHz, CDCl$_3$) δ 180.03, 138.03, 129.08, 128.58, 126.66, 46.55, 35.78; ESIMS m/z 297 ([M−H]$^−$).

Example 1, Step 4

Preparation of (2R,3R)-2,3-dibenzylbutane-1,4-diol

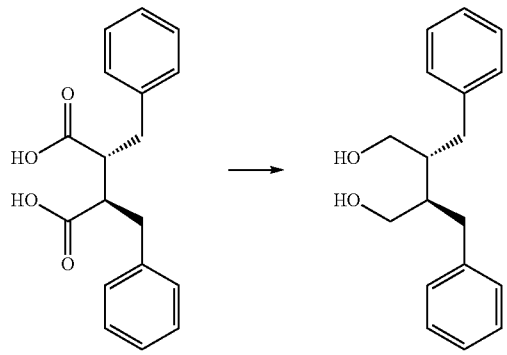 [SMILES: O=C(O)[C@H](Cc1ccccc1)[C@@H](Cc1ccccc1)C(=O)O ; OC[C@H](Cc1ccccc1)[C@H](CO)Cc1ccccc1]

An oven-dried 250 mL Schlenk flask was cooled under N$_2$ and sealed with a rubber septum. The flask was charged with anhydrous THF (40 mL) and a solution of lithium aluminum hydride (LAH, 1.0 M in THF, 26.1 mL, 26.1 mmol). The resulting solution was cooled to 0° C. in an ice bath and treated via a canula with a solution of (2R,3R)-2,3-dibenzylsuccinic acid (2.60 g, 8.72 mmol) in anhydrous THF (27 mL) over an 11 min period with an anhydrous THF (2 mL) rinse of the source flask and canula. The cold bath was removed and the reaction mixture was heated to and stirred at 60° C. for 12 h. The reaction mixture was cooled to 0° C. in an ice bath, diluted with Et$_2$O (100 mL), treated with water (1 mL), stirred for 5 min, and then treated with 15% aqueous sodium hydroxide (NaOH, 1 mL). After stirring for an additional 10 min, water (3 mL) was added, the cold bath was removed, and the resulting mixture was stirred at room temperature for 2 h. The solids were collected on filter paper in a Buchner funnel and rinsed with Et$_2$O. The filtrate was saved and the solids were suspended in THF (20 mL), warmed to 62° C., and stirred for 1 h. The reaction mixture was cooled to room temperature and the solids were collected on filter paper rinsing with Et$_2$O. The two filtrates were combined, concentrated by rotary evaporation, and the crude concentrate was purified via column chromatography (SiO$_2$, 1→35% acetone in hexanes) to give the title compound (1.52 g, 64%) as a white solid: mp 87-93° C.; $^1$H NMR (400 MHz, CDCl$_3$) δ 7.28-7.22 (m, 4H), 7.22-7.11 (m, 6H), 3.86 (s, 2H), 3.78 (dd, J=11.4, 1.8 Hz, 2H), 3.47 (dd, J=11.4, 4.5 Hz, 2H), 2.82 (dd, J=13.7, 8.6 Hz, 2H), 2.71 (dd, J=13.6, 5.8 Hz, 2H), 1.96-1.86 (m, 2H); $^{13}$C NMR (101 MHz, CDCl$_3$) δ 140.67, 129.08, 128.42, 126.01, 60.19, 44.21, 36.18; ESIMS m/z 269 ([M−H]$^−$).

Example 1, Step 5a

Preparation of (5)-methyl 2-((tert-butoxycarbonyl)amino)-3-((2R,3R)-2,3-dibenzyl-4-hydroxybutoxy)propanoate

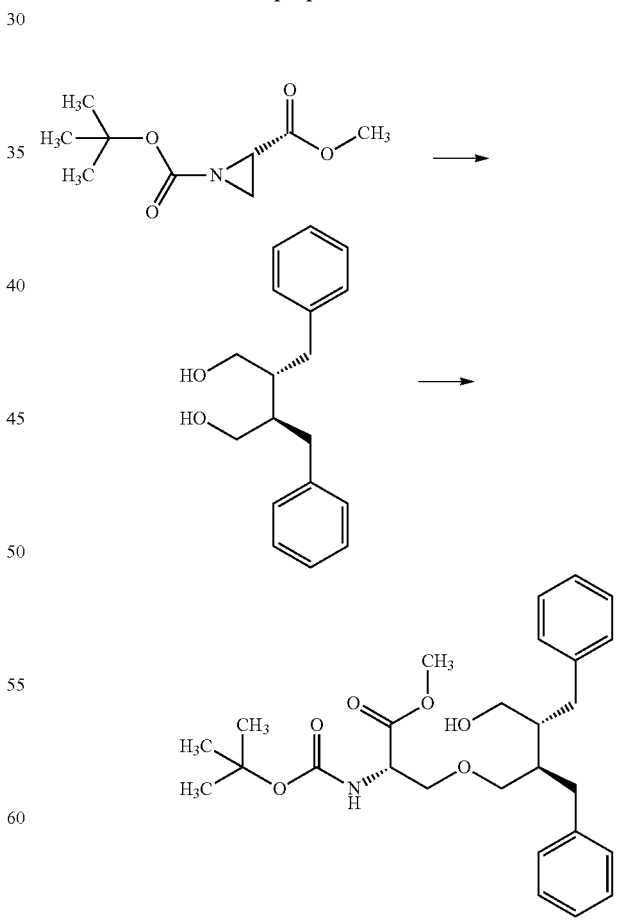

An oven-dried 100 mL Schlenk flask was cooled under N$_2$, charged with (S)-1-tert-butyl 2-methyl aziridine-1,2- dicarboxylate (706 mg, 3.51 mmol) and (2R,3R)-2,3-dibenzylbutane-1,4-diol (1.41 g, 5.22 mmol), and sealed with a rubber septum. Anhydrous CH$_2$Cl$_2$ (35 mL) was added, and the resulting mixture was cooled to −78° C. in a dry ice/acetone bath and treated with BF$_3$·O(Et)$_2$ (0.088 mL, 0.694 mmol). After stirring for 15 min, the reaction mixture was warmed to 0° C. in an ice bath and stirred for 3 h at 0° C. The reaction mixture was quenched with saturated aqueous sodium bicarbonate (NaHCO$_3$) solution (50 mL), and warmed to room temperature. The resulting mixture was diluted with water (50 mL) and extracted with CH$_2$Cl$_2$ (3×50 mL), and the combined organic extracts were washed with brine (50 mL), dried over MgSO$_4$, filtered, and concentrated by rotary evaporation. The crude concentrate was purified via column chromatography (SiO$_2$, 1→30% acetone in hexanes) to give the title compound (839 mg, 51%) as a colorless oil: $^1$H NMR (400 MHz, CDCl$_3$) δ 7.30-7.24 (m, 4H), 7.23-7.16 (m, 2H), 7.16-7.12 (m, 2H), 7.11-7.06 (m, 2H), 5.39 (d, J=8.4 Hz, 1H), 4.55-4.41 (m, 1H), 3.83-3.72 (m, 4H), 3.70-3.61 (m, 2H), 3.59-3.45 (m, 2H), 3.29 (dd, J=9.7, 5.9 Hz, 1H), 2.81-2.58 (m, 4H), 2.31 (dd, J=8.0, 4.7 Hz, 1H), 2.09-1.98 (m, 1H), 1.98-1.88 (m, 1H), 1.45 (s, 9H); $^{13}$C NMR (101 MHz, CDCl$_3$) δ 171.00, 155.43, 140.72, 140.51, 129.07, 128.97, 128.38, 126.05, 125.94, 80.18, 71.38, 70.61, 61.73, 53.97, 52.60, 44.41, 41.69, 36.07, 35.69, 28.33; ESIMS m/z 494 ([M+Na]$^+$).

Example 1, Step 5b

Preparation of (S)-methyl 2-(((benzyloxy)carbonyl)amino)-3-(((2R,3R)-3-((S)-1-hydroxyethyl)-2-(4-(trifluoromethyl)benzyl)heptyl)oxy)propanoate

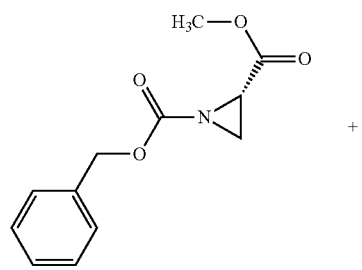

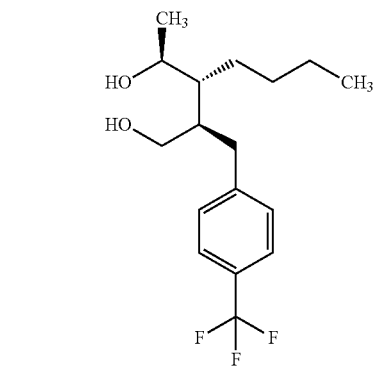

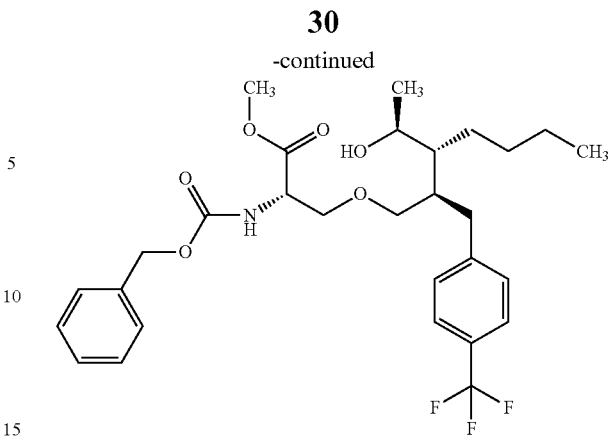

To a solution of (S)-1-benzyl 2-methyl aziridine-1,2-dicarboxylate (172 mg, 0.731 mmol) and (2R,3R,4S)-3-butyl-2-(4-(trifluoromethyl)benzyl)pentane-1,4-diol (349 mg, 1.097 mmol) in DCM (15 mL) at 0° C. was added BF$_3$·O(Et)$_2$ (18.1 μl, 0.146 mmol). The reaction was slowly warmed to room temperature over a 6 h period as the ice melted. The reaction mixture was quenched by the addition of saturated aqueous NaHCO$_3$, and extracted with EtOAc (3×). The combined organic phases were concentrated and purified by column chromatography (SiO$_2$, EtOAc in hexanes gradient) to provide the title compound (178 mg, 44%) as a colorless oil: $^1$H NMR (400 MHz, CDCl$_3$) δ 7.56-7.49 (m, 2H), 7.44-7.22 (m, 7H), 5.63 (d, J=8.6 Hz, 1H), 5.12 (d, J=1.7 Hz, 2H), 4.51 (dt, J=8.5, 3.1 Hz, 1H), 3.83-3.69 (m, 2H), 3.77 (s, 3H), 3.62 (dd, J=9.4, 3.2 Hz, 1H), 3.39 (dd, J=9.4, 3.5 Hz, 1H), 3.28 (dd, J=9.4, 6.4 Hz, 1H), 2.89 (dd, J=13.6, 5.2 Hz, 1H), 2.64 (dd, J=13.5, 9.9 Hz, 1H), 2.15-2.08 (m, 2H), 1.46-1.33 (m, 1H), 1.30-1.17 (m, 9H), 0.92-0.81 (m, 3H); $^{19}$F NMR (376 MHz, CDCl3) δ −62.28; ESIMS m/z 576.4 ([M+Na]$^+$).

Example 1, Step 6

Preparation of (S)-methyl 2-((tert-butoxycarbonyl)amino)-3-((2R,3R)-2,3-dibenzyl-4-oxobutoxy)propanoate

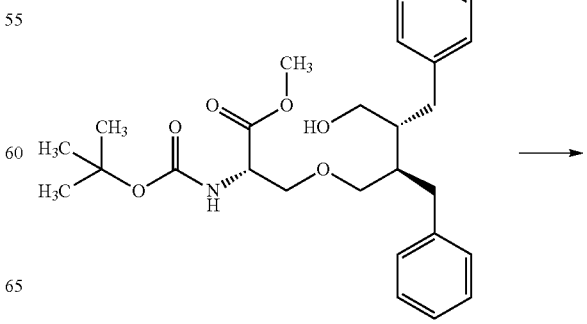

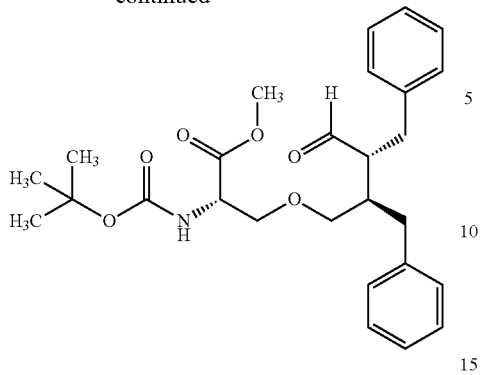

A 25 mL screw top vial was charged with (S)-methyl 2-((tert-butoxycarbonyl)amino)-3-((2R,3R)-2,3-dibenzyl-4-hydroxybutoxy)propanoate (820 mg, 1.74 mmol), anhydrous $CH_2Cl_2$ (10 mL), and anhydrous dimethyl sulfoxide (DMSO, 2 mL). The resulting mixture was cooled to 0° C. in an ice bath and treated with triethylamine (TEA, 1.20 mL, 8.61 mmol) followed by sulfurtrioxide pyridine complex (830 mg, 5.21 mmol). The reaction mixture was stirred while slowly warming as the ice melted, and after 4.5 h, the reaction mixture was diluted with saturated aqueous $NH_4Cl$ (50 mL) at 15° C. The mixture was extracted with EtOAc (3×50 mL), and the combined organic extracts were washed with brine (50 mL), dried over anhydrous $MgSO_4$, filtered, and concentrated by rotary evaporation. The crude concentrate was purified via column chromatography ($SiO_2$, 1→30% acetone in hexanes) to give the title compound (788 mg, 97%) as a colorless oil: $^1H$ NMR (400 MHz, $CDCl_3$) δ 9.72 (d, J=1.3 Hz, 1H), 7.34-7.03 (m, 10H), 5.38 (d, J=8.8 Hz, 1H), 4.49-4.39 (m, 1H), 3.81-3.70 (m, 4H), 3.55 (dd, J=9.2, 3.0 Hz, 1H), 3.46 (dd, J=9.4, 3.7 Hz, 1H), 3.27 (dd, J=9.4, 5.9 Hz, 1H), 3.13 (dd, J=16.4, 10.1 Hz, 1H), 2.83-2.62 (m, 4H), 2.33-2.21 (m, 1H), 1.46 (s, 9H); $^{13}C$ NMR (101 MHz, $CDCl_3$) δ 203.62, 171.02, 155.56, 139.41, 139.25, 129.00, 128.88, 128.58, 128.55, 126.45, 126.36, 80.05, 71.18, 69.94, 54.21, 53.96, 52.49, 41.70, 35.83, 32.37, 28.35; ESIMS m/z 492 ([M+Na]$^+$).

An oven dried 25 mL Schlenk flask was cooled under $N_2$ and was charged with (S)-methyl 2-((tert-butoxycarbonyl)amino)-3-((2R,3R)-2,3-dibenzyl-4-oxobutoxy)propanoate (280 mg, 0.596 mmol) and anhydrous $CH_2Cl_2$ (6 mL). The flask was sealed with a rubber septum, cooled to −78° C. in a dry ice/acetone bath, and the solution was treated with a solution of methylmagnesium bromide (MeMgBr, 3.0 M in $Et_2O$, 0.40 mL, 1.20 mmol). The reaction mixture was stirred while slowly warming as the dry ice sublimed and after 3 h the reaction mixture was quenched at −13° C. by the addition of saturated aqueous $NH_4Cl$ solution (10 mL) and then warmed to room temperature. The resulting mixture was diluted with water (50 mL), extracted with EtOAc (3×50 mL), and the combined organic extracts were washed with brine (50 mL), dried over anhydrous $MgSO_4$, filtered, and concentrated by rotary evaporation. The crude concentrate was purified via column chromatography ($SiO_2$, 1→30% acetone in hexanes) to give a 90:10 diastereomeric mixture of the title compound (230 mg, 79%) as a colorless oil: $^1H$ NMR (400 MHz, $CDCl_3$) δ 7.34-6.90 (m, 10H), 5.54-5.36 (m, 1H), 4.58-4.40 (m, 1H), 4.24-4.12 (m, 1H), 3.79 (s, 3H), 3.66 (d, J=9.2 Hz, 1H), 3.25 (dd, J=9.8, 5.5 Hz, 1H), 3.01 (s, 1H), 2.90 (dd, J=14.5, 4.8 Hz, 1H), 2.65 (dd, J=14.2, 9.5 Hz, 2H), 2.56 (dd, J=13.7, 6.7 Hz, 1H), 1.90 (dd, J=7.1, 4.7 Hz, 1H), 1.84-1.76 (m, 1H), 1.46 (s, 9H), 1.24 (d, J=6.5 Hz, 3H); $^{13}C$ NMR (101 MHz, $CDCl_3$) δ 170.93, 155.46, 141.33, 140.32, 128.95, 128.88, 128.37, 128.34, 126.03, 125.78, 80.19, 71.66, 70.52, 65.36, 52.63, 47.65, 40.47, 36.23, 31.95, 28.34, 21.75; ESIMS m/z 486 ([M+H]$^+$).

Example 1, Step 7

Preparation of (S)-methyl 2-((tert-butoxycarbonyl)amino)-3-(((2R,3R,4R)-2,3-dibenzyl-4-hydroxypentyl)oxy)propanoate Example 1, Step 8

Preparation of (S)-methyl 2-((tert-butoxycarbonyl)amino)-3-(((2R,3R)-2,3-dibenzyl-4-oxopentyl)oxy)propanoate

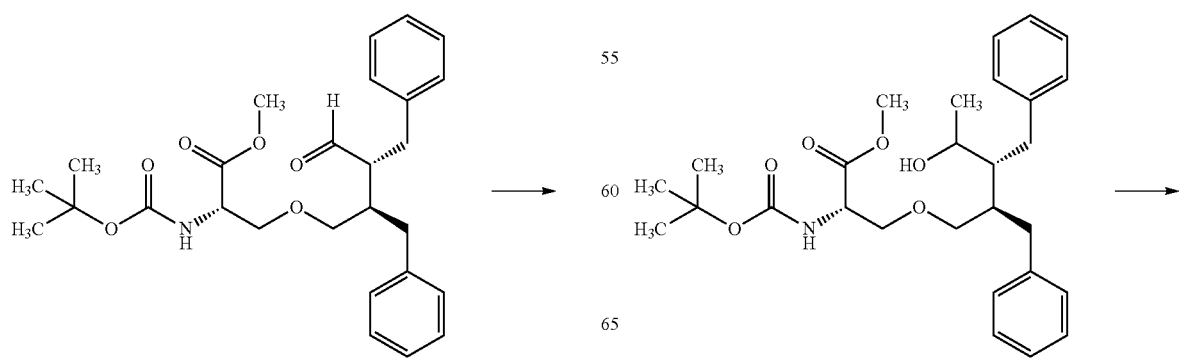

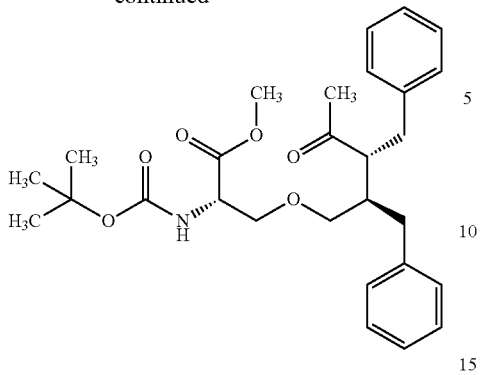

A 25 mL screw top vial was charged with (S)-methyl 2-((tert-butoxycarbonyl)amino)-3-(((2R,3R,4R)-2,3-dibenzyl-4-hydroxypentyl)oxy)propanoate (200 mg, 0.412 mmol), anhydrous $CH_2Cl_2$ (2.5 mL), and anhydrous DMSO (0.50 mL). The resulting mixture was cooled to 0° C. in an ice water bath, treated with TEA (0.30 mL, 2.15 mmol) and sulfurtrioxide pyridine complex (196 mg, 1.23), and the resulting mixture was stirred at 0° C. and slowly warmed to room temperature as the ice melted. The reaction mixture was diluted with saturated aqueous $NH_4Cl$ solution (50 mL), extracted with EtOAc (3×50 mL), and the combined organic extracts were washed with brine (50 mL), dried over anhydrous $MgSO_4$, filtered, and concentrated by rotary evaporation. The crude concentrate was purified via column chromatography ($SiO_2$, 1→30% acetone in hexanes) to give the title compound (119 mg, 60%) as a colorless oil: $^1$H NMR (400 MHz, $CDCl_3$) δ 7.35-7.05 (m, 10H), 5.36 (d, J=8.6 Hz, 1H), 4.41 (dt, J=8.6, 3.2 Hz, 1H), 3.82-3.63 (m, 4H), 3.52 (dd, J=9.3, 3.2 Hz, 1H), 3.34-3.18 (m, 2H), 3.10-2.99 (m, 1H), 2.94-2.79 (m, 3H), 2.54 (dd, J=13.7, 10.3 Hz, 1H), 2.24-2.10 (m, 1H), 1.91 (s, 3H), 1.43 (s, 9H); $^{13}$C NMR (101 MHz, $CDCl_3$) δ 212.12, 171.05, 155.39, 139.75, 139.69, 129.00, 128.92, 128.51, 128.48, 126.28, 79.99, 70.93, 70.28, 55.09, 53.98, 52.44, 42.72, 35.22, 35.01, 32.00, 28.33; ESIMS m/z 506 ([M+Na]$^+$).

Example 1, Step 9a

Preparation of (5)-methyl 2-((tert-butoxycarbonyl)amino)-3-(((2R,3R,4S)-2,3-dibenzyl-4-hydroxypentyl)oxy)propanoate

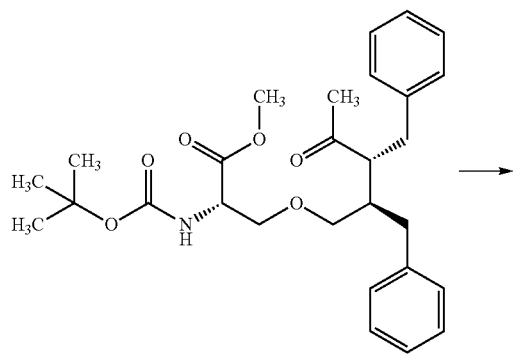

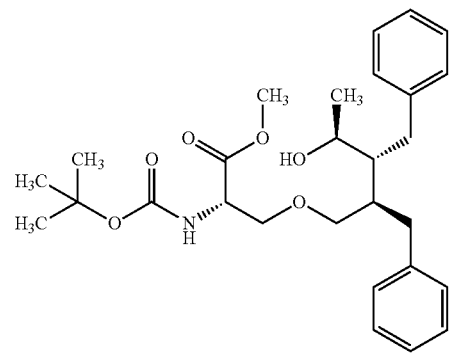

An oven-dried 10 mL Schlenk flask was cooled under $N_2$, sealed with a rubber septum, and then charged with anhydrous toluene (5.2 mL) and a solution of (R)-1-methyl-3,3-diphenylhexahydropyrrolo[1,2-c][1,3,2]oxazaborole (1.0 M in toluene, 0.012 mL, 0.012 mmol). The resulting solution was cooled to 0° C. in an ice bath and treated with borane dimethylsulfide (0.029 mL, 0.306 mmol) followed by the addition of a solution of (S)-methyl 2-((tert-butoxycarbonyl)amino)-3-(((2R,3R)-2,3-dibenzyl-4-oxopentyl)oxy)propanoate in toluene (2.6 mL) via a syringe pump over a 30 min period, and the resulting solution was stirred at 0° C. for 5 h. The reaction was quenched by the sequential addition of methanol (MeOH, 2.5 mL) and water (2.5 mL). The resulting mixture was diluted with water (50 mL), extracted with $CH_2Cl_2$ (3×50 mL), and the combined organic extracts were washed with brine (50 mL), dried over anhydrous $MgSO_4$, filtered, and concentrated by rotary evaporation. The crude concentrate was purified via column chromatography ($SiO_2$, 1→30% acetone in hexanes) to give the title compound (108 mg, 91%) as a colorless oil: $^1$H NMR (400 MHz, $CDCl_3$) δ 7.30-7.13 (m, 6H), 7.08 (d, J=7.3 Hz, 2H), 7.00 (d, J=7.2 Hz, 2H), 5.40 (d, J=8.7 Hz, 1H), 4.54-4.40 (m, 1H), 3.88-3.80 (m, 1H), 3.79-3.71 (m, 4H), 3.60 (dd, J=9.3, 3.2 Hz, 1H), 3.46 (dd, J=9.5, 3.3 Hz, 1H), 3.29 (dd, J=9.5, 6.8 Hz, 1H), 2.88 (dd, J=13.7, 5.4 Hz, 1H), 2.72 (dd, J=14.0, 6.9 Hz, 1H), 2.64-2.51 (m, 2H), 2.41-2.31 (m, 1H), 2.16-2.08 (m, 1H), 1.97-1.88 (m, 1H), 1.45 (s, 9H), 1.26 (d, J=6.2 Hz, 3H); $^{13}$C NMR (101 MHz, $CDCl_3$) δ 171.00, 155.39, 141.16, 141.14, 129.01, 128.37, 128.26, 125.86, 125.84, 80.06, 71.32, 70.95, 69.17, 53.97, 52.51, 48.08, 40.53, 36.69, 35.29, 28.33, 22.36; ESIMS m/z 486 ([M+H]$^+$).

Example 1, Step 9b

Preparation of (S)-methyl 2-(((benzyloxy)carbonyl)amino)-3-(((2R,3R)-3-((S)-1-hydroxyethyl)-2-isopentyl-6-methylheptyl)oxy)propanoate

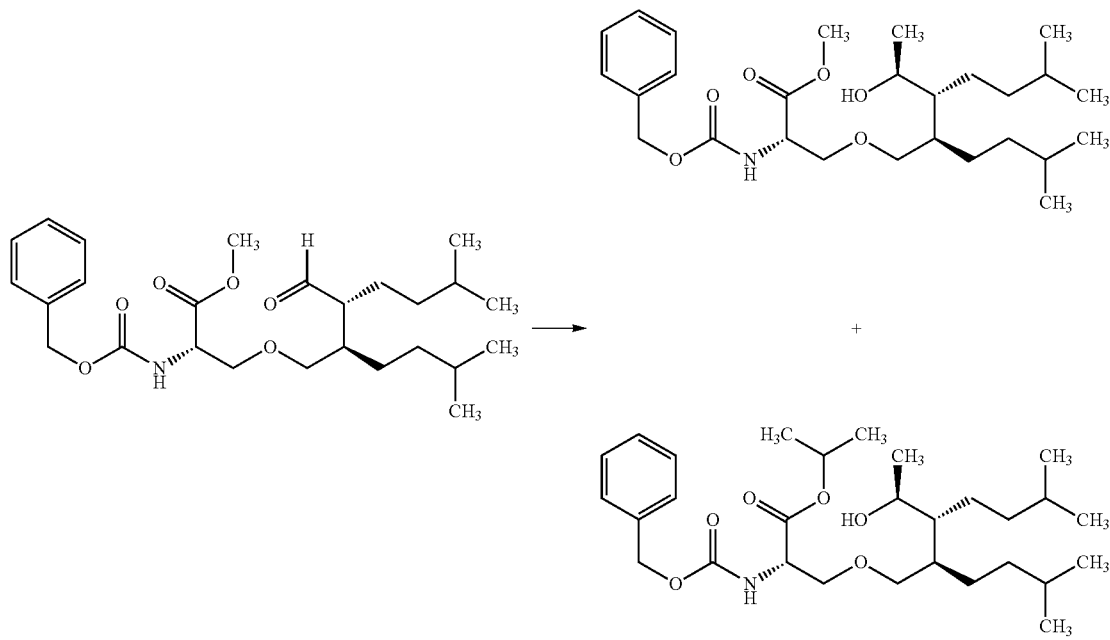

To a N₂ flushed 100 mL round bottom flask were added (S)-methyl 2-(((benzyloxy)-carbonyl)-amino)-3-((2R,3R)-3-formyl-2-isopentyl-6-methylheptyl)oxy)propanoate (380 mg, 0.820 mmol), anhydrous THF (1 mL) and CH₂Cl₂ (1 mL) and the resulting solution was cooled to −78° C. in a dry ice/acetone bath and treated dropwise via syringe with triisopropoxy(methyl)titanium (1.8 mL, 1.8 mmol, 1 M solution in THF). The reaction mixture was stirred at −78° C. for 0.5 h, warmed to −25° C., and maintained at −25° C. for 15 h. Thin layer chromatography (TLC) analysis (2:1 hexanes/EtOAc) indicated residual starting material, along with several new products. The mixture was warmed to −20° C., treated with additional triisopropoxy(methyl)titanium (1.8 mL, 1.8 mmol, 1 M solution in THF), and allowed to warm to 0° C. over a 2 h period. The reaction mixture was quenched with saturated aqueous NH₄Cl (20 mL), diluted with EtOAc (20 mL), and the phases separated. The aqueous phase was extracted with EtOAc (2×10 mL) and the combined organic extracts were washed with brine, dried over Na₂SO₄, filtered and concentrated to give the title compounds (343 mg, 87%) as diastereomeric mixtures (5:1) of the Me and i-Pr ester products as a colorless oil which was used as is in Step 10.

Methyl ester: ESIMS m/z 478 ([M−H]⁻).
Isopropyl ester: ESIMS m/z 506 ([M−H]⁻).

Example 1, Step 10

Preparation of (S)-2-((tert-butoxycarbonyl)amino)-3-(((2R,3R,4S)-2,3-dibenzyl-4-hydroxypentyl)oxy)propanoic acid

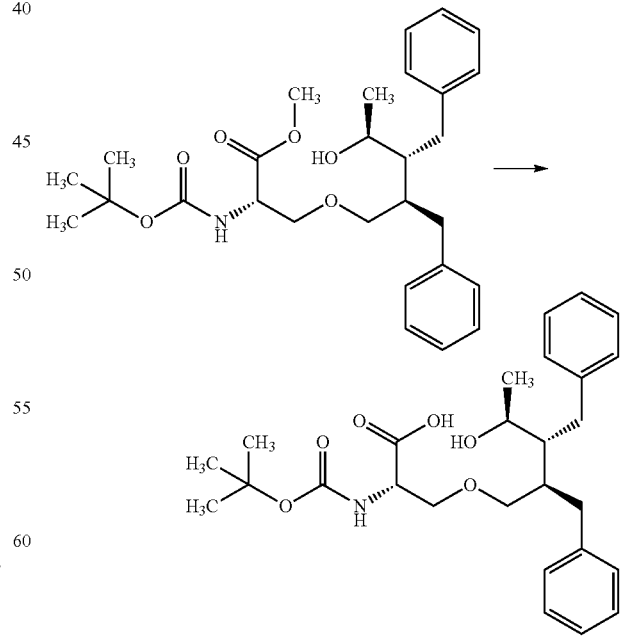

A 25 mL screw top vial was charged with (S)-methyl 2-((tert-butoxycarbonyl)amino)-3-((2R,3R,4S)-2,3-dibenzyl-4-hydroxypentyl)oxy)propanoate (98.0 mg, 0.202 mmol), THF (2 mL), water (0.75 mL), and LiOH (14.5 mg, 0.605 mmol). After stirring for 2 h, the reaction was diluted with 1.0 M HCl (50 mL) and extracted with EtOAc (3×50 mL). The combined organic extracts were washed with brine (50 mL), dried over anhydrous MgSO$_4$, filtered, and concentrated to provide the title compound (89.2 mg, 94%) as a white solid: mp 38-42° C.; $^1$H NMR (400 MHz, CDCl$_3$) δ 7.55 (s, 1H), 7.32-6.89 (m, 10H), 5.57 (d, J=7.9 Hz, 1H), 4.47 (d, J=7.9 Hz, 1H), 4.11 (q, J=7.2 Hz, 1H), 3.96-3.81 (m, 1H), 3.82-3.58 (m, 2H), 3.51 (d, J=9.7 Hz, 1H), 3.23 (t, J=8.2 Hz, 1H), 2.84-2.44 (m, 5H), 1.95 (d, J=7.2 Hz, 1H), 1.44 (s, 9H), 1.35-1.17 (m, 3H); $^{13}$C NMR (101 MHz, CDCl$_3$) δ 173.45, 155.58, 140.95, 129.04, 129.02, 128.39, 128.26, 125.88, 125.82, 80.16, 71.30, 70.64, 69.91, 53.88, 48.35, 41.09, 37.18, 35.81, 28.35, 21.91; ESIMS m/z 472 ([M+H]$^+$).

Example 1, Step 11

Preparation of tert-butyl ((3S,7R,8R,9S)-7,8-dibenzyl-9-methyl-2-oxo-1,5-dioxonan-3-yl)carbamate (Cmpd. 203)

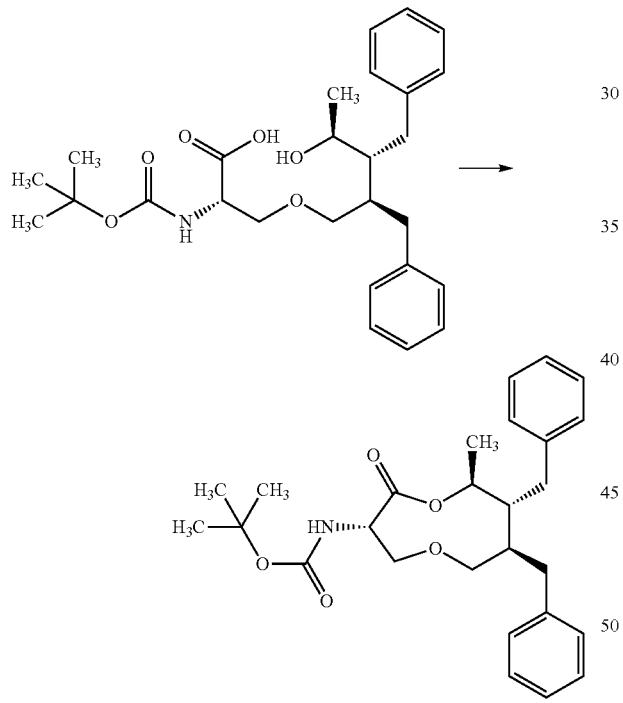

An oven-dried 100 mL Schlenk flask was cooled under N$_2$ and charged with MNBA (115 mg, 0.333 mmol), DMAP (163 mg, 1.33 mmol), and anhydrous toluene (44 mL). The flask was sealed with a rubber septum and the solution was treated with solution of (S)-2-((tert-butoxycarbonyl)amino)-3-(((2R,3R,4S)-2,3-dibenzyl-4-hydroxypentyl)oxy)propanoic acid (105 mg, 0.222 mmol) in anhydrous toluene (6 mL) via syringe pump over a 6 h period. The resulting mixture was stirred overnight at room temperature and the crude reaction mixture was filtered through Celite® to remove the solids. The filtrate was concentrated by rotary evaporation and the crude concentrate was purified via column chromatography (SiO$_2$, 1→20% acetone in hexanes) to give the title compound (74.1 mg, 74%) as a colorless oil: See Table 2 for characterization data.

Example 1, Step 12a

Preparation of (3S,7R,8R,9S)-7,8-dibenzyl-9-methyl-2-oxo-1,5-dioxonan-3-aminium chloride (Cmpd. 169)

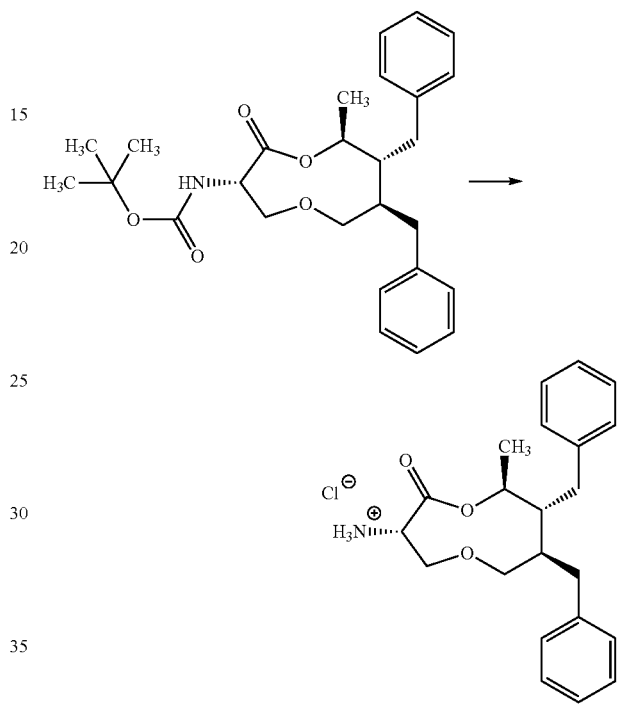

A 25 mL screw top vial was charged with tert-butyl ((3S,7R,8R,9S)-7,8-dibenzyl-9-methyl-2-oxo-1,5-dioxonan-3-yl)carbamate (291 mg, 0.642 mmol) and anhydrous CH$_2$Cl$_2$ (4 mL), and the resulting solution was treated with a solution of HCl (4.0 M in dioxane, 3.2 mL, 12.8 mmol) and stirred at room temperature for 45 min. The reaction mixture was concentrated under a gentle stream of N$_2$ to give the intermediate amine hydrochloride, (3S,7R,8R,9S)-7,8-dibenzyl-9-methyl-2-oxo-1,5-dioxonan-3-aminium chloride, (250 mg, 100%) as a white solid: See Table 2 for characterization data.

Example 1, Step 12b

Preparation of (3S,7R,8R,9S)-3-amino-8-benzyl-7-isopentyl-9-methyl-1,5-dioxonan-2-one (Cmpd 174)

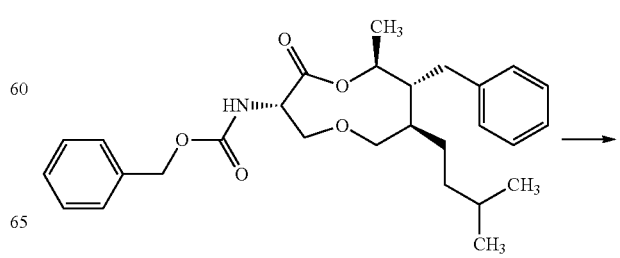

-continued

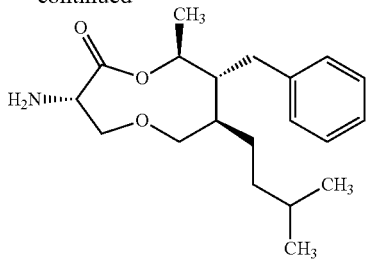

To a solution of benzyl ((3S,7R,8R,9S)-8-benzyl-7-isopentyl-9-methyl-2-oxo-1,5-dioxonan-3-yl)carbamate (609 mg, 1.30 mmol) in EtOAc (10 mL) was added 5% Pd/C (139 mg, 0.065 mmol) and the reaction was hydrogenated in a steel reactor under 500 psi of $H_2$ at room temperature for 20 h. The reaction mixture was filtered through a pad of Celite®, concentrated and dried under high vacuum to yield the title compound (360 mg, 66% yield) as a colorless oil: See Table 2 for characterization data.

Example 1, Step 12c

Preparation of (3S,7R,8R,9S)-3-amino-8-benzyl-7-(4-chlorobenzyl)-9-methyl-1,5-dioxonan-2-one (Cmpd 175)

To a solution of benzyl ((3S,7R,8R,9S)-8-benzyl-7-(4-chlorobenzyl)-9-methyl-2-oxo-1,5-dioxonan-3-yl)carbamate (10.0 mg, 0.019 mmol) in acetic acid (50 μL) was added 33 wt. % HBr in acetic acid (52.0 μL, 0.287 mmol) at 0° C. and the reaction mixture was warmed to room temperature and stirred for 30 min. The reaction mixture was diluted with EtOAc and poured into saturated aqueous $NaHCO_3$. The phases were separated and the aqueous phase was further extracted with EtOAc. The combined organics were washed with brine, dried over $Na_2SO_4$, filtered, and concentrated to yield the title compound (7.0 mg, 94%) as a pale yellow oil: See Table 2 for characterization data.

Example 1, Step 13

Preparation of N-((3S,7R,8R,9S)-7,8-dibenzyl-9-methyl-2-oxo-1,5-dioxonan-3-yl)-3-hydroxy-4-methoxypicolinamide (Cmpd. 112)

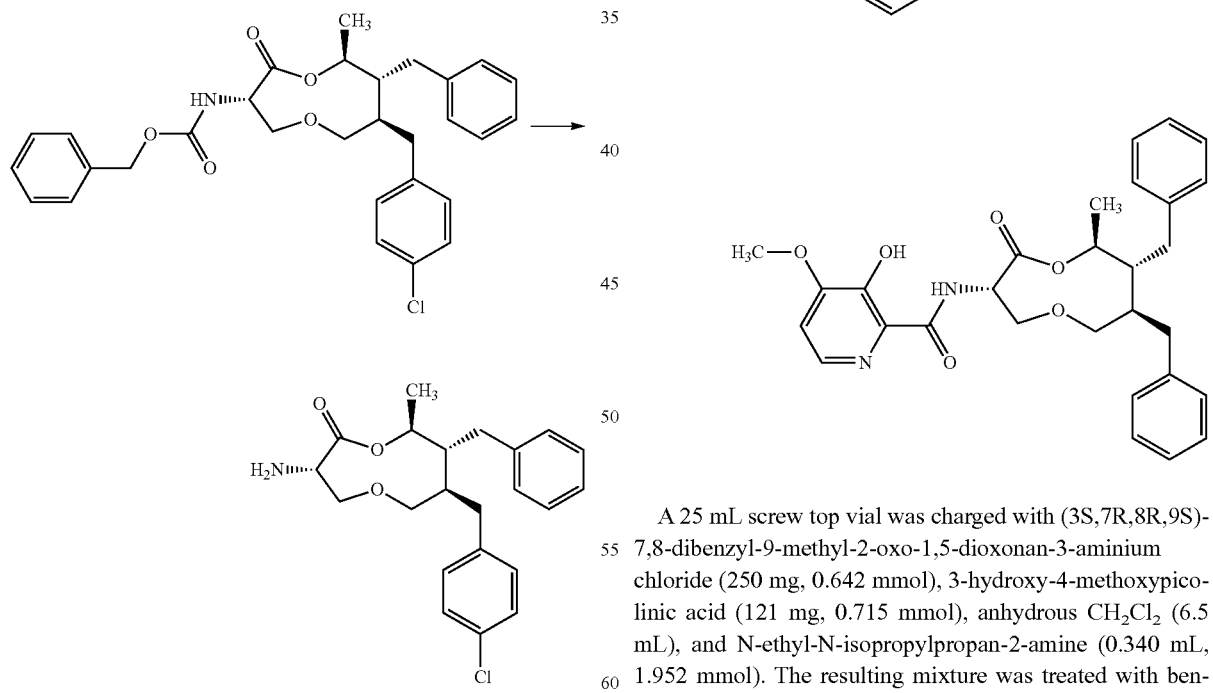

A 25 mL screw top vial was charged with (3S,7R,8R,9S)-7,8-dibenzyl-9-methyl-2-oxo-1,5-dioxonan-3-aminium chloride (250 mg, 0.642 mmol), 3-hydroxy-4-methoxypicolinic acid (121 mg, 0.715 mmol), anhydrous $CH_2Cl_2$ (6.5 mL), and N-ethyl-N-isopropylpropan-2-amine (0.340 mL, 1.952 mmol). The resulting mixture was treated with benzotriazol-1-yl-oxytripyrrolidinophosphonium hexafluorophosphate (PyBOP, 371 mg, 0.713 mmol), stirred at room temperature for 2.5 h, and the entire reaction mixture was purified via column chromatography ($SiO_2$, 2→30% acetone in hexanes) to give the title compound (268 mg, 74%) as a white solid: See Table 2 for characterization data.

Example 1, Step 14

Preparation of ((2-(((3S,7R,8R,9S)-7,8-dibenzyl-9-methyl-2-oxo-1,5-dioxonan-3-yl)carbamoyl)-4-methoxypyridin-3-yl)oxy)methyl acetate (Cmpd. 3)

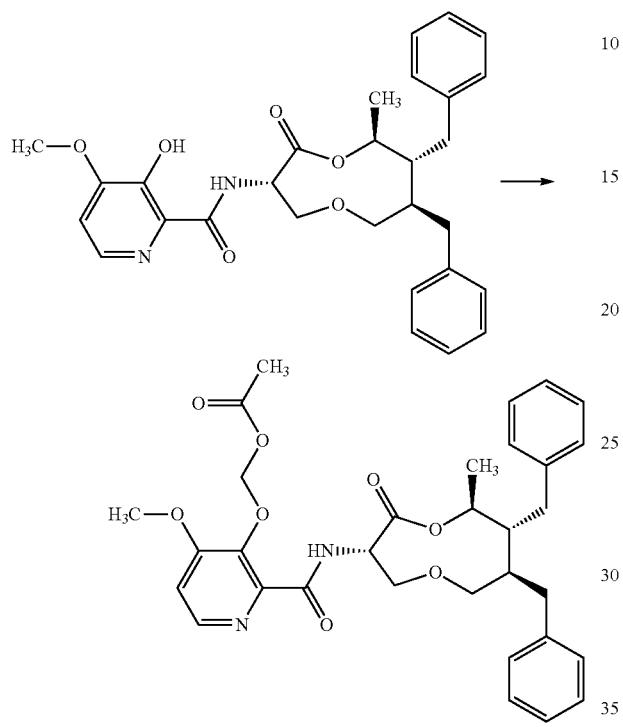

A 25 mL screw top vial was charged with N-((3S,7R,8R,9S)-7,8-dibenzyl-9-methyl-2-oxo-1,5-dioxonan-3-yl)-3-hydroxy-4-methoxypicolinamide (80.5 mg, 0.160 mmol), anhydrous acetone (1 mL), potassium carbonate (K$_2$CO$_3$, 73.7 mg, 0.533 mmol), and bromomethyl acetate (0.023 mL, 0.235 mmol), and the resulting mixture was heated to 40° C. and stirred for 16.5 h. The reaction mixture was cooled to room temperature and concentrated under a stream of N$_2$. The crude concentrate was purified via column chromatography (SiO$_2$, 1→40% acetone in hexanes) to give the title compound (58.4 mg, 64%) as a white solid: See Table 2 for characterization data.

Example 2, Step 1

Preparation of pent-3-yn-2-ol

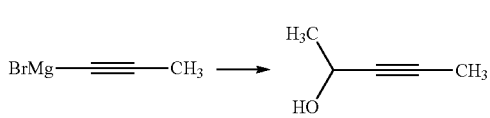

An oven-dried 250 mL Schlenk flask was cooled under N$_2$, charged with prop-1-yn-1-ylmagnesium bromide (0.5 M in THF, 100 mL, 50 mmol), and sealed with a rubber septum. The solution was cooled to 0° C. in an ice water bath and treated with acetaldehyde (2.3 mL, 41.0 mmol) via syringe pump over a 30 min period. The resulting mixture was stirred at 0° C. and allowed to slowly warm as the ice melted. After stirring for 5 h, the reaction mixture was concentrated to dryness under high vacuum. The flask containing the dried salts was cooled to 0° C. in an ice bath, whereupon Et$_2$O (50 mL) and saturated aqueous NH$_4$Cl solution (100 mL) were sequentially added, and the mixture was stirred to dissolve the solids. The phases were separated and the aqueous phase was extracted with Et$_2$O (3×50 mL). The combined organic phases were dried over anhydrous MgSO$_4$, filtered, and concentrated by rotary evaporation at 20° C. and 450 mbar to give a mixture of the title compound and residual THF and Et$_2$O, which was used without further purification: $^1$H NMR (400 MHz, CDCl$_3$) δ 4.48 (qdq, J=6.7, 4.2, 2.1 Hz, 1H), 2.31 (d, J=5.1 Hz, 1H), 1.84 (d, J =2.1 Hz, 3H), 1.42 (d, J=6.6 Hz, 3H); ESIMS m/z 83 [(M−H)$^-$].

Example 2, Step 2

Preparation of (Z)-pent-3-en-2-ol

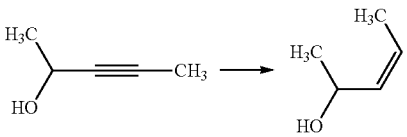

A 250 mL round bottom flask was charged with pent-3-yn-2-ol, pentane (120 mL), and quinoline (0.017 M in pentane, 13.5 mL, 0.228 mmol) followed by Lindlar catalyst (1.2 g), and the flask was sealed with a rubber septum and the reaction mixture placed under balloon pressure of hydrogen gas (H$_2$). The mixture was stirred at room temperature for 23 h, occasionally tilting the flask to ensure the catalyst remained suspended in the solvent. The solids were removed by filtration through a pad of Celite® and rinsed with pentane. The filtrate was concentrated by rotary evaporation at 20° C. and 450 mbar to ~10 mL total volume to give a mixture of the title compound and residual THF, pentane, and Et$_2$O, which was used without further purification: $^1$H NMR (400 MHz, CDCl$_3$) δ 5.58-5.40 (m, 2H), 4.74-4.63 (m, 1H), 1.68 (dd, J=6.7, 1.4 Hz, 3H), 1.50 (d, J =3.5 Hz, 1H), 1.25 (d, J=6.3 Hz, 3H); ESIMS: m/z=86 [M$^+$].

Example 2, Step 3

Preparation of (Z)-pent-3-en-2-yl 3-phenylpropiolate

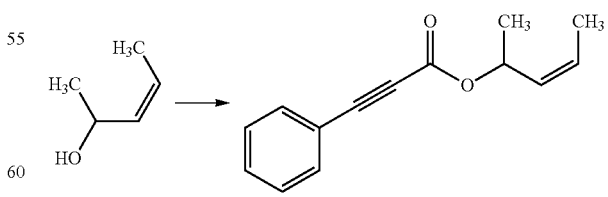

A 500 mL round bottom flask was charged with (Z)-pent-3-en-2-ol, anhydrous CH$_2$Cl$_2$ (200 mL), 3-phenylpropionic acid (5.99 g, 41.0 mmol), and DMAP (250 mg, 2.05 mmol), and the mixture was treated with 3-(((ethylimino)methylene)amino)-N,N-dimethylpropan-1-aminium chloride (11.8 g, 61.6 mmol). The resulting yellow solution was stirred at room temperature for 7 h, and was then sequentially washed with saturated aqueous NH₄Cl solution (100 mL), a 2:1 mixture of saturated aqueous NH₄Cl solution and water (150 mL), water (100 mL), saturated aqueous NaHCO₃ solution (100 mL), and brine (100 mL). The organic phase was dried over anhydrous MgSO₄, filtered, and concentrated by rotary evaporation. The crude concentrate was purified via column chromatography (SiO₂, 1→20% acetone in hexanes) to give the title compound (1.47 g, 17% over 3 steps) as a yellow oil: $^1$H NMR (400 MHz, CDCl₃) δ 7.61-7.55 (m, 2H), 7.46-7.40 (m, 1H), 7.40-7.33 (m, 2H), 5.87-5.78 (m, 1H), 5.71-5.58 (m, 1H), 5.46 (ddq, J=10.6, 8.5, 1.7 Hz, 1H), 1.74 (dd, J=7.0, 1.8 Hz, 3H), 1.38 (d, J=6.4 Hz, 3H); $^{13}$C NMR (101 MHz, CDCl₃) δ 153.42, 132.93, 130.52, 129.43, 128.53, 128.27, 119.74, 85.81, 80.96, 68.90, 20.55, 13.36; ESIMS m/z 214 [M⁺].

Example 2, Step 4

Preparation of (4R,5S,Z)-3-benzylidene-5-methyl-4-vinyldihydrofuran-2(3H)-one

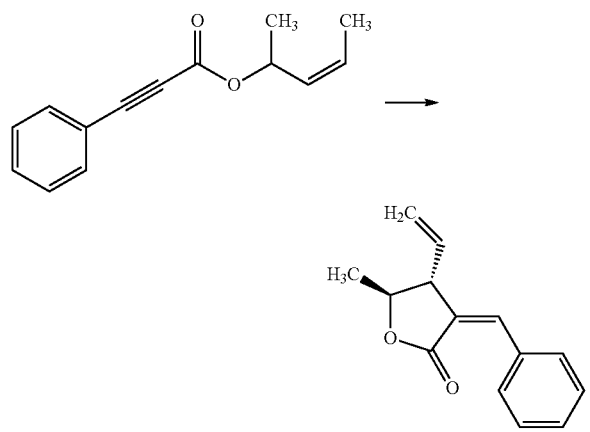

An oven-dried 250 mL Schlenk flask was cooled under N₂ and charged with anhydrous 1,2-dichloroethane (DCE, 89 mL), chloro(1,5-cyclooctadiene)rhodium(I) dimer (116 mg, 0.235 mmol), and (R)-(+)-(1,1'-binaphthalene-2,2'-diyl)bis(diphenylphosphine) ((R)-BINAP, 291 mg, 0.467 mmol). To the resulting red solution was added (Z)-pent-3-en-2-yl 3-phenylpropiolate (2.09 g, 9.75 mmol), and the reaction mixture was stirred at room temperature for 5 min and then treated with a solution of silver hexafluorostibate (0.034 M in DCE, 19 mL 0.646 mmol). After stirring for 50 min, the entire reaction mixture was purified via column chromatography (SiO₂, 1→30% acetone in hexanes) to give the title compound (605 mg, 58%) as a colorless oil: $^1$H NMR (400 MHz, CDCl₃) δ 7.89-7.82 (m, 2H), 7.41-7.30 (m, 3H), 6.74 (d, J=2.9 Hz, 1H), 5.70 (ddd, J=16.9, 10.1, 8.6 Hz, 1H), 5.37 (dd, J=10.1, 1.6 Hz, 1H), 5.32 (ddd, J=16.9, 1.3, 0.6 Hz, 1H), 4.29 (dq, J=8.2, 6.2 Hz, 1H), 3.33 (td, J=8.4, 2.9 Hz, 1H), 1.46 (d, J=6.2 Hz, 3H); $^{13}$C NMR (101 MHz, CDCl₃) δ 168.26, 140.26, 134.80, 133.47, 130.83, 129.67, 128.38, 128.16, 120.77, 78.08, 55.95, 19.42; ESIMS m/z 215 ([M+H]⁺).

Example 2, Step 5

Preparation of (3R,4R,5S)-3-benzyl-5-methyl-4-vinyldihydrofuran-2(3H)-one

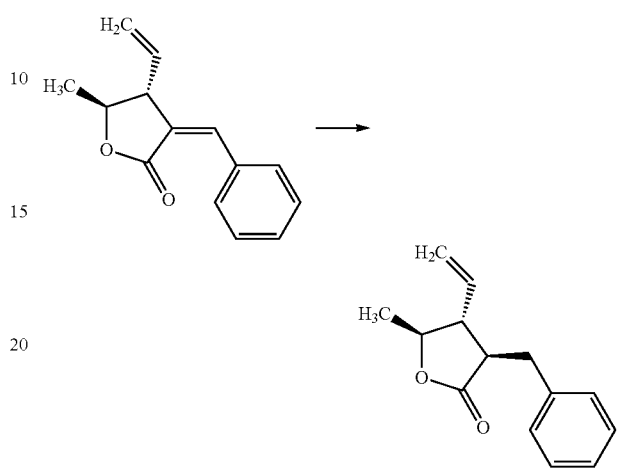

An oven-dried 50 mL Schlenk flask was cooled under N₂, charged with (4R,5S,Z)-3-benzylidene-5-methyl-4-vinyldihydrofuran-2(3H)-one (605 mg, 2.82 mmol) and anhydrous THF (28 mL), and the flask was sealed with a rubber septum. The resulting solution was cooled to −78° C. in a dry ice/acetone bath, treated with a solution of lithium tri-sec-butylhydroborate (1.0 M in THF, 2.87 mL, 2.87 mmol), and stirred at −78° C. for 3 h. The reaction mixture was treated with saturated aqueous NH₄Cl solution (30 mL), warmed to room temperature, and stirred for 30 min. The crude mixture was diluted with water (50 mL) and extracted with Et₂O (3×50 mL). The combined organic extracts were washed with brine (50 mL), dried over anhydrous MgSO₄, filtered, and concentrated by rotary evaporation. The crude concentrate was purified via column chromatography (SiO₂, 1→25% acetone in hexanes) to give the title compound (526 mg, 86%) as a colorless oil: $^1$H NMR (400 MHz, CDCl₃) δ 7.33-7.15 (m, 5H), 5.52 (ddd, J=17.0, 10.3, 8.5 Hz, 1H), 5.11 (ddd, J =10.3, 1.3, 0.5 Hz, 1H), 5.13-5.03 (m, 1H), 4.13 (dq, J=9.6, 6.1 Hz, 1H), 3.08-2.98 (m, 2H), 2.78 (dt, J=11.4, 5.6 Hz, 1H), 2.32 (dt, J=11.9, 9.0 Hz, 1H), 1.27 (d, J=6.1 Hz, 3H); $^{13}$C NMR (101 MHz, CDCl₃) δ 176.92, 137.66, 134.65, 129.71, 128.42, 126.64, 119.29, 78.51, 53.18, 48.12, 33.68, 18.25; ESIMS m/z 216 ([M+H]⁺).

Example 2, Step 6

Preparation of (2R,3R,4S)-2-benzyl-3-vinylpentane-1,4-diol

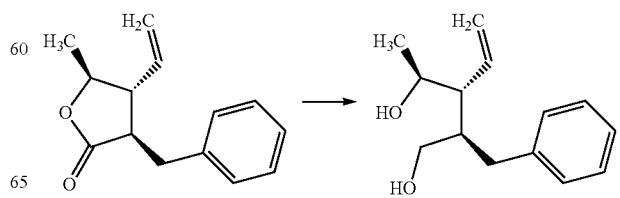

An oven-dried 100 mL Schlenk flask was cooled under N$_2$, sealed with a rubber septum, and charged with lithium aluminum hydride (LAH, 1.0 M in THF, 18.5 mL, 18.5 mmol) and anhydrous THF (18 mL). The colorless solution was cooled to 0° C. in an ice water bath and treated with a solution of (3R,4R,5S)-3-benzyl-5-methyl-4-vinyldihydrofuran-2(3H)-one (2.03 g, 9.39 mmol) in anhydrous THF (18 mL) via a canula over a 5 min period. The reaction mixture was stirred at 0° C. for 30 min, warmed to room temperature, stirred for 4 h, and slowly poured into a mixture of ice (150 g) and saturated aqueous NH$_4$Cl solution (100 mL). The resulting mixture was extracted with CH$_2$Cl$_2$ (1×100 mL and 1×50 mL), and the combined organic extracts were washed with water (100 mL) and brine (100 mL), dried over anhydrous Na$_2$SO$_4$, filtered, concentrated by rotary evaporation, and dried under high vacuum to give the title compound (1.94 g, 94%) as a white solid: mp 79-83° C.; $^1$H NMR (400 MHz, CDCl$_3$) δ 7.31-7.26 (m, 2H), 7.24-7.15 (m, 3H), 5.68 (dt, J=17.0, 10.1 Hz, 1H), 5.23 (dd, J=10.3, 2.1 Hz, 1H), 5.18 (ddd, J=17.0, 2.1, 0.6 Hz, 1H), 3.90 (s, 1H), 3.68-3.58 (m, 1H), 3.51-3.40 (m, 1H), 2.87 (dd, J=13.7, 4.0 Hz, 1H), 2.43 (dd, J=13.7, 10.6 Hz, 1H), 2.31 (ddd, J=9.9, 8.4, 5.4 Hz, 1H), 2.17-2.08 (m, 1H), 1.82 (s, 1H), 1.71 (s, 1H), 1.20 (d, J=6.2 Hz, 3H); $^{13}$C NMR (101 MHz, CDCl$_3$) δ 141.14, 137.20, 129.11, 128.41, 125.98, 118.72, 67.73, 62.60, 53.69, 43.69, 34.24, 22.32; EIMS m/z 220 [M$^+$].

Example 3, Step 1

Preparation of (3R,4S,5S)-3-benzyl-4-(hydroxymethyl)-5-methyldihydrofuran-2(3H)-one

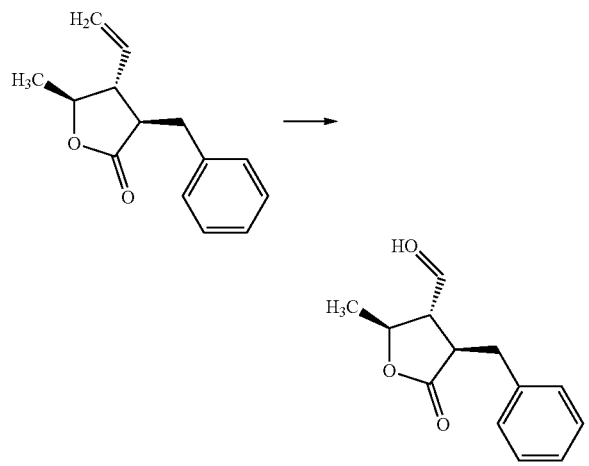

A 250 mL, three neck round bottom flask was charged with (3R,4R,5S)-3-benzyl-5-methyl-4-vinyldihydrofuran-2(3H)-one (1.38 g, 6.38 mmol), CH$_2$Cl$_2$ (30 mL), and MeOH (60 mL), and the resulting colorless solution was cooled to −78° C. in a dry ice/acetone bath. Ozone was bubbled through the reaction solution for 1 hour resulting in a deep blue solution. The reaction mixture was purged of excess ozone with N$_2$ to give a colorless solution and treated with solution of sodium borohydride (NaBH$_4$, 1.37 g, 36.2 mmol), sodium acetate (NaOAc, 979 mg, 11.9 mmol), and sodium bicarbonate (NaHCO$_3$, 137 mg, 1.63 mmol) in water (30 mL). The cold bath was removed, and the reaction was allowed to stir at room temperature for 3 h. The reaction mixture was diluted with EtOAc (200 mL), washed with brine (2×100 mL), dried over anhydrous MgSO$_4$, filtered, and concentrated by rotary evaporation. The crude concentrate was purified via column chromatography (SiO$_2$, 1→40% acetone in hexanes) to give the title compound (894 mg, 64%) as a colorless oil: $^1$H NMR (400 MHz, CDCl$_3$) δ 7.33-7.26 (m, 2H), 7.26-7.19 (m, 3H), 4.39 (dq, J=8.6, 6.2 Hz, 1H), 3.47 (dt, J=11.1, 3.9 Hz, 1H), 3.31 (dt, J=10.7, 5.0 Hz, 1H), 3.27-3.13 (m, 1H), 2.99-2.85 (m, 2H), 2.15-2.09 (m, 1H), 1.94 (dddd, J=10.1, 8.9, 5.3, 3.7 Hz, 1H), 1.31 (d, J=6.2 Hz, 3H); $^{13}$C NMR (101 MHz, CDCl$_3$) δ 178.21, 138.02, 129.16, 128.72, 126.85, 77.42, 60.53, 49.84, 43.77, 35.44, 20.19; EIMS m/z 220 [M$^+$].

Example 4, Step 1

Preparation of (3R,4S,5S)-3-benzyl-5-methyl-4-(((2-methylallyl)oxy)methyl)dihydrofuran-2(3H)-one

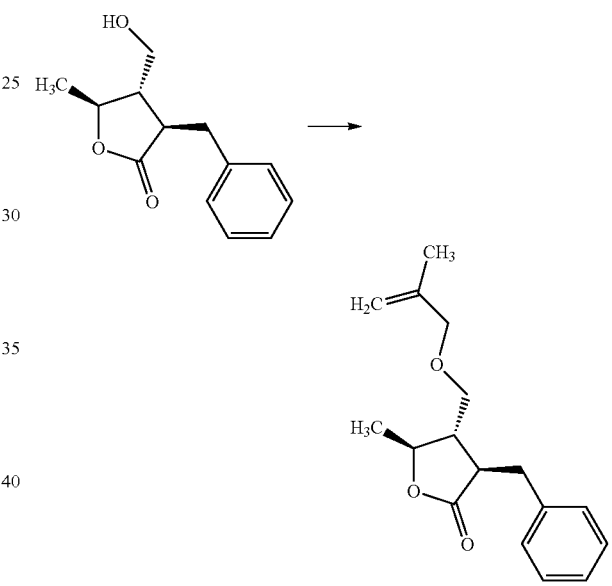

An oven-dried 50 mL Schlenk flask was cooled under N$_2$ and charged with (3R,4S,5S)-3-benzyl-4-(hydroxymethyl)-5-methyldihydrofuran-2(3H)-one (917 mg, 4.16 mmol), tert-butyl(2-methallyl) carbonate (1.47 g, 8.54 mmol), anhydrous THF (20 mL), tris(dibenzylidineacetone)dipalladium (0) chloroform adduct (Pd$_2$(dba)$_3$.CHCl$_3$, 214 mg, 0.207 mmol), and bis(diphenylphosphino)ferrocene (dppf, 230 mg, 0.415 mmol). The resulting mixture was heated to 60° C. and stirred for 17 h, cooled to room temperature, and concentrated by rotary evaporation. The crude concentrate was purified via column chromatography (SiO$_2$, 1→25% acetone in hexanes) to give the title compound (911 mg, 80%) as a yellow oil: $^1$H NMR (400 MHz, CDCl$_3$) δ 7.32-7.25 (m, 2H), 7.25-7.19 (m, 3H), 4.84 (h, J=1.1 Hz, 2H), 4.36 (dq, J=8.7, 6.2 Hz, 1H), 3.72-3.58 (m, 2H), 3.26-3.15 (m, 2H), 3.01 (dd, J=9.7, 5.7 Hz, 1H), 2.97-2.84 (m, 2H), 2.03-1.95 (m, 1H), 1.66 (t, J=1.3 Hz, 3H), 1.31 (d, J=6.2 Hz, 3H); $^{13}$C NMR (101 MHz, CDCl$_3$) δ 177.66, 141.62, 138.07, 129.22, 128.61, 126.74, 112.24, 77.57, 75.10, 68.02, 48.40, 44.07, 35.53, 20.12, 19.41; EIMS m/z 274 [M$^+$].

Example 5, Step 1

Preparation of tert-butyl ((3S,7R,8S,9S)-7-benzyl-8-(isobutoxymethyl)-9-methyl-2-oxo-1,5-dioxonan-3-yl)carbamate (Cmpd. 207)

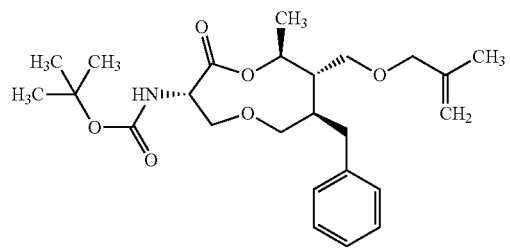

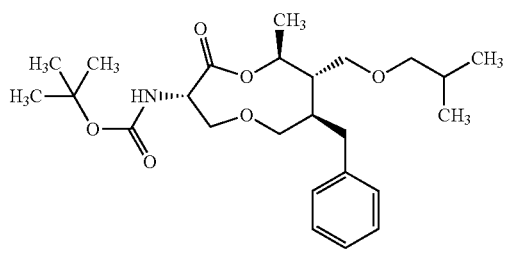

A 25 mL screw top vial was charged with tert-butyl ((3S,7R,8S,9S)-7-benzyl-9-methyl-8-(((2-methylallyl)oxy)methyl)-2-oxo-1,5-dioxonan-3-yl)carbamate (103 mg, 0.230 mmol), EtOAc (2 mL), and palladium on carbon (Pd/C, 10%, 25 mg, 0.023 mmol). The vial was sealed with a septum cap and the reaction mixture was placed under balloon pressure of H$_2$ and stirred at room temperature for 16 h. The solids were removed from the reaction mixture by filtration through a pad of Celite®, rinsing with CH$_2$Cl$_2$. The filtrate was concentrated under a stream of N$_2$ and dried under high vacuum to give the title compound (100 mg, 97%) as a colorless oil: See Table 2 for characterization data.

Example 6, Step 1

Preparation of (3R,4S,5S)-3-benzyl-5-methyl-4-(((triisopropylsilyl)oxy)methyl)dihydrofuran-2(3H)-one

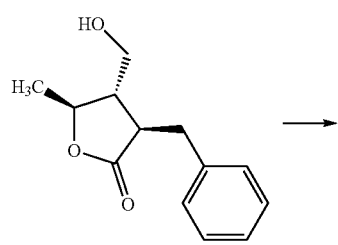

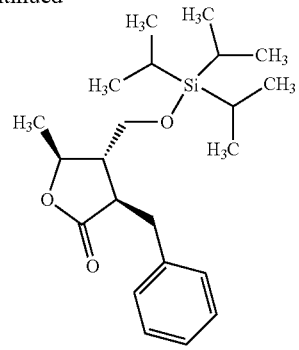

A 250 mL round bottom flask was charged with (3R,4S,5S)-3-benzyl-4-(hydroxymethyl)-5-methyldihydrofuran-2(3H)-one (5.64 g, 25.6 mmol) and anhydrous CH$_2$Cl$_2$ (100 mL). The flask was sealed with a rubber septum, purged with N$_2$, and the mixture was cooled to 0° C. in an ice bath and treated with 2,6-dimethylpyridine (3.6 mL, 30.9 mmol) and triisopropylsilyl trifluoromethanesulfonate (7.64 mL, 28.2 mmol). The reaction mixture was stirred at 0° C. and slowly allowed to warm to room temperature as the ice melted. After 22.5 h, the reaction mixture was washed with saturated aqueous NH$_4$Cl solution (50 mL), washed with brine (50 mL), dried by passing through a Biotage phase separator cartridge, and then concentrated by rotary evaporation. The crude concentrate was purified via column chromatography (SiO$_2$, 1→15% acetone in hexanes) to give the title compound (9.64 g, 100%) as a colorless oil: $^1$H NMR (400 MHz, CDCl$_3$) δ 7.30-7.24 (m, 2H), 7.23-7.16 (m, 3H), 4.40 (dq, J=8.4, 6.2 Hz, 1H), 3.47 (dd, J=10.3, 3.5 Hz, 1H), 3.37 (dd, J=10.3, 5.6 Hz, 1H), 3.21 (dd, J=13.1, 4.1 Hz, 1H), 2.96-2.86 (m, 1H), 2.85 (dd, J=13.1, 8.1 Hz, 1H), 1.99-1.87 (m, 1H), 1.32 (d, J=6.2 Hz, 3H), 1.02-0.94 (m, 21H); $^{13}$C NMR (101 MHz, CDCl$_3$) δ 177.68, 138.08, 129.04, 128.56, 126.61, 77.33, 61.64, 50.40, 43.46, 35.72, 17.83, 17.81, 17.61, 11.66; ESIMS m/z 377 ([M+H]$^+$).

Example 7, Step 1

Preparation of tert-butyl ((3S,7R,8S,9S)-7-benzyl-8-(hydroxymethyl)-9-methyl-2-oxo-1,5-dioxonan-3-yl)carbamate

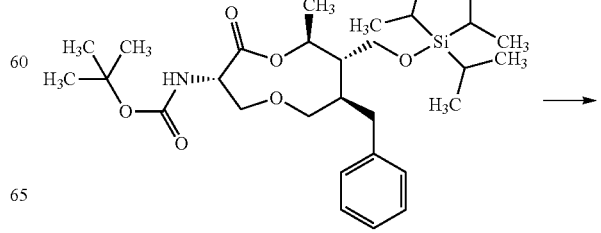

-continued

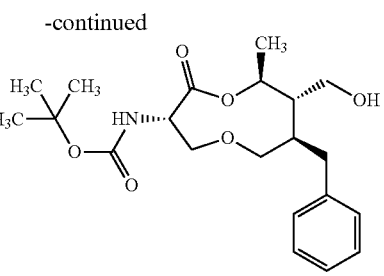

A 25 mL screw top vial was charged with tert-butyl ((3S,7R,8S,9S)-7-benzyl-9-methyl-2-oxo-8-(((triisopropylsilyl)oxy)methyl)-1,5-dioxonan-3-yl)carbamate (346 mg, 0.628 mmol) and anhydrous THF (6 mL). The vial was sealed with a septum cap, placed under an atmosphere of $N_2$, and cooled to 0° C. in an ice water bath. The resulting mixture was treated with tetrabutylammonium fluoride (TBAF, 1.0 M in THF, 1.26 mL, 1.26 mmol) and stirred at 0° C. for 2 h. The reaction mixture was diluted with a 1:1 mixture of water and brine (50 mL) and extracted with $CH_2Cl_2$ (3×50 mL), and the combined organic extracts were dried over anhydrous $MgSO_4$, filtered, and concentrated by rotary evaporation. The crude concentrate was purified via column chromatography ($SiO_2$, 1→40% acetone in hexanes) to give the title compound (215 mg, 87%) as a white solid: mp 95-99° C.; $^1$H NMR (400 MHz, $CDCl_3$) δ 7.31-7.24 (m, 2H), 7.22-7.15 (m, 3H), 5.16 (d, J=8.3 Hz, 1H), 5.14-5.06 (m, 1H), 4.54 (q, J=8.0 Hz, 1H), 4.03 (dd, J=11.7, 7.4 Hz, 1H), 3.87-3.70 (m, 2H), 3.56 (dd, J=10.9, 5.4 Hz, 1H), 3.19 (d, J=10.8 Hz, 1H), 3.13 (dd, J =11.7, 8.3 Hz, 1H), 2.77 (dd, J=13.6, 4.6 Hz, 1H), 2.66 (dd, J=13.7, 10.4 Hz, 1H), 2.09 (s, 1H), 1.93 (qd, J=9.0, 7.1, 4.5 Hz, 1H), 1.70 (tt, J=8.0, 3.5 Hz, 1H), 1.49 (d, J=6.4 Hz, 3H), 1.42 (s, 9H); $^{13}$C NMR (101 MHz, $CDCl_3$) δ 172.77, 154.95, 140.10, 129.04, 128.30, 126.04, 80.03, 74.44, 72.21, 71.70, 61.65, 52.35, 49.48, 41.44, 37.17, 28.22, 19.93.

Example 7, Step 2

Preparation of tert-butyl ((3S,7R,8S,9S)-7-benzyl-9-methyl-2-oxo-8-(phenoxymethyl)-1,5-dioxonan-3-yl)carbamate (Cmpd. 238)

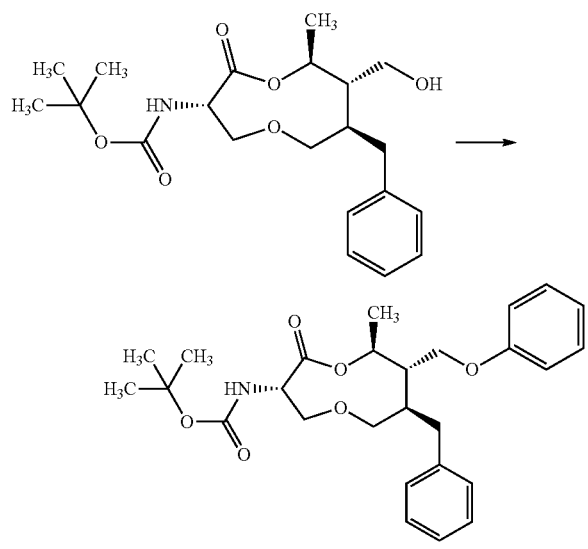

A 25 mL screw top vial was charged with tert-butyl ((3S,7R,8S,9S)-7-benzyl-8-(hydroxymethyl)-9-methyl-2-oxo-1,5-dioxonan-3-yl)carbamate (164.7 mg, 0.419 mmol), phenol (63.8 mg, 0.678 mmol), triphenylphosphine (157 mg, 0.599 mmol), and anhydrous THF (5 mL), and the resulting mixture was stirred to dissolve the solids. The resulting solution was cooled to 0° C. in an ice water bath and treated with (E)-diisopropyl diazene-1,2-dicarboxylate (0.110 mL, 0.559 mmol). The reaction mixture was stirred at 0° C. and allowed to slowly warm to room temperature as the ice melted over a 16 h period. The mixture was concentrated under a stream of $N_2$ and the crude concentrate was purified via column chromatography ($SiO_2$, 1→20% acetone in hexanes) to give the title compound (171 mg, 87%) as a colorless oil: See Table 2 for characterization data.

Example 8, Step 1

Preparation of (4R,5S)-4-butyl-5-methyldihydrofuran-2(3H)-one

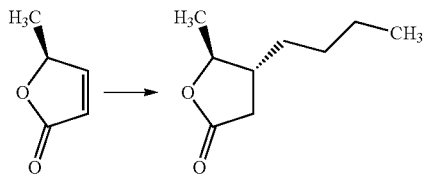

To a suspension of copper(I) iodide (CuI, 6.08 g, 31.9 mmol) in $Et_2O$ (35 mL) at −78° C. was added n-BuLi (2.5 M in hexanes, 25.6 mL, 64.0 mmol) dropwise, and the reaction mixture was warmed to −30° C. and stirred between −30 and −20° C. for 30 min. The resulting homogenous, dark-brown solution was cooled to −78° C. and treated with a solution of (S)-5-methylfuran-2(5H)-one (2.09 g, 21.3 mmol) in $Et_2O$ (8 mL). The reaction mixture was stirred at −78° C. for 2 h, at which time thin layer chromatography (TLC) analysis showed the reaction to be complete. The reaction mixture was quenched with saturated aqueous $NH_4Cl$ solution and filtered through Celite® to remove the inorganic salts. The filtrate was extracted with $Et_2O$ (3×) and the combined organic extracts were dried over $Na_2SO_4$, filtered, concentrated, and the crude concentrate was purified via column chromatography ($SiO_2$, 0→30% EtOAc in hexanes) to give the title compound (2.92 g, 88%) as a colorless oil: $^1$H NMR (400 MHz, $CDCl_3$) δ 4.21 (dq, J=7.6, 6.2 Hz, 1H), 2.68 (dd, J=17.4, 8.2 Hz, 1H), 2.22 (dd, J=17.4, 9.7 Hz, 1H), 2.14-2.00 (m, 1H), 1.62-1.49 (m, 1H), 1.40 (d, J=6.2 Hz, 3H), 1.38-1.26 (m, 5H), 0.91 (t, J=7.0 Hz, 3H); $^{13}$C NMR (101 MHz, $CDCl_3$) δ 176.51, 82.16, 43.27, 35.44, 32.11, 29.76, 22.55, 19.80, 13.82; [α]D=−44.2° (a=−0.177, c=0.4, $CDCl_3$).

Example 8, Step 2

(3R,4R,5S)-3-benzyl-4-butyl-5-methyldihydrofuran-2(3H)-one

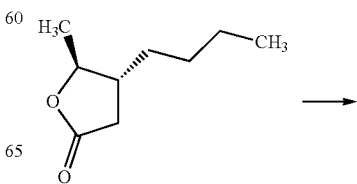

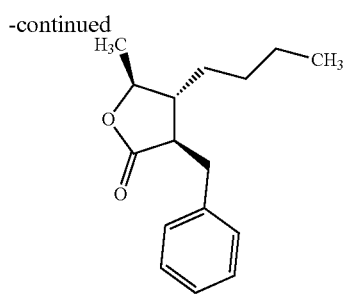

To a solution of diisopropylamine (958 microliters (µL), 6.84 mmol) in THF (11 mL) at −78° C. was added n-BuLi (2.5 M in hexanes, 2.74 mL, 6.85 mmol). The reaction mixture was stirred at 0° C. for 15 min, cooled to −78° C., and treated with (4R,5S)-4-butyl-5-methyldihydrofuran-2 (3H)-one (890 mg, 5.70 mmol). The mixture was stirred at −78° C. for 30 min, treated with benzyl bromide (1016 µl, 8.55 mmol), and the resulting solution was slowly warmed to room temperature overnight. The reaction mixture was quenched with saturated aqueous NH$_4$Cl solution, extracted with Et$_2$O (3×), and the combined organic extracts were concentrated and the residue was purified via column chromatography (SiO$_2$, 0→5% EtOAc in hexanes) to give the title compound (950 mg, 68%) as a colorless oil: $^1$H NMR (400 MHz, CDCl$_3$) δ 7.38-7.10 (m, 5H), 4.12 (dq, J=8.2, 6.2 Hz, 1H), 3.12 (dd, J=14.0, 5.4 Hz, 1H), 2.98 (dd, J=14.0, 6.6 Hz, 1H), 2.63 (ddd, J=10.1, 6.6, 5.4 Hz, 1H), 1.81-1.73 (m, 1H), 1.33-1.26 (m, 2H), 1.26 (d, J=6.2 Hz, 3H), 1.22-1.12 (m, 4H), 0.85-0.79 (m, 3H); $^{13}$C NMR (101 MHz, CDCl$_3$) 178.11, 138.11, 129.37, 128.54, 126.69, 80.24, 67.96, 48.07, 46.82, 35.64, 31.70, 28.96, 25.61, 22.77, 20.72, 13.80.

Example 9, Step 1

Preparation of 2-(((3S,7R,8S,9S)-7-benzyl-9-methyl-2-oxo-8-(phenoxymethyl)-1,5-dioxonan-3-yl)carbamoyl)-4-methoxypyridin-3-yl acetate (Cmpd. 95)

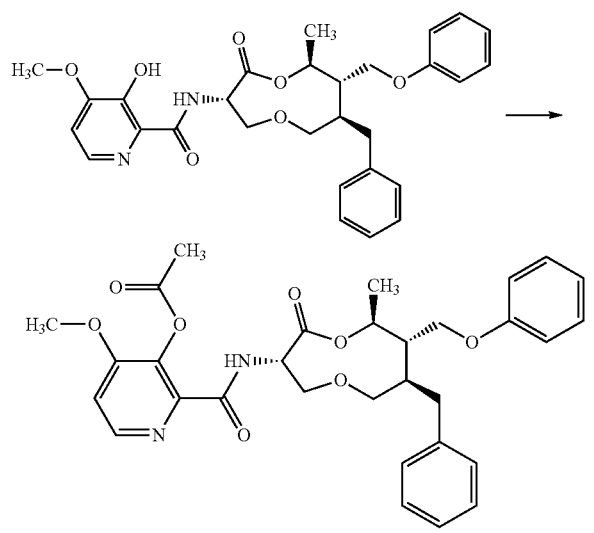

A 25 mL screw top vial was charged with N-((3S,7R,8S, 9S)-7-benzyl-9-methyl-2-oxo-8-(phenoxymethyl)-1,5-dioxonan-3-yl)-3-hydroxy-4-methoxypicolinamide (94.4 mg, 0.181 mmol), DMAP (7.5 mg, 0.061 mmol), anhydrous CH$_2$Cl$_2$ (2 mL) and TEA (0.051 mL, 0.336 mmol). The resulting mixture was treated with acetyl chloride (0.019 mL, 0.267 mmol) and stirred at room temperature for 16.5 h. The entire crude reaction mixture was purified via column chromatography (SiO$_2$, 2→40% acetone in hexanes) to give the title compound (86.3 mg, 85%) as a white solid: See Table 2 for characterization data.

Example 10, Step 1

Preparation of ((2-(((3S,7R,8R,9S)-8-cyclopentyl-7-isopentyl-9-methyl-2-oxo-1,5-dioxonan-3-yl)carbamoyl)-4-methoxypyridin-3-yl)oxy)methyl isobutyrate (Cmpd. 94)

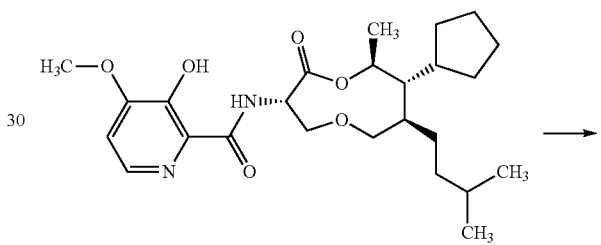

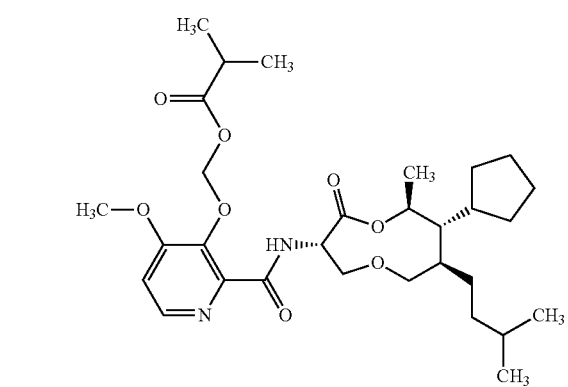

A 25 mL screw top vial was charged with N-((3S,7R,8R, 9S)-8-cyclopentyl-7-isopentyl-9-methyl-2-oxo-1,5-dioxonan-3-yl)-3-hydroxy-4-methoxypicolinamide (72.1 mg, 0.156 mmol), sodium carbonate (Na$_2$CO$_3$, 36.9 mg, 0.348 mmol), sodium iodide (NaI, 8.1 mg, 0.054 mmol), anhydrous acetone (2 mL) and chloromethyl isobutyrate (35.0 mg, 0.256 mmol). The resulting mixture was heated to 50° C. and stirred at that temperature for 17 h. The crude reaction mixture was cooled to room temperature and concentrated under a stream of N$_2$. The crude concentrate was purified via column chromatography (SiO$_2$, 1-35% acetone in hexanes) to give the title compound (66.1 mg, 75%) as a colorless oil: See Table 2 for characterization data.

Example 11, Step 1

Preparation of 2-(((3S,7R,8R,9S)-8-cyclopentyl-7-isopentyl-9-methyl-2-oxo-1,5-dioxonan-3-yl)carbamoyl)-4-methoxypyridin-3-yl isobutyrate (Cmpd. 92)

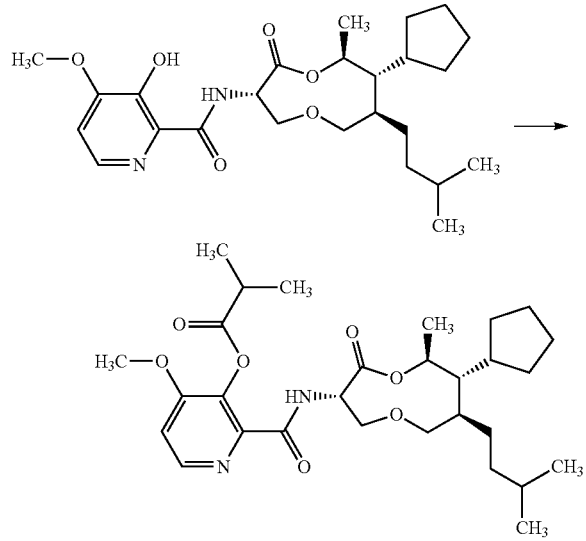

A 25 mL screw top vial was charged with N-((3S,7R,8R, 9S)-8-cyclopentyl-7-isopentyl-9-methyl-2-oxo-1,5-dioxonan-3-yl)-3-hydroxy-4-methoxypicolinamide (81.7 mg, 0.177 mmol), DMAP (5.7 mg, 0.047 mmol), anhydrous CH₂Cl₂ (2 mL) and TEA (0.049 mL, 0.352 mmol). The resulting mixture was treated with isobutyryl chloride (0.028 mL, 0.267 mmol) and stirred at room temperature for 19 h. The entire crude reaction mixture was purified via column chromatography (SiO₂, 1→40% acetone in hexanes) to give the title compound (87.9 mg, 93%) as a white solid: See Table 2 for characterization data.

Example 12, Step 1

Preparation of 2-(((3S,7R,8R,9S)-7-(4-chlorobenzyl)-8-cyclopentyl-9-methyl-2-oxo-1,5-dioxonan-3-yl)carbamoyl)-4-methoxypyridin-3-yl 3-methoxypropanoate (Cmpd. 106)

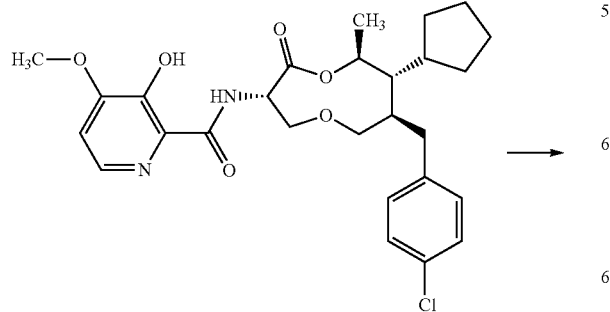

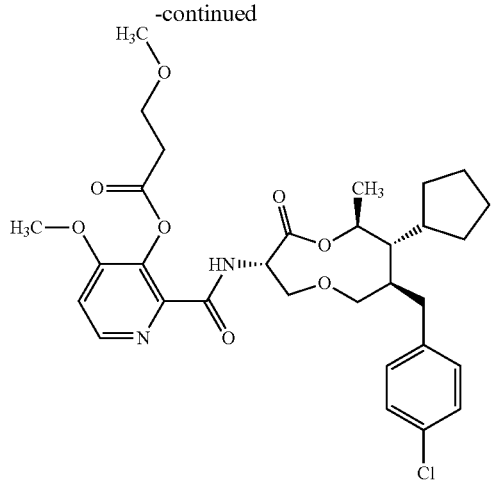

A 25 mL screw top vial was charged with N-((3S,7R,8R, 9S)-7-(4-chlorobenzyl)-8-cyclopentyl-9-methyl-2-oxo-1,5-dioxonan-3-yl)-3-hydroxy-4-methoxypicolinamide (50.7 mg, 0.098 mmol), DMAP (2.4 mg, 0.020 mmol), anhydrous CH₂Cl₂ (1 mL) and TEA (0.027 mL, 0.194 mmol). The resulting mixture was treated with 3-methoxypropanoyl chloride (20.4 mg, 0.166 mmol) and stirred at room temperature for 16.5 h. The entire crude reaction mixture was purified via column chromatography (SiO₂, 2→40% acetone in hexanes) to give the title compound (14.3 mg, 24%) as a colorless oil: See Table 2 for characterization data.

Example 13, Step 1

Preparation of ((2-(((3S,7R,8R,9S)-7-(4-chlorobenzyl)-8-cyclopentyl-9-methyl-2-oxo-1,5-dioxonan-3-yl)carbamoyl)-4-methoxypyridin-3-yl)oxy)methyl 2-ethoxyacetate (Cmpd. 90)

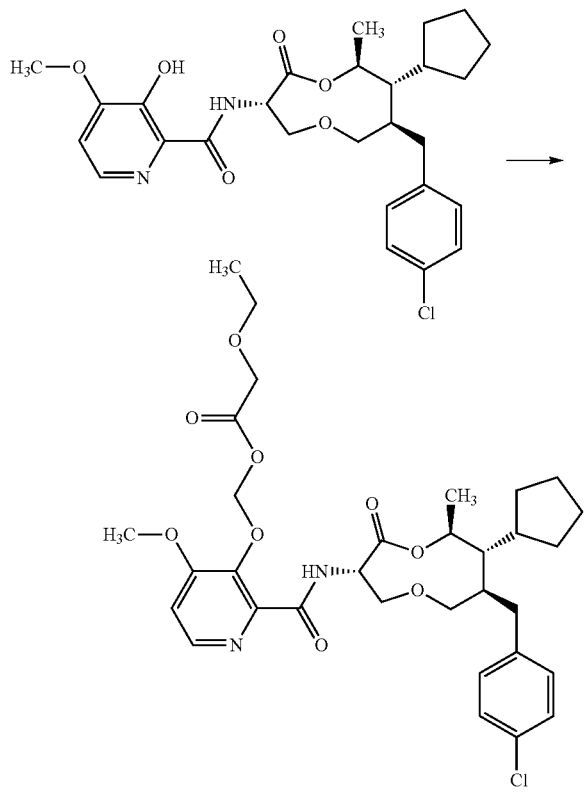

A 25 mL screw top vial was charged with N-((3S,7R,8R,9S)-7-(4-chlorobenzyl)-8-cyclopentyl-9-methyl-2-oxo-1,5-dioxonan-3-yl)-3-hydroxy-4-methoxypicolinamide (100 mg, 0.193 mmol), $Na_2CO_3$ (38.9 mg, 0.367 mmol), NaI (9.1 mg, 0.061 mmol), anhydrous acetone (2 mL) and chloromethyl 2-ethoxyacetate (42.0 mg, 0.275 mmol), and the resulting mixture was heated to 50° C. and stirred at that temperature for 17.5 h. The crude reaction mixture was cooled to room temperature, concentrated under a stream of $N_2$, and the crude concentrate was purified via column chromatography ($SiO_2$, 1-35% acetone in hexanes) to give the title compound (68.4 mg, 56%) as a white solid: See Table 2 for characterization data.

Example A

Evaluation of Fungicidal Activity: Leaf Blotch of Wheat (*Mycosphaerella graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia triticina*; Synonym: *Puccinia recondite* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% relative humidity for 48 hr, and then moved to a greenhouse set at 20° C. for disease to develop. Fungicide formulation, application and disease assessment on the sprayed leaves followed the procedures as described in the Example A.

Example E

Evaluation of Fungicidal Activity: Grape Powdery Mildew (*Uncinula necator*; Bayer code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G

Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H

Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example I

Evaluation of Fungicidal Activity: Wheat Powdery Mildew (*Blumeria graminis* f. Sp. *Tritici*; Synonym: *Erysiphe graminis* f. Sp. *Tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J

Evaluation of Fungicidal Activity: Barley Powdery Mildew (*Blumeria graminis* f. Sp. *hordei*; Synonym: *Erysiphe graminis* f. Sp. *hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L

Evaluation of Fungicidal Activity: Rice Blast (*Magnaporthe grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M

Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N

Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure and Appearance

| Compound Number | Structure | Prepared According to Example | Appearance |
|---|---|---|---|
| 1 | 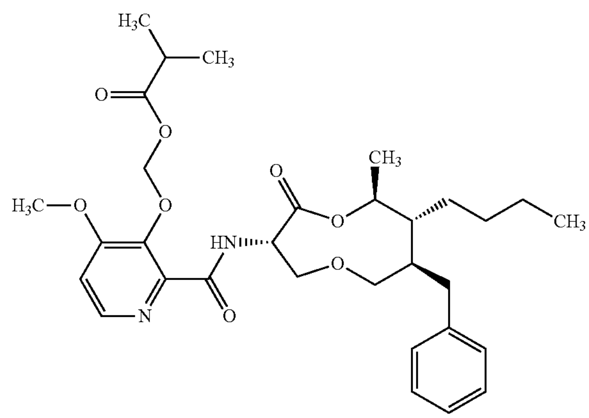 [SMILES: CCCC[C@@H]1[C@@H](Cc2ccccc2)COC[C@H](NC(=O)c2nccc(OC)c2OCOC(=O)C(C)C)C(=O)O[C@H]1C] | Example 10, Step 1 | Colorless Oil |
| 2 | 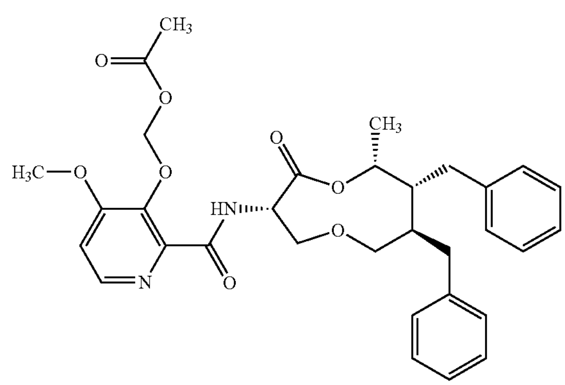 [SMILES: COc1ccnc(C(=O)N[C@H]2COC[C@H](Cc3ccccc3)[C@@H](Cc3ccccc3)[C@@H](C)OC2=O)c1OCOC(C)=O] | Example 1, Step 14 | Colorless Oil |
| 3 | 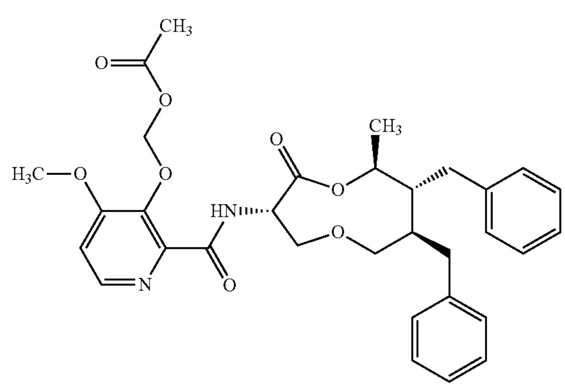 [SMILES: COc1ccnc(C(=O)N[C@H]2COC[C@H](Cc3ccccc3)[C@@H](Cc3ccccc3)[C@H](C)OC2=O)c1OCOC(C)=O] | Example 1, Step 14 | White Solid |

TABLE 1-continued

Compound Structure and Appearance

| Compound Number | Structure | Prepared According to Example | Appearance |
|---|---|---|---|
| 4 | 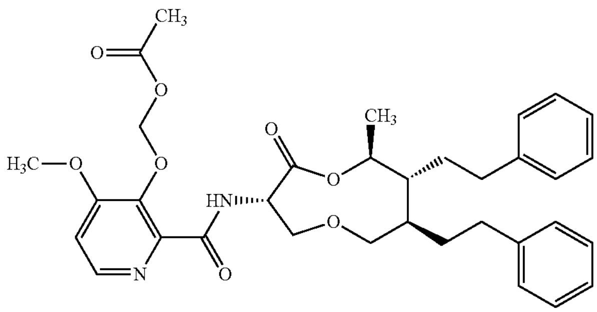 [SMILES: COc1ccnc(C(=O)N[C@H]2COC[C@H](CCc3ccccc3)[C@@H](CCc3ccccc3)[C@H](C)OC2=O)c1OCOC(C)=O] | Example 1, Step 14 | Pale Yellow Solid |
| 5 | 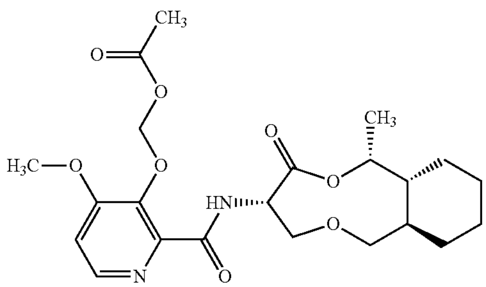 [SMILES: COc1ccnc(C(=O)N[C@H]2COC[C@@H]3CCCC[C@H]3[C@@H](C)OC2=O)c1OCOC(C)=O] | Example 1, Step 14 | White Foam |
| 6 | 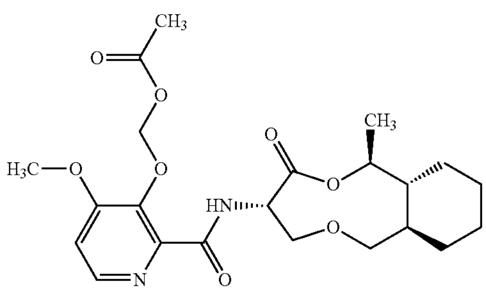 [SMILES: COc1ccnc(C(=O)N[C@H]2COC[C@@H]3CCCC[C@H]3[C@H](C)OC2=O)c1OCOC(C)=O] | Example 1, Step 14 | White Foam |
| 7 | 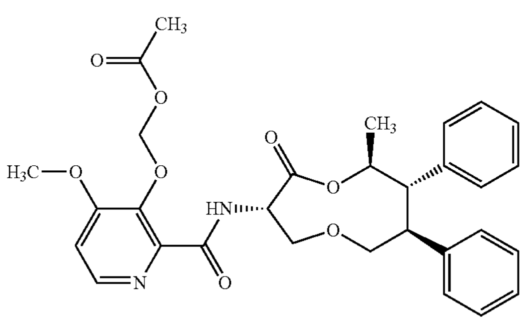 [SMILES: COc1ccnc(C(=O)N[C@H]2COC[C@H](c3ccccc3)[C@@H](c3ccccc3)[C@H](C)OC2=O)c1OCOC(C)=O] | Example 1, Step 14 | White Solid |
| 8 | 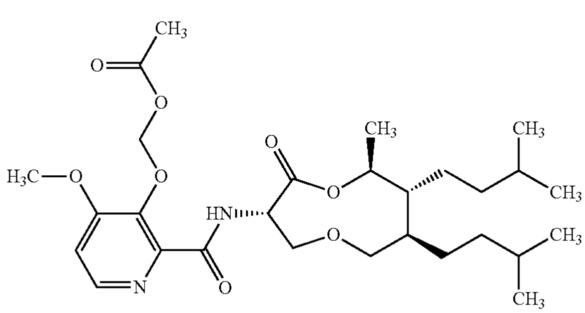 [SMILES: COc1ccnc(C(=O)N[C@H]2COC[C@H](CCC(C)C)[C@@H](CCC(C)C)[C@H](C)OC2=O)c1OCOC(C)=O] | Example 1, Step 14 | Colorless Oil |

TABLE 1-continued

Compound Structure and Appearance

| Compound Number | Structure | Prepared According to Example | Appearance |
|---|---|---|---|
| 9 | 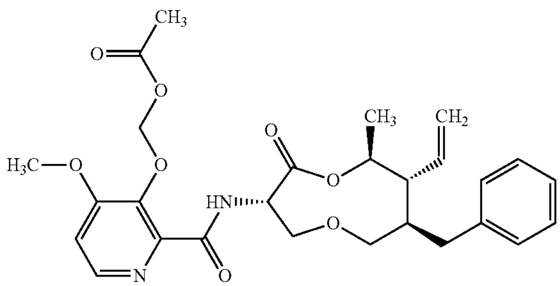 [SMILES: C=C[C@@H]1[C@@H](Cc2ccccc2)COC[C@H](NC(=O)c2nccc(OC)c2OCOC(C)=O)C(=O)O[C@H]1C] | Example 1, Step 14 | White Solid |
| 10 | 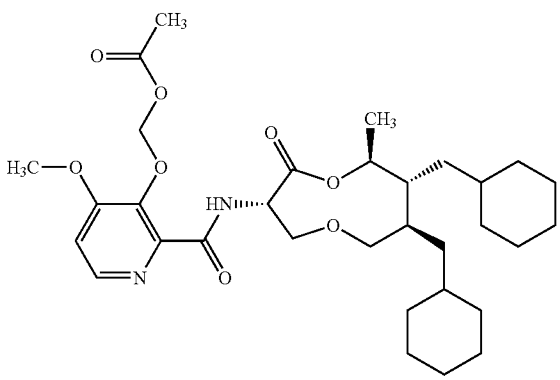 [SMILES: COc1ccnc(C(=O)N[C@H]2COC[C@H](CC3CCCCC3)[C@@H](CC3CCCCC3)[C@H](C)OC2=O)c1OCOC(C)=O] | Example 1, Step 14 | White Solid |
| 11 | 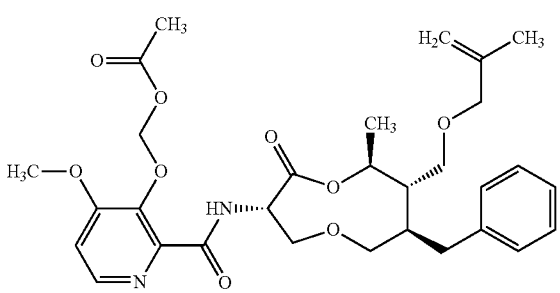 [SMILES: C=C(C)COC[C@@H]1[C@@H](Cc2ccccc2)COC[C@H](NC(=O)c2nccc(OC)c2OCOC(C)=O)C(=O)O[C@H]1C] | Example 1, Step 14 | White Solid |
| 12 | 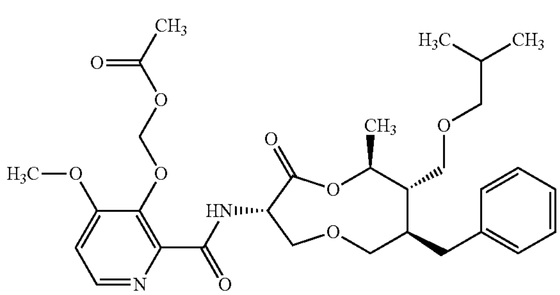 [SMILES: COc1ccnc(C(=O)N[C@H]2COC[C@H](Cc3ccccc3)[C@@H](COCC(C)C)[C@H](C)OC2=O)c1OCOC(C)=O] | Example 1, Step 14 | Colorless Oil |

TABLE 1-continued

Compound Structure and Appearance

| Compound Number | Structure | Prepared According to Example | Appearance |
|---|---|---|---|
| 13 | 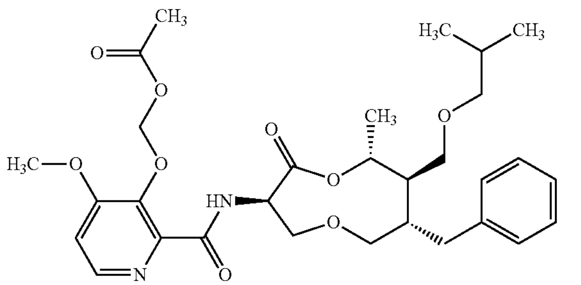 [SMILES: COc1ccnc(C(=O)N[C@@H]2COC[C@@H](Cc3ccccc3)[C@H](COCC(C)C)[C@@H](C)OC2=O)c1OCOC(C)=O] | Example 1, Step 14 | White Solid |
| 14 | 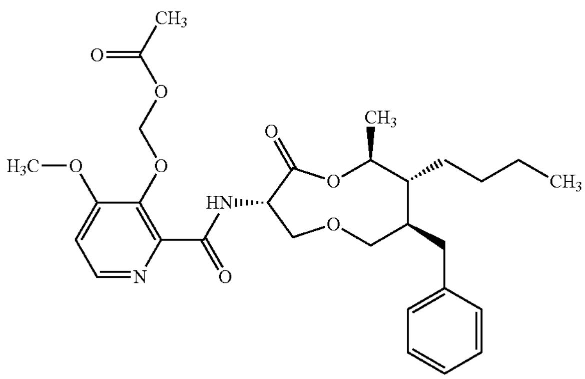 [SMILES: CCCC[C@@H]1[C@@H](Cc2ccccc2)COC[C@H](NC(=O)c2nccc(OC)c2OCOC(C)=O)C(=O)O[C@H]1C] | Example 1, Step 14 | Colorless Oil |
| 15 | 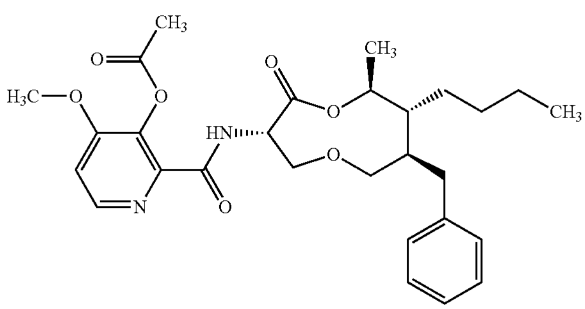 [SMILES: CCCC[C@@H]1[C@@H](Cc2ccccc2)COC[C@H](NC(=O)c2nccc(OC)c2OC(C)=O)C(=O)O[C@H]1C] | Example 9, Step 1 | White Foam |
| 16 | 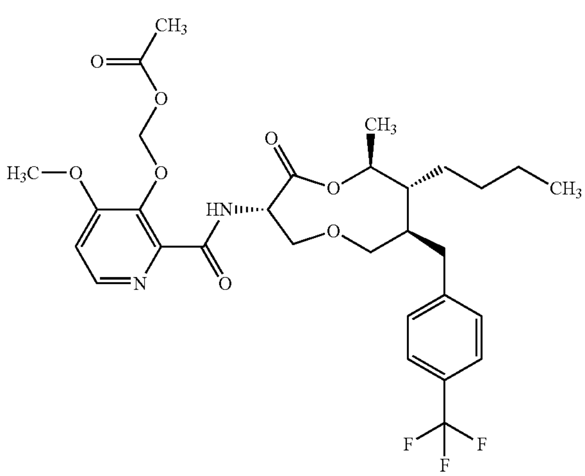 [SMILES: CCCC[C@@H]1[C@@H](Cc2ccc(C(F)(F)F)cc2)COC[C@H](NC(=O)c2nccc(OC)c2OCOC(C)=O)C(=O)O[C@H]1C] | Example 1, Step 14 | White Foam |

TABLE 1-continued
Compound Structure and Appearance
| Compound Number | Structure | Prepared According to Example | Appearance |
|---|---|---|---|
| 17 | 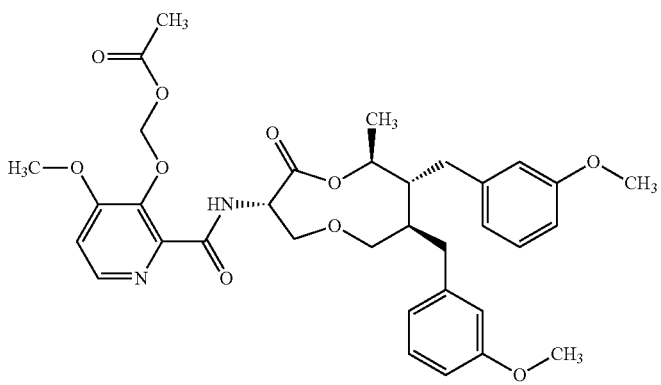 | Example 1, Step 14 | White Solid |
| 18 | 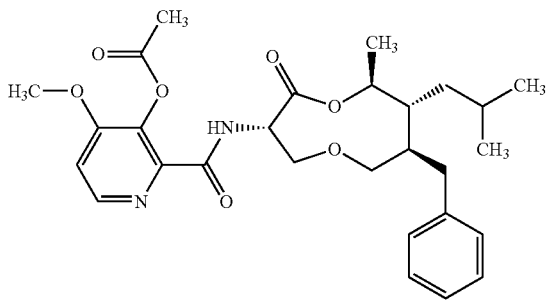 [SMILES: COc1ccnc(C(=O)N[C@H]2COC[C@H](Cc3ccccc3)[C@@H](CC(C)C)[C@H](C)OC2=O)c1OC(C)=O] | Example 9, Step 1 | Colorless Foam |
| 19 | 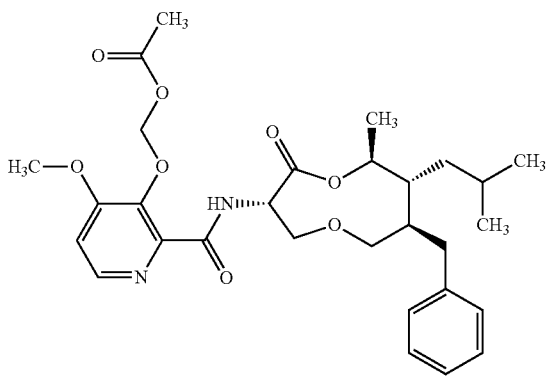 [SMILES: COc1ccnc(C(=O)N[C@H]2COC[C@H](Cc3ccccc3)[C@@H](CC(C)C)[C@H](C)OC2=O)c1OCOC(C)=O] | Example 1, Step 14 | Colorless Oil |
| 20 | 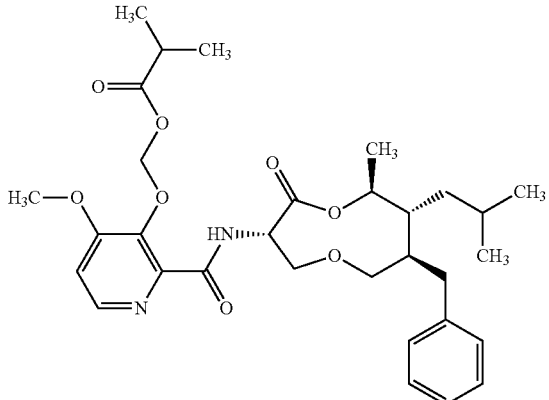 | Example 10, Step 1 | Colorless Oil |

TABLE 1-continued
Compound Structure and Appearance
| Compound Number | Structure | Prepared According to Example | Appearance |
|---|---|---|---|
| 21 | 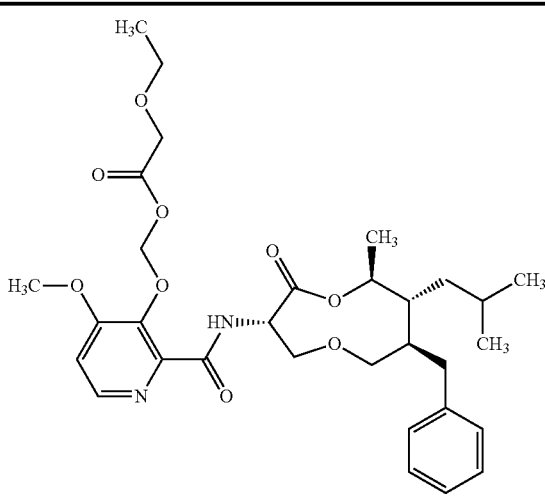 | Example 13, Step 1 | Colorless Oil |
| 22 | 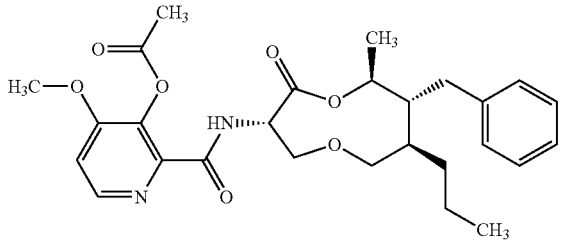 [SMILES: CCC[C@H]1COC[C@H](NC(=O)c2nccc(OC)c2OC(C)=O)C(=O)O[C@@H](C)[C@@H]1Cc1ccccc1] | Example 9, Step 1 | Colorless Oil |
| 23 | 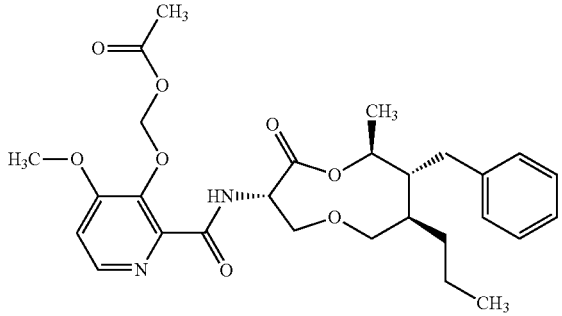 [SMILES: CCC[C@H]1COC[C@H](NC(=O)c2nccc(OC)c2OCOC(C)=O)C(=O)O[C@@H](C)[C@@H]1Cc1ccccc1] | Example 1, Step 14 | Colorless Oil |
| 24 | 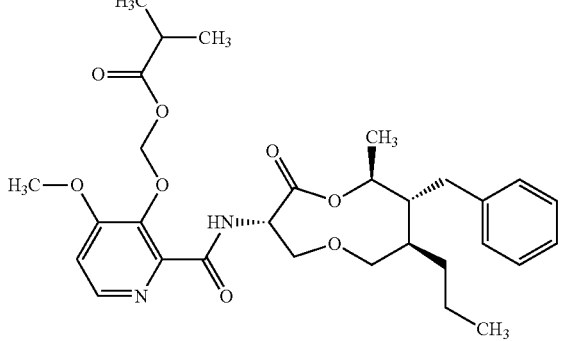 [SMILES: CCC[C@H]1COC[C@H](NC(=O)c2nccc(OC)c2OCOC(=O)C(C)C)C(=O)O[C@@H](C)[C@@H]1Cc1ccccc1] | Example 10, Step 1 | Colorless Oil |

TABLE 1-continued

Compound Structure and Appearance

| Compound Number | Structure | Prepared According to Example | Appearance |
|---|---|---|---|
| 25 | 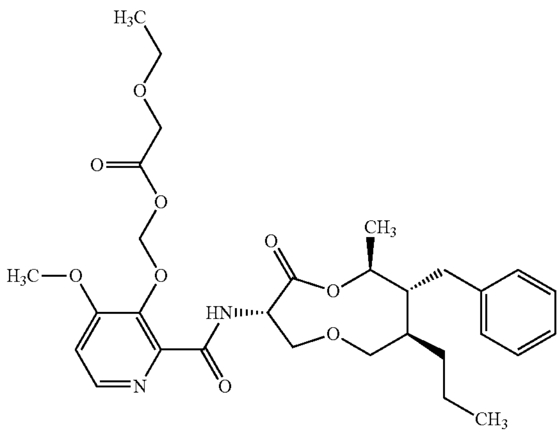 [SMILES: CCC[C@H]1COC[C@H](NC(=O)c2nccc(OC)c2OCOC(=O)COCC)C(=O)O[C@@H](C)[C@@H]1Cc1ccccc1] | Example 13, Step 1 | Colorless Oil |
| 26 | 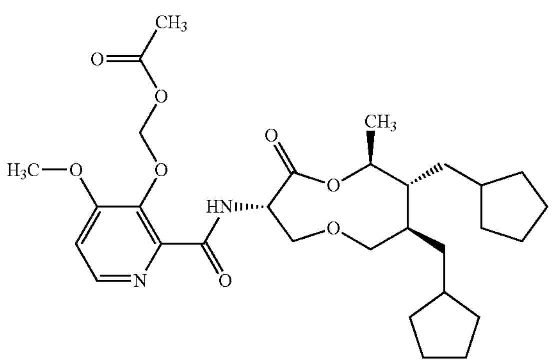 [SMILES: COc1ccnc(C(=O)N[C@H]2COC[C@H](CC3CCCC3)[C@@H](CC3CCCC3)[C@H](C)OC2=O)c1OCOC(C)=O] | Example 1, Step 14 | Yellow Oil |
| 27 | 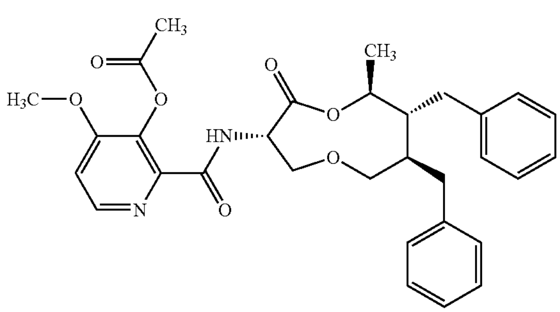 [SMILES: COc1ccnc(C(=O)N[C@H]2COC[C@H](Cc3ccccc3)[C@@H](Cc3ccccc3)[C@H](C)OC2=O)c1OC(C)=O] | Example 9, Step 1 | White Solid |

TABLE 1-continued

Compound Structure and Appearance

| Compound Number | Structure | Prepared According to Example | Appearance |
|---|---|---|---|
| 28 | 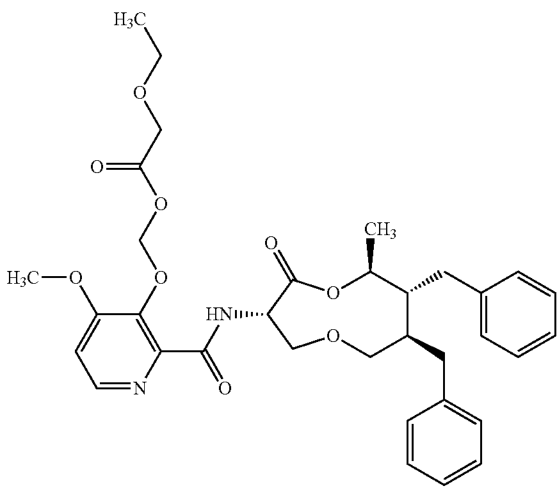 [SMILES: CCOCC(=O)OCOc1c(OC)ccnc1C(=O)N[C@H]1COC[C@H](Cc2ccccc2)[C@@H](Cc2ccccc2)[C@H](C)OC1=O] | Example 13, Step 1 | Colorless Oil |
| 29 | 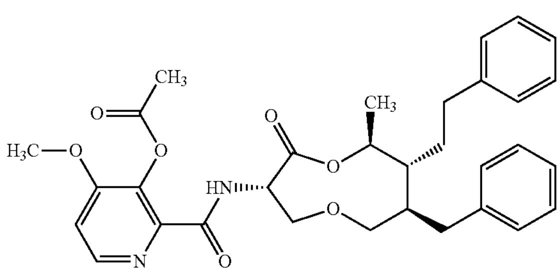 [SMILES: COc1ccnc(C(=O)N[C@H]2COC[C@H](Cc3ccccc3)[C@@H](CCc3ccccc3)[C@H](C)OC2=O)c1OC(C)=O] | Example 9, Step 1 | Colorless Oil |
| 30 | 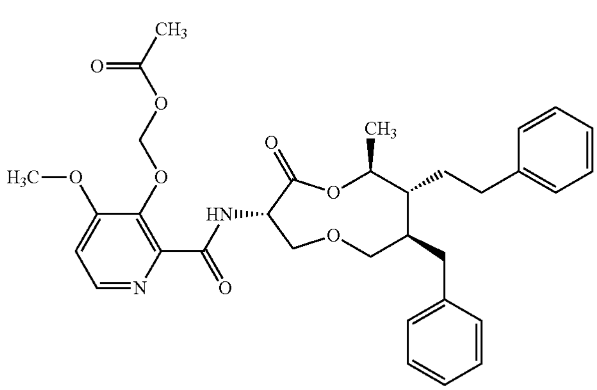 [SMILES: COc1ccnc(C(=O)N[C@H]2COC[C@H](Cc3ccccc3)[C@@H](CCc3ccccc3)[C@H](C)OC2=O)c1OCOC(C)=O] | Example 1, Step 14 | Colorless Oil |

TABLE 1-continued

Compound Structure and Appearance

| Compound Number | Structure | Prepared According to Example | Appearance |
|---|---|---|---|
| 31 | 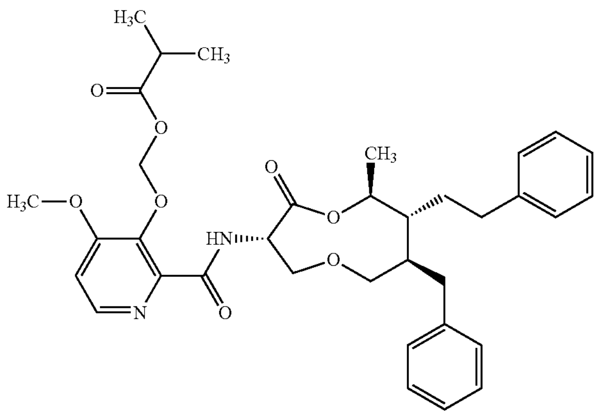 [SMILES: COc1ccnc(C(=O)N[C@H]2COC[C@H](Cc3ccccc3)[C@@H](CCc3ccccc3)[C@H](C)OC2=O)c1OCOC(=O)C(C)C] | Example 10, Step 1 | Colorless Oil |
| 32 | 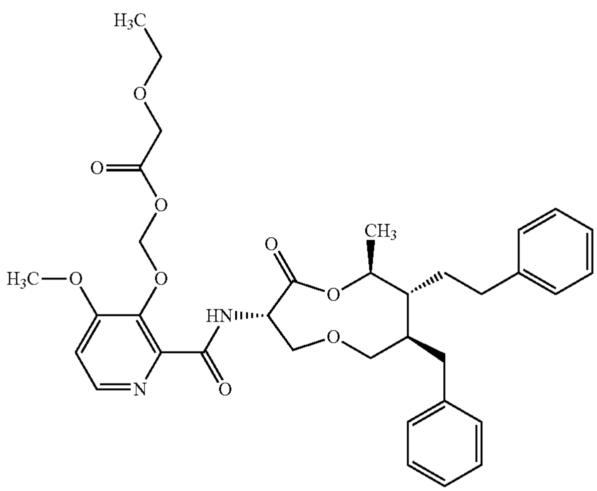 [SMILES: CCOCC(=O)OCOc1c(OC)ccnc1C(=O)N[C@H]1COC[C@H](Cc2ccccc2)[C@@H](CCc2ccccc2)[C@H](C)OC1=O] | Example 13, Step 1 | Colorless Oil |
| 33 | 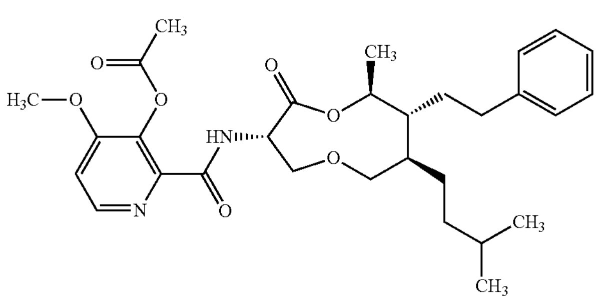 [SMILES: COc1ccnc(C(=O)N[C@H]2COC[C@H](CCC(C)C)[C@@H](CCc3ccccc3)[C@H](C)OC2=O)c1OC(C)=O] | Example 9, Step 1 | Colorless Oil |

TABLE 1-continued

| Compound Number | Structure | Prepared According to Example | Appearance |
|---|---|---|---|
| 34 | 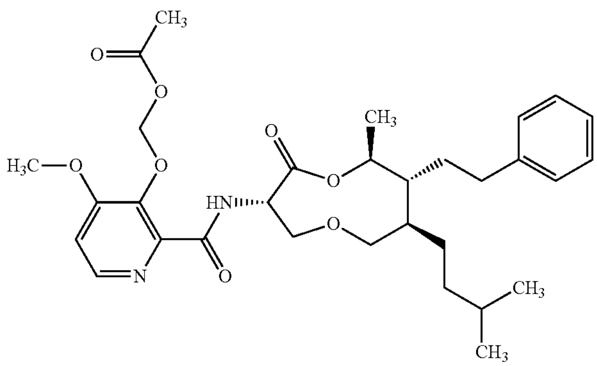 [SMILES: COc1ccnc(C(=O)N[C@H]2COC[C@H](CCC(C)C)[C@@H](CCc3ccccc3)[C@H](C)OC2=O)c1OCOC(C)=O] | Example 1, Step 14 | Colorless Oil |
| 35 | 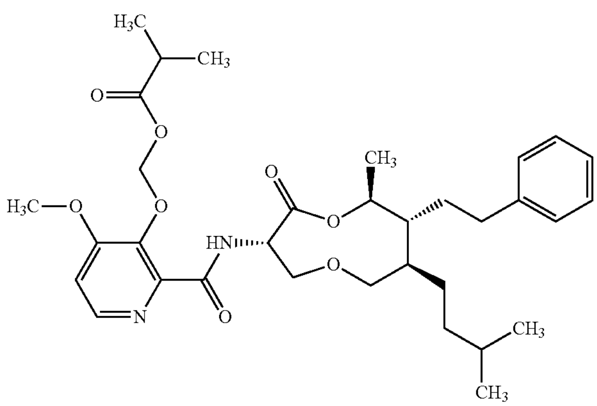 [SMILES: COc1ccnc(C(=O)N[C@H]2COC[C@H](CCC(C)C)[C@@H](CCc3ccccc3)[C@H](C)OC2=O)c1OCOC(=O)C(C)C] | Example 10, Step 1 | Colorless Oil |
| 36 | 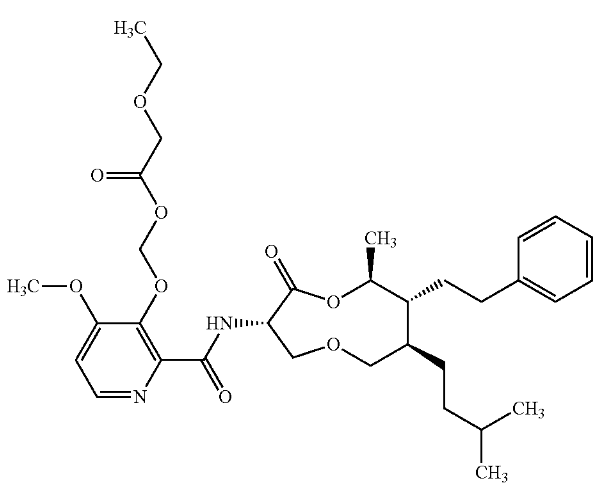 [SMILES: CCOCC(=O)OCOc1c(OC)ccnc1C(=O)N[C@H]1COC[C@H](CCC(C)C)[C@@H](CCc2ccccc2)[C@H](C)OC1=O] | Example 13, Step 1 | Colorless Oil |

TABLE 1-continued

Compound Structure and Appearance

| Compound Number | Structure | Prepared According to Example | Appearance |
|---|---|---|---|
| 37 | 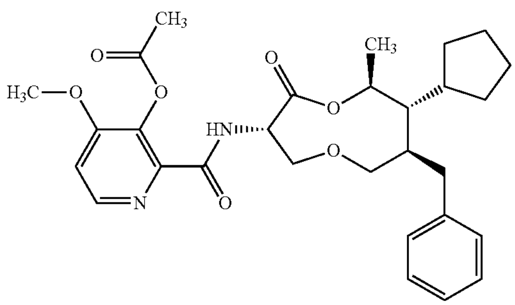 [SMILES: COc1ccnc(C(=O)N[C@H]2COC[C@H](Cc3ccccc3)[C@@H](C3CCCC3)[C@H](C)OC2=O)c1OC(C)=O] | Example 9, Step 1 | Colorless Oil |
| 38 | 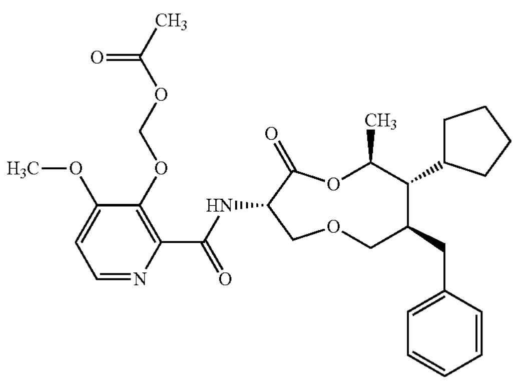 [SMILES: COc1ccnc(C(=O)N[C@H]2COC[C@H](Cc3ccccc3)[C@@H](C3CCCC3)[C@H](C)OC2=O)c1OCOC(C)=O] | Example 1, Step 14 | Colorless Oil |
| 39 | 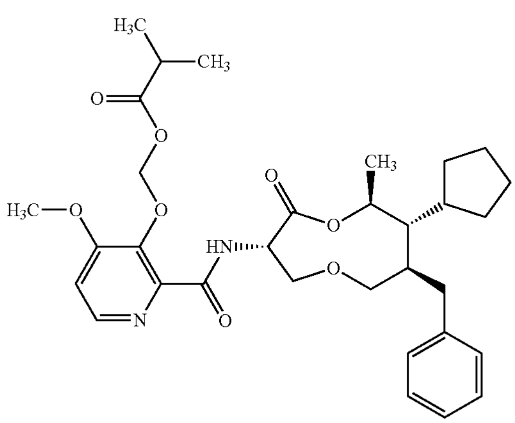 [SMILES: COc1ccnc(C(=O)N[C@H]2COC[C@H](Cc3ccccc3)[C@@H](C3CCCC3)[C@H](C)OC2=O)c1OCOC(=O)C(C)C] | Example 10, Step 1 | Colorless Oil |

TABLE 1-continued

Compound Structure and Appearance

| Compound Number | Structure | Prepared According to Example | Appearance |
|---|---|---|---|
| 40 | 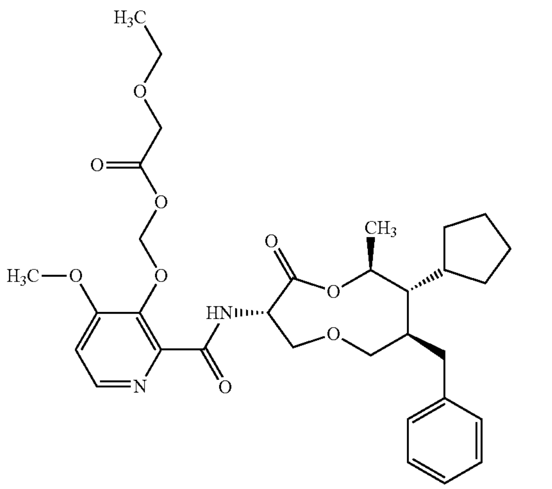 [SMILES: CCOCC(=O)OCOc1c(OC)ccnc1C(=O)N[C@H]1COC[C@H](Cc2ccccc2)[C@@H](C2CCCC2)[C@H](C)OC1=O] | Example 13, Step 1 | Colorless Oil |
| 41 | 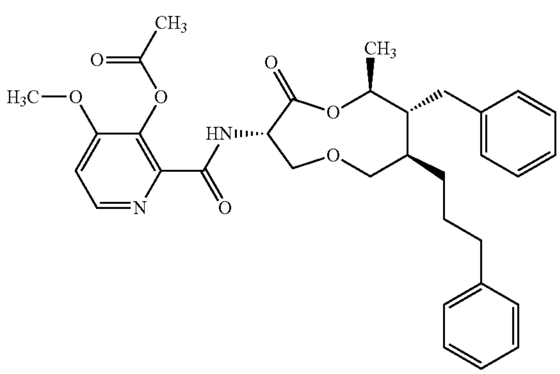 [SMILES: COc1ccnc(C(=O)N[C@H]2COC[C@H](CCCc3ccccc3)[C@@H](Cc3ccccc3)[C@H](C)OC2=O)c1OC(C)=O] | Example 9, Step 1 | Colorless Oil |
| 42 | 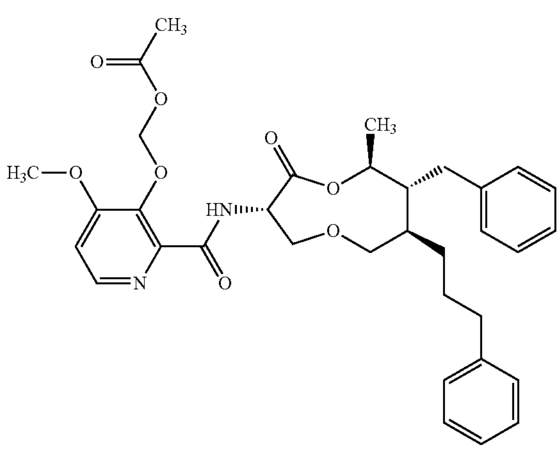 [SMILES: COc1ccnc(C(=O)N[C@H]2COC[C@H](CCCc3ccccc3)[C@@H](Cc3ccccc3)[C@H](C)OC2=O)c1OCOC(C)=O] | Example 1, Step 14 | Colorless Oil |

TABLE 1-continued
Compound Structure and Appearance
| Compound Number | Structure | Prepared According to Example | Appearance |
|---|---|---|---|
| 43 | 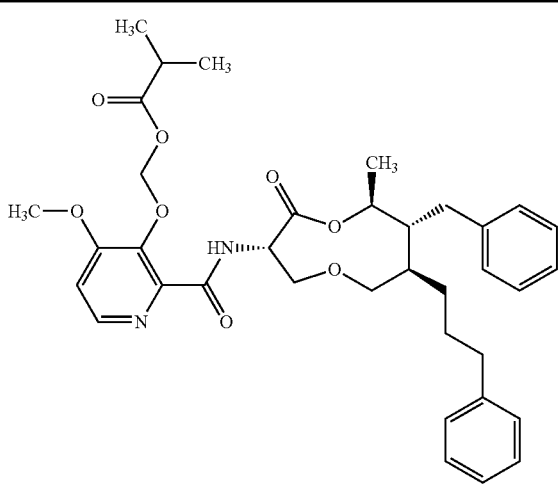 | Example 10, Step 1 | Colorless Oil |
| 44 | 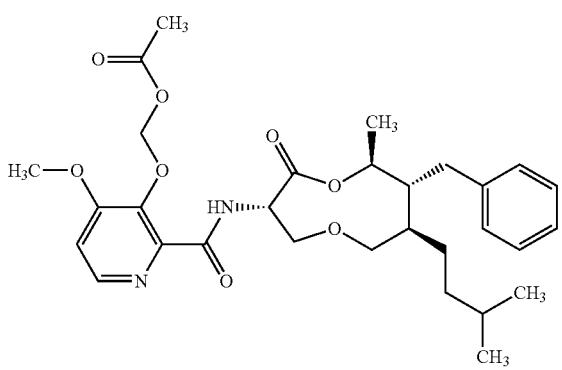 [SMILES: COc1ccnc(C(=O)N[C@H]2COC[C@H](CCC(C)C)[C@@H](Cc3ccccc3)[C@H](C)OC2=O)c1OCOC(C)=O] | Example 1, Step 14 | Colorless Oil |
| 45 | 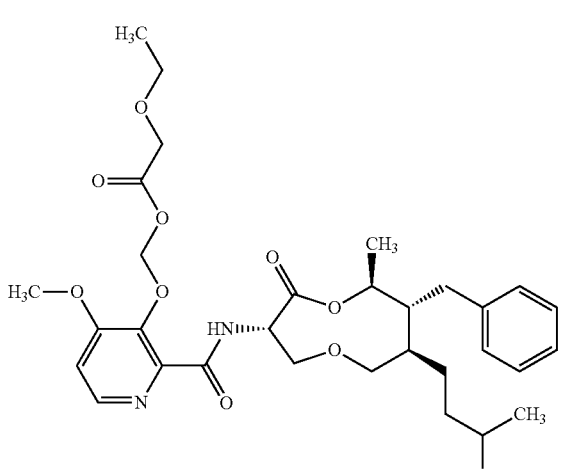 | Example 13, Step 1 | Colorless Oil |

TABLE 1-continued

Compound Structure and Appearance

| Compound Number | Structure | Prepared According to Example | Appearance |
|---|---|---|---|
| 46 | 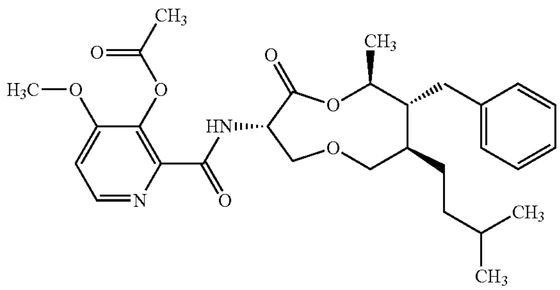 [SMILES: COc1ccnc(C(=O)N[C@H]2COC[C@H](CCC(C)C)[C@@H](Cc3ccccc3)[C@H](C)OC2=O)c1OC(C)=O] | Example 9, Step 1 | Pale Yellow Oil |
| 47 | 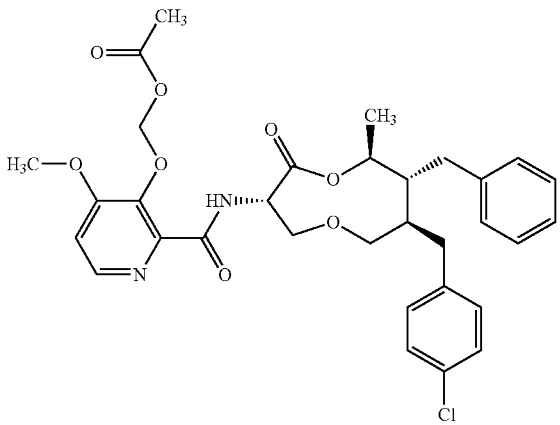 [SMILES: COc1ccnc(C(=O)N[C@H]2COC[C@H](Cc3ccc(Cl)cc3)[C@@H](Cc3ccccc3)[C@H](C)OC2=O)c1OCOC(C)=O] | Example 1, Step 14 | White Solid |
| 48 | 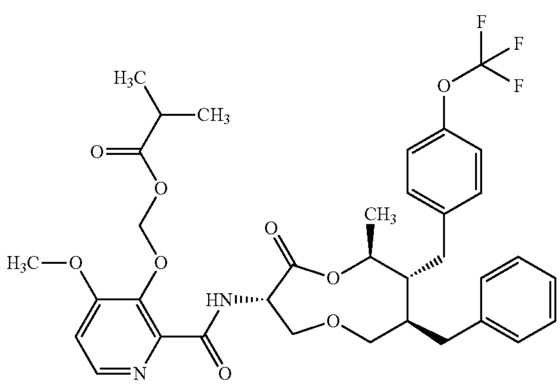 [SMILES: COc1ccnc(C(=O)N[C@H]2COC[C@H](Cc3ccccc3)[C@@H](Cc3ccc(OC(F)(F)F)cc3)[C@H](C)OC2=O)c1OCOC(=O)C(C)C] | Example 10, Step 1 | Colorless Oil |
| 49 | 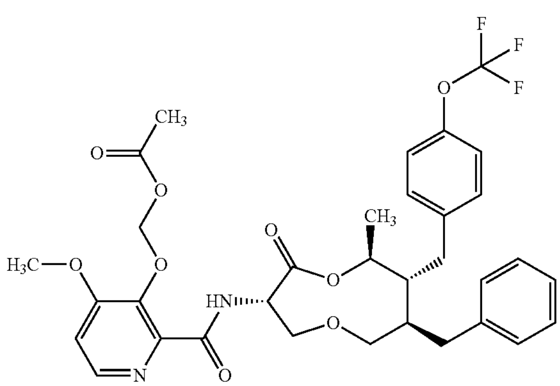 [SMILES: COc1ccnc(C(=O)N[C@H]2COC[C@H](Cc3ccccc3)[C@@H](Cc3ccc(OC(F)(F)F)cc3)[C@H](C)OC2=O)c1OCOC(C)=O] | Example 1, Step 14 | Pale Yellow Oil |

TABLE 1-continued

| Compound Number | Structure | Prepared According to Example | Appearance |
|---|---|---|---|
| 50 | 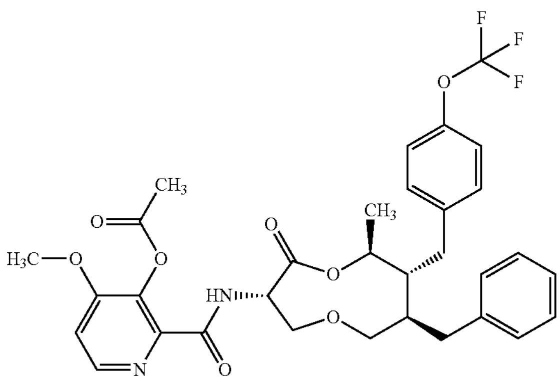 [SMILES: COc1ccnc(C(=O)N[C@H]2COC[C@H](Cc3ccccc3)[C@@H](Cc3ccc(OC(F)(F)F)cc3)[C@H](C)OC2=O)c1OC(C)=O] | Example 9, Step 1 | Colorless Oil |
| 51 | 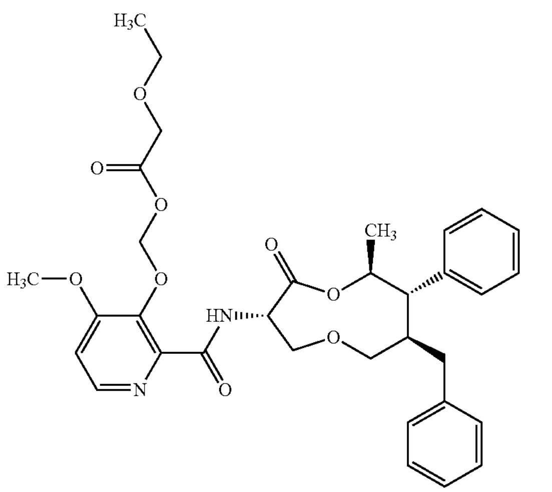 [SMILES: CCOCC(=O)OCOc1c(OC)ccnc1C(=O)N[C@H]1COC[C@H](Cc2ccccc2)[C@@H](c2ccccc2)[C@H](C)OC1=O] | Example 13, Step 1 | Colorless Oil |
| 52 | 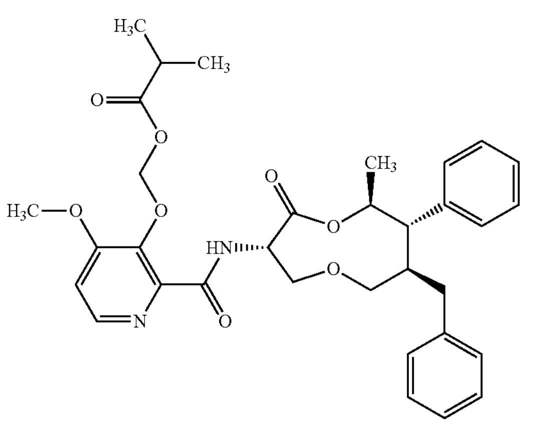 [SMILES: COc1ccnc(C(=O)N[C@H]2COC[C@H](Cc3ccccc3)[C@@H](c3ccccc3)[C@H](C)OC2=O)c1OCOC(=O)C(C)C] | Example 10, Step 1 | White Solid |

TABLE 1-continued

Compound Structure and Appearance

| Compound Number | Structure | Prepared According to Example | Appearance |
|---|---|---|---|
| 53 | 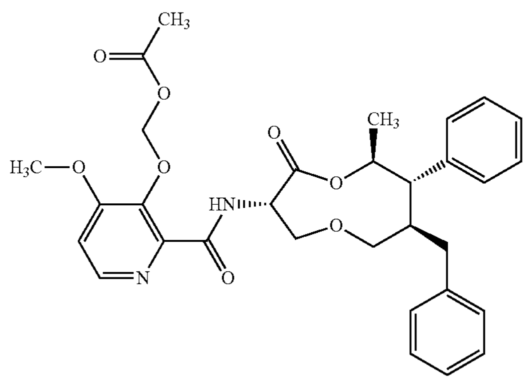 [SMILES: COc1ccnc(C(=O)N[C@H]2COC[C@H](Cc3ccccc3)[C@@H](c3ccccc3)[C@H](C)OC2=O)c1OCOC(C)=O] | Example 1, Step 14 | Colorless Oil |
| 54 | 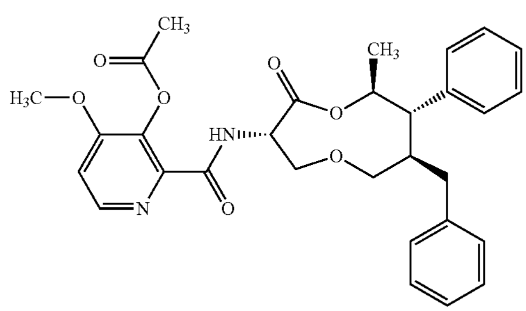 [SMILES: COc1ccnc(C(=O)N[C@H]2COC[C@H](Cc3ccccc3)[C@@H](c3ccccc3)[C@H](C)OC2=O)c1OC(C)=O] | Example 9, Step 1 | White Solid |
| 55 | 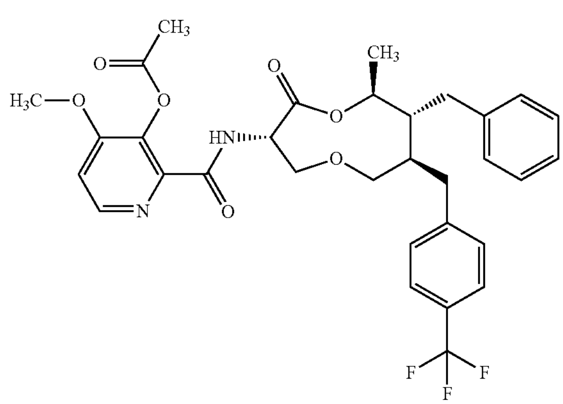 [SMILES: COc1ccnc(C(=O)N[C@H]2COC[C@H](Cc3ccc(C(F)(F)F)cc3)[C@@H](Cc3ccccc3)[C@H](C)OC2=O)c1OC(C)=O] | Example 9, Step 1 | Colorless Oil |

TABLE 1-continued

Compound Structure and Appearance

| Compound Number | Structure | Prepared According to Example | Appearance |
|---|---|---|---|
| 56 | 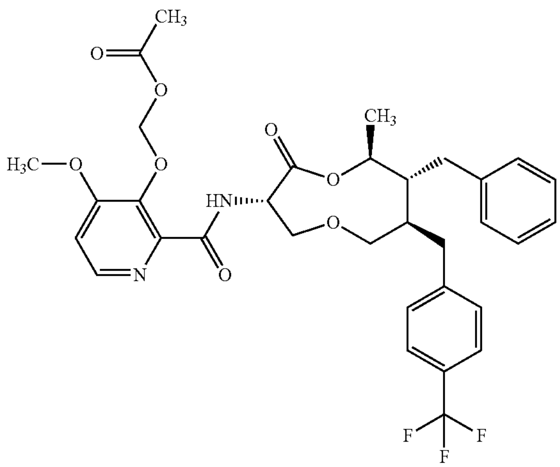 [SMILES: COc1ccnc(C(=O)N[C@H]2COC[C@H](Cc3ccc(C(F)(F)F)cc3)[C@@H](Cc3ccccc3)[C@H](C)OC2=O)c1OCOC(C)=O] | Example 1, Step 14 | Colorless Oil |
| 57 | 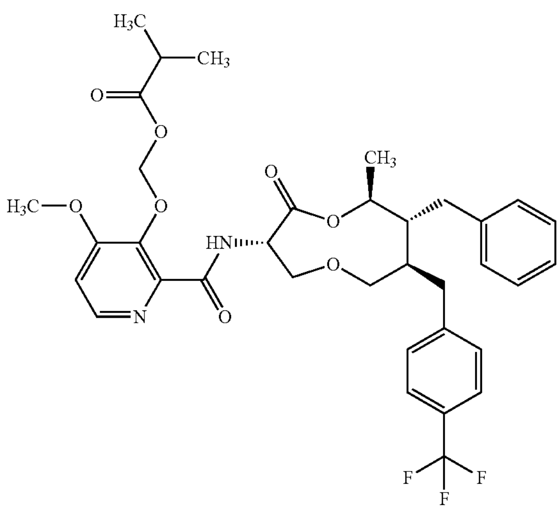 [SMILES: COc1ccnc(C(=O)N[C@H]2COC[C@H](Cc3ccc(C(F)(F)F)cc3)[C@@H](Cc3ccccc3)[C@H](C)OC2=O)c1OCOC(=O)C(C)C] | Example 10, Step 1 | Colorless Oil |
| 58 | 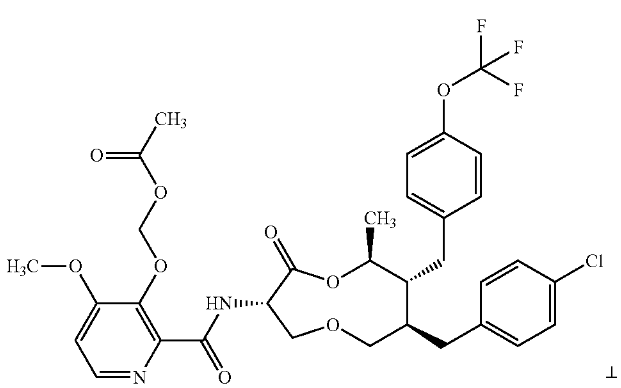 [SMILES: COc1ccnc(C(=O)N[C@H]2COC[C@H](Cc3ccc(Cl)cc3)[C@@H](Cc3ccc(OC(F)(F)F)cc3)[C@H](C)OC2=O)c1OCOC(C)=O] | Example 1, Step 14 | White Solid |

TABLE 1-continued
Compound Structure and Appearance
| Compound Number | Structure | Prepared According to Example | Appearance |
|---|---|---|---|
| 59 | 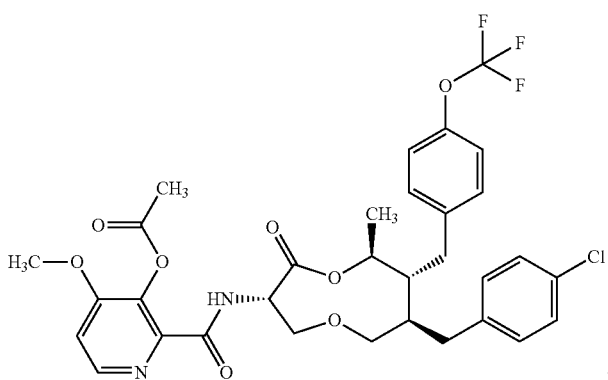 | Example 9, Step 1 | White Solid |
| 60 | 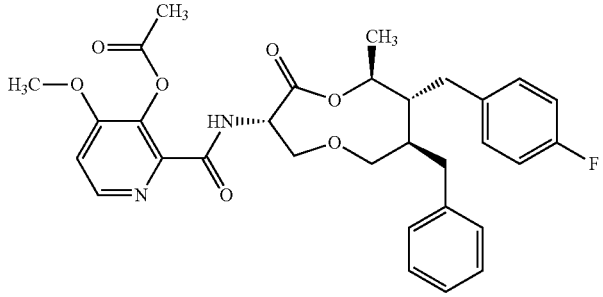 [SMILES: COc1ccnc(C(=O)N[C@H]2COC[C@H](Cc3ccccc3)[C@@H](Cc3ccc(F)cc3)[C@H](C)OC2=O)c1OC(C)=O] | Example 9, Step 1 | Colorless Oil |
| 61 | 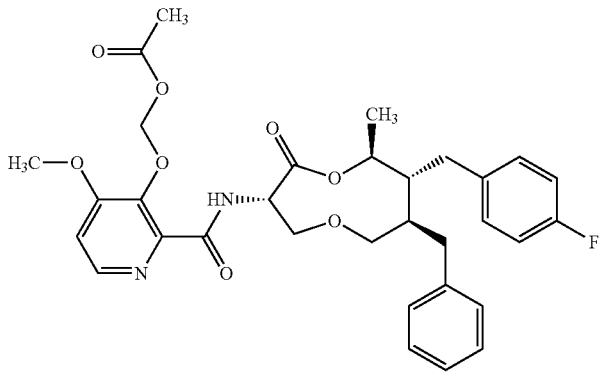 [SMILES: COc1ccnc(C(=O)N[C@H]2COC[C@H](Cc3ccccc3)[C@@H](Cc3ccc(F)cc3)[C@H](C)OC2=O)c1OCOC(C)=O] | Example 1, Step 14 | Colorless Oil |
| 62 | 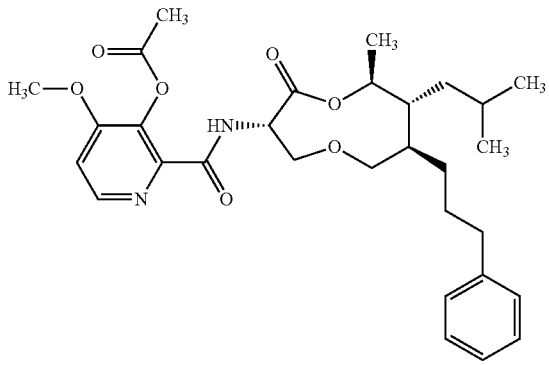 [SMILES: COc1ccnc(C(=O)N[C@H]2COC[C@H](CCCc3ccccc3)[C@@H](CC(C)C)[C@H](C)OC2=O)c1OC(C)=O] | Example 9, Step 1 | Colorless Oil |

TABLE 1-continued

Compound Structure and Appearance

| Compound Number | Structure | Prepared According to Example | Appearance |
|---|---|---|---|
| 63 | 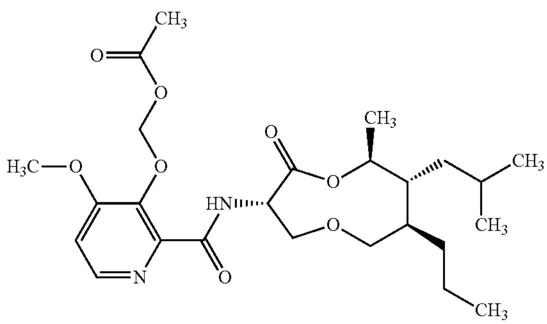 [SMILES: CCC[C@H]1COC[C@H](NC(=O)c2nccc(OC)c2OCOC(C)=O)C(=O)O[C@@H](C)[C@@H]1CC(C)C] | Example 1, Step 14 | Off White Foam |
| 64 | 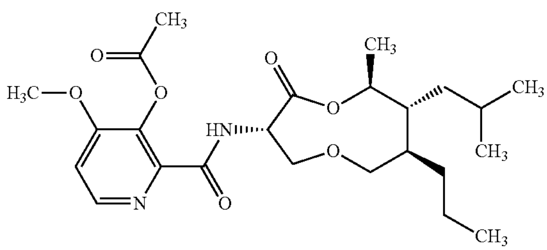 [SMILES: CCC[C@H]1COC[C@H](NC(=O)c2nccc(OC)c2OC(C)=O)C(=O)O[C@@H](C)[C@@H]1CC(C)C] | Example 9, Step 1 | Light Orange Foam |
| 65 | 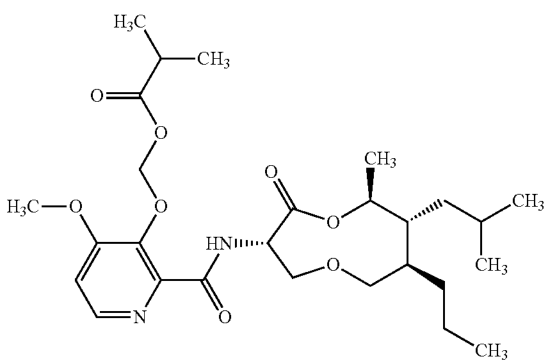 [SMILES: CCC[C@H]1COC[C@H](NC(=O)c2nccc(OC)c2OCOC(=O)C(C)C)C(=O)O[C@@H](C)[C@@H]1CC(C)C] | Example 10, Step 1 | Off White Foam |
| 66 | 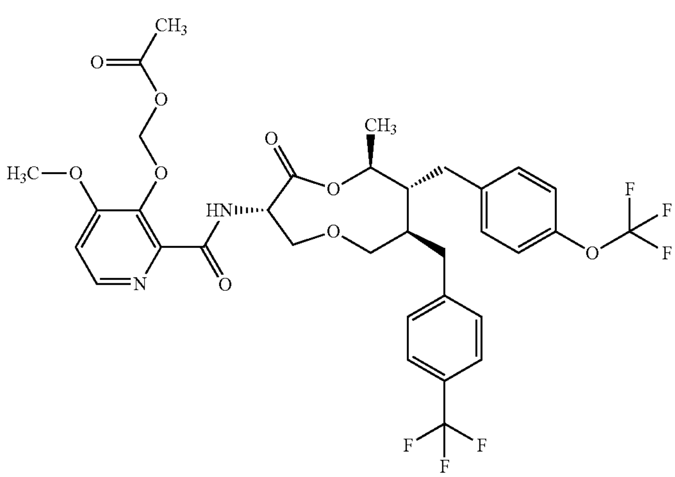 [SMILES: COc1ccnc(C(=O)N[C@H]2COC[C@H](Cc3ccc(C(F)(F)F)cc3)[C@@H](Cc3ccc(OC(F)(F)F)cc3)[C@H](C)OC2=O)c1OCOC(C)=O] | Example 1, Step 14 | White Solid |

… 97 …

TABLE 1-continued

Compound Structure and Appearance

| Compound Number | Structure | Prepared According to Example | Appearance |
|---|---|---|---|
| 67 | [structure] | Example 1, Step 14 | White Solid |
| 68 | [structure] | Example 1, Step 14 | White Solid |
| 69 | [structure] | Example 9, Step 1 | White Solid |
| 70 | [structure] | Example 10, Step 1 | White Solid |

TABLE 1-continued

Compound Structure and Appearance

| Compound Number | Structure | Prepared According to Example | Appearance |
|---|---|---|---|
| 71 | 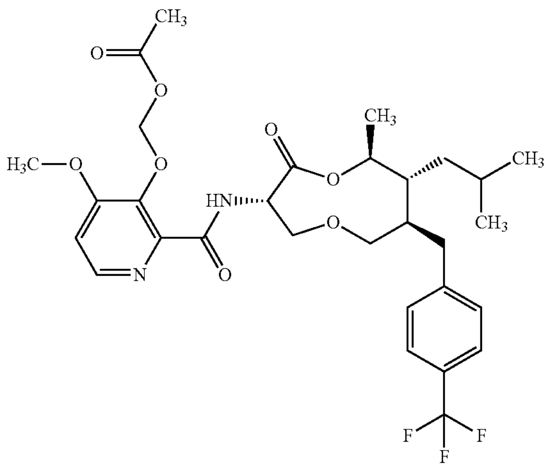 [SMILES: COc1ccnc(C(=O)N[C@H]2COC[C@H](Cc3ccc(C(F)(F)F)cc3)[C@@H](CC(C)C)[C@H](C)OC2=O)c1OCOC(C)=O] | Example 1, Step 14 | White Solid |
| 72 | 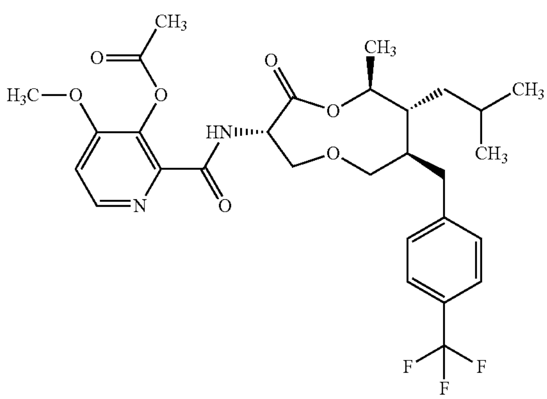 [SMILES: COc1ccnc(C(=O)N[C@H]2COC[C@H](Cc3ccc(C(F)(F)F)cc3)[C@@H](CC(C)C)[C@H](C)OC2=O)c1OC(C)=O] | Example 9, Step 1 | White Solid |
| 73 | 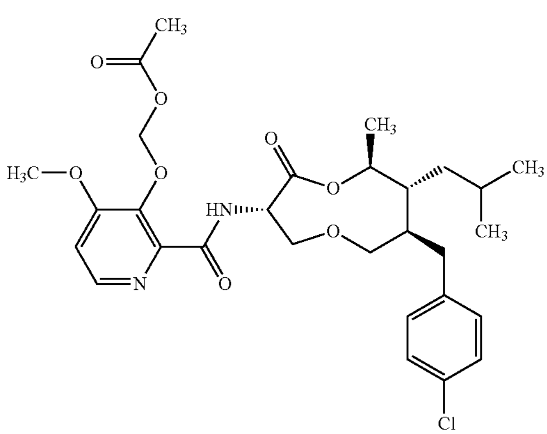 [SMILES: COc1ccnc(C(=O)N[C@H]2COC[C@H](Cc3ccc(Cl)cc3)[C@@H](CC(C)C)[C@H](C)OC2=O)c1OCOC(C)=O] | Example 1, Step 14 | Colorless Solid |

TABLE 1-continued

Compound Structure and Appearance

| Compound Number | Structure | Prepared According to Example | Appearance |
|---|---|---|---|
| 74 | 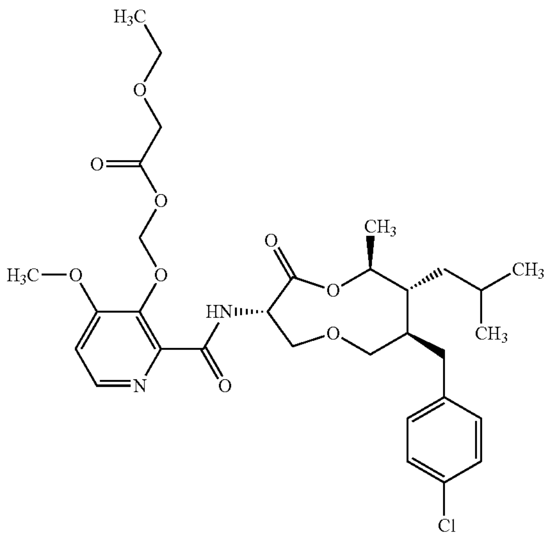 [SMILES: CCOCC(=O)OCOc1c(OC)ccnc1C(=O)N[C@H]1COC[C@H](Cc2ccc(Cl)cc2)[C@@H](CC(C)C)[C@H](C)OC1=O] | Example 13, Step 1 | Colorless Oil |
| 75 | 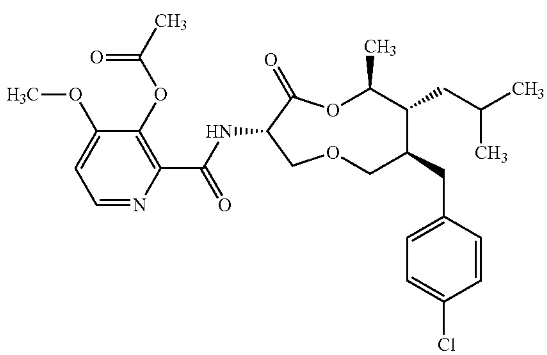 [SMILES: COc1ccnc(C(=O)N[C@H]2COC[C@H](Cc3ccc(Cl)cc3)[C@@H](CC(C)C)[C@H](C)OC2=O)c1OC(C)=O] | Example 9, Step 1 | Off-White Solid |
| 76 | 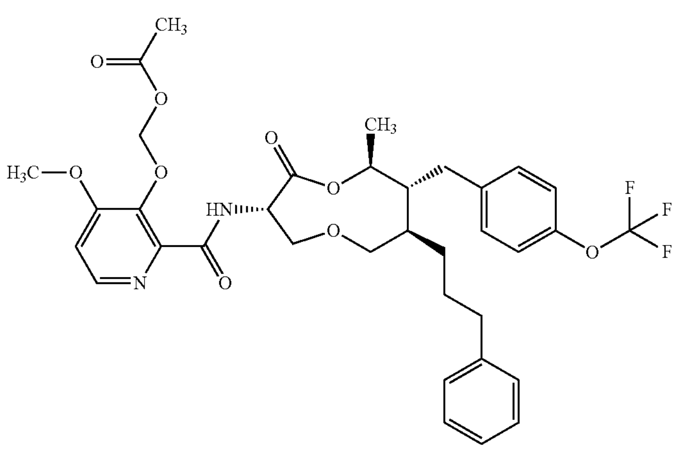 [SMILES: COc1ccnc(C(=O)N[C@H]2COC[C@H](CCCc3ccccc3)[C@@H](Cc3ccc(OC(F)(F)F)cc3)[C@H](C)OC2=O)c1OCOC(C)=O] | Example 1, Step 14 | Colorless Oil |

TABLE 1-continued

| Compound Number | Structure | Prepared According to Example | Appearance |
|---|---|---|---|
| 77 | 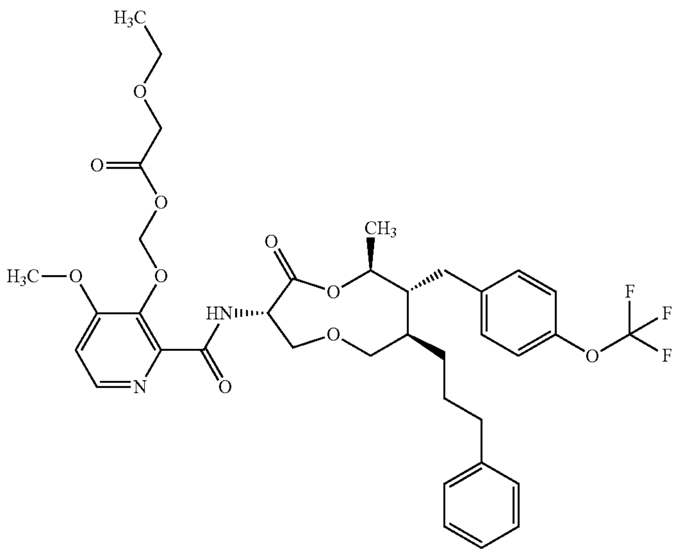 [SMILES: CCOCC(=O)OCOc1c(OC)ccnc1C(=O)N[C@H]1COC[C@H](CCCc2ccccc2)[C@@H](Cc2ccc(OC(F)(F)F)cc2)[C@H](C)OC1=O] | Example 13, Step 1 | Colorless Oil |
| 78 | 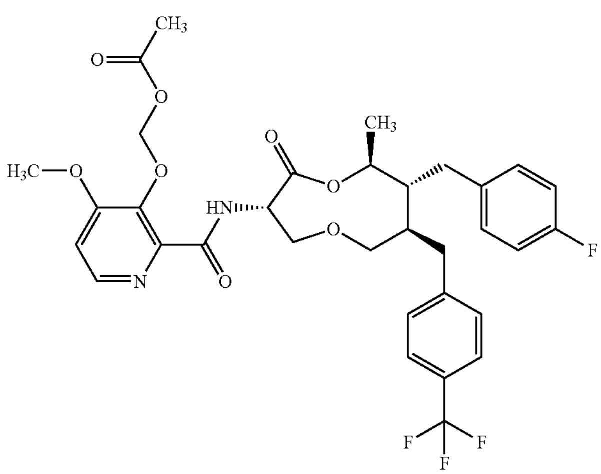 [SMILES: COc1ccnc(C(=O)N[C@H]2COC[C@H](Cc3ccc(C(F)(F)F)cc3)[C@@H](Cc3ccc(F)cc3)[C@H](C)OC2=O)c1OCOC(C)=O] | Example 1, Step 14 | White Foam |
| 79 | 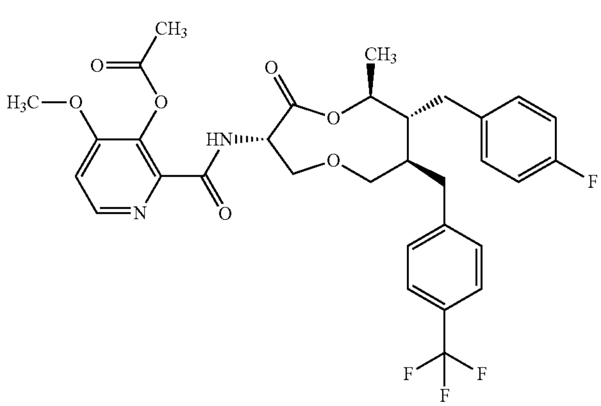 [SMILES: COc1ccnc(C(=O)N[C@H]2COC[C@H](Cc3ccc(C(F)(F)F)cc3)[C@@H](Cc3ccc(F)cc3)[C@H](C)OC2=O)c1OC(C)=O] | Example 9, Step 1 | Light Yellow Foam |

TABLE 1-continued
Compound Structure and Appearance
| Compound Number | Structure | Prepared According to Example | Appearance |
|---|---|---|---|
| 80 | 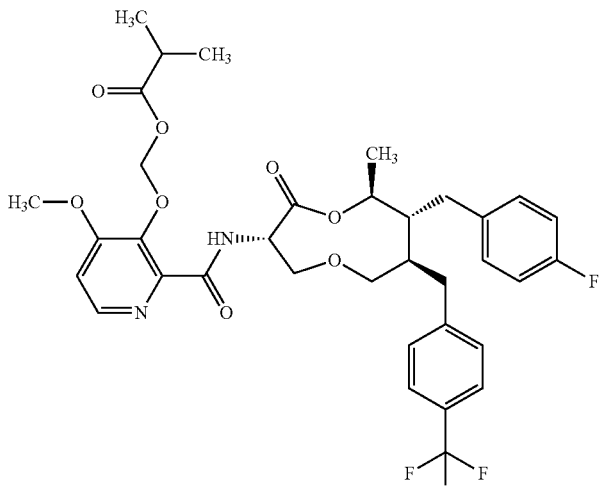 | Example 10, Step 1 | White Foam |
| 81 | 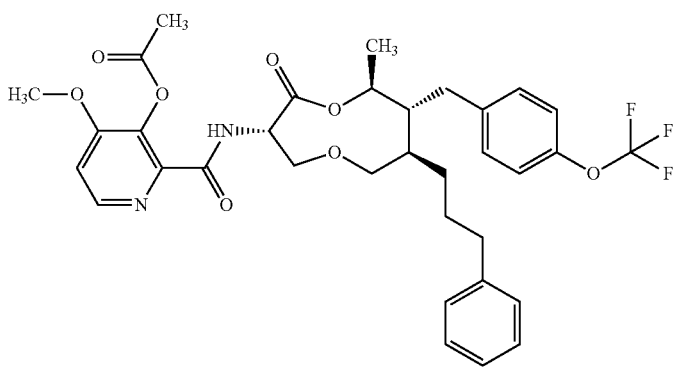 [SMILES: COc1ccnc(C(=O)N[C@H]2COC[C@H](CCCc3ccccc3)[C@@H](Cc3ccc(OC(F)(F)F)cc3)[C@H](C)OC2=O)c1OC(C)=O] | Example 9, Step 1 | Pale Yellow Sticky Solid |
| 82 | 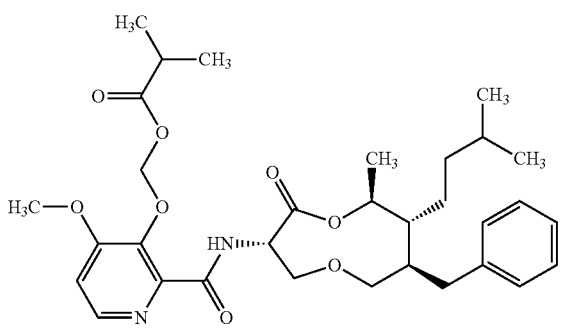 [SMILES: COc1ccnc(C(=O)N[C@H]2COC[C@H](Cc3ccccc3)[C@@H](CCC(C)C)[C@H](C)OC2=O)c1OCOC(=O)C(C)C] | Example 10, Step 1 | Colorless Oil |

TABLE 1-continued

Compound Structure and Appearance

| Compound Number | Structure | Prepared According to Example | Appearance |
|---|---|---|---|
| 83 | 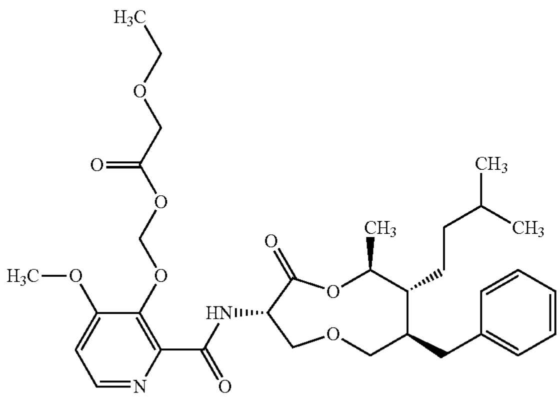 [SMILES: CCOCC(=O)OCOc1c(OC)ccnc1C(=O)N[C@H]1COC[C@H](Cc2ccccc2)[C@@H](CCC(C)C)[C@H](C)OC1=O] | Example 13, Step 1 | Colorless Oil |
| 84 | 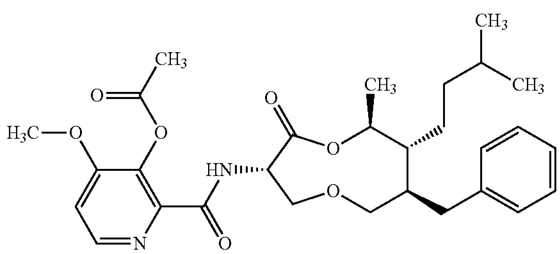 [SMILES: COc1ccnc(C(=O)N[C@H]2COC[C@H](Cc3ccccc3)[C@@H](CCC(C)C)[C@H](C)OC2=O)c1OC(C)=O] | Example 9, Step 1 | Colorless Oil |
| 85 | 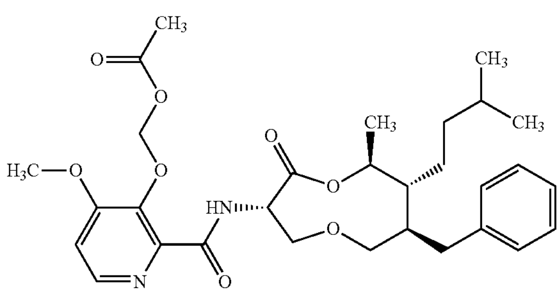 [SMILES: COc1ccnc(C(=O)N[C@H]2COC[C@H](Cc3ccccc3)[C@@H](CCC(C)C)[C@H](C)OC2=O)c1OCOC(C)=O] | Example 1, Step 14 | Colorless Oil |
| 86 | 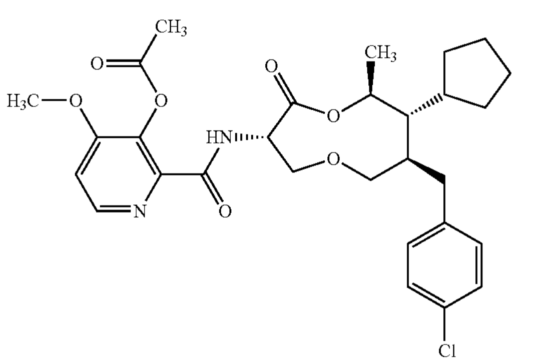 [SMILES: COc1ccnc(C(=O)N[C@H]2COC[C@H](Cc3ccc(Cl)cc3)[C@@H](C3CCCC3)[C@H](C)OC2=O)c1OC(C)=O] | Example 9, Step 1 | White Solid |

TABLE 1-continued

Compound Structure and Appearance

| Compound Number | Structure | Prepared According to Example | Appearance |
|---|---|---|---|
| 87 | 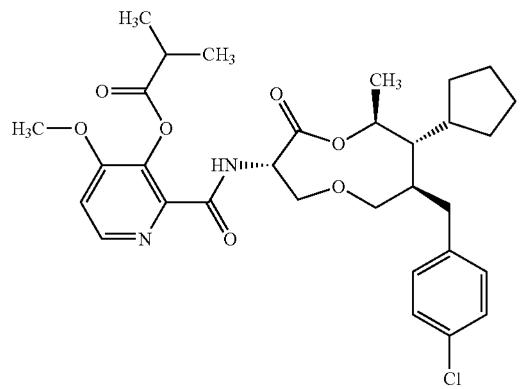 [SMILES: COc1ccnc(C(=O)N[C@H]2COC[C@H](Cc3ccc(Cl)cc3)[C@@H](C3CCCC3)[C@H](C)OC2=O)c1OC(=O)C(C)C] | Example 11, Step 1 | White Solid |
| 88 | 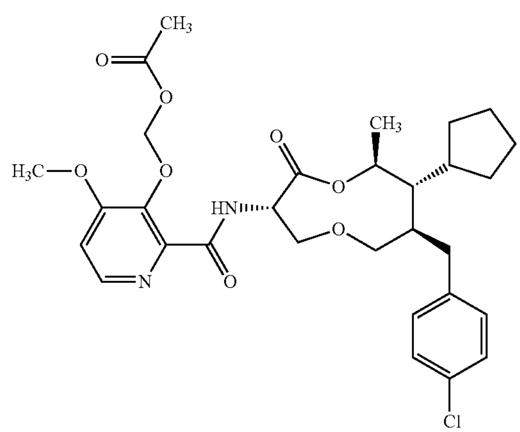 [SMILES: COc1ccnc(C(=O)N[C@H]2COC[C@H](Cc3ccc(Cl)cc3)[C@@H](C3CCCC3)[C@H](C)OC2=O)c1OCOC(C)=O] | Example 1, Step 14 | White Solid |
| 89 | 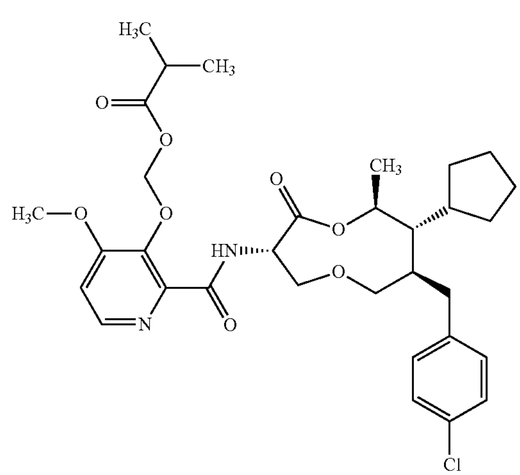 [SMILES: COc1ccnc(C(=O)N[C@H]2COC[C@H](Cc3ccc(Cl)cc3)[C@@H](C3CCCC3)[C@H](C)OC2=O)c1OCOC(=O)C(C)C] | Example 10, Step 1 | White Solid |

TABLE 1-continued

Compound Structure and Appearance

| Compound Number | Structure | Prepared According to Example | Appearance |
| --- | --- | --- | --- |
| 90 | 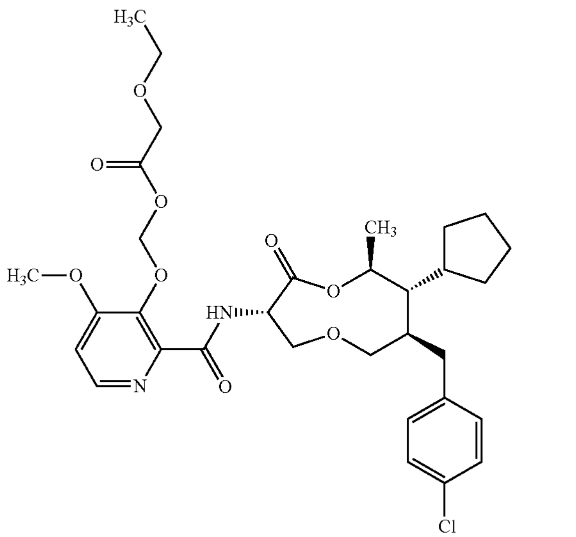 [SMILES: CCOCC(=O)OCOc1c(OC)ccnc1C(=O)N[C@H]1COC[C@H](Cc2ccc(Cl)cc2)[C@@H](C2CCCC2)[C@H](C)OC1=O] | Example 13, Step 1 | White Solid |
| 91 | 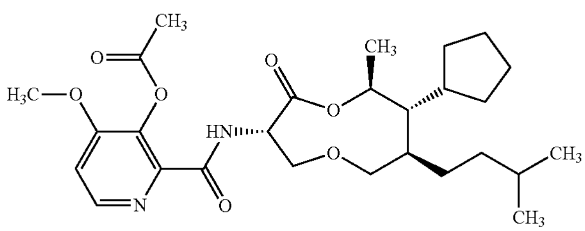 [SMILES: COc1ccnc(C(=O)N[C@H]2COC[C@H](CCC(C)C)[C@@H](C3CCCC3)[C@H](C)OC2=O)c1OC(C)=O] | Example 9, Step 1 | White Solid |
| 92 | 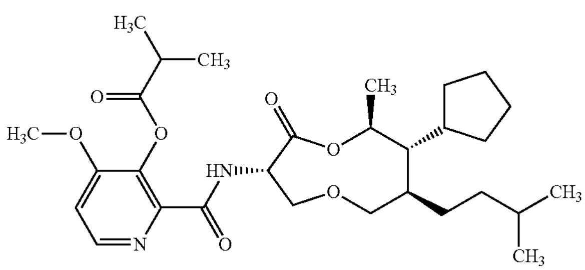 [SMILES: COc1ccnc(C(=O)N[C@H]2COC[C@H](CCC(C)C)[C@@H](C3CCCC3)[C@H](C)OC2=O)c1OC(=O)C(C)C] | Example 11, Step 1 | White Solid |
| 93 | 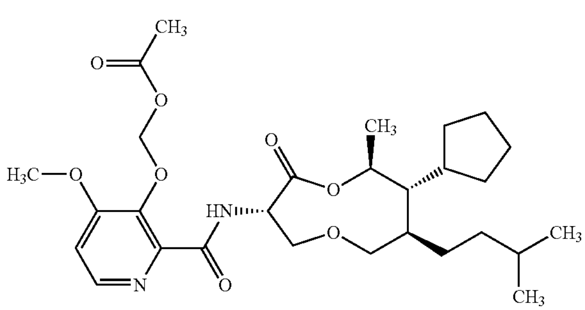 [SMILES: COc1ccnc(C(=O)N[C@H]2COC[C@H](CCC(C)C)[C@@H](C3CCCC3)[C@H](C)OC2=O)c1OCOC(C)=O] | Example 1, Step 14 | Pale Yellow Solid |

TABLE 1-continued

Compound Structure and Appearance

| Compound Number | Structure | Prepared According to Example | Appearance |
|---|---|---|---|
| 94 | 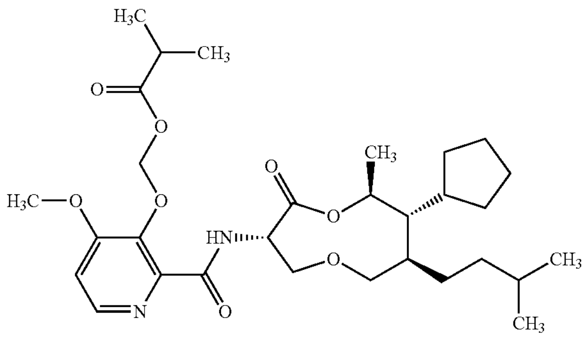 [SMILES: COc1ccnc(C(=O)N[C@H]2COC[C@H](CCC(C)C)[C@@H](C3CCCC3)[C@H](C)OC2=O)c1OCOC(=O)C(C)C] | Example 10, Step 1 | Colorless Oil |
| 95 | 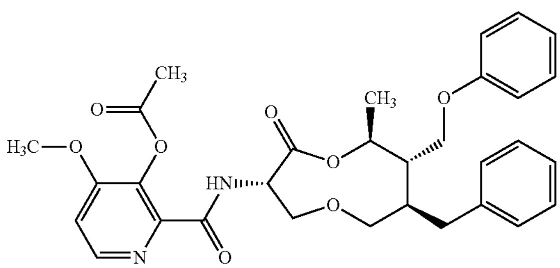 [SMILES: COc1ccnc(C(=O)N[C@H]2COC[C@H](Cc3ccccc3)[C@@H](COc3ccccc3)[C@H](C)OC2=O)c1OC(C)=O] | Example 9, Step 1 | White Solid |
| 96 | 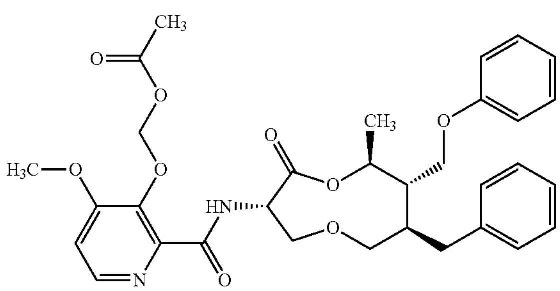 [SMILES: COc1ccnc(C(=O)N[C@H]2COC[C@H](Cc3ccccc3)[C@@H](COc3ccccc3)[C@H](C)OC2=O)c1OCOC(C)=O] | Example 1, Step 14 | White Solid |
| 97 | 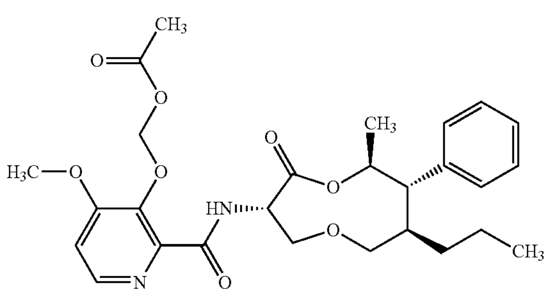 [SMILES: CCC[C@H]1COC[C@H](NC(=O)c2nccc(OC)c2OCOC(C)=O)C(=O)O[C@@H](C)[C@@H]1c1ccccc1] | Example 1, Step 14 | White Foam |
| 98 | 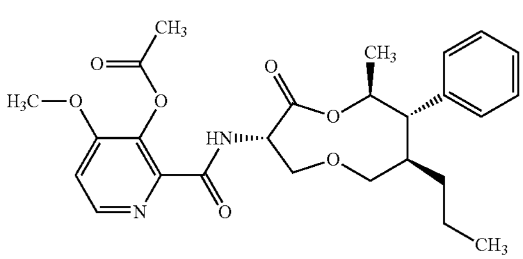 [SMILES: CCC[C@H]1COC[C@H](NC(=O)c2nccc(OC)c2OC(C)=O)C(=O)O[C@@H](C)[C@@H]1c1ccccc1] | Example 9, Step 1 | White Foam |

TABLE 1-continued

Compound Structure and Appearance

| Compound Number | Structure | Prepared According to Example | Appearance |
|---|---|---|---|
| 99 | 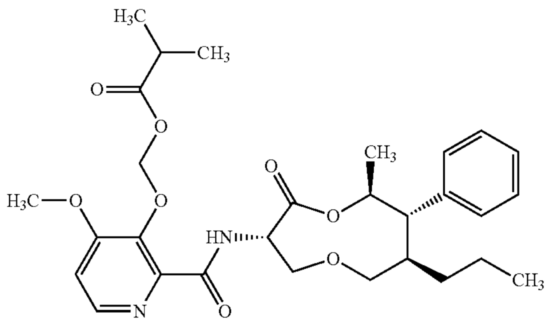 [SMILES: CCC[C@H]1COC[C@H](NC(=O)c2nccc(OC)c2OCOC(=O)C(C)C)C(=O)O[C@@H](C)[C@@H]1c1ccccc1] | Example 10, Step 1 | White Foam |
| 100 | 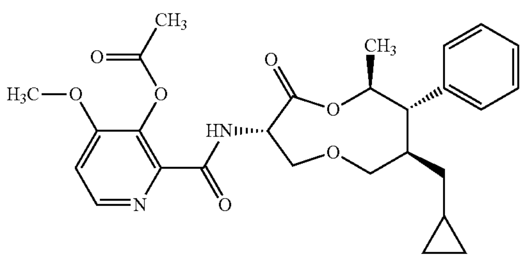 [SMILES: COc1ccnc(C(=O)N[C@H]2COC[C@H](CC3CC3)[C@@H](c3ccccc3)[C@H](C)OC2=O)c1OC(C)=O] | Example 9, Step 1 | Colorless Oil |
| 101 | 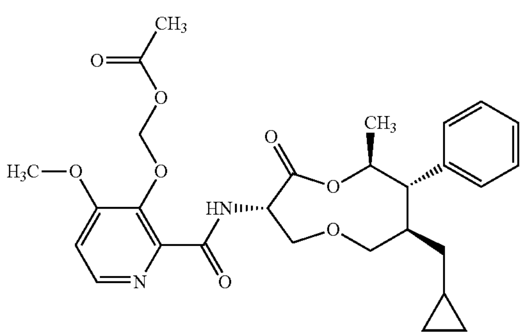 [SMILES: COc1ccnc(C(=O)N[C@H]2COC[C@H](CC3CC3)[C@@H](c3ccccc3)[C@H](C)OC2=O)c1OCOC(C)=O] | Example 1, Step 14 | Colorless Oil |
| 102 | 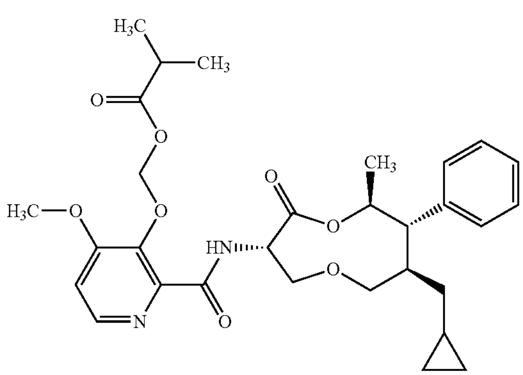 [SMILES: COc1ccnc(C(=O)N[C@H]2COC[C@H](CC3CC3)[C@@H](c3ccccc3)[C@H](C)OC2=O)c1OCOC(=O)C(C)C] | Example 10, Step 1 | Colorless Oil |

TABLE 1-continued

Compound Structure and Appearance

| Compound Number | Structure | Prepared According to Example | Appearance |
|---|---|---|---|
| 103 | 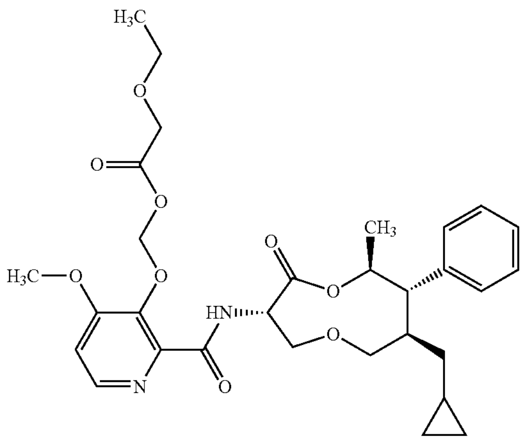 [SMILES: CCOCC(=O)OCOc1c(OC)ccnc1C(=O)N[C@H]1COC[C@H](CC2CC2)[C@@H](c2ccccc2)[C@H](C)OC1=O] | Example 13, Step 1 | Colorless Oil |
| 104 | 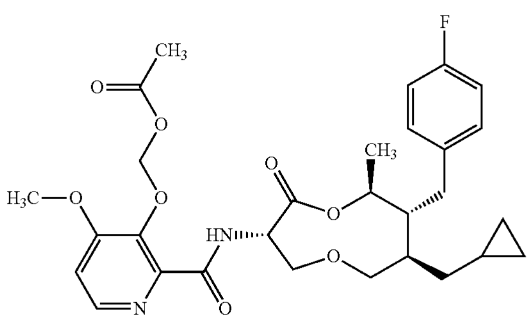 [SMILES: COc1ccnc(C(=O)N[C@H]2COC[C@H](CC3CC3)[C@@H](Cc3ccc(F)cc3)[C@H](C)OC2=O)c1OCOC(C)=O] | Example 1, Step 14 | White Foam |
| 105 | 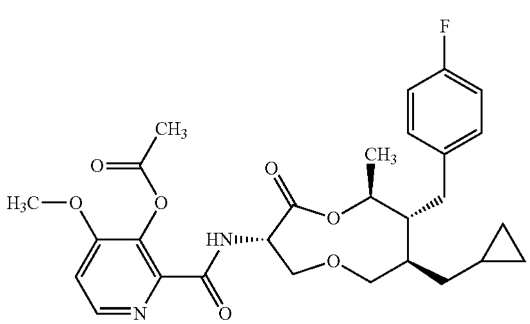 [SMILES: COc1ccnc(C(=O)N[C@H]2COC[C@H](CC3CC3)[C@@H](Cc3ccc(F)cc3)[C@H](C)OC2=O)c1OC(C)=O] | Example 9, Step 1 | Light Orange Foam |

TABLE 1-continued

Compound Structure and Appearance

| Compound Number | Structure | Prepared According to Example | Appearance |
|---|---|---|---|
| 106 | 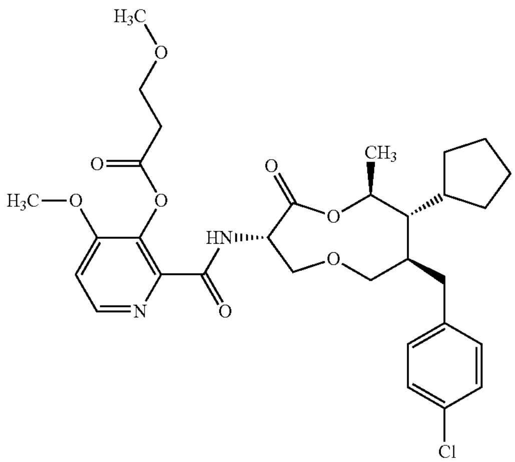 [SMILES: COCCC(=O)Oc1c(OC)ccnc1C(=O)N[C@H]1COC[C@H](Cc2ccc(Cl)cc2)[C@@H](C2CCCC2)[C@H](C)OC1=O] | Example 12, Step 1 | White Solid |
| 107 | 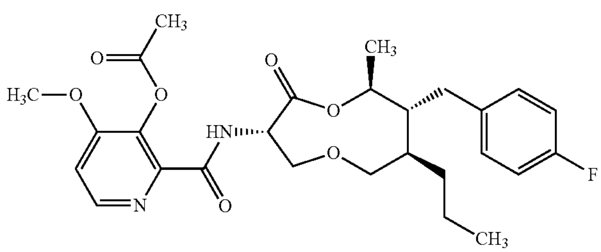 [SMILES: CCC[C@H]1COC[C@H](NC(=O)c2nccc(OC)c2OC(C)=O)C(=O)O[C@@H](C)[C@@H]1Cc1ccc(F)cc1] | Example 9, Step 1 | White Solid |
| 108 | 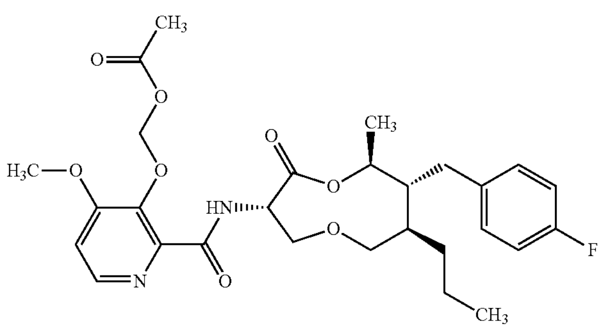 [SMILES: CCC[C@H]1COC[C@H](NC(=O)c2nccc(OC)c2OCOC(C)=O)C(=O)O[C@@H](C)[C@@H]1Cc1ccc(F)cc1] | Example 1, Step 14 | White Solid |
| 109 | 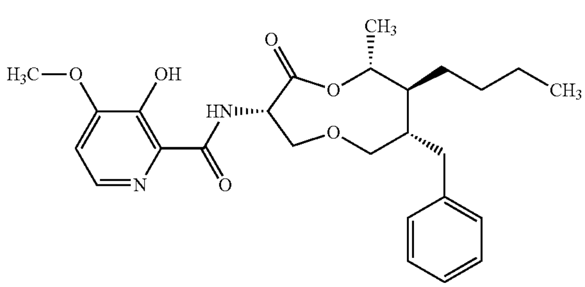 [SMILES: CCCC[C@H]1[C@H](Cc2ccccc2)COC[C@H](NC(=O)c2nccc(OC)c2O)C(=O)O[C@@H]1C] | Example 1, Step 13 | Colorless Oil |

TABLE 1-continued

Compound Structure and Appearance

| Compound Number | Structure | Prepared According to Example | Appearance |
|---|---|---|---|
| 110 | 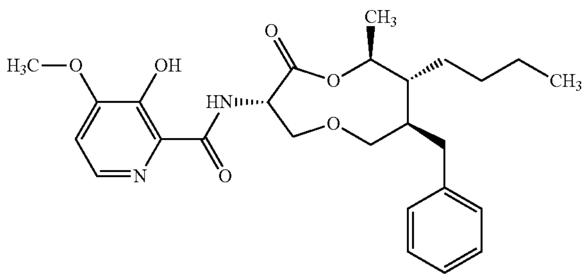 [SMILES: CCCC[C@@H]1[C@@H](Cc2ccccc2)COC[C@H](NC(=O)c2nccc(OC)c2O)C(=O)O[C@H]1C] | Example 1, Step 13 | Dark Brown Oil |
| 111 | 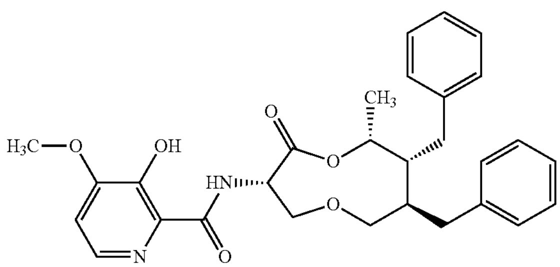 [SMILES: COc1ccnc(C(=O)N[C@H]2COC[C@H](Cc3ccccc3)[C@@H](Cc3ccccc3)[C@@H](C)OC2=O)c1O] | Example 1, Step 13 | Tacky White Solid |
| 112 | 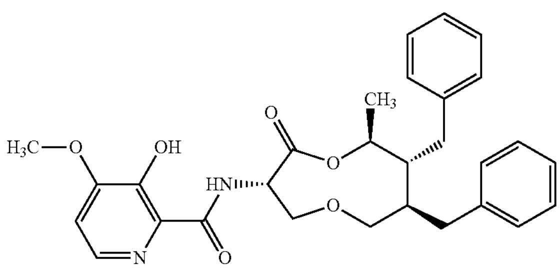 [SMILES: COc1ccnc(C(=O)N[C@H]2COC[C@H](Cc3ccccc3)[C@@H](Cc3ccccc3)[C@H](C)OC2=O)c1O] | Example 1, Step 13 | White Solid |
| 113 | 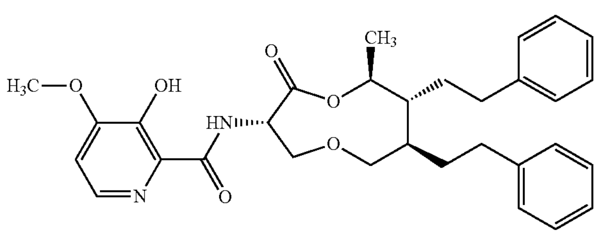 [SMILES: COc1ccnc(C(=O)N[C@H]2COC[C@H](CCc3ccccc3)[C@@H](CCc3ccccc3)[C@H](C)OC2=O)c1O] | Example 1, Step 13 | White Solid |
| 114 | 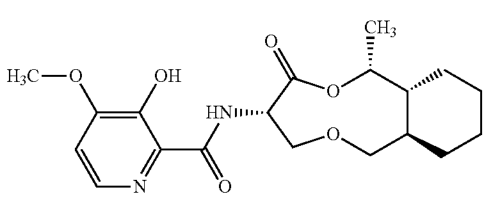 [SMILES: COc1ccnc(C(=O)N[C@H]2COC[C@@H]3CCCC[C@H]3[C@@H](C)OC2=O)c1O] | Example 1, Step 13 | Clear Oil |
| 115 | 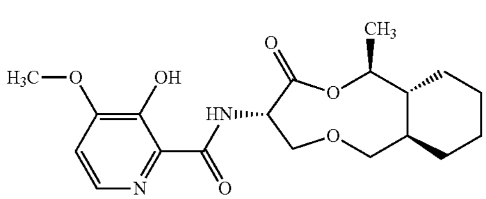 [SMILES: COc1ccnc(C(=O)N[C@H]2COC[C@@H]3CCCC[C@H]3[C@H](C)OC2=O)c1O] | Example 1, Step 13 | White Powder |

TABLE 1-continued

Compound Structure and Appearance

| Compound Number | Structure | Prepared According to Example | Appearance |
|---|---|---|---|
| 116 | 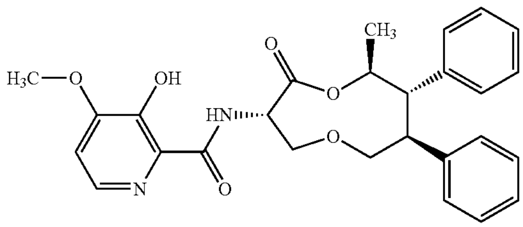 [SMILES: COc1ccnc(C(=O)N[C@H]2COC[C@H](c3ccccc3)[C@@H](c3ccccc3)[C@H](C)OC2=O)c1O] | Example 1, Step 13 | White Solid |
| 117 | 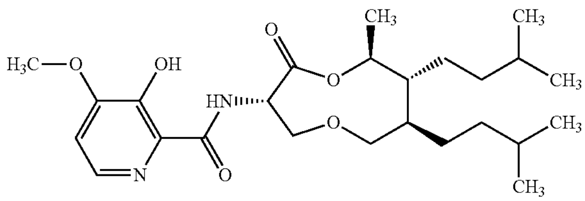 [SMILES: COc1ccnc(C(=O)N[C@H]2COC[C@H](CCC(C)C)[C@@H](CCC(C)C)[C@H](C)OC2=O)c1O] | Example 1, Step 13 | Yellow Oil |
| 118 | 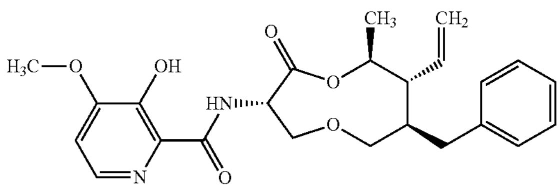 [SMILES: C=C[C@@H]1[C@@H](Cc2ccccc2)COC[C@H](NC(=O)c2nccc(OC)c2O)C(=O)O[C@H]1C] | Example 1, Step 13 | White Solid |
| 119 | 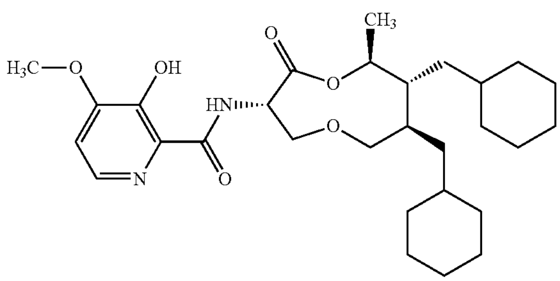 [SMILES: COc1ccnc(C(=O)N[C@H]2COC[C@H](CC3CCCCC3)[C@@H](CC3CCCCC3)[C@H](C)OC2=O)c1O] | Example 1, Step 13 | White Solid |
| 120 | 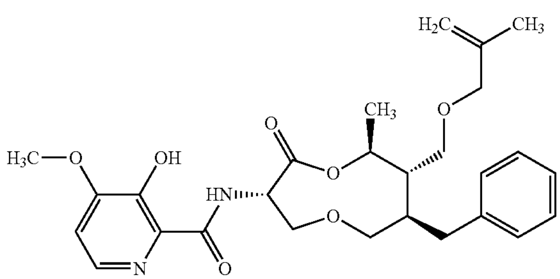 [SMILES: C=C(C)COC[C@@H]1[C@@H](Cc2ccccc2)COC[C@H](NC(=O)c2nccc(OC)c2O)C(=O)O[C@H]1C] | Example 1, Step 13 | Colorless Oil |
| 121 | 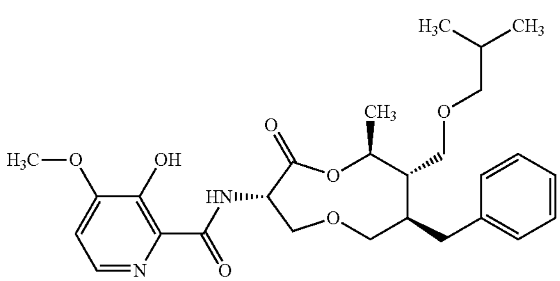 [SMILES: COc1ccnc(C(=O)N[C@H]2COC[C@H](Cc3ccccc3)[C@@H](COCC(C)C)[C@H](C)OC2=O)c1O] | Example 1, Step 13 | Colorless Oil |

TABLE 1-continued

Compound Structure and Appearance

| Compound Number | Structure | Prepared According to Example | Appearance |
|---|---|---|---|
| 122 | 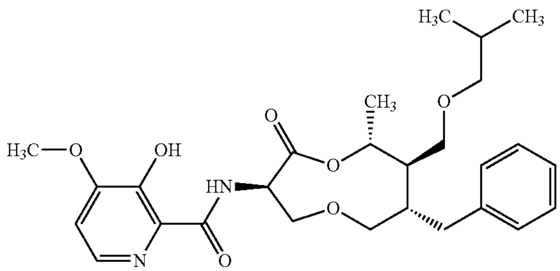 [SMILES: COc1ccnc(C(=O)N[C@@H]2COC[C@@H](Cc3ccccc3)[C@H](COCC(C)C)[C@@H](C)OC2=O)c1O] | Example 1, Step 13 | Colorless Oil |
| 123 | 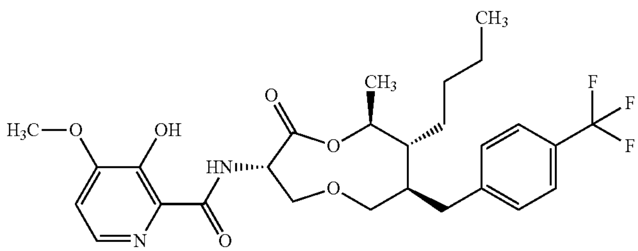 [SMILES: CCCC[C@@H]1[C@@H](Cc2ccc(C(F)(F)F)cc2)COC[C@H](NC(=O)c2nccc(OC)c2O)C(=O)O[C@H]1C] | Example 1, Step 13 | White Foam |
| 124 | 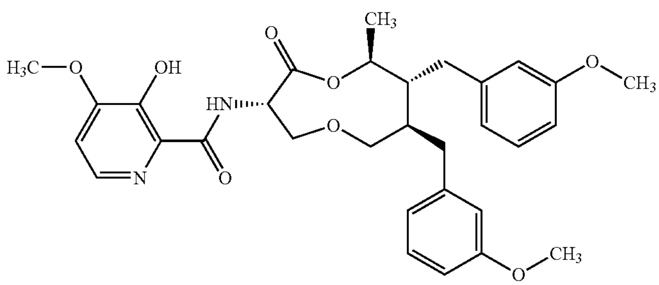 | Example 1, Step 13 | White Solid |
| 125 | 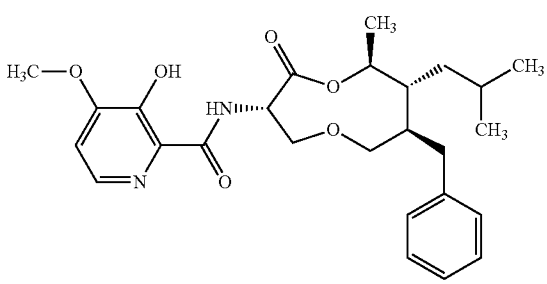 [SMILES: COc1ccnc(C(=O)N[C@H]2COC[C@H](Cc3ccccc3)[C@@H](CC(C)C)[C@H](C)OC2=O)c1O] | Example 1, Step 13 | White Foam |
| 126 | 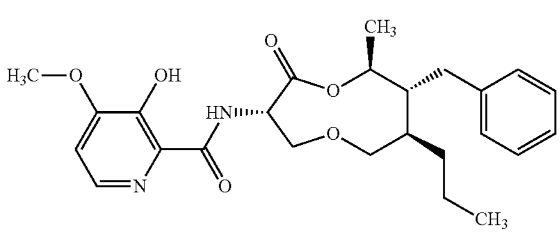 [SMILES: CCC[C@H]1COC[C@H](NC(=O)c2nccc(OC)c2O)C(=O)O[C@@H](C)[C@@H]1Cc1ccccc1] | Example 1, Step 13 | Colorless Oil |

TABLE 1-continued

Compound Structure and Appearance

| Compound Number | Structure | Prepared According to Example | Appearance |
|---|---|---|---|
| 127 | 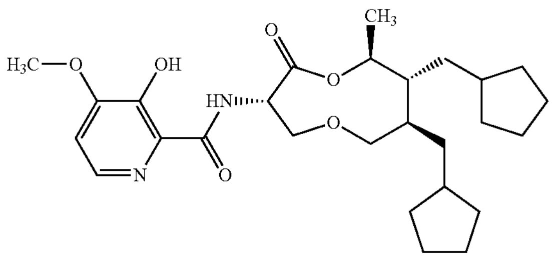 [SMILES: COc1ccnc(C(=O)N[C@H]2COC[C@H](CC3CCCC3)[C@@H](CC3CCCC3)[C@H](C)OC2=O)c1O] | Example 1, Step 13 | Colorless Oil |
| 128 | 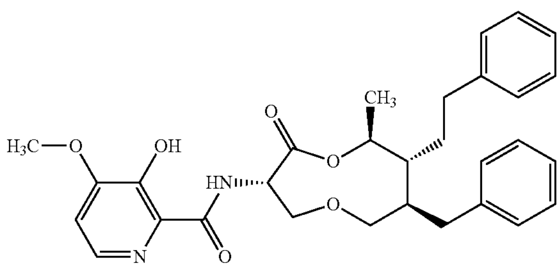 [SMILES: COc1ccnc(C(=O)N[C@H]2COC[C@H](Cc3ccccc3)[C@@H](CCc3ccccc3)[C@H](C)OC2=O)c1O] | Example 1, Step 13 | Colorless Oil |
| 129 | 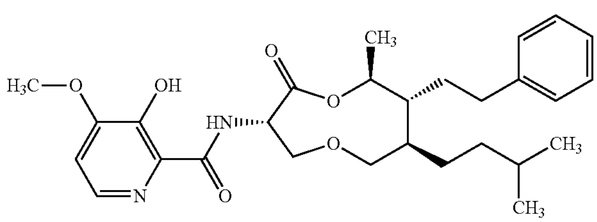 [SMILES: COc1ccnc(C(=O)N[C@H]2COC[C@H](CCC(C)C)[C@@H](CCc3ccccc3)[C@H](C)OC2=O)c1O] | Example 1, Step 13 | Colorless Foam |
| 130 | 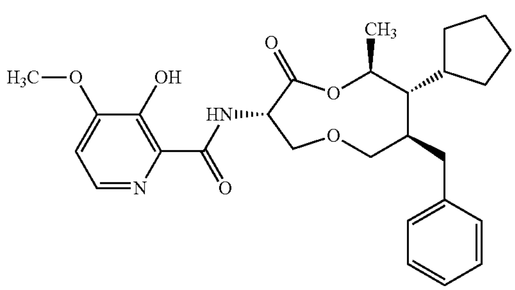 [SMILES: COc1ccnc(C(=O)N[C@H]2COC[C@H](Cc3ccccc3)[C@@H](C3CCCC3)[C@H](C)OC2=O)c1O] | Example 1, Step 13 | Colorless Foam |
| 131 | 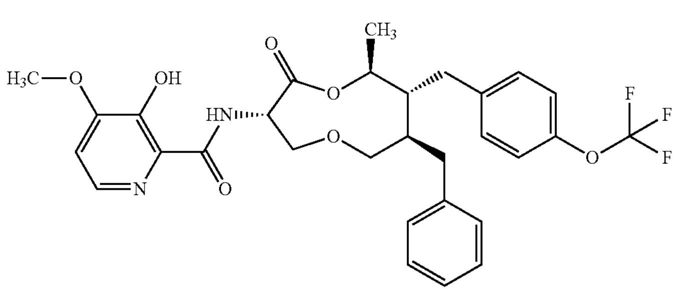 [SMILES: COc1ccnc(C(=O)N[C@H]2COC[C@H](Cc3ccccc3)[C@@H](Cc3ccc(OC(F)(F)F)cc3)[C@H](C)OC2=O)c1O] | Example 1, Step 13 | White Solid |

TABLE 1-continued

Compound Structure and Appearance

| Compound Number | Structure | Prepared According to Example | Appearance |
|---|---|---|---|
| 132 | 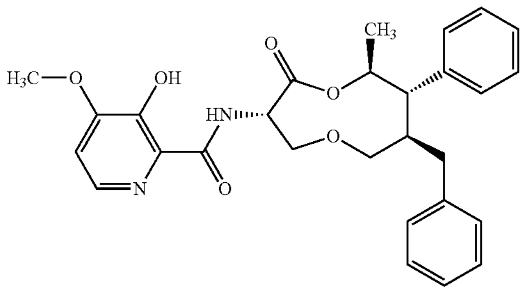 [SMILES: COc1ccnc(C(=O)N[C@H]2COC[C@H](Cc3ccccc3)[C@@H](c3ccccc3)[C@H](C)OC2=O)c1O] | Example 1, Step 13 | White Solid |
| 133 | 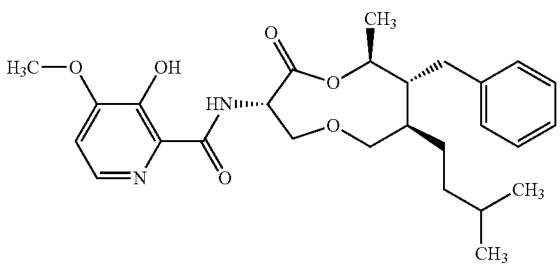 [SMILES: COc1ccnc(C(=O)N[C@H]2COC[C@H](CCC(C)C)[C@@H](Cc3ccccc3)[C@H](C)OC2=O)c1O] | Example 1, Step 13 | Pale Yellow Oil |
| 134 | 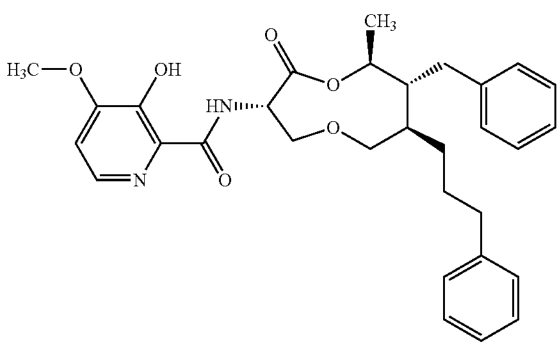 [SMILES: COc1ccnc(C(=O)N[C@H]2COC[C@H](CCCc3ccccc3)[C@@H](Cc3ccccc3)[C@H](C)OC2=O)c1O] | Example 1, Step 13 | Colorless Oil |
| 135 | 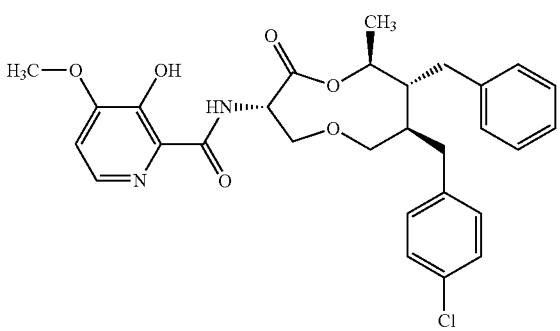 [SMILES: COc1ccnc(C(=O)N[C@H]2COC[C@H](Cc3ccc(Cl)cc3)[C@@H](Cc3ccccc3)[C@H](C)OC2=O)c1O] | Example 1, Step 13 | White Solid |

TABLE 1-continued

Compound Structure and Appearance

| Compound Number | Structure | Prepared According to Example | Appearance |
|---|---|---|---|
| 136 | 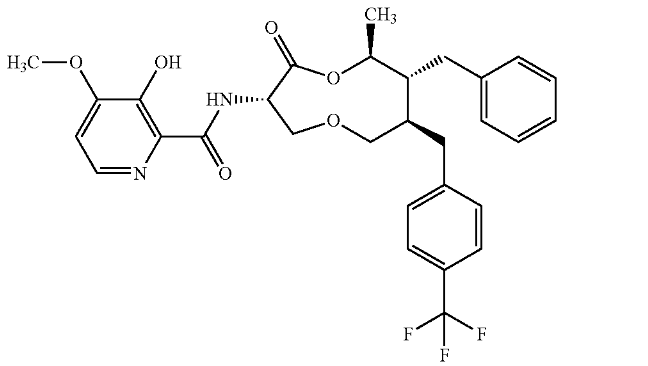 [SMILES: COc1ccnc(C(=O)N[C@H]2COC[C@H](Cc3ccc(C(F)(F)F)cc3)[C@@H](Cc3ccccc3)[C@H](C)OC2=O)c1O] | Example 1, Step 13 | Colorless Oil |
| 137 | 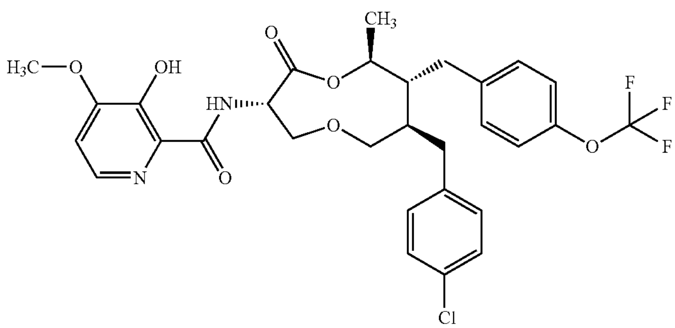 [SMILES: COc1ccnc(C(=O)N[C@H]2COC[C@H](Cc3ccc(Cl)cc3)[C@@H](Cc3ccc(OC(F)(F)F)cc3)[C@H](C)OC2=O)c1O] | Example 1, Step 13 | White Solid |
| 138 | 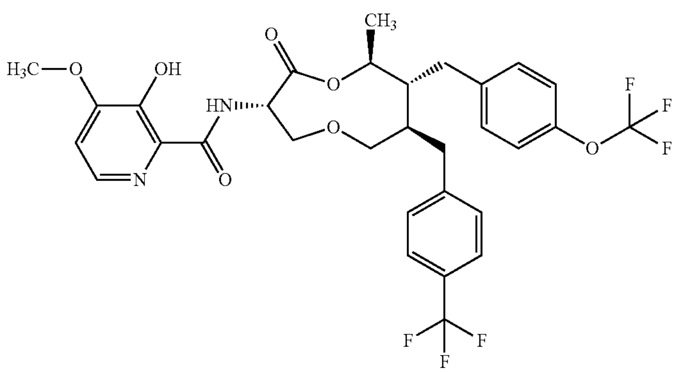 [SMILES: COc1ccnc(C(=O)N[C@H]2COC[C@H](Cc3ccc(C(F)(F)F)cc3)[C@@H](Cc3ccc(OC(F)(F)F)cc3)[C@H](C)OC2=O)c1O] | Example 1, Step 13 | Tacky White Solid |
| 139 | 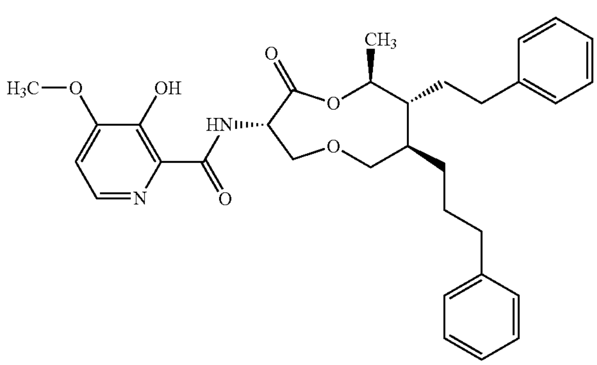 [SMILES: COc1ccnc(C(=O)N[C@H]2COC[C@H](CCCc3ccccc3)[C@@H](CCc3ccccc3)[C@H](C)OC2=O)c1O] | Example 1, Step 13 | White Solid |

TABLE 1-continued

Compound Structure and Appearance

| Compound Number | Structure | Prepared According to Example | Appearance |
|---|---|---|---|
| 140 | 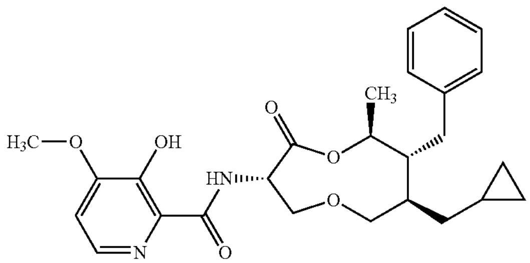 [SMILES: COc1ccnc(C(=O)N[C@H]2COC[C@H](CC3CC3)[C@@H](Cc3ccccc3)[C@H](C)OC2=O)c1O] | Example 1, Step 13 | White Solid |
| 141 | 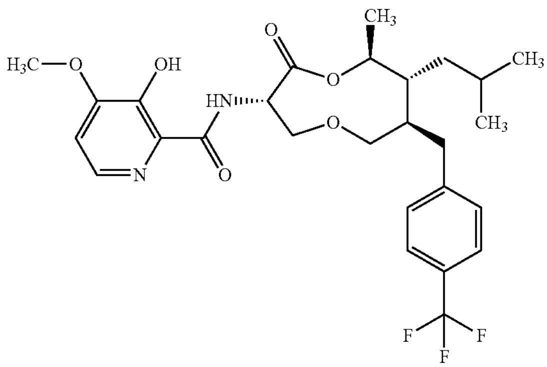 [SMILES: COc1ccnc(C(=O)N[C@H]2COC[C@H](Cc3ccc(C(F)(F)F)cc3)[C@@H](CC(C)C)[C@H](C)OC2=O)c1O] | Example 1, Step 13 | White Solid |
| 142 | 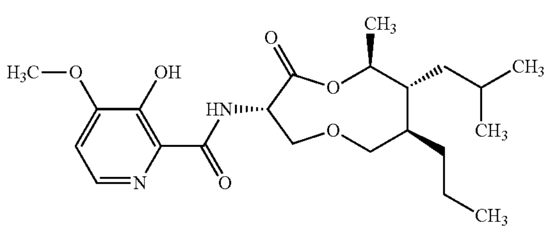 [SMILES: CCC[C@H]1COC[C@H](NC(=O)c2nccc(OC)c2O)C(=O)O[C@@H](C)[C@@H]1CC(C)C] | Example 1, Step 13 | White Powder |
| 143 | 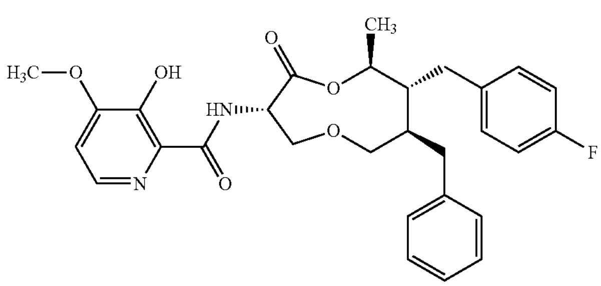 [SMILES: COc1ccnc(C(=O)N[C@H]2COC[C@H](Cc3ccccc3)[C@@H](Cc3ccc(F)cc3)[C@H](C)OC2=O)c1O] | Example 1, Step 13 | Colorless Oil |
| 144 | 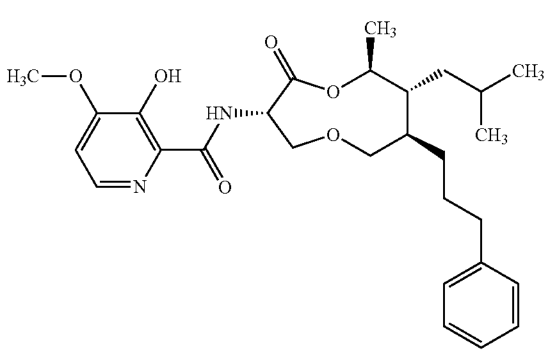 [SMILES: COc1ccnc(C(=O)N[C@H]2COC[C@H](CCCc3ccccc3)[C@@H](CC(C)C)[C@H](C)OC2=O)c1O] | Example 1, Step 13 | Colorless Oil |

TABLE 1-continued

Compound Structure and Appearance

| Compound Number | Structure | Prepared According to Example | Appearance |
|---|---|---|---|
| 145 | 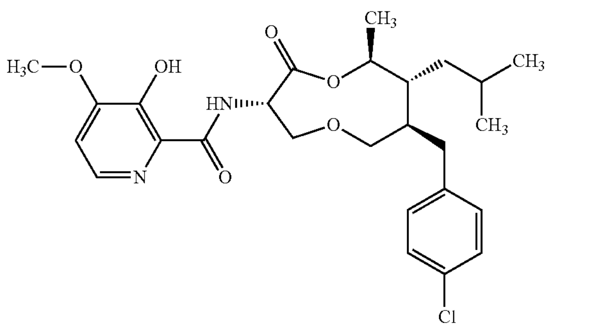 [SMILES: COc1ccnc(C(=O)N[C@H]2COC[C@H](Cc3ccc(Cl)cc3)[C@@H](CC(C)C)[C@H](C)OC2=O)c1O] | Example 1, Step 13 | Colorless Solid |
| 146 | 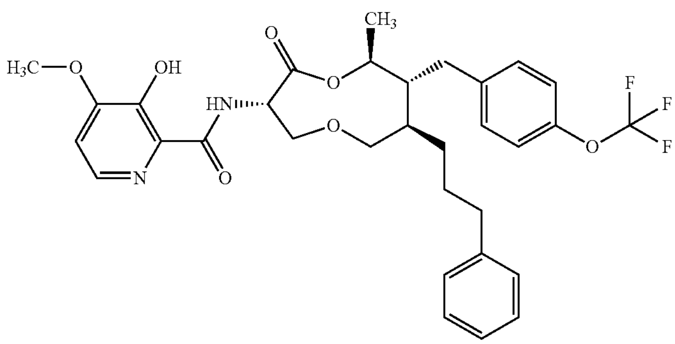 [SMILES: COc1ccnc(C(=O)N[C@H]2COC[C@H](CCCc3ccccc3)[C@@H](Cc3ccc(OC(F)(F)F)cc3)[C@H](C)OC2=O)c1O] | Example 1, Step 13 | Colorless Solid |
| 147 | 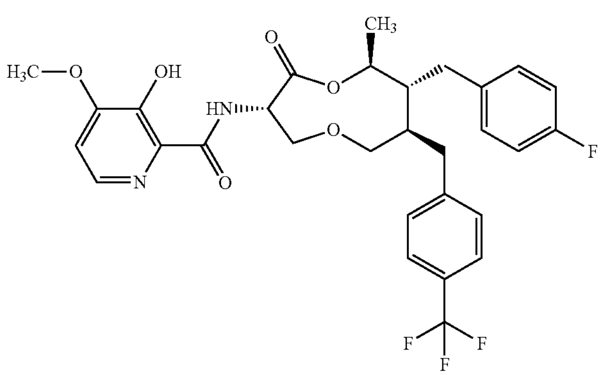 [SMILES: COc1ccnc(C(=O)N[C@H]2COC[C@H](Cc3ccc(C(F)(F)F)cc3)[C@@H](Cc3ccc(F)cc3)[C@H](C)OC2=O)c1O] | Example 1, Step 13 | White Foam |
| 148 | 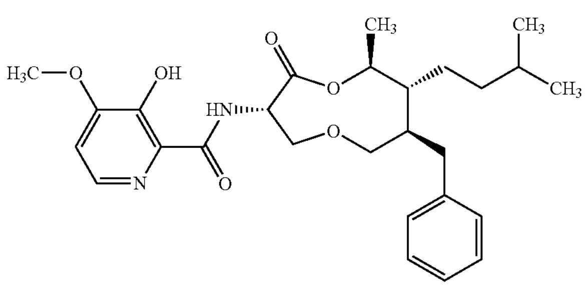 [SMILES: COc1ccnc(C(=O)N[C@H]2COC[C@H](Cc3ccccc3)[C@@H](CCC(C)C)[C@H](C)OC2=O)c1O] | Example 1, Step 13 | Colorless Oil |

TABLE 1-continued

Compound Structure and Appearance

| Compound Number | Structure | Prepared According to Example | Appearance |
|---|---|---|---|
| 149 | 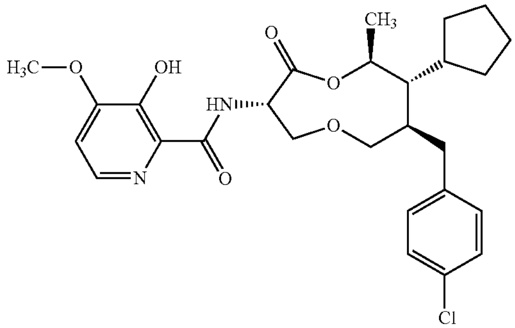 [SMILES: COc1ccnc(C(=O)N[C@H]2COC[C@H](Cc3ccc(Cl)cc3)[C@@H](C3CCCC3)[C@H](C)OC2=O)c1O] | Example 1, Step 13 | White Solid |
| 150 | 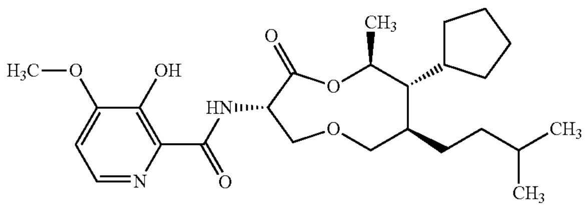 [SMILES: COc1ccnc(C(=O)N[C@H]2COC[C@H](CCC(C)C)[C@@H](C3CCCC3)[C@H](C)OC2=O)c1O] | Example 1, Step 13 | White Solid |
| 151 | 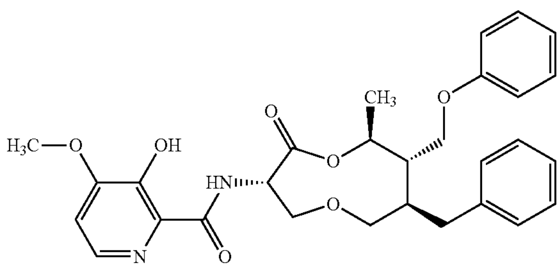 [SMILES: COc1ccnc(C(=O)N[C@H]2COC[C@H](Cc3ccccc3)[C@@H](COc3ccccc3)[C@H](C)OC2=O)c1O] | Example 1, Step 13 | White Solid |
| 152 | 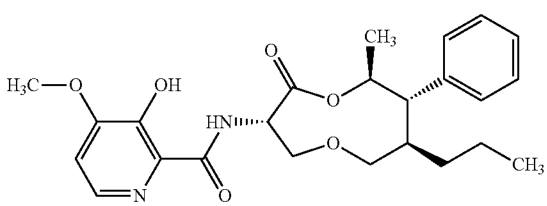 [SMILES: CCC[C@H]1COC[C@H](NC(=O)c2nccc(OC)c2O)C(=O)O[C@@H](C)[C@@H]1c1ccccc1] | Example 1, Step 13 | White Foam |
| 153 | 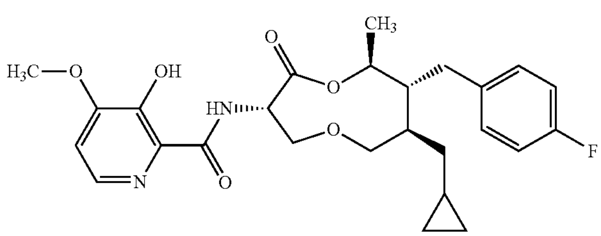 [SMILES: COc1ccnc(C(=O)N[C@H]2COC[C@H](CC3CC3)[C@@H](Cc3ccc(F)cc3)[C@H](C)OC2=O)c1O] | Example 1, Step 13 | Off White Foam |
| 154 | 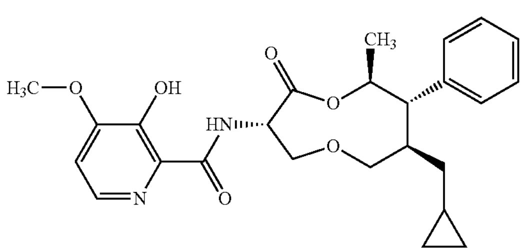 [SMILES: COc1ccnc(C(=O)N[C@H]2COC[C@H](CC3CC3)[C@@H](c3ccccc3)[C@H](C)OC2=O)c1O] | Example 1, Step 13 | Colorless Oil |

TABLE 1-continued

Compound Structure and Appearance

| Compound Number | Structure | Prepared According to Example | Appearance |
|---|---|---|---|
| 155 | 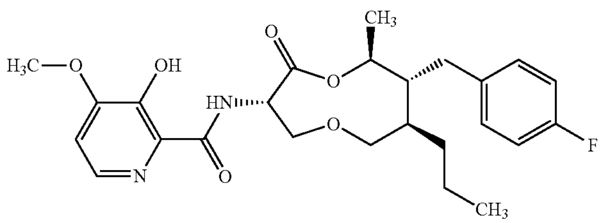 [SMILES: CCC[C@H]1COC[C@H](NC(=O)c2nccc(OC)c2O)C(=O)O[C@@H](C)[C@@H]1Cc1ccc(F)cc1] | Example 1, Step 13 | White Solid |
| 156 | 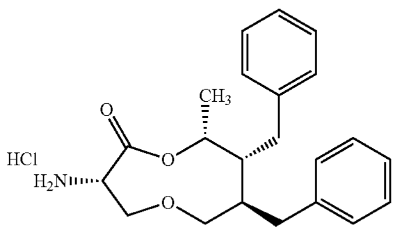 [SMILES: Cl ; C[C@H]1OC(=O)[C@@H](N)COC[C@H](Cc2ccccc2)[C@H]1Cc1ccccc1] | Example 1, Step 12a | White Solid |
| 157 | 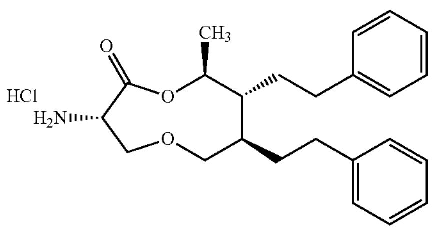 [SMILES: Cl ; C[C@@H]1OC(=O)[C@@H](N)COC[C@H](CCc2ccccc2)[C@H]1CCc1ccccc1] | Example 1, Step 12a | White Solid |
| 158 | 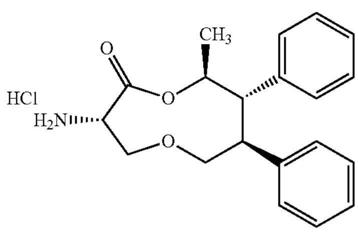 [SMILES: Cl ; C[C@@H]1OC(=O)[C@@H](N)COC[C@H](c2ccccc2)[C@H]1c1ccccc1] | Example 1, Step 12a | White Solid |
| 159 | 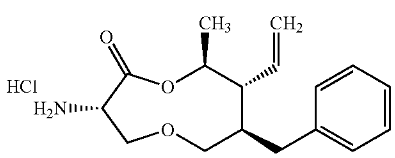 [SMILES: Cl ; C=C[C@@H]1[C@@H](Cc2ccccc2)COC[C@H](N)C(=O)O[C@H]1C] | Example 1, Step 12a | White Solid |
| 160 | 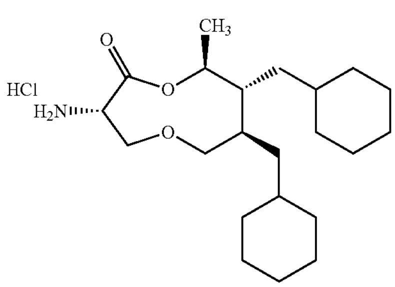 [SMILES: Cl ; C[C@@H]1OC(=O)[C@@H](N)COC[C@H](CC2CCCCC2)[C@H]1CC1CCCCC1] | Example 1, Step 12a | White Solid |

TABLE 1-continued

Compound Structure and Appearance

| Compound Number | Structure | Prepared According to Example | Appearance |
|---|---|---|---|
| 161 | 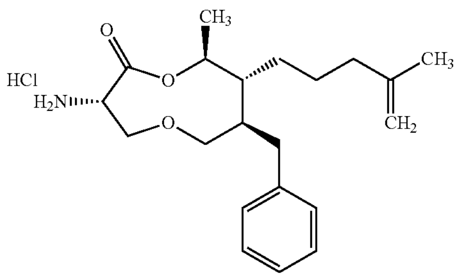 [SMILES: Cl ; C=C(C)CCC[C@@H]1[C@@H](Cc2ccccc2)COC[C@H](N)C(=O)O[C@H]1C] | Example 1, Step 12a | White Solid |
| 162 | 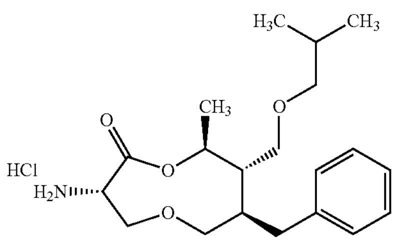 [SMILES: Cl ; CC(C)COC[C@@H]1[C@@H](Cc2ccccc2)COC[C@H](N)C(=O)O[C@H]1C] | Example 1, Step 12a | White Solid |
| 163 | 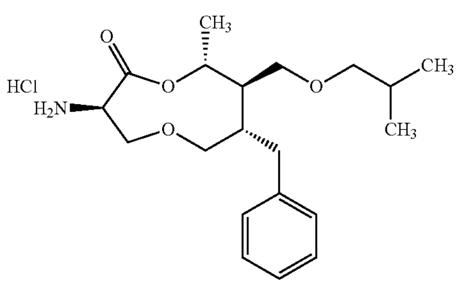 [SMILES: Cl ; CC(C)COC[C@H]1[C@H](Cc2ccccc2)COC[C@@H](N)C(=O)O[C@@H]1C] | Example 1, Step 12a | Tacky Brown Solid |
| 164 | 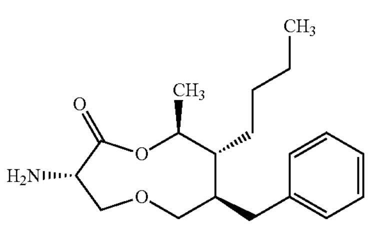 [SMILES: CCCC[C@@H]1[C@@H](Cc2ccccc2)COC[C@H](N)C(=O)O[C@H]1C] | Example 1, Step 12b | Light Yellow Oil |
| 165 | 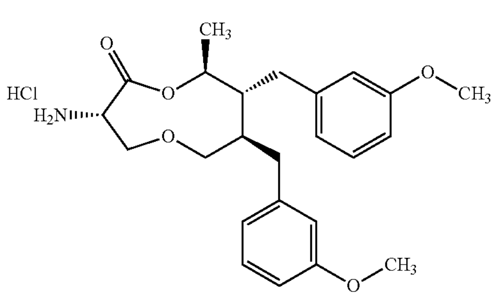 [SMILES: Cl ; COc1cccc(C[C@H]2COC[C@H](N)C(=O)O[C@@H](C)[C@@H]2Cc2cccc(OC)c2)c1] | Example 1, Step 12a | White Solid |

TABLE 1-continued

Compound Structure and Appearance

| Compound Number | Structure | Prepared According to Example | Appearance |
|---|---|---|---|
| 166 | 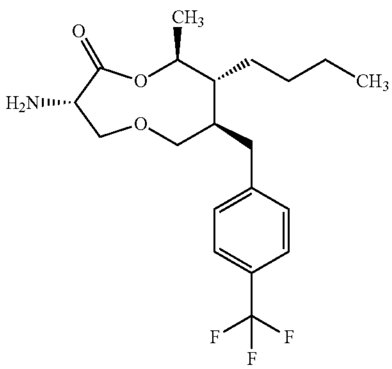 [SMILES: CCCC[C@@H]1[C@@H](Cc2ccc(C(F)(F)F)cc2)COC[C@H](N)C(=O)O[C@H]1C] | Example 1, Step 12b | White Solid |
| 167 | 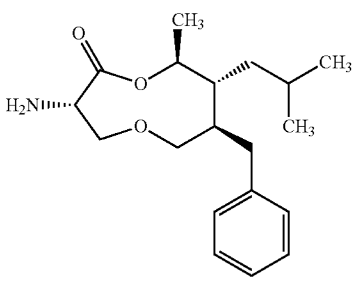 [SMILES: CC(C)C[C@@H]1[C@@H](Cc2ccccc2)COC[C@H](N)C(=O)O[C@H]1C] | Example 1, Step 12b | Colorless Oil |
| 168 | 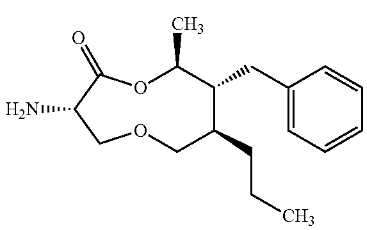 [SMILES: CCC[C@H]1COC[C@H](N)C(=O)O[C@@H](C)[C@@H]1Cc1ccccc1] | Example 1, Step 12b | Colorless Oil |
| 169 | 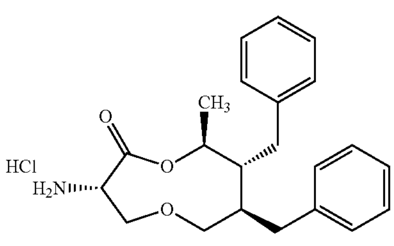 [SMILES: Cl ; C[C@@H]1OC(=O)[C@@H](N)COC[C@H](Cc2ccccc2)[C@H]1Cc1ccccc1] | Example 1, Step 12a | White Solid |
| 170 | 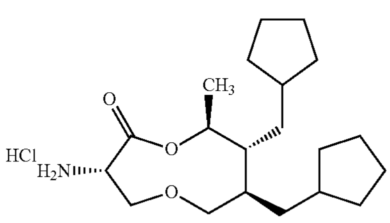 [SMILES: Cl ; C[C@@H]1OC(=O)[C@@H](N)COC[C@H](CC2CCCC2)[C@H]1CC1CCCC1] | Example 1, Step 12a | White Solid |

TABLE 1-continued

Compound Structure and Appearance

| Compound Number | Structure | Prepared According to Example | Appearance |
|---|---|---|---|
| 171 | 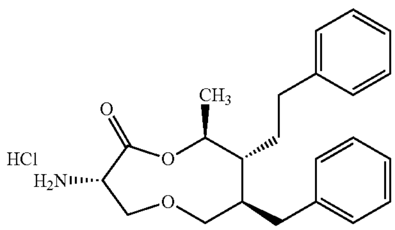 | Example 1, Step 12a | White Foam |
| 172 | 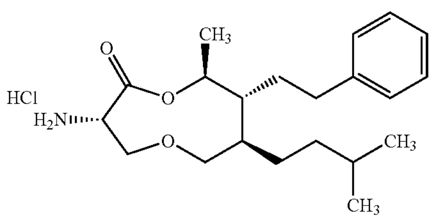 [SMILES: Cl ; CC(C)CC[C@H]1COC[C@H](N)C(=O)O[C@@H](C)[C@@H]1CCc1ccccc1] | Example 1, Step 12a | White Foam |
| 173 | 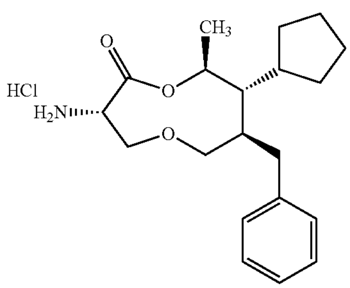 [SMILES: Cl ; C[C@@H]1OC(=O)[C@@H](N)COC[C@H](Cc2ccccc2)[C@H]1C1CCCC1] | Example 1, Step 12a | White Foam |
| 174 | 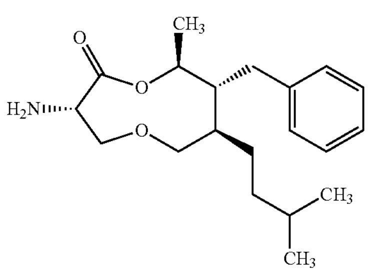 [SMILES: CC(C)CC[C@H]1COC[C@H](N)C(=O)O[C@@H](C)[C@@H]1Cc1ccccc1] | Example 1, Step 12b | Colorless Oil |
| 175 | 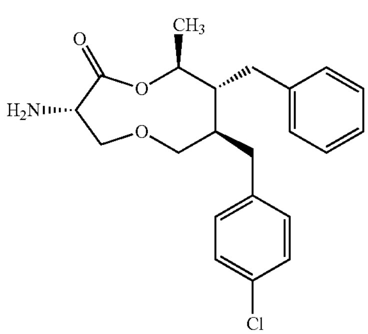 [SMILES: C[C@@H]1OC(=O)[C@@H](N)COC[C@H](Cc2ccc(Cl)cc2)[C@H]1Cc1ccccc1] | Example 1, Step 12c | Pale Yellow Oil |

TABLE 1-continued

| Compound Number | Structure | Prepared According to Example | Appearance |
|---|---|---|---|
| 176 | 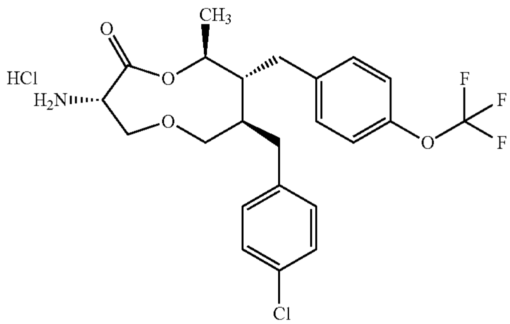 [SMILES: Cl ; C[C@@H]1OC(=O)[C@@H](N)COC[C@H](Cc2ccc(Cl)cc2)[C@H]1Cc1ccc(OC(F)(F)F)cc1] | Example 1, Step 12a | White Solid |
| 177 | 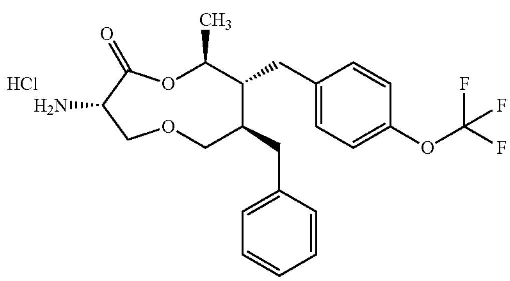 [SMILES: Cl ; C[C@@H]1OC(=O)[C@@H](N)COC[C@H](Cc2ccccc2)[C@H]1Cc1ccc(OC(F)(F)F)cc1] | Example 1, Step 12a | White Solid |
| 178 | 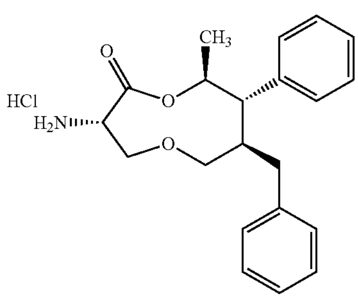 [SMILES: Cl ; C[C@@H]1OC(=O)[C@@H](N)COC[C@H](Cc2ccccc2)[C@H]1c1ccccc1] | Example 1, Step 12a | White Solid |
| 179 | 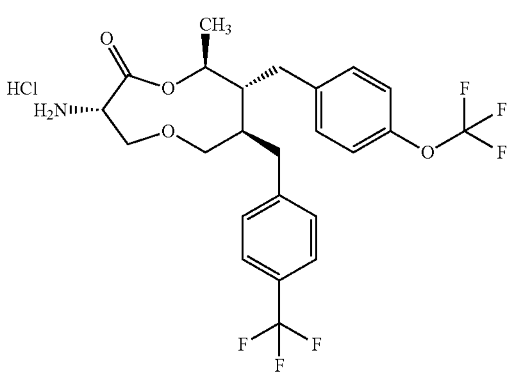 [SMILES: Cl ; C[C@@H]1OC(=O)[C@@H](N)COC[C@H](Cc2ccc(C(F)(F)F)cc2)[C@H]1Cc1ccc(OC(F)(F)F)cc1] | Example 1, Step 12a | White Solid |

TABLE 1-continued
Compound Structure and Appearance
| Compound Number | Structure | Prepared According to Example | Appearance |
|---|---|---|---|
| 180 | 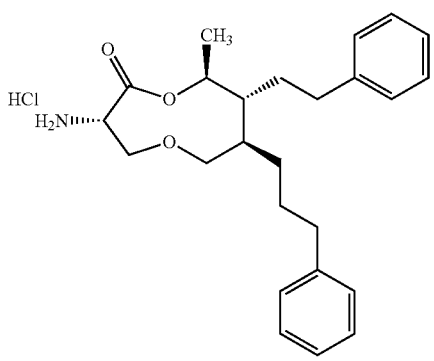 [SMILES: Cl ; C[C@@H]1OC(=O)[C@@H](N)COC[C@H](CCCc2ccccc2)[C@H]1CCc1ccccc1] | Example 1, Step 12a | White Solid |
| 181 | 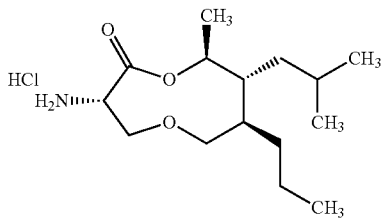 [SMILES: Cl ; CCC[C@H]1COC[C@H](N)C(=O)O[C@@H](C)[C@@H]1CC(C)C] | Example 1, Step 12a | Yellow Foam |
| 182 | 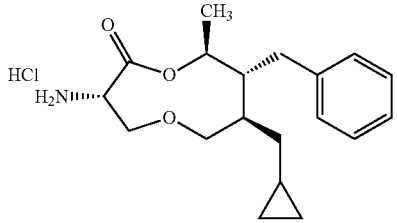 [SMILES: Cl ; C[C@@H]1OC(=O)[C@@H](N)COC[C@H](CC2CC2)[C@H]1Cc1ccccc1] | Example 1, Step 12a | White Solid |
| 183 | 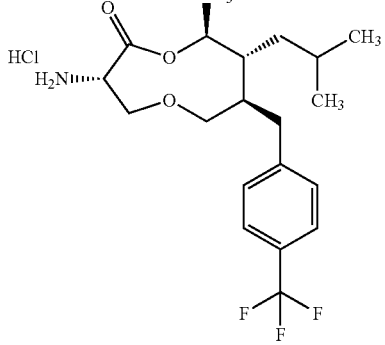 | Example 1, Step 12a | White Solid |
| 184 | 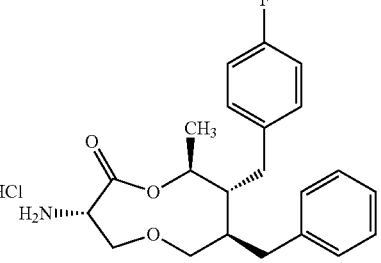 | Example 1, Step 12a | Colorless Gel |

TABLE 1-continued

Compound Structure and Appearance

| Compound Number | Structure | Prepared According to Example | Appearance |
|---|---|---|---|
| 185 | 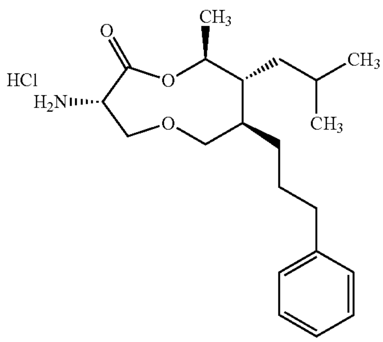 [SMILES: Cl ; CC(C)C[C@@H]1[C@@H](CCCc2ccccc2)COC[C@H](N)C(=O)O[C@H]1C] | Example 1, Step 12a | White Solid |
| 186 | 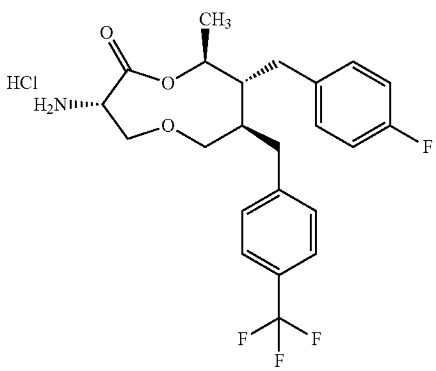 [SMILES: Cl ; C[C@@H]1OC(=O)[C@@H](N)COC[C@H](Cc2ccc(C(F)(F)F)cc2)[C@H]1Cc1ccc(F)cc1] | Example 1, Step 12a | Off White Powder |
| 187 | 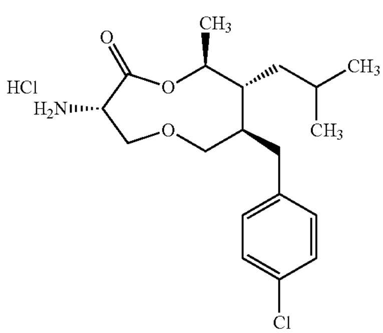 [SMILES: Cl ; CC(C)C[C@@H]1[C@@H](Cc2ccc(Cl)cc2)COC[C@H](N)C(=O)O[C@H]1C] | Example 1, Step 12a | White Solid |
| 188 | 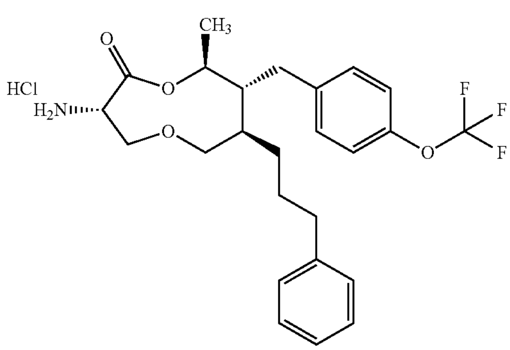 [SMILES: Cl ; C[C@@H]1OC(=O)[C@@H](N)COC[C@H](CCCc2ccccc2)[C@H]1Cc1ccc(OC(F)(F)F)cc1] | Example 1, Step 12a | White Solid |

TABLE 1-continued

Compound Structure and Appearance

| Compound Number | Structure | Prepared According to Example | Appearance |
|---|---|---|---|
| 189 | 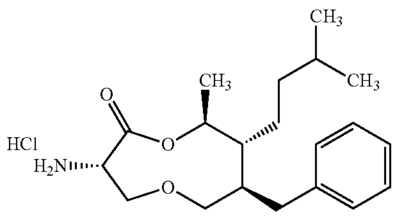 [SMILES: Cl ; CC(C)CC[C@@H]1[C@@H](Cc2ccccc2)COC[C@H](N)C(=O)O[C@H]1C] | Example 1, Step 12a | White Solid |
| 190 | 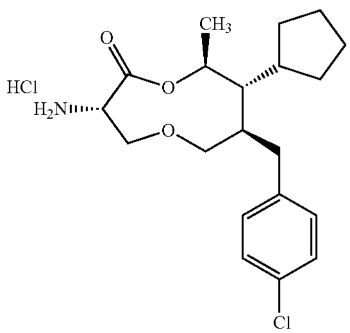 [SMILES: Cl ; C[C@@H]1OC(=O)[C@@H](N)COC[C@H](Cc2ccc(Cl)cc2)[C@H]1C1CCCC1] | Example 1, Step 12a | White Solid |
| 191 | 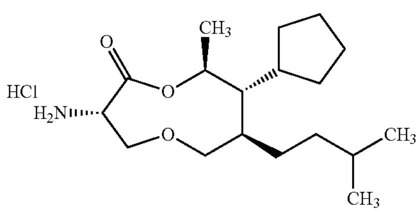 [SMILES: Cl ; CC(C)CC[C@H]1COC[C@H](N)C(=O)O[C@@H](C)[C@@H]1C1CCCC1] | Example 1, Step 12a | White Solid |
| 192 | 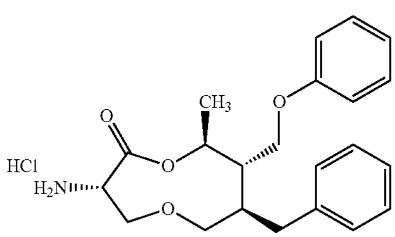 [SMILES: Cl ; C[C@@H]1OC(=O)[C@@H](N)COC[C@H](Cc2ccccc2)[C@H]1COc1ccccc1] | Example 1, Step 12a | White Solid |
| 193 | 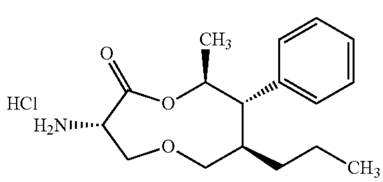 | Example 1, Step 12a | Off White Solid |
| 194 | 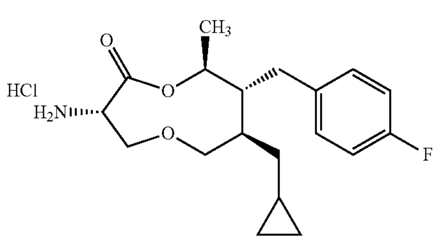 [SMILES: Cl ; C[C@@H]1OC(=O)[C@@H](N)COC[C@H](CC2CC2)[C@H]1Cc1ccc(F)cc1] | Example 1, Step 12a | White Powder |

TABLE 1-continued
Compound Structure and Appearance
| Compound Number | Structure | Prepared According to Example | Appearance |
|---|---|---|---|
| 195 | 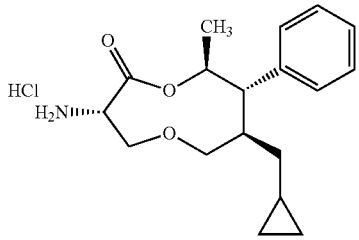 [SMILES: Cl ; C[C@@H]1OC(=O)[C@@H](N)COC[C@H](CC2CC2)[C@H]1c1ccccc1] | Example 1, Step 12a | White Solid |
| 196 | 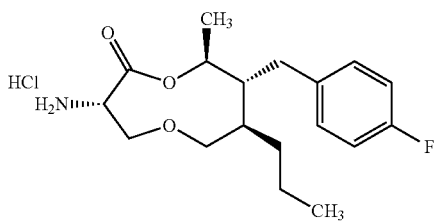 | Example 1, Step 12a | White Solid |
| 197 | 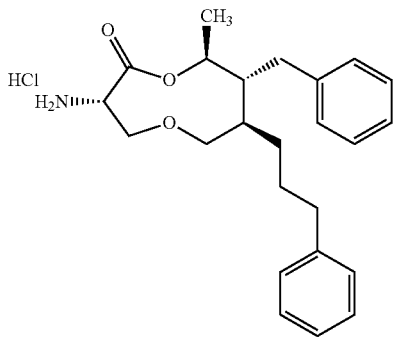 [SMILES: Cl ; C[C@@H]1OC(=O)[C@@H](N)COC[C@H](CCCc2ccccc2)[C@H]1Cc1ccccc1] | Example 1, Step 12a | Colorless Oil |
| 198 | 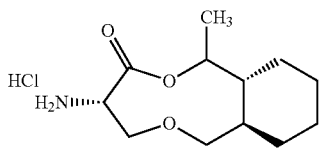 [SMILES: Cl ; CC1OC(=O)[C@@H](N)COC[C@@H]2CCCC[C@@H]12] | Example 1, Step 12a | Off White Powder |
| 199 | 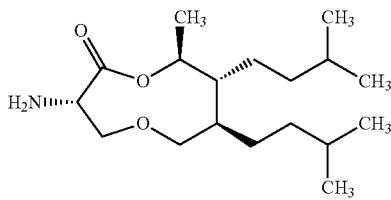 | Example 1, Step 12b | Colorless Oil |
| 200 | 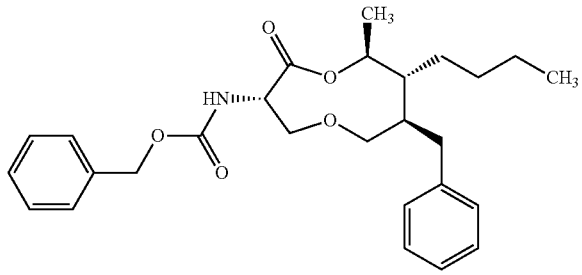 [SMILES: CCCC[C@@H]1[C@@H](Cc2ccccc2)COC[C@H](NC(=O)OCc2ccccc2)C(=O)O[C@H]1C] | Example 8, Steps 1, 2; Example 2, Step 6; Example 1, Steps 5b, 10, 11 | Colorless Oil |

TABLE 1-continued

Compound Structure and Appearance

| Compound Number | Structure | Prepared According to Example | Appearance |
|---|---|---|---|
| 201 | 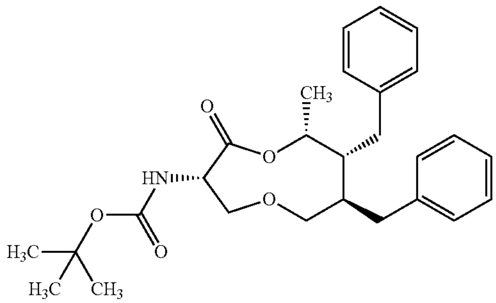 [SMILES: C[C@H]1OC(=O)[C@@H](NC(=O)OC(C)(C)C)COC[C@H](Cc2ccccc2)[C@H]1Cc1ccccc1] | Example 1, Steps 1, 2, 3, 4, 5a, 6, 7, 10, 11 | Colorless Oil |
| 202 | 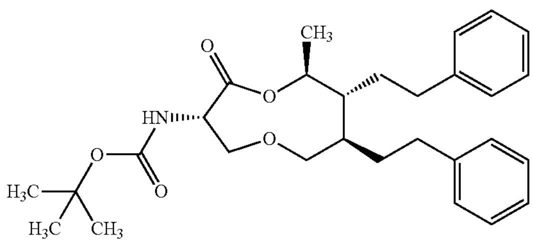 [SMILES: C[C@@H]1OC(=O)[C@@H](NC(=O)OC(C)(C)C)COC[C@H](CCc2ccccc2)[C@H]1CCc1ccccc1] | Example 1, Steps 1, 2, 3, 4, 5a, 6, 7, 8, 9a, 10, 11 | Colorless Oil |
| 203 | 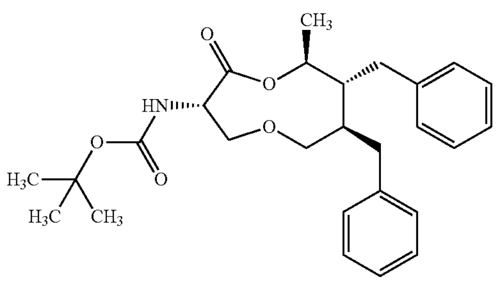 [SMILES: C[C@@H]1OC(=O)[C@@H](NC(=O)OC(C)(C)C)COC[C@H](Cc2ccccc2)[C@H]1Cc1ccccc1] | Example 1, Steps 1, 2, 3, 4, 5a, 6, 7, 8, 9a, 10, 11 | White Solid |
| 204 | 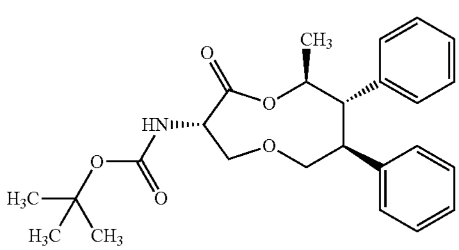 [SMILES: C[C@@H]1OC(=O)[C@@H](NC(=O)OC(C)(C)C)COC[C@H](c2ccccc2)[C@H]1c1ccccc1] | Example 1, Steps 1, 2, 3, 4, 5a, 6, 7, 8, 9a, 10, 11 | White Solid |
| 205 | 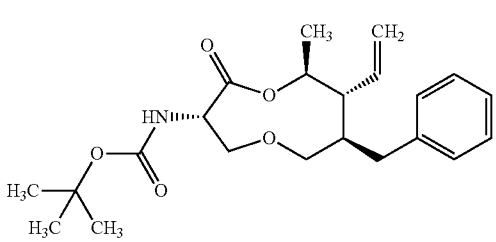 [SMILES: C=C[C@@H]1[C@@H](Cc2ccccc2)COC[C@H](NC(=O)OC(C)(C)C)C(=O)O[C@H]1C] | Example 2, Steps 1, 2, 3, 4, 5, 6; Example 1, Steps 5a, 10, 11 | White Solid |

TABLE 1-continued

Compound Structure and Appearance

| Compound Number | Structure | Prepared According to Example | Appearance |
|---|---|---|---|
| 206 | 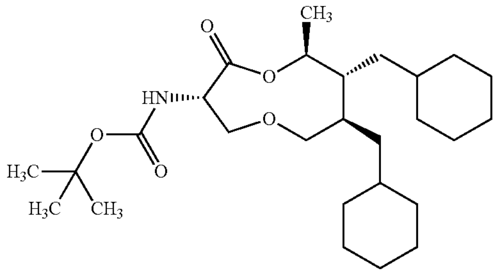 [SMILES: C[C@@H]1OC(=O)[C@@H](NC(=O)OC(C)(C)C)COC[C@H](CC2CCCCC2)[C@H]1CC1CCCCC1] | Example 1, Steps 1, 2, 3, 4, 5a, 6, 7, 8, 9, 10, 11 | White Solid |
| 207 | 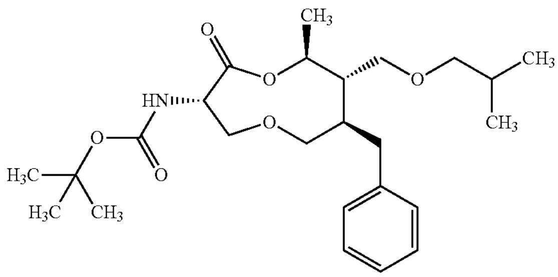 [SMILES: CC(C)COC[C@@H]1[C@@H](Cc2ccccc2)COC[C@H](NC(=O)OC(C)(C)C)C(=O)O[C@H]1C] | Example 2, Steps 1, 2, 3, 4, 5; Example 3, Step 1; Example 4, Step 1; Example 2, Step 6; Example 1, Steps 5a, 10, 11; Example 5, Step 1 | Colorless Oil |
| 208 | 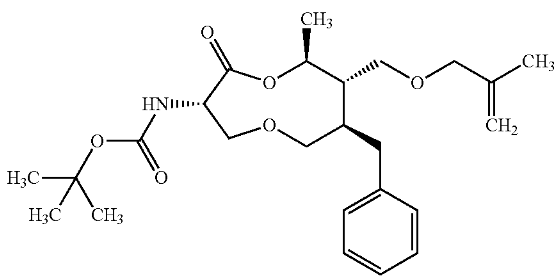 [SMILES: C=C(C)COC[C@@H]1[C@@H](Cc2ccccc2)COC[C@H](NC(=O)OC(C)(C)C)C(=O)O[C@H]1C] | Example 2, Steps 1, 2, 3, 4, 5; Example 3, Step 1; Example 4, Step 1; Example 2, Step 6; Example 1, Steps 5a, 10, 11 | White Solid |
| 209 | 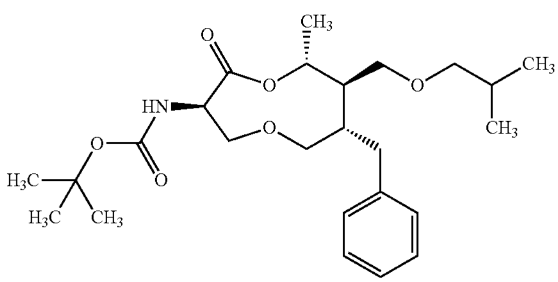 [SMILES: CC(C)COC[C@H]1[C@H](Cc2ccccc2)COC[C@@H](NC(=O)OC(C)(C)C)C(=O)O[C@@H]1C] | Example 2, Steps 1, 2, 3, 4, 5; Example 3, Step 1; Example 4, Step 1; Example 2, Step 6; Example 1, Steps 5a, 10, 11; Example 5, Step 1 | Colorless Oil |
| 210 | 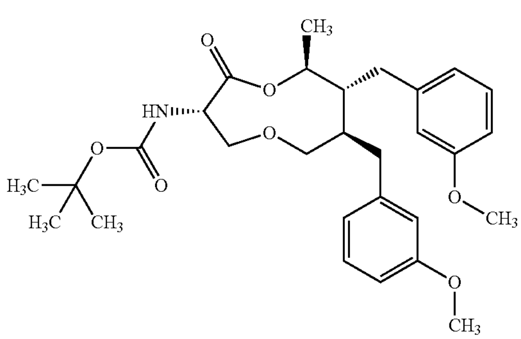 [SMILES: COc1cccc(C[C@H]2COC[C@H](NC(=O)OC(C)(C)C)C(=O)O[C@@H](C)[C@@H]2Cc2cccc(OC)c2)c1] | Example 1, Steps 1, 2, 3, 4, 5a, 6, 7, 8, 9, 10, 11 | Colorless Oil |

TABLE 1-continued

Compound Structure and Appearance

| Compound Number | Structure | Prepared According to Example | Appearance |
|---|---|---|---|
| 211 | 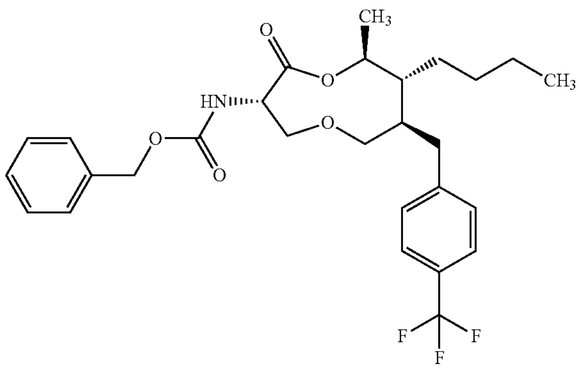 [SMILES: CCCC[C@@H]1[C@@H](Cc2ccc(C(F)(F)F)cc2)COC[C@H](NC(=O)OCc2ccccc2)C(=O)O[C@H]1C] | Example 8, Steps 1, 2; Example 2, Step 6; Steps 5b, 10, 11 | Colorless Oil |
| 212 | 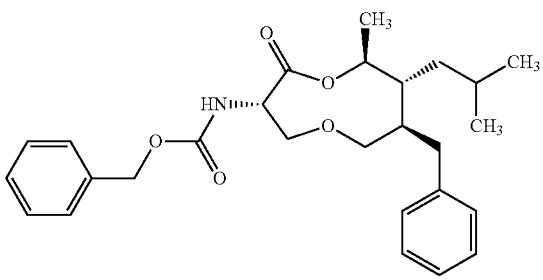 [SMILES: CC(C)C[C@@H]1[C@@H](Cc2ccccc2)COC[C@H](NC(=O)OCc2ccccc2)C(=O)O[C@H]1C] | Example 8, Steps 1, 2; Example 2, Step 6; Example 1, Steps 5b, 10, 11 | Colorless Oil |
| 213 | 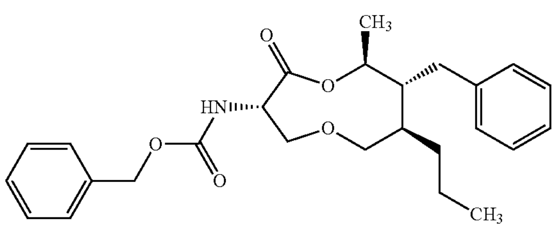 [SMILES: CCC[C@H]1COC[C@H](NC(=O)OCc2ccccc2)C(=O)O[C@@H](C)[C@@H]1Cc1ccccc1] | Example 8, Steps 1, 2; Example 2, Step 6; Example 1, Steps 5b, 10, 11 | Colorless Oil |
| 214 | 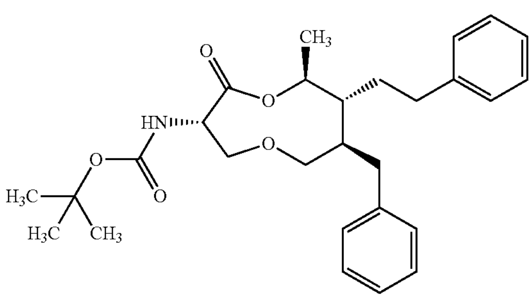 [SMILES: C[C@@H]1OC(=O)[C@@H](NC(=O)OC(C)(C)C)COC[C@H](Cc2ccccc2)[C@H]1CCc1ccccc1] | Example 8, Steps 1, 2; Example 2, Step 6; Example 1, Steps 5a, 10, 11 | Colorless Gel |
| 215 | 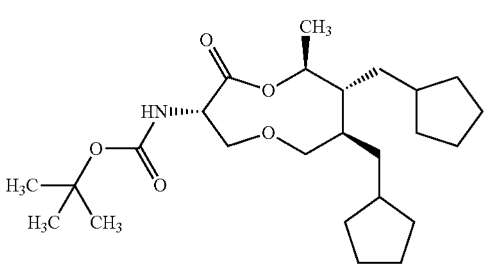 [SMILES: C[C@@H]1OC(=O)[C@@H](NC(=O)OC(C)(C)C)COC[C@H](CC2CCCC2)[C@H]1CC1CCCC1] | Example 1, Steps 1, 2, 3, 4, 5a, 6, 7, 8, 9, 10, 11 | Colorless Oil |

TABLE 1-continued

Compound Structure and Appearance

| Compound Number | Structure | Prepared According to Example | Appearance |
|---|---|---|---|
| 216 | 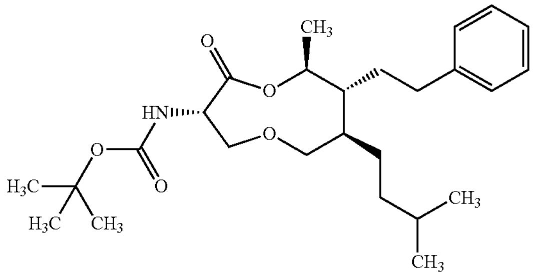 [SMILES: CC(C)CC[C@H]1COC[C@H](NC(=O)OC(C)(C)C)C(=O)O[C@@H](C)[C@@H]1CCc1ccccc1] | Example 8, Steps 1, 2; Example 2, Step 6; Example 1, Steps 5a, 10, 11 | Colorless Oil |
| 217 | 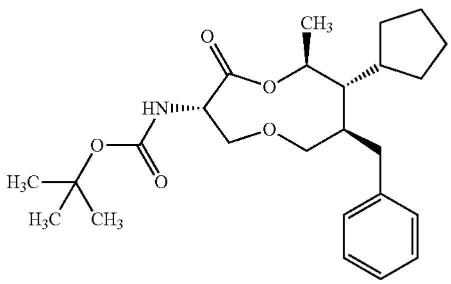 [SMILES: C[C@@H]1OC(=O)[C@@H](NC(=O)OC(C)(C)C)COC[C@H](Cc2ccccc2)[C@H]1C1CCCC1] | Example 8, Steps 1, 2; Example 2, Step 6; Example 1, Steps 5a, 10, 11 | Colorless Oil |
| 218 | 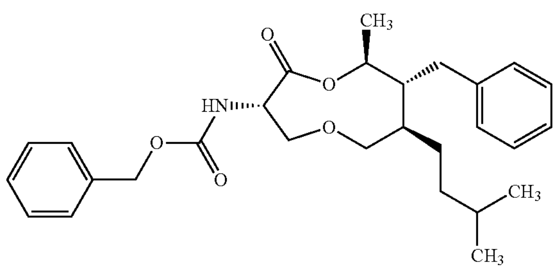 [SMILES: CC(C)CC[C@H]1COC[C@H](NC(=O)OCc2ccccc2)C(=O)O[C@@H](C)[C@@H]1Cc1ccccc1] | Example 8, Steps 1, 2; Example 2, Step 6; Example 1, Steps 5b, 10, 11 | Pale Yellow Oil |
| 219 | 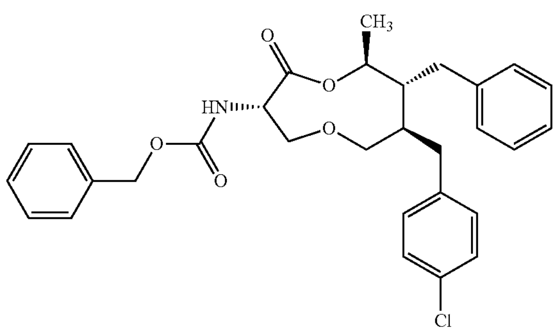 [SMILES: C[C@@H]1OC(=O)[C@@H](NC(=O)OCc2ccccc2)COC[C@H](Cc2ccc(Cl)cc2)[C@H]1Cc1ccccc1] | Example 8, Steps 1, 2; Example 2, Step 6; Example 1, Steps 5b, 10, 11 | Pale Yellow Oil |
| 220 | 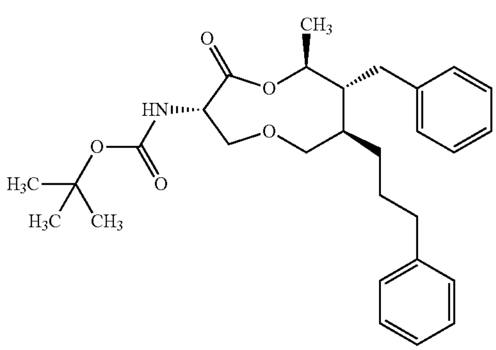 [SMILES: C[C@@H]1OC(=O)[C@@H](NC(=O)OC(C)(C)C)COC[C@H](CCCc2ccccc2)[C@H]1Cc1ccccc1] | Example 8, Steps 1, 2; Example 2, Step 6; Example 1, Steps 5a, 10, 11 | Colorless Oil |

TABLE 1-continued

Compound Structure and Appearance

| Compound Number | Structure | Prepared According to Example | Appearance |
|---|---|---|---|
| 221 | 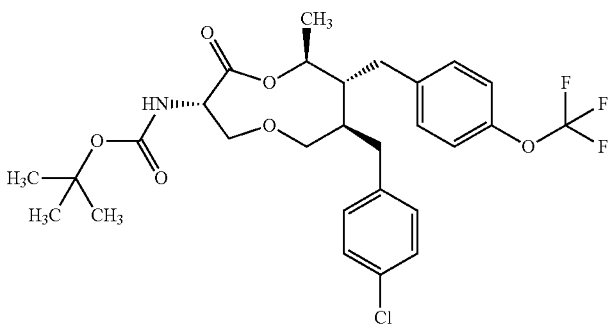 [SMILES: C[C@@H]1OC(=O)[C@@H](NC(=O)OC(C)(C)C)COC[C@H](Cc2ccc(Cl)cc2)[C@H]1Cc1ccc(OC(F)(F)F)cc1] | Example 8, Steps 1, 2; Example 2, Step 6; Example 1 Steps 5a, 10, 11 | Colorless Oil |
| 222 | 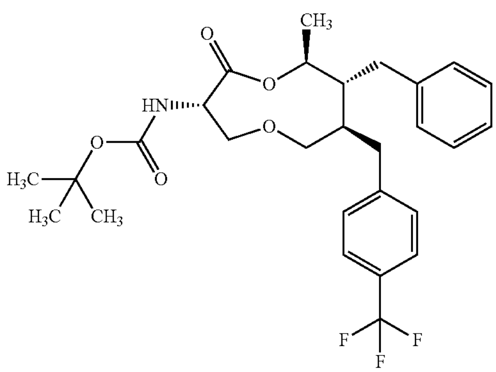 [SMILES: C[C@@H]1OC(=O)[C@@H](NC(=O)OC(C)(C)C)COC[C@H](Cc2ccc(C(F)(F)F)cc2)[C@H]1Cc1ccccc1] | Example 8, Steps 1, 2; Example 2, Step 6; Example 1, Steps 5a, 10, 11 | Colorless Oil |
| 223 | 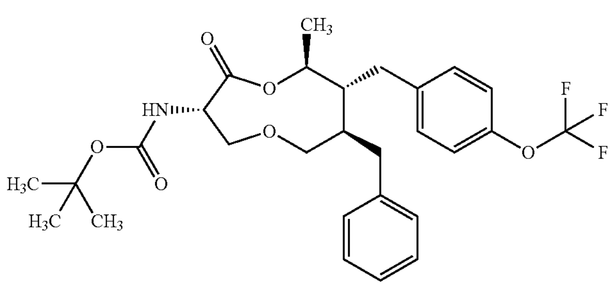 [SMILES: C[C@@H]1OC(=O)[C@@H](NC(=O)OC(C)(C)C)COC[C@H](Cc2ccccc2)[C@H]1Cc1ccc(OC(F)(F)F)cc1] | Example 8 Steps 1, 2; Example 2 Step 6; Example 1 Steps 5a, 10, 11 | White Solid |
| 224 | 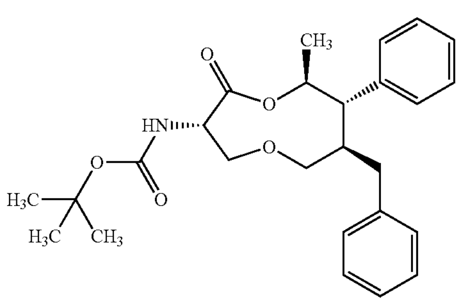 [SMILES: C[C@@H]1OC(=O)[C@@H](NC(=O)OC(C)(C)C)COC[C@H](Cc2ccccc2)[C@H]1c1ccccc1] | Example 8, Steps 1, 2; Example 2, Step 6; Example 1, Steps 5a, 10, 11 | White Solid |

TABLE 1-continued

Compound Structure and Appearance

| Compound Number | Structure | Prepared According to Example | Appearance |
|---|---|---|---|
| 225 | 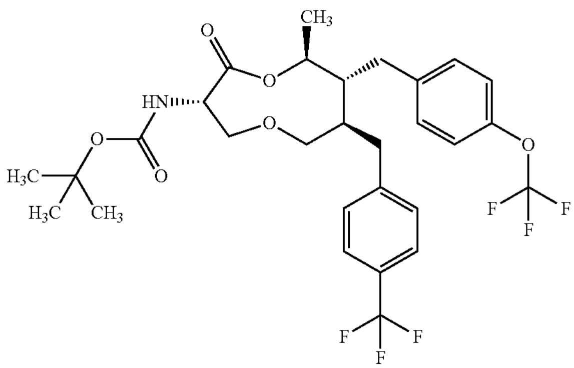 [SMILES: C[C@@H]1OC(=O)[C@@H](NC(=O)OC(C)(C)C)COC[C@H](Cc2ccc(C(F)(F)F)cc2)[C@H]1Cc1ccc(OC(F)(F)F)cc1] | Example 8, Steps 1, 2; Example 2, Step 6; Example 1, Steps 5a, 10, 11 | White Solid |
| 226 | 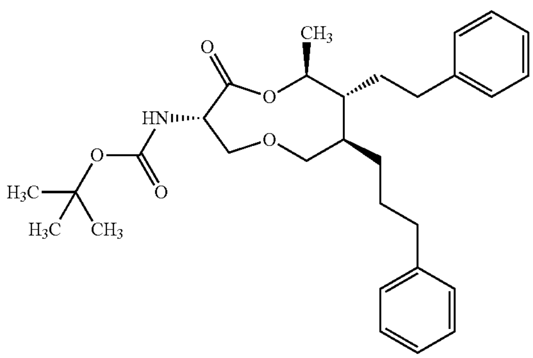 [SMILES: C[C@@H]1OC(=O)[C@@H](NC(=O)OC(C)(C)C)COC[C@H](CCCc2ccccc2)[C@H]1CCc1ccccc1] | Example 8, Steps 1, 2; Example 2, Step 6; Example 1, Steps 5a, 10, 11 | Colorless Oil |
| 227 | 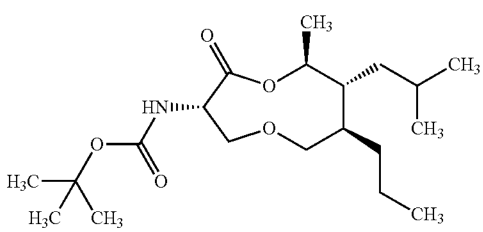 [SMILES: CCC[C@H]1COC[C@H](NC(=O)OC(C)(C)C)C(=O)O[C@@H](C)[C@@H]1CC(C)C] | Example 8, Steps 1, 2; Example 2, Step 6; Example 1, Steps 5a, 10, 11 | Colorless Oil |
| 228 | 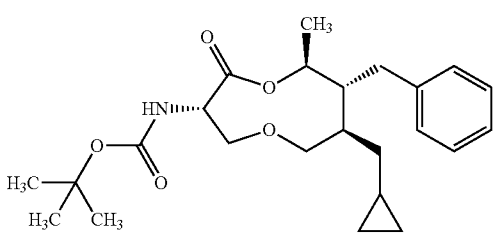 [SMILES: C[C@@H]1OC(=O)[C@@H](NC(=O)OC(C)(C)C)COC[C@H](CC2CC2)[C@H]1Cc1ccccc1] | Example 8, Steps 1, 2; Example 2, Step 6; Example 1, Steps 5a, 10, 11 | Colorless Oil |

TABLE 1-continued

Compound Structure and Appearance

| Compound Number | Structure | Prepared According to Example | Appearance |
|---|---|---|---|
| 229 | 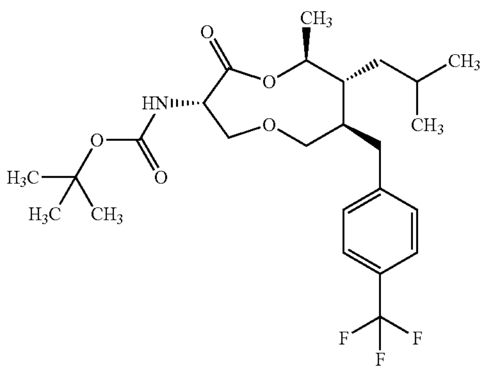 [SMILES: CC(C)C[C@@H]1[C@@H](Cc2ccc(C(F)(F)F)cc2)COC[C@H](NC(=O)OC(C)(C)C)C(=O)O[C@H]1C] | Example 8, Steps 1, 2; Example 2, Step 6; Example 1, Steps 5a, 10, 11 | White Solid |
| 230 | 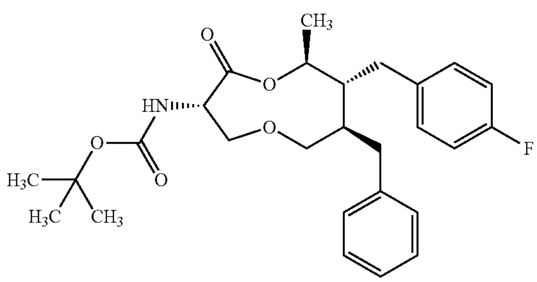 [SMILES: C[C@@H]1OC(=O)[C@@H](NC(=O)OC(C)(C)C)COC[C@H](Cc2ccccc2)[C@H]1Cc1ccc(F)cc1] | Example 8, Steps 1, 2; Example 2, Step 6; Example 1, Steps 5a, 10, 11 | Colorless Oil |
| 231 | 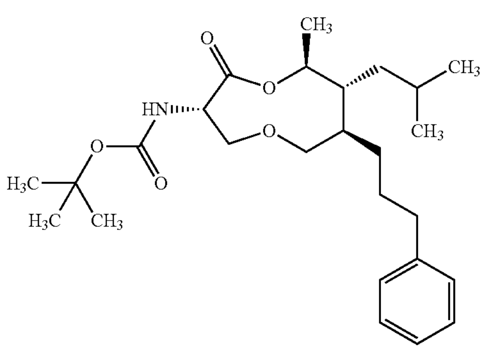 [SMILES: CC(C)C[C@@H]1[C@@H](CCCc2ccccc2)COC[C@H](NC(=O)OC(C)(C)C)C(=O)O[C@H]1C] | Example 8, Steps 1, 2; Example 2, Step 6; Example 1, Steps 5a, 10, 11 | Colorless Oil |
| 232 | 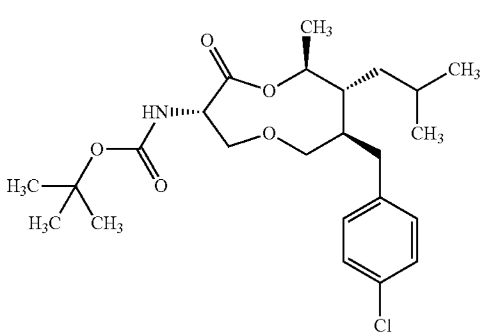 [SMILES: CC(C)C[C@@H]1[C@@H](Cc2ccc(Cl)cc2)COC[C@H](NC(=O)OC(C)(C)C)C(=O)O[C@H]1C] | Example 8, Steps 1, 2; Example 2, Step 6; Example 1, Steps 5a, 10, 11 | Colorless Oil |

TABLE 1-continued

Compound Structure and Appearance

| Compound Number | Structure | Prepared According to Example | Appearance |
|---|---|---|---|
| 233 | 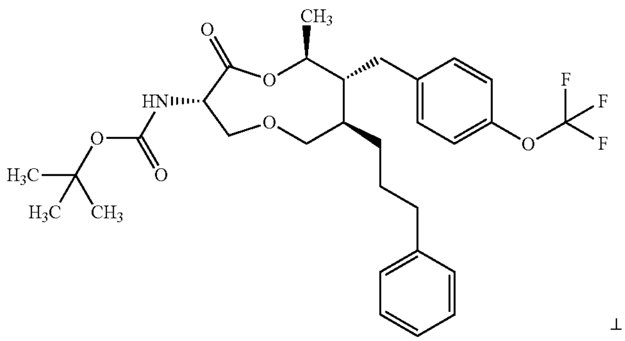 [SMILES: C[C@@H]1OC(=O)[C@@H](NC(=O)OC(C)(C)C)COC[C@H](CCCc2ccccc2)[C@H]1Cc1ccc(OC(F)(F)F)cc1] | Example 8, Steps 1, 2; Example 2, Step 6; Example 1, Steps 5a, 10, 11 | Colorless Oil |
| 234 | 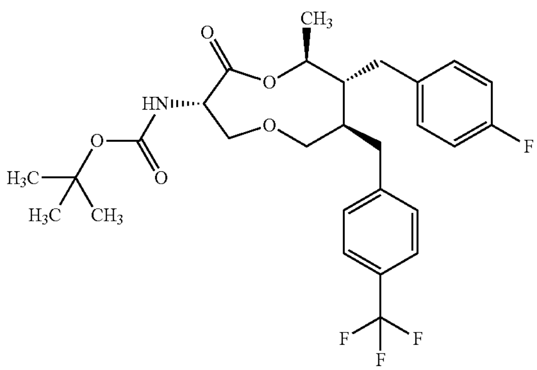 [SMILES: C[C@@H]1OC(=O)[C@@H](NC(=O)OC(C)(C)C)COC[C@H](Cc2ccc(C(F)(F)F)cc2)[C@H]1Cc1ccc(F)cc1] | Example 8, Steps 1, 2; Example 2, Step 6; Example 1, Steps 5a, 10, 11 | White Foam |
| 235 | 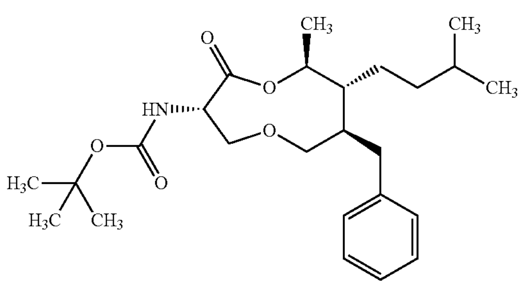 [SMILES: CC(C)CC[C@@H]1[C@@H](Cc2ccccc2)COC[C@H](NC(=O)OC(C)(C)C)C(=O)O[C@H]1C] | Example 8, Steps 1, 2; Example 2, Step 6; Example 1, Steps 5a, 10, 11 | Colorless Oil |
| 236 | 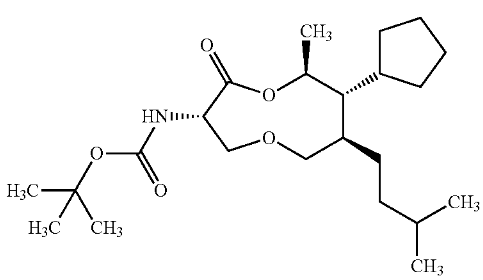 [SMILES: CC(C)CC[C@H]1COC[C@H](NC(=O)OC(C)(C)C)C(=O)O[C@@H](C)[C@@H]1C1CCCC1] | Example 8, Steps 1, 2; Example 2, Step 6; Example 1, Steps 5a, 10, 11 | Colorless Oil |

TABLE 1-continued

Compound Structure and Appearance

| Compound Number | Structure | Prepared According to Example | Appearance |
|---|---|---|---|
| 237 | 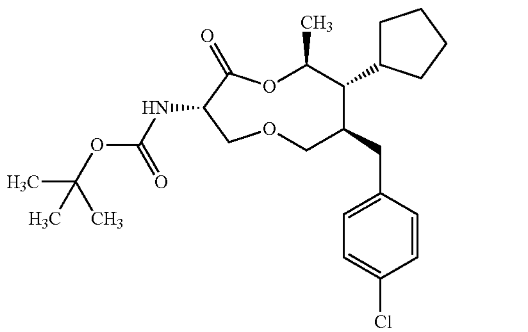 [SMILES: C[C@@H]1OC(=O)[C@@H](NC(=O)OC(C)(C)C)COC[C@H](Cc2ccc(Cl)cc2)[C@H]1C1CCCC1] | Example 8, Steps 1, 2; Example 2, Step 6; Example 1, Steps 5a, 10, 11 | White Solid |
| 238 | 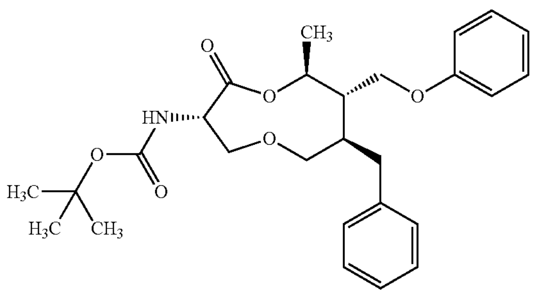 | Example 2, Steps 1, 2, 3, 4, 5; Example 3, Step 1; Example 6, Step 1; Example 2, Step 6; Example 1, Steps 5a, 10, 11; Example 7, Steps 1, 2 | Colorless Oil |
| 239 | 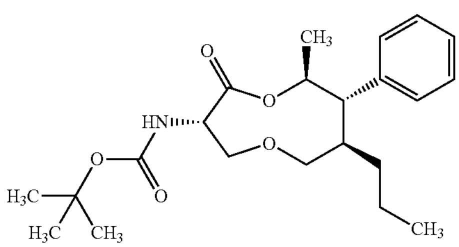 [SMILES: CCC[C@H]1COC[C@H](NC(=O)OC(C)(C)C)C(=O)O[C@@H](C)[C@@H]1c1ccccc1] | Example 8, Steps 1, 2; Example 2, Step 6; Example 1, Steps 5a, 10, 11 | White Foam |
| 240 | 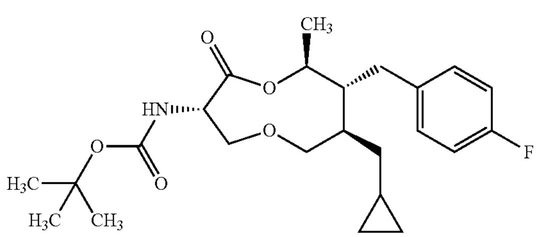 [SMILES: C[C@@H]1OC(=O)[C@@H](NC(=O)OC(C)(C)C)COC[C@H](CC2CC2)[C@H]1Cc1ccc(F)cc1] | Example 8, Steps 1, 2; Example 2, Step 6; Example 1, Steps 5a, 10, 11 | White Foam |
| 241 | 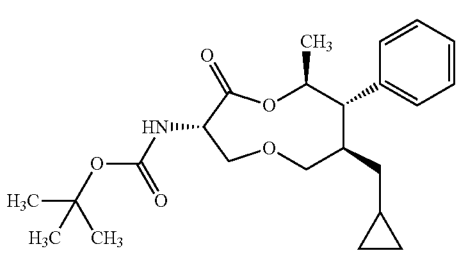 [SMILES: C[C@@H]1OC(=O)[C@@H](NC(=O)OC(C)(C)C)COC[C@H](CC2CC2)[C@H]1c1ccccc1] | Example 8, Steps 1, 2; Example 2, Step 6; Example 1, Steps 5a, 10, 11 | Colorless Oil |

TABLE 1-continued

Compound Structure and Appearance

| Compound Number | Structure | Prepared According to Example | Appearance |
|---|---|---|---|
| 242 | 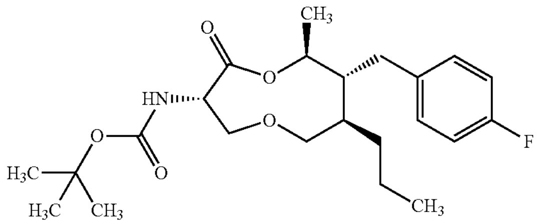 [SMILES: CCC[C@H]1COC[C@H](NC(=O)OC(C)(C)C)C(=O)O[C@@H](C)[C@@H]1Cc1ccc(F)cc1] | Example 8, Steps 1, 2; Example 2 Step 6; Example 1, Steps 5a, 10, 11 | Colorless Oil |
| 243 | 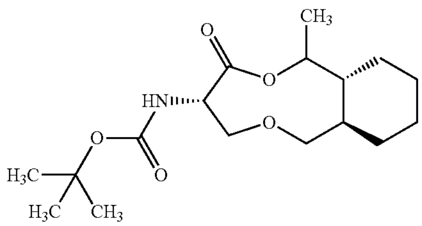 [SMILES: CC1OC(=O)[C@@H](NC(=O)OC(C)(C)C)COC[C@@H]2CCCC[C@@H]12] | Example 1, Steps 4, 5a, 6, 9b, 10, 11 | Colorless Oil |
| 244 | 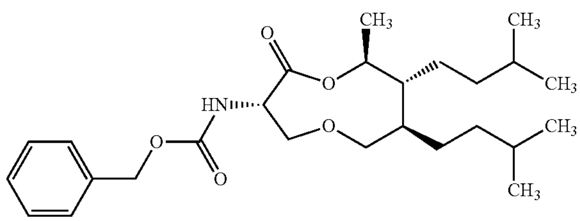 [SMILES: CC(C)CC[C@H]1COC[C@H](NC(=O)OCc2ccccc2)C(=O)O[C@@H](C)[C@@H]1CCC(C)C] | Example 1, Steps 1, 2, 3, 4, 5b, 6, 9b, 10, 11 | Colorless Oil |

TABLE 2

Analytical Data

| Cmpd. No. | MP (° C.) | IR (cm$^{-1}$) | MASS | NMR ($^{1}$H, $^{13}$C or $^{19}$F) |
|---|---|---|---|---|
| 1 | — | — | ESIMS m/z 570 [M]$^+$ | $^{1}$H NMR (400 MHz, CDCl$_3$) δ 8.39 (d, J = 8.2 Hz, 1H), 8.27 (d, J = 5.4 Hz, 1H), 7.32-7.27 (m, 2H), 7.20 (t, J = 7.3 Hz, 3H), 6.93 (d, J = 5.4 Hz, 1H), 5.77 (dd, J = 8.6, 1.8 Hz, 2H), 5.00 (q, J = 8.2 Hz, 1H), 4.95-4.85 (m, 1H), 4.13 (dd, J = 11.5, 7.7 Hz, 1H), 3.89 (d, J = 3.2 Hz, 3H), 3.58 (dd, J = 10.4, 4.7 Hz, 1H), 3.31-3.19 (m, 2H), 2.82 (d, J = 12.5 Hz, 1H), 2.60-2.50 (m, 2H), 1.70 (d, J = 4.3 Hz, 2H), 1.64-1.47 (m, 2H), 1.42 (d, J = 6.3 Hz, 3H), 1.33 (dd, J = 11.4, 6.1 Hz, 2H), 1.29-1.19 (m, 2H), 1.14 (d, J = 7.0 Hz, 6H), 0.93 (t, J = 7.0 Hz, 3H) $^{13}$C NMR (101 MHz, CDCl$_3$) δ 176.26, 172.20, 163.12, 160.19, 145.61, 144.16, 141.88, 140.44, 129.35, 129.13 (2), 128.34 (2), 126.02, 109.60, 89.77, 76.19, 70.89, 56.14, 51.17, 47.20, 44.43, 37.11, 33.86, 29.77, 27.28, 23.44, 20.17, 18.68 (2), 13.99 |
| 2 | — | — | ESIMS m/z 577 [M + H]$^+$ | $^{1}$H NMR (400 MHz, CDCl$_3$) δ 8.86 (d, J = 7.8 Hz, 1H), 8.26 (d, J = 5.4 Hz, 1H), 7.30-7.11 (m, 6H), 7.05-6.98 (m, 2H), 6.95 (d, J = 5.4 Hz, 1H), 6.89-6.81 (m, 2H), 5.75 (s, 2H), 5.34 (q, J = 6.9 Hz, 1H), 4.82 (ddd, J = 7.9, 4.6, 2.3 Hz, 1H), 4.05 (dd, J = 12.2, 4.6 Hz, 1H), 3.95-3.84 (m, 4H), 3.76 (d, J = 11.8 Hz, 1H), 3.44 (dd, J = 10.5, 7.7 Hz, 1H), 3.11 (d, J = 14.2 Hz, 1H), 2.93 (dd, J = 14.2, 10.7 Hz, 1H), 2.67-2.55 (m, 1H), 2.42 (t, J = 11.4 Hz, 1H), 2.07 (s, 3H), |

TABLE 2-continued

Analytical Data

| Cmpd. No. | MP (°C.) | IR (cm$^{-1}$) | MASS | NMR ($^1$H, $^{13}$C or $^{19}$F) |
|---|---|---|---|---|
| | | | | 2.01-1.77 (m, 2H), 1.45 (d, J = 6.6 Hz, 3H) $^{13}$C NMR (101 MHz, CDCl$_3$) δ 170.28, 169.73, 162.61, 160.36, 145.68, 144.32, 142.04, 140.39, 139.65, 129.05, 128.81, 128.36, 128.22, 125.90, 109.68, 89.51, 73.62, 72.02, 56.18, 55.28, 39.86, 36.33, 33.90, 29.22, 20.83, 14.15 |
| 3 | 56-60 | — | ESIMS m/z 577 [M + H]$^+$ | $^1$H NMR (400 MHz, CDCl$_3$) δ 8.35 (d, J = 8.1 Hz, 1H), 8.27 (d, J = 5.3 Hz, 1H), 7.35-7.13 (m, 8H), 7.11-7.05 (m, 2H), 6.94 (d, J = 5.4 Hz, 1H), 5.78-5.68 (m, 2H), 5.10-4.94 (m, 2H), 4.20 (dd, J = 11.6, 7.5 Hz, 1H), 3.89 (s, 3H), 3.64 (dd, J = 11.0, 5.8 Hz, 1H), 3.28-3.19 (m, 2H), 2.89-2.66 (m, 4H), 2.18-2.09 (m, 1H), 2.06 (s, 3H), 1.84-1.72 (m, 1H), 1.39 (d, J = 6.4 Hz, 3H) $^{13}$C NMR (101 MHz, CDCl$_3$) δ 171.97, 170.17, 163.08, 160.12, 145.68, 143.84, 142.12, 140.10, 139.89, 129.04, 128.99, 128.47, 128.15, 126.22, 125.89, 109.63, 89.29, 76.07, 71.26, 70.94, 56.11, 51.18, 48.59, 45.45, 38.47, 37.31, 21.21, 20.79 |
| 4 | 42-47 | — | ESIMS m/z 605 [M + H]$^+$ | $^1$H NMR (400 MHz, CDCl$_3$) δ 8.43 (d, J = 8.1 Hz, 1H), 8.29 (d, J = 5.4 Hz, 1H), 7.33-7.23 (m, 4H), 7.18 (d, J = 7.4 Hz, 4H), 7.04 (d, J = 7.5 Hz, 2H), 6.96 (d, J = 5.4 Hz, 1H), 5.78-5.72 (m, 2H), 5.14-4.90 (m, 2H), 4.19 (dd, J = 11.7, 7.4 Hz, 1H), 3.97-3.84 (m, 4H), 3.54 (d, J = 10.6 Hz, 1H), 3.47 (dd, J = 11.8, 7.9 Hz, 1H), 2.80 (ddd, J = 14.0, 9.0, 5.2 Hz, 1H), 2.52 (dt, J = 13.7, 8.3 Hz, 1H), 2.47-2.34 (m, 2H), 2.08 (s, 3H), 1.90-1.51 (m, 6H), 1.46 (d, J = 6.2 Hz, 3H) $^{13}$C NMR (101 MHz, CDCl$_3$) δ 172.02, 170.29, 163.23, 160.23, 145.82, 143.96, 142.26, 142.09, 142.02, 128.47, 128.46, 128.17, 125.97, 125.93, 109.75, 89.42, 75.93, 74.31, 71.53, 56.23, 51.58, 46.92, 41.34, 33.11, 32.96, 32.28, 31.34, 20.91, 20.36 |
| 5 | — | — | ESIMS m/z 451 [M + H]$^+$ | $^1$H NMR (400 MHz, CDCl$_3$) δ 8.76 (d, J = 7.4 Hz, 1H), 8.31 (d, J = 5.3 Hz, 1H), 6.95 (d, J = 5.4 Hz, 1H), 5.74 (m, 2H), 5.04 (dt, J = 7.7, 4.5 Hz, 1H), 4.97 (qd, J = 6.8, 3.5 Hz, 1H), 4.03 (d, J = 4.5 Hz, 2H), 3.92 (dd, J = 3.4, 6.4 Hz, 1H), 3.91 (m, 3H), 3.73 (d, J = 9.5 Hz, 1H), 2.29 (ddd, J = 12.5, 8.0, 3.0 Hz, 1H), 2.07 (s, 3H), 1.72 (dd, J = 8.1, 4.3 Hz, 2H), 1.56 (m, 2H), 1.47-1.39 (m, 2H), 1.30 (d, J = 6.8 Hz, 3H), 1.27-1.16 (m, 2H), 1.01 (td, J = 12.4, 3.3 Hz, 1H) $^{13}$C NMR (101 MHz, CDCl$_3$) δ 170.56, 170.25, 163.22, 160.18, 145.85, 143.87, 142.44, 109.60, 89.49, 79.22, 77.94, 75.01, 56.18, 53.33, 39.54, 39.35, 32.14, 29.50, 26.58, 26.09, 20.87, 13.66 |
| 6 | — | — | ESIMS m/z 451 [M + H]$^+$ | $^1$H NMR (400 MHz, CDCl$_3$) δ 8.54 (d, J = 7.9 Hz, 1H), 8.28 (d, J = 5.3 Hz, 1H), 6.95 (d, J = 5.4 Hz, 1H), 5.74 (m, 2H), 5.14 (td, J = 7.7, 5.7 Hz, 1H), 4.76 (dq, J = 9.3, 6.4 Hz, 1H), 4.02 (dd, J = 11.8, 7.5 Hz, 1H), 3.91 (s, 3H), 3.68 (dd, J = 11.8, 5.8 Hz, 1H), 3.63-3.56 (m, 2H), 2.07 (s, 3H), 1.80-1.68 (m, 4H), 1.63 (bd, J = 13.2 Hz, 1H), 1.42-1.16 (m, 3H), 1.35 (d, J = 6.4 Hz, 3H), 1.03-0.83 (m, 2H) $^{13}$C NMR (101 MHz, CDCl$_3$) δ 171.39, 170.25, 163.25, 160.20, 145.82, 143.88, 142.31, 109.65, 89.46, 80.62, 78.00, 72.41, 56.19, 52.35, 49.54, 44.29, 31.98, 29.10, 26.35, 25.91, 20.87, 19.84 |
| 7 | 59-64 | — | ESIMS m/z 549 [M + H]$^+$ | $^1$H NMR (400 MHz, CDCl$_3$) δ 8.55 (d, J = 8.1 Hz, 1H), 8.31 (d, J = 5.3 Hz, 1H), 7.20-6.76 (m, 11H), 5.76 (s, 2H), 5.40-5.27 (m, 2H), 4.23-4.09 (m, 2H), 3.98-3.85 (m, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | 4H), 3.70 (dd, J = 11.7, 7.0 Hz, 1H), 3.15-3.05 (m, 2H), 2.08 (s, 3H), 1.10 (d, J = 6.3 Hz, 3H) $^{13}$C NMR (101 MHz, CDCl$_3$) δ 172.00, 170.26, 163.31, 160.24, 145.84, 143.97, 142.63, 142.19, 140.97, 128.27, 128.15, 127.61, 126.47, 126.12, 109.77, 89.44, 77.23, 77.18, 71.65, 58.64, 56.22, 53.31, 51.85, 30.93, 20.89 |
| 8 | — | — | ESIMS m/z 537 [M + H]⁺ | $^{1}$H NMR (400 MHz, CDCl$_3$) δ 8.43 (d, J = 8.0 Hz, 1H), 8.29 (d, J = 5.4 Hz, 1H), 6.95 (d, J = 5.4 Hz, 1H), 5.77-5.70 (m, 2H), 5.04 (q, J = 7.4 Hz, 1H), 4.95-4.85 (m, 1H), 4.10 (dd, J = 11.7, 7.5 Hz, 1H), 3.91 (s, 3H), 3.72 (dd, J = 10.2, 6.0 Hz, 1H), 3.55-3.43 (m, 2H), 2.07 (s, 3H), 1.53-1.01 (m, 12H), 1.38 (d, J = 6.4 Hz, 3H), 0.89 (m, 12H) $^{13}$C NMR (101 MHz, CDCl$_3$) δ 171.95, 170.28, 163.18, 160.20, 145.78, 143.92, 142.32, 109.64, 89.45, 77.21, 76.50, 71.70, 56.19, 51.75, 46.98, 42.18, 35.72, 33.60, 29.10, 28.76, 28.38, 27.20, 22.81, 22.53, 22.47, 22.38, 20.89, 20.23 |
| 9 | 42-48 | — | ESIMS m/z 513 [M + H]⁺ | $^{1}$H NMR (400 MHz, CDCl$_3$) δ 8.39 (d, J = 8.2 Hz, 1H), 8.27 (d, J = 5.4 Hz, 1H), 7.33-7.23 (m, 2H), 7.22-7.10 (m, 3H), 6.94 (d, J = 5.4 Hz, 1H), 5.72 (s, 2H), 5.54 (dt, J = 17.0, 10.0 Hz, 1H), 5.27 (dd, J = 10.3, 1.7 Hz, 1H), 5.20 (dd, J = 17.1, 1.7 Hz, 1H), 5.07 (q, J = 7.8 Hz, 1H), 4.92 (dq, J = 9.9, 6.3 Hz, 1H), 4.06 (dd, J = 11.6, 7.6 Hz, 1H), 3.90 (s, 3H), 3.58 (dd, J = 10.3, 6.1 Hz, 1H), 3.50 (dd, J = 10.3, 1.8 Hz, 1H), 3.38 (dd, J = 11.6, 7.7 Hz, 1H), 2.93 (dd, J = 14.1, 3.3 Hz, 1H), 2.31-2.19 (m, 2H), 2.06 (s, 3H), 1.72 (tdd, J = 10.3, 5.0, 2.1 Hz, 1H), 1.35 (d, J = 6.3 Hz, 3H) $^{13}$C NMR (101 MHz, CDCl$_3$) δ 172.05, 170.26, 163.18, 160.20, 145.78, 143.92, 142.19, 140.21, 138.02, 129.10, 128.34, 126.03, 119.08, 109.71, 89.40, 75.42, 72.96, 71.31, 56.20, 55.69, 51.53, 45.03, 36.90, 20.94, 20.88 |
| 10 | 50-56 | — | ESIMS m/z 589 [M + H]⁺ | $^{1}$H NMR (400 MHz, CDCl$_3$) δ 8.38 (d, J = 8.2 Hz, 1H), 8.28 (d, J = 5.4 Hz, 1H), 6.96 (d, J = 5.4 Hz, 1H), 5.78-5.70 (m, 2H), 5.00 (q, J = 8.0 Hz, 1H), 4.82 (dq, J = 8.9, 6.4 Hz, 1H), 4.15 (dd, J = 11.6, 7.5 Hz, 1H), 3.91 (s, 3H), 3.74 (dd, J = 10.7, 5.7 Hz, 1H), 3.41-3.31 (m, 2H), 2.07 (s, 3H), 1.92-1.59 (m, 14H), 1.55-1.43 (m, 1H), 1.43-0.71 (m, 16H) $^{13}$C NMR (101 MHz, CDCl$_3$) δ 172.08, 170.26, 163.13, 160.18, 145.76, 143.90, 142.28, 109.67, 89.39, 77.65, 73.90, 71.34, 56.19, 51.41, 45.52, 42.07, 40.25, 38.64, 36.88, 34.96, 34.83, 34.41, 33.44, 32.55, 26.65, 26.50, 26.49, 26.43, 26.21, 20.88, 20.66 |
| 11 | 35-40 | — | ESIMS m/z 571 [M + H]⁺ | $^{1}$H NMR (400 MHz, CDCl$_3$) δ 8.31 (d, J = 8.2 Hz, 1H), 8.27 (d, J = 5.3 Hz, 1H), 7.33-7.23 (m, 2H), 7.24-7.15 (m, 3H), 6.95 (d, J = 5.4 Hz, 1H), 5.75-5.71 (m, 2H), 5.09 (dq, J = 9.3, 6.4 Hz, 1H), 4.98-4.89 (m, 3H), 4.20 (dd, J = 11.6, 7.5 Hz, 1H), 3.90 (s, 3H), 3.89-3.79 (m, 2H), 3.62-3.50 (m, 3H), 3.24-3.12 (m, 2H), 2.81 (dd, J = 13.5, 4.0 Hz, 1H), 2.75-2.61 (m, 1H), 2.07 (s, 3H), 2.04-1.94 (m, 1H), 1.86-1.73 (m, 4H), 1.46 (d, J = 6.3 Hz, 3H) $^{13}$C NMR (101 MHz, CDCl$_3$) δ 172.27, 170.27, 163.15, 160.19, 145.75, 143.91, 142.24, 141.88, 140.38, 129.18, 128.31, 126.01, 112.56, 109.69, 89.39, 75.55, 75.27, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 12 | — | — | ESIMS m/z 573 [M + H]$^+$ | 71.38, 70.86, 68.91, 56.20, 51.14, 48.54, 42.09, 37.00, 20.89, 19.66, 19.64 $^1$H NMR (400 MHz, CDCl$_3$) δ 8.35-8.29 (m, 1H), 8.27 (d, J = 5.4 Hz, 1H), 7.31-7.24 (m, 2H), 7.23-7.15 (m, 3H), 6.95 (d, J = 5.4 Hz, 1H), 5.76-5.70 (m, 2H), 5.07 (dq, J = 9.3, 6.3 Hz, 1H), 4.98-4.90 (m, 1H), 4.19 (dd, J = 11.6, 7.5 Hz, 1H), 3.90 (s, 3H), 3.62-3.49 (m, 3H), 3.25-3.07 (m, 4H), 2.82 (dd, J = 13.6, 3.7 Hz, 1H), 2.66 (dd, J = 13.6, 10.9 Hz, 1H), 2.06 (s, 3H), 2.04-1.94 (m, 1H), 1.85 (dq, J = 13.3, 6.6 Hz, 1H), 1.76 (tt, J = 9.3, 2.8 Hz, 1H), 1.45 (d, J = 6.3 Hz, 3H), 0.91 (d, J = 6.7 Hz, 6H) $^{13}$C NMR (101 MHz, CDCl$_3$) δ 172.31, 170.27, 163.15, 160.18, 145.77, 143.89, 142.26, 140.51, 129.16, 128.30, 125.98, 109.70, 89.37, 78.43, 75.52, 71.60, 70.93, 69.44, 56.20, 51.19, 42.10, 36.89, 28.39, 20.88, 19.60, 19.43, 19.41 |
| 13 | 44-48 | — | ESIMS m/z 573 [M + H]$^+$ | $^1$H NMR (400 MHz, CDCl$_3$) δ 8.31 (d, J = 8.3 Hz, 1H), 8.27 (d, J = 5.4 Hz, 1H), 7.32-7.24 (m, 2H), 7.23-7.17 (m, 3H), 6.94 (d, J = 5.4 Hz, 1H), 5.77-5.70 (m, 2H), 5.07 (dq, J = 9.3, 6.3 Hz, 1H), 5.00-4.89 (m, 1H), 4.19 (dd, J = 11.6, 7.5 Hz, 1H), 3.90 (s, 3H), 3.61-3.50 (m, 3H), 3.24-3.08 (m, 4H), 2.82 (dd, J = 13.6, 3.7 Hz, 1H), 2.66 (dd, J = 13.6, 11.0 Hz, 1H), 2.07 (s, 3H), 2.04-1.93 (m, 1H), 1.86 (hept, J = 6.7 Hz, 1H), 1.80-1.72 (m, 1H), 1.45 (d, J = 6.3 Hz, 3H), 0.91 (d, J = 6.7 Hz, 6H) $^{13}$C NMR (101 MHz, CDCl$_3$) δ 172.27, 170.23, 163.10, 160.14, 145.71, 143.86, 142.23, 140.47, 129.12, 128.26, 125.93, 109.62, 89.35, 78.39, 75.48, 71.54, 70.89, 69.41, 56.14, 51.15, 48.61, 42.06, 36.85, 28.35, 20.84, 19.56, 19.38, 19.36 |
| 14 | — | — | HRMS-FAB (m/z) [M + H]$^+$ calcd for C$_{29}$H$_{39}$N$_2$O$_8$, 543.2706; found, 543.2717 | $^1$H NMR (400 MHz, CDCl$_3$) δ 8.34 (d, J = 8.2 Hz, 1H), 8.27 (d, J = 5.4 Hz, 1H), 7.34-7.26 (m, 2H), 7.22-7.17 (m, 3H), 6.95 (d, J = 5.3 Hz, 1H), 5.73 (s, 2H), 5.05-4.95 (m, 1H), 4.90 (dq, J = 9.3, 6.2 Hz, 1H), 4.13 (dd, J = 11.6, 7.6 Hz, 1H), 3.90 (s, 3H), 3.58 (dd, J = 10.6, 4.8 Hz, 1H), 3.31-3.20 (m, 2H), 2.82 (dd, J = 13.7, 2.8 Hz, 1H), 2.55 (dd, J = 13.8, 10.3 Hz, 1H), 2.06 (s, 3H), 1.75-1.66 (m, 2H), 1.65-1.45 (m, 2H), 1.42 (d, J = 6.3 Hz, 3H), 1.40-1.19 (m, 4H), 0.93 (t, J = 7.0 Hz, 3H) $^{13}$C NMR (101 MHz, CDCl$_3$) δ 172.19, 170.28, 163.16, 160.20, 145.77, 143.93, 142.23, 140.43, 129.13, 128.35, 126.03, 109.69, 89.40, 76.20, 72.14, 70.91, 56.20, 51.22, 47.23, 44.44, 37.12, 29.77, 27.28, 23.44, 20.89, 20.18, 14.00 |
| 15 | — | — | HRMS-FAB (m/z) [M + H]$^+$ calcd for C$_{28}$H$_{37}$N$_2$O$_7$, 513.2601; found, 513.2618 | $^1$H NMR (400 MHz, CDCl$_3$) δ 8.51 (d, J = 8.5 Hz, 1H), 8.32 (d, J = 5.4 Hz, 1H), 7.33-7.26 (m, 2H), 7.24-7.13 (m, 3H), 6.99 (d, J = 5.5 Hz, 1H), 4.97 (td, J = 8.6, 7.6 Hz, 1H), 4.89 (dq, J = 9.0, 6.3 Hz, 1H), 4.09 (dd, J = 11.6, 7.6 Hz, 1H), 3.89 (s, 3H), 3.57 (dd, J = 10.5, 5.0 Hz, 1H), 3.32-3.15 (m, 2H), 2.81 (dd, J = 13.8, 3.0 Hz, 1H), 2.61-2.45 (m, 1H), 2.39 (s, 3H), 1.75-1.45 (m, 4H), 1.41 (d, J = 6.3 Hz, 3H), 1.38-1.20 (m, 4H), 0.93 (t, J = 7.0 Hz, 3H) $^{13}$C NMR (101 MHz, CDCl$_3$) δ 172.09, 168.87, 162.65, 159.42, 146.73, 141.21, 140.42, 137.49, 129.13, 128.34, 126.03, 109.89, 76.20, 72.12, 70.91, 56.29, 51.01, 47.24, 44.42, 37.15, 29.80, 27.29, 23.44, 20.75, 20.18, 14.00 |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 16 | — | — | HRMS-FAB (m/z) [M + H]$^+$ calcd for C$_{30}$H$_{38}$F$_3$N$_2$O$_8$, 611.2580; found. 611.2609 | $^1$H NMR (400 MHz, CDCl$_3$) δ 8.34 (d, J = 8.2 Hz, 1H), 8.27 (d, J = 5.4 Hz, 1H), 7.58-7.51 (m, 2H), 7.32 (d, J = 8.0 Hz, 2H), 6.96 (d, J = 5.4 Hz, 1H), 5.73 (d, J = 0.9 Hz, 2H), 5.11-4.85 (m, 2H), 4.19-4.13 (m, 1H), 3.91 (s, 3H), 3.54 (dd, J = 10.8, 4.3 Hz, 1H), 3.29-3.14 (m, 2H), 2.91-2.78 (m, 1H), 2.75-2.63 (m, 1H), 2.07 (s, 3H), 1.76-1.67 (m, 2H), 1.64-1.48 (m, 2H), 1.43 (d, J = 6.3 Hz, 3H), 1.40-1.24 (m, 4H), 0.94 (t, J = 7.0 Hz, 3H) $^{19}$F NMR (376 MHz, CDCl$_3$) δ −62.31 |
| 17 | 51-55 | — | ESIMS m/z 637 [M + H]$^+$ | $^1$H NMR (400 MHz, CDCl$_3$) δ 8.33 (d, J = 8.2 Hz, 1H), 8.25 (d, J = 5.3 Hz, 1H), 7.21 (td, J = 7.5, 1.5 Hz, 1H), 7.13 (t, J = 7.9 Hz, 1H), 6.93 (d, J = 5.4 Hz, 1H), 6.83-6.61 (m, 6H), 5.72 (s, 2H), 5.08-4.93 (m, 2H), 4.20 (dd, J = 11.6, 7.5 Hz, 1H), 3.88 (s, 3H), 3.78 (s, 3H), 3.74 (s, 3H), 3.66 (dd, J = 10.9, 5.8 Hz, 1H), 3.23 (dd, J = 11.7, 8.7 Hz, 2H), 2.87-2.62 (m, 4H), 2.15-2.07 (m, 1H), 2.05 (s, 3H), 1.83-1.72 (m, 1H), 1.40 (d, J = 6.4 Hz, 3H) $^{13}$C NMR (101 MHz, CDCl$_3$) δ 171.89, 170.06, 163.06, 160.10, 159.63, 159.41, 145.63, 143.79, 142.15, 141.72, 141.46, 129.37, 129.01, 121.41, 121.34, 114.98, 114.56, 111.45, 111.30, 109.62, 89.25, 76.00, 71.35, 70.95, 56.07, 55.01, 54.95, 51.20, 48.47, 45.30, 38.55, 37.39, 21.14, 20.72 |
| 18 | — | — | HRMS-FAB (m/z) [M + H]$^+$ calcd for C$_{28}$H$_{37}$N$_2$O$_7$, 513.2601; found, 513.2600 | $^1$H NMR (400 MHz, CDCl$_3$) δ 8.50 (d, J = 8.7 Hz, 1H), 8.32 (d, J = 5.4 Hz, 1H), 7.33-7.16 (m, 5H), 6.99 (d, J = 5.4 Hz, 1H), 4.95 (td, J = 8.7, 7.6 Hz, 1H), 4.86 (dq, J = 8.8, 6.4 Hz, 1H), 4.14 (dd, J = 11.6, 7.5 Hz, 1H), 3.89 (s, 3H), 3.59 (dd, J = 10.9, 5.4 Hz, 1H), 3.19 (dd, J = 11.5, 9.0 Hz, 2H), 2.84 (dd, J = 13.7, 3.6 Hz, 1H), 2.68-2.54 (m, 1H), 2.39 (s, 3H), 1.76-1.63 (m, 2H), 1.62-1.53 (m, 1H), 1.43 (d, J = 6.4 Hz, 3H), 1.41-1.34 (m, 1H), 1.20 (ddd, J = 14.7, 8.7, 3.4 Hz, 1H), 0.96 (d, J = 6.5 Hz, 3H), 0.93 (d, J = 6.6 Hz, 3H) $^{13}$C NMR (101 MHz, CDCl$_3$) δ 172.05, 168.89, 162.64, 159.43, 146.73, 141.24, 140.58, 137.50, 129.13, 128.31, 126.01, 109.89, 77.19, 71.33, 71.09, 56.29, 51.04, 47.32, 45.61, 42.17, 36.95, 27.07, 23.62, 22.50, 20.75, 20.61 |
| 19 | — | — | HRMS-FAB (m/z) [M + H]$^+$ calcd for C$_{29}$H$_{39}$N$_2$O$_8$, 543.2706; found, 543.2704 | $^1$H NMR (400 MHz, CDCl$_3$) δ 8.37-8.30 (m, 1H), 8.27 (d, J = 5.3 Hz, 1H), 7.34-7.17 (m, 5H), 6.94 (d, J = 5.4 Hz, 1H), 5.73 (d, J = 1.3 Hz, 2H), 5.03-4.93 (m, 1H), 4.87 (dq, J = 8.9, 6.4 Hz, 1H), 4.17 (dd, J = 11.6, 7.5 Hz, 1H), 3.90 (s, 3H), 3.60 (dd, J = 10.9, 5.3 Hz, 1H), 3.29-3.14 (m, 2H), 2.86 (dd, J = 13.8, 3.6 Hz, 1H), 2.63 (dd, J = 13.7, 11.1 Hz, 1H), 2.07 (s, 3H), 1.76-1.63 (m, 2H), 1.62-1.52 (m, 1H), 1.44 (d, J = 6.4 Hz, 3H), 1.39 (ddd, J = 14.7, 6.9, 5.2 Hz, 1H), 1.20 (ddd, J = 14.7, 8.8, 3.4 Hz, 1H), 0.97 (d, J = 6.5 Hz, 3H), 0.93 (d, J = 6.6 Hz, 3H) $^{13}$C NMR (101 MHz, CDCl$_3$) δ 172.14, 170.28, 163.15, 160.21, 145.75, 143.94, 142.24, 140.57, 129.13, 128.31, 126.01, 109.69, 89.41, 77.22, 71.34, 71.08, 56.20, 51.24, 47.36, 45.58, 42.15, 36.90, 27.10, 23.64, 22.47, 20.89, 20.58 |
| 20 | — | — | HRMS-FAB (m/z) [M + H]$^+$ calcd for C$_{31}$H$_{43}$N$_2$O$_8$, | $^1$H NMR (400 MHz, CDCl$_3$) δ 8.39 (d, J = 8.2 Hz, 1H), 8.26 (d, J = 5.3 Hz, 1H), 7.36-7.17 (m, 5H), 6.93 (d, J = 5.4 Hz, 1H), 5.82-5.66 (m, 2H), 5.04-4.94 (m, 1H), 4.87 (dq, J = 8.9, 6.4 Hz, 1H), 4.17 (dd, J = 11.6, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | 571.3019; found, 571.3018 | 7.6 Hz, 1H), 3.88 (s, 3H), 3.60 (dd, J = 10.9, 5.3 Hz, 1H), 3.27-3.13 (m, 2H), 2.85 (dd, J = 13.8, 3.6 Hz, 1H), 2.63 (dd, J = 13.7, 11.2 Hz, 1H), 2.62-2.48 (m, 1H), 1.76-1.65 (m, 2H), 1.61-1.52 (m, 1H), 1.44 (d, J = 6.4 Hz, 3H), 1.42-1.35 (m, 1H), 1.26-1.17 (m, 1H), 1.14 (d, J = 7.0 Hz, 6H), 0.97 (dd, J = 6.6, 1.1 Hz, 3H), 0.93 (d, J = 6.6 Hz, 3H) $^{13}$C NMR (101 MHz, CDCl$_3$) δ 176.24, 172.14, 163.12, 160.19, 145.61, 144.15, 141.90, 140.57, 129.13, 128.31, 126.00, 109.63, 89.75, 77.20, 71.29, 71.06, 56.15, 51.21, 47.37, 45.57, 42.15, 36.89, 33.86, 27.10, 23.64, 22.46, 20.58, 18.68 |
| 21 | — | — | HRMS-FAB (m/z) [M + H]$^+$ calcd for C$_{31}$H$_{43}$N$_2$O$_9$, 587.2968; found, 587.2963 | $^1$H NMR (400 MHz, CDCl$_3$) δ 8.35 (d, J = 8.2 Hz, 1H), 8.26 (d, J = 5.3 Hz, 1H), 7.31-7.17 (m, 5H), 6.95 (d, J = 5.4 Hz, 1H), 5.81 (s, 2H), 4.97 (td, J = 8.8, 7.5 Hz, 1H), 4.87 (dq, J = 8.9, 6.4 Hz, 1H), 4.17 (dd, J = 11.6, 7.6 Hz, 1H), 4.10 (s, 2H), 3.90 (s, 3H), 3.62-3.56 (m, 3H), 3.20 (ddd, J = 11.7, 5.6, 4.1 Hz, 2H), 2.85 (dd, J = 13.7, 3.6 Hz, 1H), 2.63 (dd, J = 13.7, 11.2 Hz, 1H), 1.77-1.65 (m, 2H), 1.61-1.52 (m, 1H), 1.44 (d, J = 6.4 Hz, 3H), 1.43-1.35 (m, 1H), 1.23 (t, J = 7.0 Hz, 3H), 1.19 (dd, J = 8.9, 3.4 Hz, 1H), 0.97 (d, J = 6.6 Hz, 3H), 0.93 (d, J = 6.5 Hz, 3H) $^{13}$C NMR (101 MHz, CDCl$_3$) δ 172.10, 170.07, 163.10, 160.11, 145.79, 143.90, 142.08, 140.56, 129.13, 128.31, 126.01, 109.79, 89.40, 77.22, 77.09, 71.31, 71.06, 67.80, 67.20, 56.23, 51.21, 47.37, 45.57, 42.15, 36.89, 27.10, 23.64, 22.46, 20.58, 15.01 |
| 22 | — | — | HRMS-FAB (m/z) [M + H]$^+$ calcd for C$_{27}$H$_{35}$N$_2$O$_7$, 499.2444; found, 499.2443 | $^1$H NMR (400 MHz, CDCl$_3$) δ 8.57 (d, J = 8.1 Hz, 1H), 8.33 (d, J = 5.4 Hz, 1H), 7.33-7.17 (m, 5H), 7.00 (d, J = 5.5 Hz, 1H), 5.07-4.92 (m, 2H), 4.14 (dd, J = 11.6, 7.4 Hz, 1H), 3.89 (s, 3H), 3.83 (dd, J = 10.7, 5.7 Hz, 1H), 3.47-3.32 (m, 2H), 2.80-2.66 (m, 2H), 2.39 (s, 3H), 2.04-1.94 (m, 1H), 1.56-1.33 (m, 4H), 1.30 (d, J = 6.4 Hz, 3H), 1.27-1.17 (m, 1H), 0.84 (t, J = 6.9 Hz, 3H) $^{13}$C NMR (101 MHz, CDCl$_3$) δ 171.85, 168.88, 162.65, 159.43, 146.74, 141.24, 140.45, 137.51, 128.95, 128.44, 126.11, 109.89, 76.26, 73.66, 71.48, 56.30, 51.30, 48.99, 43.54, 38.41, 33.78, 21.43, 20.74, 20.34, 14.26 |
| 23 | — | — | HRMS-FAB (m/z) [M + H]$^+$ calcd for C$_{28}$H$_{37}$N$_2$O$_8$, 529.2550; found, 529.2545 | $^1$H NMR (400 MHz, CDCl$_3$) δ 8.40 (d, J = 8.1 Hz, 1H), 8.28 (d, J = 5.4 Hz, 1H), 7.33-7.17 (m, 5H), 6.95 (d, J = 5.4 Hz, 1H), 5.81-5.69 (m, 2H), 5.09-4.93 (m, 2H), 4.18 (dd, J = 11.6, 7.4 Hz, 1H), 3.91 (s, 3H), 3.84 (dd, J = 10.9, 5.4 Hz, 1H), 3.47-3.33 (m, 2H), 2.81-2.66 (m, 2H), 2.07 (s, 3H), 2.00 (tt, J = 7.2, 3.8 Hz, 1H), 1.56-1.35 (m, 4H), 1.31 (d, J = 6.4 Hz, 3H), 1.24-1.15 (m, 1H), 0.85 (t, J = 6.9 Hz, 3H) $^{13}$C NMR (101 MHz, CDCl$_3$) δ 171.94, 170.27, 163.17, 160.21, 145.77, 143.94, 142.25, 140.43, 128.94, 128.44, 126.11, 109.70, 89.40, 76.29, 73.65, 71.48, 56.20, 51.51, 48.96, 43.55, 38.36, 33.73, 21.41, 20.88, 20.35, 14.25 |
| 24 | — | — | HRMS-FAB (m/z) [M + H]$^+$ calcd for C$_{30}$H$_{41}$N$_2$O$_8$, 557.2863; found, 557.2862 | $^1$H NMR (400 MHz, CDCl$_3$) δ 8.46 (d, J = 8.1 Hz, 1H), 8.27 (d, J = 5.3 Hz, 1H), 7.33-7.17 (m, 5H), 6.94 (d, J = 5.4 Hz, 1H), 5.83-5.70 (m, 2H), 5.09-4.94 (m, 2H), 4.18 (dd, J = 11.6, 7.4 Hz, 1H), 3.89 (s, 3H), 3.84 (dd, J = 10.8, 5.3 Hz, 1H), 3.47-3.33 (m, 2H), 2.82-2.66 (m, 2H), 2.54 (hept, J = 7.0 Hz, 1H), 2.01 (qd, J = 7.2, 4.8 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1.57-1.34 (m, 4H), 1.31 (d, J = 6.4 Hz, 3H), 1.29-1.17 (m, 1H), 1.14 (d, J = 7.0 Hz, 6H), 0.85 (t, J = 7.0 Hz, 3H), $^{13}$C NMR (101 MHz, CDCl$_3$) δ 176.23, 171.94, 163.13, 160.19, 145.63, 144.15, 141.91, 140.43, 128.94, 128.43, 126.10, 109.65, 89.75, 76.27, 73.60, 71.46, 56.15, 51.48, 48.96, 43.55, 38.37, 33.85, 33.72, 21.41, 20.36, 18.67, 14.25 |
| 25 | — | — | HRMS-FAB (m/z) [M + H]$^+$ calcd for C$_{30}$H$_{41}$N$_2$O$_9$, 573.2812; found, 573.2816 | $^1$H NMR (400 MHz, CDCl$_3$) δ 8.41 (d, J = 8.1 Hz, 1H), 8.27 (d, J = 5.4 Hz, 1H), 7.33-7.17 (m, 5H), 6.95 (d, J = 5.4 Hz, 1H), 5.81 (d, J = 0.6 Hz, 2H), 5.07-4.94 (m, 2H), 4.17 (dd, J = 11.6, 7.4 Hz, 1H), 4.10 (s, 2H), 3.90 (s, 3H), 3.84 (dd, J = 10.9, 5.3 Hz, 1H), 3.59 (q, J = 7.0 Hz, 2H), 3.47-3.34 (m, 2H), 2.81-2.65 (m, 2H), 2.01 (qd, J = 7.1, 4.8 Hz, 1H), 1.57-1.36 (m, 4H), 1.31 (d, J = 6.5 Hz, 3H), 1.29-1.25 (m, 1H), 1.22 (t, J = 7.0 Hz, 3H), 0.85 (t, J = 7.0 Hz, 3H) $^{13}$C NMR (101 MHz, CDCl$_3$) δ 171.91, 170.06, 163.11, 160.12, 145.81, 143.90, 142.09, 140.41, 128.94, 128.44, 126.11, 109.80, 89.41, 76.28, 73.64, 71.47, 67.80, 67.19, 56.24, 51.50, 48.97, 43.55, 38.37, 33.73, 21.41, 20.35, 15.00, 14.25 |
| 26 | — | — | ESIMS m/z 561 [M + H]$^+$ | $^1$H NMR (400 MHz, CDCl$_3$) δ 8.36 (d, J = 8.1 Hz, 1H), 8.26 (d, J = 5.4 Hz, 1H), 6.93 (d, J = 5.5 Hz, 1H), 5.77-5.66 (m, 2H), 5.02-4.83 (m, 2H), 4.15 (dd, J = 11.6, 7.3 Hz, 1H), 3.96-3.83 (m, 4H), 3.78 (dd, J = 10.9, 5.6 Hz, 1H), 3.41-3.28 (m, 2H), 2.05 (s, 3H), 1.96-1.20 (m, 20H), 1.04 (tdt, J = 12.0, 9.2, 5.7 Hz, 6H) $^{13}$C NMR (101 MHz, CDCl$_3$) δ 171.96, 170.20, 163.07, 160.13, 145.69, 143.85, 142.24, 109.60, 89.33, 76.87, 73.72, 71.48, 56.12, 51.48, 47.35, 43.33, 38.76, 37.53, 34.59, 33.66, 33.60, 33.18, 32.10, 31.51, 25.01, 24.90, 24.78, 24.73, 22.58, 20.81 |
| 27 | 67-71 | — | ESIMS m/z 547 [M + H]$^+$ | $^1$H NMR (400 MHz, CDCl$_3$) δ 8.54 (d, J = 8.5 Hz, 1H), 8.33 (d, J = 5.4 Hz, 1H), 7.35-7.29 (m, 2H), 7.27-7.21 (m, 5H), 7.20-7.15 (m, 1H), 7.11-7.06 (m, 2H), 6.99 (d, J = 5.5 Hz, 1H), 5.05 (dq, J = 8.5, 6.5 Hz, 1H), 4.98 (td, J = 8.7, 7.5 Hz, 1H), 4.18 (dd, J = 11.6, 7.5 Hz, 1H), 3.89 (s, 3H), 3.64 (dd, J = 10.9, 5.8 Hz, 1H), 3.26-3.17 (m, 2H), 2.87-2.68 (m, 4H), 2.40 (s, 3H), 2.13 (ddd, J = 14.1, 7.9, 6.2 Hz, 1H), 1.86-1.70 (m, 1H), 1.39 (d, J = 6.5 Hz, 3H) $^{13}$C NMR (101 MHz, CDCl$_3$) δ 171.89, 168.80, 162.58, 159.35, 146.66, 141.12, 140.13, 139.91, 137.43, 129.07, 129.02, 128.49, 128.16, 126.24, 125.90, 109.84, 76.05, 71.23, 70.97, 56.22, 50.99, 48.65, 45.47, 38.54, 37.37, 21.24, 20.67 |
| 28 | — | — | ESIMS m/z 621 [M + H]$^+$ | $^1$H NMR (400 MHz, CDCl$_3$) δ 8.36 (d, J = 8.2 Hz, 1H), 8.27 (d, J = 5.3 Hz, 1H), 7.35-7.28 (m, 2H), 7.27-7.20 (m, 5H), 7.20-7.14 (m, 1H), 7.11-7.05 (m, 2H), 6.94 (d, J = 5.4 Hz, 1H), 5.81 (s, 2H), 5.09-4.93 (m, 2H), 4.20 (dd, J = 11.6, 7.5 Hz, 1H), 4.10 (s, 2H), 3.90 (s, 3H), 3.64 (dd, J = 11.1, 5.8 Hz, 1H), 3.59 (q, J = 7.1 Hz, 2H), 3.27-3.17 (m, 2H), 2.88-2.81 (m, 2H), 2.81-2.71 (m, 2H), 2.14 (ddd, J = 13.9, 7.8, 6.5 Hz, 1H), 1.84-1.72 (m, 1H), 1.39 (d, J = 6.4 Hz, 3H), 1.23 (t, J = 7.0 Hz, 3H) $^{13}$C NMR (101 MHz, CDCl$_3$) δ 172.01, 170.03, 163.08, 160.10, 145.76, 143.90, 142.03, 140.16, 139.95, 129.11, 129.05, 128.53, 128.21, 126.29, 125.95, 109.75, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 89.39, 76.14, 71.27, 71.00, 67.77, 67.17, 56.20, 51.21, 48.65, 45.53, 38.54, 37.36, 21.26, 14.98 |
| 29 | — | — | HRMS-FAB (m/z) [M + H]$^+$ calcd for C$_{32}$H$_{37}$N$_2$O$_7$, 561.2601; found, 561.2602 | $^1$H NMR (400 MHz, CDCl$_3$) δ 8.52 (d, J = 8.5 Hz, 1H), 8.32 (d, J = 5.3 Hz, 1H), 7.35-7.14 (m, 10H), 6.99 (d, J = 5.4 Hz, 1H), 5.05-4.93 (m, 2H), 4.11 (dd, J = 11.6, 7.6 Hz, 1H), 3.89 (s, 3H), 3.61 (d, J = 10.5, 5.0 Hz, 1H), 3.38-3.18 (m, 2H), 2.84 (dd, J = 13.8, 3.0 Hz, 1H), 2.69 (ddd, J = 13.8, 11.7, 5.1 Hz, 1H), 2.56 (ddd, J = 13.8, 10.5, 6.8 Hz, 2H), 2.39 (s, 3H), 1.99-1.71 (m, 4H), 1.50 (d, J = 6.3 Hz, 3H) $^{13}$C NMR (101 MHz, CDCl$_3$) δ 172.12, 168.88, 162.66, 159.48, 146.74, 141.96, 141.19, 140.25, 137.54, 129.14, 128.60, 128.44, 128.21, 126.15, 126.10, 109.95, 75.94, 72.11, 70.94, 56.34, 51.03, 47.13, 44.60, 37.21, 32.66, 31.83, 20.76, 20.34 |
| 30 | — | — | HRMS-FAB (m/z) [M + H]$^+$ calcd for C$_{33}$H$_{39}$N$_2$O$_8$, 591.2706; found, 591.2702 | $^1$H NMR (400 MHz, CDCl$_3$) δ 8.35 (d, J = 8.2 Hz, 1H), 8.27 (d, J = 5.3 Hz, 1H), 7.33-7.15 (m, 10H), 6.95 (d, J = 5.4 Hz, 1H), 5.73 (d, J = 1.1 Hz, 2H), 5.08-4.96 (m, 2H), 4.15 (dd, J = 11.6, 7.6 Hz, 1H), 3.90 (s, 3H), 3.63 (dd, J = 10.5, 4.6 Hz, 1H), 3.37-3.23 (m, 2H), 2.91-2.80 (m, 1H), 2.70 (ddd, J = 13.7, 11.6, 5.0 Hz, 1H), 2.64-2.51 (m, 2H), 2.07 (s, 3H), 1.98-1.79 (m, 4H), 1.52 (d, J = 6.3 Hz, 3H) $^{13}$C NMR (101 MHz, CDCl$_3$) δ 172.21, 170.29, 163.20, 160.22, 145.79, 143.95, 142.24, 141.95, 140.26, 129.13, 128.59, 128.44, 128.20, 126.14, 126.10, 109.73, 89.41, 75.94, 72.14, 70.95, 56.22, 51.24, 47.13, 44.62, 37.18, 32.64, 31.83, 20.90, 20.33 |
| 31 | — | — | HRMS-FAB (m/z) [M + H]$^+$ calcd for C$_{35}$H$_{43}$N$_2$O$_8$, 619.3019; found, 619.3009 | $^1$H NMR (400 MHz, CDCl$_3$) δ 8.41 (d, J = 8.2 Hz, 1H), 8.27 (d, J = 5.3 Hz, 1H), 7.34-7.15 (m, 10H), 6.94 (d, J = 5.4 Hz, 1H), 5.86-5.71 (m, 2H), 5.09-4.95 (m, 2H), 4.14 (dd, J = 11.6, 7.6 Hz, 1H), 3.88 (s, 3H), 3.68-3.59 (m, 1H), 3.36-3.22 (m, 2H), 2.89-2.80 (m, 1H), 2.70 (ddd, J = 13.5, 11.6, 5.0 Hz, 1H), 2.63-2.48 (m, 3H), 1.98-1.80 (m, 4H), 1.52 (d, J = 6.3 Hz, 3H), 1.14 (d, J = 7.0 Hz, 6H) $^{13}$C NMR (101 MHz, CDCl$_3$) δ 176.23, 172.22, 163.17, 160.22, 145.64, 144.18, 141.95, 141.91, 140.27, 129.13, 128.59, 128.43, 128.20, 126.14, 126.10, 109.67, 89.77, 75.91, 72.08, 70.95, 56.16, 51.21, 47.13, 44.63, 37.18, 33.87, 32.65, 31.85, 20.32, 18.69 |
| 32 | — | — | HRMS-FAB (m/z) [M + H]$^+$ calcd for C$_{35}$H$_{43}$N$_2$O$_9$, 635.2968; found, 635.2963 | $^1$H NMR (400 MHz, CDCl$_3$) δ 8.36 (d, J = 8.2 Hz, 1H), 8.27 (d, J = 5.4 Hz, 1H), 7.35-7.14 (m, 10H), 6.95 (d, J = 5.4 Hz, 1H), 5.81 (s, 2H), 5.10-4.95 (m, 2H), 4.14 (dd, J = 11.6, 7.7 Hz, 1H), 4.10 (s, 2H), 3.90 (s, 3H), 3.67-3.53 (m, 3H), 3.38-3.20 (m, 2H), 2.85 (dd, J = 13.8, 2.9 Hz, 1H), 2.70 (ddd, J = 13.6, 11.4, 5.0 Hz, 1H), 2.57 (qd, J = 11.6, 11.0, 5.4 Hz, 2H), 1.99-1.77 (m, 4H), 1.52 (d, J = 6.3 Hz, 3H), 1.23 (t, J = 7.0 Hz, 3H) $^{13}$C NMR (101 MHz, CDCl$_3$) δ 172.19, 170.07, 163.15, 160.14, 145.82, 143.92, 142.10, 141.94, 140.26, 129.13, 128.59, 128.43, 128.20, 126.14, 126.10, 109.82, 89.42, 75.93, 72.09, 70.94, 67.81, 67.20, 56.24, 51.21, 47.12, 44.63, 37.17, 32.64, 31.84, 20.32, 15.02 |
| 33 | — | — | ESIMS m/z 541 [M + H]$^+$ | $^1$H NMR (400 MHz, CDCl$_3$) δ 8.62 (d, J = 8.4 Hz, 1H), 8.33 (d, J = 5.4 Hz, 1H), 7.33-7.12 (m, 5H), 7.00 (d, J = 5.5 Hz, 1H), 5.12-4.94 (m, 2H), 4.08 (dd, J = 11.7, 7.5 Hz, 1H), 3.89 (s, 3H), 3.74 (dd, J = 10.2, 6.1 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1H), 3.59-3.51 (m, 1H), 3.48 (dd, J = 11.7, 7.4 Hz, 1H), 2.55 (dddd, J = 32.2, 13.8, 11.5, 5.4 Hz, 2H), 2.39 (s, 3H), 1.81-1.63 (m, 3H), 1.57-1.48 (m, 2H), 1.46 (d, J = 6.3 Hz, 3H), 1.42-1.21 (m, 3H), 1.12-1.04 (m, 1H), 0.90 (d, J = 5.0 Hz, 3H), 0.88 (d, J = 5.0 Hz, 3H) $^{13}$C NMR (101 MHz, CDCl$_3$) δ 171.88, 168.86, 162.70, 159.43, 146.77, 142.18, 141.22, 137.52, 128.52, 128.15, 125.99, 109.92, 76.24, 75.76, 71.66, 56.30, 51.50, 46.89, 42.52, 35.78, 32.28, 31.53, 29.18, 28.41, 22.83, 22.42, 20.74, 20.40 |
| 34 | — | — | HRMS-FAB (m/z) [M + H]$^+$ calcd for C$_{31}$H$_{43}$N$_2$O$_8$, 571.3019; found, 571.3015 | $^1$H NMR (400 MHz, CDCl$_3$) δ 8.45 (d, J = 8.1 Hz, 1H), 8.29 (d, J = 5.3 Hz, 1H), 7.34-7.12 (m, 5H), 6.96 (d, J = 5.4 Hz, 1H), 5.80-5.70 (m, 2H), 5.13-4.97 (m, 2H), 4.12 (dd, J = 11.7, 7.4 Hz, 1H), 3.91 (s, 3H), 3.76 (dd, J = 10.3, 6.1 Hz, 1H), 3.59-3.53 (m, 1H), 3.50 (dd, J = 11.7, 7.4 Hz, 1H), 2.67-2.45 (m, 2H), 2.07 (s, 3H), 1.85-1.62 (m, 3H), 1.59-1.49 (m, 2H), 1.48 (d, J = 6.3 Hz, 2H), 1.44-1.22 (m, 3H), 1.09 (ddt, J = 12.9, 11.3, 5.8 Hz, 1H), 0.90 (d, J = 4.7 Hz, 3H), 0.89 (d, J = 4.7 Hz, 3H) $^{13}$C NMR (101 MHz, CDCl$_3$) δ 171.97, 170.27, 163.21, 160.21, 145.81, 143.92, 142.27, 142.17, 128.52, 128.14, 125.99, 109.71, 89.41, 76.23, 75.78, 71.69, 56.21, 51.74, 46.90, 42.55, 35.80, 32.27, 31.53, 29.15, 28.40, 22.82, 22.42, 20.89, 20.39 |
| 35 | — | — | HRMS-FAB (m/z) [M + H]$^+$ calcd for C$_{33}$H$_{47}$N$_2$O$_8$, 599.3332; found, 599.3308 | $^1$H NMR (400 MHz, CDCl$_3$) δ 8.50 (d, J = 8.2 Hz, 1H), 8.28 (d, J = 5.4 Hz, 1H), 7.34-7.11 (m, 5H), 6.95 (d, J = 5.4 Hz, 1H), 5.85-5.71 (m, 2H), 5.13-4.97 (m, 2H), 4.11 (dd, J = 11.6, 7.4 Hz, 1H), 3.89 (s, 3H), 3.76 (dd, J = 10.3, 6.1 Hz, 1H), 3.55 (dd, J = 10.2, 1.6 Hz, 1H), 3.50 (dd, J = 11.7, 7.4 Hz, 1H), 2.67-2.44 (m, 3H), 1.80-1.67 (m, 2H), 1.58-1.50 (m, 2H), 1.48 (d, J = 6.3 Hz, 3H), 1.45-1.22 (m, 4H), 1.15 (d, J = 7.0 Hz, 6H), 1.13-1.02 (m, 1H), 0.90 (d, J = 4.7 Hz, 3H), 0.89 (d, J = 4.7 Hz, 3H) $^{13}$C NMR (101 MHz, CDCl$_3$) δ 176.24, 171.98, 163.18, 160.21, 145.66, 144.16, 142.18, 141.92, 128.52, 128.15, 125.99, 109.65, 89.78, 76.22, 75.71, 71.67, 56.15, 51.70, 46.89, 42.55, 35.81, 33.86, 32.27, 31.53, 29.15, 28.40, 22.82, 22.42, 20.39, 18.69 |
| 36 | — | — | HRMS-FAB (m/z) [M + H]$^+$ calcd for C$_{33}$H$_{47}$N$_2$O$_9$, 615.3281; found, 615.3277 | $^1$H NMR (400 MHz, CDCl$_3$) δ 8.46 (d, J = 8.1 Hz, 1H), 8.28 (d, J = 5.3 Hz, 1H), 7.34-7.13 (m, 5H), 6.96 (d, J = 5.4 Hz, 1H), 5.82 (s, 2H), 5.11-4.95 (m, 2H), 4.18-4.07 (m, 3H), 3.90 (s, 3H), 3.76 (dd, J = 10.3, 6.0 Hz, 1H), 3.59 (q, J = 7.0 Hz, 2H), 3.57-3.53 (m, 1H), 3.50 (dd, J = 11.7, 7.4 Hz, 1H), 2.67-2.45 (m, 2H), 1.83-1.63 (m, 3H), 1.58-1.49 (m, 2H), 1.48 (d, J = 6.3 Hz, 3H), 1.45-1.26 (m, 3H), 1.23 (t, J = 7.0 Hz, 3H), 1.17-1.02 (m, 1H), 0.90 (d, J = 4.8 Hz, 3H), 0.89 (d, J = 4.8 Hz, 3H) $^{13}$C NMR (101 MHz, CDCl$_3$) δ 171.94, 170.05, 163.16, 160.13, 145.85, 143.89, 142.16, 142.12, 128.52, 128.14, 125.99, 109.81, 89.43, 76.23, 75.75, 71.68, 67.80, 67.20, 56.24, 51.71, 46.91, 42.55, 35.82, 32.28, 31.53, 29.15, 28.40, 22.83, 22.42, 20.40, 15.02 |
| 37 | — | — | HRMS-FAB (m/z) [M + H]$^+$ calcd for | $^1$H NMR (400 MHz, CDCl$_3$) δ 8.54 (d, J = 8.4 Hz, 1H), 8.32 (d, J = 5.4 Hz, 1H), 7.33-7.15 (m, 5H), 6.99 (d, J = 5.4 Hz, 1H), 5.37-5.21 (m, 1H), 4.92 (ddd, J = 9.3, 8.3, 7.0 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
|  |  |  | C$_{29}$H$_{37}$N$_2$O$_7$, 525.2601; found, 525.2593 | 1H), 4.25 (dd, J = 11.5, 7.0 Hz, 1H), 3.90 (s, 3H), 3.83 (dd, J = 11.6, 6.6 Hz, 1H), 3.15 (td, J = 13.3, 12.6, 10.2 Hz, 3H), 2.72 (dd, J = 13.4, 4.9 Hz, 1H), 2.40 (s, 3H), 2.10-1.91 (m, 3H), 1.71-1.50 (m, 6H), 1.45 (d, J = 6.7 Hz, 3H), 1.34-1.15 (m, 1H), 0.97 (td, J = 7.7, 7.1, 4.4 Hz, 1H) $^{13}$C NMR (101 MHz, CDCl$_3$) δ 171.85, 168.90, 162.65, 159.45, 146.73, 141.26, 141.17, 137.51, 129.21, 128.18, 125.87, 109.89, 74.47, 71.96, 71.53, 56.30, 52.68, 51.63, 43.50, 43.39, 38.37, 31.34, 29.99, 24.86, 24.76, 22.25, 20.75 |
| 38 | — | — | HRMS-FAB (m/z) [M + H]$^+$ calcd for C$_{30}$H$_{39}$N$_2$O$_8$, 555.2706; found, 555.2701 | $^1$H NMR (400 MHz, CDCl$_3$) δ 8.37 (d, J = 8.1 Hz, 1H), 8.27 (d, J = 5.4 Hz, 1H), 7.34-7.14 (m, 5H), 6.95 (d, J = 5.4 Hz, 1H), 5.80-5.69 (m, 2H), 5.26 (qd, J = 6.6, 4.9 Hz, 1H), 4.95 (ddd, J = 9.4, 8.1, 7.0 Hz, 1H), 4.28 (dd, J = 11.5, 7.0 Hz, 1H), 3.90 (s, 3H), 3.84 (dd, J = 11.6, 6.6 Hz, 1H), 3.27-3.04 (m, 3H), 2.73 (dd, J = 13.4, 4.9 Hz, 1H), 2.08 (s, 3H), 2.07-1.89 (m, 3H), 1.71-1.48 (m, 6H), 1.46 (d, J = 6.7 Hz, 3H), 1.31-1.18 (m, 1H), 1.02-0.93 (m, 1H) $^{13}$C NMR (101 MHz, CDCl$_3$) δ 171.93, 170.28, 163.16, 160.24, 145.76, 143.97, 142.26, 141.14, 129.19, 128.19, 125.88, 109.69, 89.45, 74.49, 71.93, 71.59, 56.20, 52.60, 51.82, 43.48, 43.36, 38.37, 31.31, 29.97, 24.86, 24.75, 22.25, 20.90 |
| 39 | — | — | ESIMS m/z 583 [M + H]$^+$ | $^1$H NMR (400 MHz, CDCl$_3$) δ 8.42 (d, J = 8.1 Hz, 1H), 8.26 (d, J = 5.3 Hz, 1H), 7.37-7.14 (m, 5H), 6.94 (d, J = 5.4 Hz, 1H), 5.86-5.70 (m, 2H), 5.27 (qt, J = 6.6, 3.2 Hz, 1H), 4.95 (ddd, J = 9.4, 8.1, 7.0 Hz, 1H), 4.28 (dd, J = 11.5, 7.0 Hz, 1H), 3.89 (s, 3H), 3.88-3.80 (m, 1H), 3.26-3.08 (m, 3H), 2.73 (dd, J = 13.4, 4.9 Hz, 1H), 2.55 (hept, J = 7.0 Hz, 1H), 2.10-1.94 (m, 3H), 1.72-1.48 (m, 6H), 1.46 (d, J = 6.6 Hz, 3H), 1.33-1.23 (m, 1H), 1.15 (d, J = 7.0 Hz, 6H), 1.01-0.93 (m, 1H) $^{13}$C NMR (101 MHz, CDCl$_3$) δ 176.25, 171.94, 163.13, 160.23, 145.62, 144.19, 141.92, 141.15, 129.20, 128.18, 125.87, 109.63, 89.82, 74.48, 71.92, 71.56, 56.15, 52.60, 51.81, 43.49, 43.36, 38.36, 33.87, 31.32, 29.97, 24.86, 24.75, 22.25, 18.69 |
| 40 | — | — | ESIMS m/z 599 [M + H]$^+$ | $^1$H NMR (400 MHz, CDCl$_3$) δ 8.38 (d, J = 8.1 Hz, 1H), 8.26 (d, J = 5.4 Hz, 1H), 7.34-7.15 (m, 5H), 6.95 (d, J = 5.4 Hz, 1H), 5.86-5.76 (m, 2H), 5.27 (td, J = 6.7, 5.1 Hz, 1H), 4.93 (ddd, J = 9.3, 8.1, 7.0 Hz, 1H), 4.28 (dd, J = 11.6, 7.0 Hz, 1H), 4.11 (s, 2H), 3.90 (s, 3H), 3.84 (dd, J = 11.5, 6.5 Hz, 1H), 3.60 (q, J = 7.0 Hz, 2H), 3.25-3.08 (m, 3H), 2.73 (dd, J = 13.4, 4.9 Hz, 1H), 2.12-1.92 (m, 3H), 1.73-1.49 (m, 6H), 1.46 (d, J = 6.6 Hz, 3H), 1.35-1.26 (m, 1H), 1.24 (t, J = 7.0 Hz, 3H), 1.05-0.91 (m, 1H) $^{13}$C NMR (101 MHz, CDCl$_3$) δ 171.91, 170.08, 163.10, 160.14, 145.80, 143.93, 142.10, 141.13, 129.19, 128.18, 125.88, 109.78, 89.45, 74.50, 71.91, 71.56, 67.81, 67.21, 56.24, 52.59, 51.80, 43.47, 43.36, 38.36, 31.32, 29.95, 24.86, 24.75, 22.24, 15.02 |
| 41 | — | — | HRMS-FAB (m/z) [M + H]$^+$ calcd for C$_{33}$H$_{39}$N$_2$O$_7$, 575.2757; found, 575.2746 | $^1$H NMR (400 MHz, CDCl$_3$) δ 8.63-8.49 (m, 1H), 8.32 (d, J = 5.4 Hz, 1H), 7.32-7.08 (m, 10H), 6.99 (d, J = 5.5 Hz, 1H), 5.10-4.90 (m, 2H), 4.13 (dd, J = 11.7, 7.3 Hz, 1H), 3.88 (s, 3H), 3.81 (dd, J = 10.8, 5.5 Hz, 1H), 3.46-3.31 (m, 2H), 2.75-2.64 (m, 2H), 2.50 (t, J = 7.3 Hz, 2H), 2.38 (s, 3H), 2.02-1.94 (m, 1H), 1.74-1.66 (m, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1.59-1.38 (m, 3H), 1.31 (d, J = 6.4 Hz, 3H), 1.30-1.17 (m, 1H) $^{13}$C NMR (101 MHz, CDCl$_3$) δ 171.80, 168.90, 162.67, 159.44, 146.77, 142.34, 141.22, 140.28, 137.52, 128.98, 128.47, 128.37, 128.29, 126.15, 125.73, 109.92, 76.10, 73.79, 71.60, 56.31, 51.37, 49.02, 43.63, 38.38, 36.06, 31.24, 29.10, 21.41, 20.76 |
| 42 | — | — | HRMS-FAB (m/z) [M + H]$^+$ calcd for C$_{34}$H$_{41}$N$_2$O$_8$, 605.2863; found, 605.2859 | $^1$H NMR (400 MHz, CDCl$_3$) δ 8.40 (d, J = 8.1 Hz, 1H), 8.27 (d, J = 5.3 Hz, 1H), 7.32-7.09 (m, 10H), 6.94 (d, J = 5.4 Hz, 1H), 5.81-5.65 (m, 2H), 5.07-4.94 (m, 2H), 4.17 (dd, J = 11.7, 7.3 Hz, 1H), 3.90 (s, 3H), 3.83 (dd, J = 10.9, 5.3 Hz, 1H), 3.45-3.35 (m, 2H), 2.74-2.65 (m, 2H), 2.51 (t, J = 7.3 Hz, 2H), 2.06 (s, 3H), 2.03-1.96 (m, 1H), 1.75-1.67 (m, 1H), 1.59-1.40 (m, 3H), 1.32 (d, J = 6.4 Hz, 3H), 1.29-1.23 (m, 1H) $^{13}$C NMR (101 MHz, CDCl$_3$) δ 171.90, 170.30, 163.18, 160.22, 145.79, 143.95, 142.34, 142.25, 140.27, 128.97, 128.48, 128.37, 128.29, 126.16, 125.73, 109.72, 89.41, 76.14, 73.81, 71.60, 56.21, 51.59, 49.00, 43.64, 38.34, 36.06, 31.22, 29.11, 21.39, 20.90 |
| 43 | — | — | HRMS-FAB (m/z) [M + H]$^+$ calcd for C$_{36}$H$_{45}$N$_2$O$_8$, 633.3176; found, 633.3171 | $^1$H NMR (400 MHz, CDCl$_3$) δ 8.46 (d, J = 8.1 Hz, 1H), 8.27 (d, J = 5.3 Hz, 1H), 7.31-7.10 (m, 10H), 6.93 (d, J = 5.4 Hz, 1H), 5.84-5.72 (m, 2H), 5.08-4.94 (m, 2H), 4.17 (dd, J = 11.7, 7.4 Hz, 1H), 3.88 (s, 3H), 3.83 (dd, J = 10.9, 5.4 Hz, 1H), 3.44-3.33 (m, 2H), 2.69 (d, J = 6.0 Hz, 2H), 2.58-2.49 (m, 3H), 2.04-1.95 (m, 1H), 1.78-1.66 (m, 1H), 1.58-1.39 (m, 3H), 1.32 (d, J = 6.4 Hz, 3H), 1.30-1.25 (m, 1H), 1.14 (d, J = 7.0 Hz, 6H) $^{13}$C NMR (101 MHz, CDCl$_3$) δ 176.25, 171.91, 163.14, 160.21, 145.64, 144.17, 142.34, 141.90, 140.28, 128.97, 128.47, 128.37, 128.28, 126.15, 125.73, 109.66, 89.76, 76.11, 73.73, 71.58, 56.16, 51.55, 48.99, 43.64, 38.35, 36.05, 33.86, 31.20, 29.12, 21.38, 18.69 |
| 44 | — | (Neat) 3375, 2952, 1753, 1677, 1504, 1381, 1201 | HRMS-ESI (m/z) [M]$^+$ calcd for C$_{30}$H$_{40}$N$_2$O$_8$, 556.2785; found, 556.2790 | $^1$H NMR (400 MHz, CDCl$_3$) δ 8.41 (d, J = 8.1 Hz, 1H), 8.28 (d, J = 5.4 Hz, 1H), 7.33-7.26 (m, 2H), 7.22-7.17 (m, 3H), 6.95 (d, J = 5.4 Hz, 1H), 5.77-5.70 (m, 2H), 5.07-4.96 (m, 2H), 4.17 (dd, J = 11.6, 7.4 Hz, 1H), 3.91 (s, 3H), 3.83 (dd, J = 10.8, 5.0 Hz, 1H), 3.46-3.36 (m, 2H), 2.77-2.68 (m, 2H), 2.07 (s, 3H), 2.07-1.97 (m, 1H), 1.54-1.35 (m, 4H), 1.33 (d, J = 6.4 Hz, 3H), 1.31-1.19 (m, 1H), 1.11-0.96 (m, 1H), 0.83 (d, J = 6.6 Hz, 3H), 0.83 (d, J = 6.6 Hz, 3H) |
| 45 | — | (Neat) 3375, 2952, 1740, 1677, 1504, 1382, 1127 | ESIMS m/z 601.5 [M + H]$^+$ | $^1$H NMR (400 MHz, CDCl$_3$) δ 8.42 (d, J = 8.2 Hz, 1H), 8.28 (d, J = 5.4 Hz, 1H), 7.32-7.26 (m, 2H), 7.23-7.16 (m, 3H), 6.95 (d, J = 5.4 Hz, 1H), 5.83-5.79 (m, 2H), 5.06-4.95 (m, 2H), 4.16 (dd, J = 11.6, 7.3 Hz, 1H), 4.10 (s, 2H), 3.90 (s, 3H), 3.83 (dd, J = 10.7, 5.2 Hz, 1H), 3.59 (q, J = 7.0 Hz, 2H), 3.46-3.36 (m, 2H), 2.76-2.69 (m, 2H), 2.07-1.97 (m, 1H), 1.52-1.36 (m, 4H), 1.33 (d, J = 6.4 Hz, 3H), 1.30-1.21 (m, 1H), 1.23 (t, J = 7.0 Hz, 3H), 1.10-0.97 (m, 1H), 0.84 (d, J = 6.6 Hz, 3H), 0.83 (d, J = 6.5 Hz, 3H) |
| 46 | — | (Neat) 3376, 2953, 1771, 1678, 1507, | HRMS-ESI (m/z) [M]$^+$ calcd for C$_{29}$H$_{38}$N$_2$O$_7$, 526.2679; | $^1$H NMR (400 MHz, CDCl$_3$) δ 8.58 (d, J = 8.2 Hz, 1H), 8.33 (d, J = 5.4 Hz, 1H), 7.32-7.25 (m, 2H), 7.22-7.17 (m, 3H), 7.00 (d, J = 5.5 Hz, 1H), 5.06-4.93 (m, 2H), 4.13 (dd, J = 11.6, 7.4 Hz, 1H), 3.89 (s, 3H), 3.86-3.78 (m, 1H), 3.45-3.35 (m, 2H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | 1367, 1195 | found, 526.2674 | 2.75-2.69 (m, 2H), 2.38 (s, 3H), 2.05-1.95 (m, 1H), 1.52-1.36 (m, 4H), 1.32 (d, J = 6.4 Hz, 3H), 1.29-1.22 (m, 1H), 1.11-0.97 (m, 1H), 0.83 (d, J = 6.6 Hz, 3H), 0.83 (d, J = 6.5 Hz, 3H) |
| 47 | 88-90 | (Neat) 3372, 2936, 1754, 1678, 1505, 1381, 1204 | HRMS-ESI (m/z) [M]$^+$ calcd for C$_{32}$H$_{35}$ClN$_2$O$_8$, 610.2082; found, 610.2069 | $^1$H NMR (400 MHz, CDCl$_3$) δ 8.34 (d, J = 8.2 Hz, 1H), 8.27 (d, J = 5.4 Hz, 1H), 7.35-7.28 (m, 2H), 7.26-7.16 (m, 5H), 7.00-6.93 (m, 3H), 5.77-5.71 (m, 2H), 5.09-4.92 (m, 2H), 4.21 (dd, J = 11.6, 7.4 Hz, 1H), 3.91 (s, 3H), 3.60 (dd, J = 11.1, 5.6 Hz, 1H), 3.25-3.13 (m, 2H), 2.90-2.60 (m, 4H), 2.16-2.06 (m, 1H), 2.07 (s, 3H), 1.77-1.67 (m, 1H), 1.40 (d, J = 6.4 Hz, 3H) |
| 48 | — | — | ESIMS m/z 689 [M + H]$^+$ | $^1$H NMR (400 MHz, CDCl$_3$) δ 8.43 (d, J = 8.1 Hz, 1H), 8.26 (d, J = 5.4 Hz, 1H), 7.26-7.12 (m, 7H), 7.07-7.02 (m, 2H), 6.94 (d, J = 5.4 Hz, 1H), 5.80-5.72 (m, 2H), 5.11-5.03 (m, 1H), 5.01 (q, J = 8.4 Hz, 1H), 4.20 (dd, J = 11.6, 7.5 Hz, 1H), 3.88 (s, 3H), 3.71 (dd, J = 10.9, 6.4 Hz, 1H), 3.35-3.24 (m, 2H), 2.86-2.70 (m, 4H), 2.54 (hept, J = 7.0 Hz, 1H), 2.09 (p, J = 6.6 Hz, 1H), 1.87-1.74 (m, 1H), 1.39 (d, J = 6.5 Hz, 3H), 1.14 (d, J = 7.0 Hz, 6H) $^{13}$C NMR (101 MHz, CDCl$_3$) δ 176.19, 171.97, 163.10, 160.17, 147.61 (q, J = 1.6 Hz), 145.58, 144.14, 141.77, 139.88, 138.87, 130.27, 128.98, 128.26, 126.04, 124.36-116.45 (m), 121.00, 109.61, 89.70, 75.80, 71.65, 71.19, 56.09, 51.28, 48.60, 45.24, 38.38, 37.49, 33.80, 21.39, 18.62 $^{19}$F NMR (376 MHz, CDCl$_3$) δ −57.89 |
| 49 | — | — | ESIMS m/z 661 [M + H]$^+$ | $^1$H NMR (400 MHz, CDCl$_3$) δ 8.37 (d, J = 8.1 Hz, 1H), 8.27 (d, J = 5.4 Hz, 1H), 7.28-7.11 (m, 7H), 7.08-7.01 (m, 2H), 6.95 (d, J = 5.4 Hz, 1H), 5.77-5.69 (m, 2H), 5.11-4.97 (m, 2H), 4.21 (dd, J = 11.6, 7.5 Hz, 1H), 3.90 (s, 3H), 3.71 (dd, J = 10.8, 6.3 Hz, 1H), 3.36-3.24 (m, 2H), 2.89-2.69 (m, 4H), 2.15-2.02 (m, 4H), 1.86-1.75 (m, 1H), 1.39 (d, J = 6.5 Hz, 3H) $^{13}$C NMR (101 MHz, CDCl$_3$) δ 171.96, 170.22, 163.13, 160.17, 147.60 (q, J = 1.9 Hz), 145.71, 143.91, 142.10, 139.86, 138.85, 130.26, 128.97, 128.25, 126.04, 120.99, 124.69-116.49 (m), 109.67, 89.34, 75.81, 71.68, 71.19, 56.14, 51.30, 48.60, 45.22, 38.36, 37.49, 21.38, 20.82 $^{19}$F NMR (376 MHz, CDCl$_3$) δ −57.89 |
| 50 | — | — | ESIMS m/z 631 [M + H]$^+$ | $^1$H NMR (400 MHz, CDCl$_3$) δ 8.55 (d, J = 8.2 Hz, 1H), 8.33 (d, J = 5.5 Hz, 1H), 7.26-7.12 (m, 7H), 7.05-7.02 (m, 2H), 7.00 (d, J = 5.5 Hz, 1H), 5.13-5.01 (m, 1H), 4.99 (td, J = 8.5, 7.5 Hz, 1H), 4.18 (dd, J = 11.7, 7.5 Hz, 1H), 3.90 (s, 3H), 3.70 (dd, J = 10.8, 6.4 Hz, 1H), 3.28 (dd, J = 11.5, 8.8 Hz, 2H), 2.90-2.69 (m, 4H), 2.40 (s, 3H), 2.08 (p, J = 6.9 Hz, 1H), 1.81 (dtt, J = 11.4, 8.2, 3.8 Hz, 1H), 1.39 (d, J = 6.5 Hz, 3H) $^{13}$C NMR (101 MHz, CDCl$_3$) δ 171.90, 168.85, 162.64, 159.42, 147.64 (q, J = 1.9 Hz), 146.71, 141.14, 139.90, 138.87, 137.50, 130.30, 129.00, 128.27, 126.06, 121.02, 124.53-116.35 (m), 109.88, 75.79, 71.67, 71.22, 56.26, 51.11, 48.66, 45.24, 38.45, 37.56, 21.42, 20.70 $^{19}$F NMR (376 MHz, CDCl$_3$) δ −57.90 |
| 51 | — | — | ESIMS m/z 607 [M + H]$^+$ | $^1$H NMR (400 MHz, CDCl$_3$) δ 8.45 (d, J = 8.2 Hz, 1H), 8.27 (d, J = 5.4 Hz, 1H), 7.40-7.33 (m, 2H), 7.31-7.10 (m, 6H), 6.97-6.92 (m, 3H), 5.81 (s, 2H), 5.21 (dq, J = 10.4, 6.4 Hz, 1H), 5.16 (q, J = 7.7 Hz, 1H), 4.09 (s, 2H), 4.09 (dd, J = 10.9, 3.2 Hz, 1H), 3.89 (s, 3H), 3.72-3.64 (m, 2H), 3.59 (q, J = 7.0 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 2H), 3.46 (dd, J = 11.7, 7.6 Hz, 1H), 2.74 (t, J = 10.0 Hz, 1H), 2.50 (d, J = 11.4 Hz, 1H), 2.22-2.09 (m, 2H), 1.22 (t, J = 7.03 Hz, 3H), 1.05 (d, J = 6.3 Hz, 3H) $^{13}$C NMR (101 MHz, CDCl$_3$) δ 171.95, 169.97, 163.09, 160.06, 145.77, 143.82, 141.96, 141.72, 139.90, 128.92, 128.82, 128.52, 128.18, 127.11, 125.94, 109.75, 89.34, 76.84, 73.26, 71.19, 67.72, 67.12, 57.48, 56.17, 51.43, 37.06, 31.51, 20.86, 14.94 |
| 52 | 69-73 | — | ESIMS m/z 591 [M + H]$^+$ | $^1$H NMR (400 MHz, CDCl$_3$) δ 8.49 (d, J = 8.2 Hz, 1H), 8.29-8.24 (m, 1H), 7.39-7.33 (m, 2H), 7.30-7.09 (m, 6H), 6.97-6.91 (m, 3H), 5.81-5.72 (m, 2H), 5.25-5.12 (m, 2H), 4.08 (dd, J = 11.6, 7.8 Hz, 1H), 3.88 (s, 3H), 3.73-3.65 (m, 2H), 3.46 (dd, J = 11.7, 7.6 Hz, 1H), 2.73 (t, J = 10.0 Hz, 1H), 2.54 (p, J = 7.0 Hz, 1H), 2.50 (d, J = 11.7 Hz, 1H), 2.22-2.08 (m, 2H), 1.13 (d, J = 7.1 Hz, 6H), 1.05 (d, J = 6.3 Hz, 3H) $^{13}$C NMR (101 MHz, CDCl$_3$) δ 176.15, 171.98, 163.11, 160.14, 145.58, 144.09, 141.78, 141.75, 139.92, 128.91, 128.83, 128.55, 128.19, 127.10, 125.94, 109.60, 89.68, 76.82, 73.23, 71.19, 57.48, 56.09, 51.43, 47.27, 37.07, 33.79, 20.87, 18.61 |
| 53 | — | — | ESIMS m/z 563 [M + H]$^+$ | $^1$H NMR (400 MHz, CDCl$_3$) δ 8.43 (d, J = 8.2 Hz, 1H), 8.27 (d, J = 5.4 Hz, 1H), 7.36 (dd, J = 8.0, 6.8 Hz, 2H), 7.29-7.09 (m, 6H), 6.96-6.91 (m, 3H), 5.73 (d, J = 0.7 Hz, 2H), 5.25-5.13 (m, 2H), 4.08 (dd, J = 11.7, 7.8 Hz, 1H), 3.90 (s, 3H), 3.74-3.64 (m, 2H), 3.46 (dd, J = 11.7, 7.5 Hz, 1H), 2.73 (t, J = 10.1 Hz, 1H), 2.54-2.46 (m, 1H), 2.21-2.13 (m, 2H), 2.06 (s, 3H), 1.05 (d, J = 6.3 Hz, 3H) $^{13}$C NMR (101 MHz, CDCl$_3$) δ 171.98, 170.19, 163.15, 160.14, 145.73, 143.86, 142.13, 141.74, 139.91, 128.92, 128.83, 128.52, 128.19, 127.11, 125.94, 109.66, 89.33, 76.85, 73.30, 71.21, 57.50, 56.13, 51.48, 47.26, 37.08, 22.59, 20.81 |
| 54 | 99-103 | — | ESIMS m/z 533 [M + H]$^+$ | $^1$H NMR (400 MHz, CDCl$_3$) δ 8.62 (d, J = 8.5 Hz, 1H), 8.33 (d, J = 5.5 Hz, 1H), 7.40-7.33 (m, 2H), 7.30-7.10 (m, 6H), 7.00 (d, J = 5.5 Hz, 1H), 6.96-6.91 (m, 2H), 5.24-5.11 (m, 2H), 4.05 (dd, J = 11.7, 7.8 Hz, 1H), 3.89 (s, 3H), 3.72-3.65 (m, 2H), 3.45 (dd, J = 11.7, 7.5 Hz, 1H), 2.72 (t, J = 10.1 Hz, 1H), 2.54-2.46 (m, 1H), 2.40 (s, 3H), 2.20-2.07 (m, 2H), 1.05 (d, J = 6.3 Hz, 3H) $^{13}$C NMR (101 MHz, CDCl$_3$) δ 171.88, 168.79, 162.64, 159.36, 146.70, 141.74, 141.08, 139.90, 137.46, 128.92, 128.83, 128.53, 128.20, 127.11, 125.96, 109.86, 76.86, 73.28, 71.17, 57.49, 56.23, 51.23, 47.23, 37.10, 20.87, 20.67 |
| 55 | — | — | HRMS-FAB (m/z) [M + H]$^+$ calcd for C$_{32}$H$_{34}$F$_3$N$_2$O$_7$, 615.2318; found, 615.2321 | $^1$H NMR (400 MHz, CDCl$_3$) δ 8.53 (d, J = 8.8 Hz, 1H), 8.33 (d, J = 5.4 Hz, 1H), 7.51-7.09 (m, 9H), 7.00 (d, J = 5.5 Hz, 1H), 5.04 (dq, J = 8.2, 6.4 Hz, 1H), 4.94 (ddd, J = 9.0, 8.3, 7.4 Hz, 1H), 4.19 (dd, J = 11.6, 7.4 Hz, 1H), 3.90 (s, 3H), 3.58 (dd, J = 11.2, 5.6 Hz, 1H), 3.25-3.10 (m, 2H), 2.94-2.62 (m, 4H), 2.40 (s, 3H), 2.11 (dq, J = 8.5, 6.6 Hz, 1H), 1.82-1.71 (m, 1H), 1.42 (d, J = 6.4 Hz, 3H) $^{19}$F NMR (376 MHz, CDCl$_3$) δ −62.30 |
| 56 | — | — | HRMS-FAB (m/z) [M + H]$^+$ | $^1$H NMR (400 MHz, CDCl$_3$) δ 8.35 (d, J = 8.1 Hz, 1H), 8.27 (d, J = 5.4 Hz, 1H), 7.50-7.10 (m, 9H), 6.95 (d, J = 5.4 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | calcd for C$_{33}$H$_{36}$F$_3$N$_2$O$_8$, 645.2424; found, 645.2419 | 5.74 (d, J = 1.0 Hz, 2H), 5.05 (dq, J = 8.4, 6.4 Hz, 1H), 4.97 (dt, J = 9.0, 7.7 Hz, 1H), 4.23 (dd, J = 11.6, 7.4 Hz, 1H), 3.91 (s, 3H), 3.59 (dd, J = 11.2, 5.6 Hz, 1H), 3.28-3.10 (m, 2H), 2.99-2.64 (m, 4H), 2.16-2.10 (m, 1H), 2.07 (s, 3H), 1.80-1.72 (m, 1H), 1.43 (d, J = 6.4 Hz, 3H) $^{19}$F NMR (376 MHz, CDCl$_3$) δ −62.29 |
| 57 | — | — | HRMS-FAB (m/z) [M + H]$^+$ calcd for C$_{35}$H$_{40}$F$_3$N$_2$O$_8$, 673.2738; found, 673.2739 | $^1$H NMR (400 MHz, CDCl$_3$) δ 8.41 (d, J = 8.2 Hz, 1H), 8.27 (d, J = 5.3 Hz, 1H), 7.52-7.10 (m, 9H), 6.94 (d, J = 5.4 Hz, 1H), 5.79-5.75 (m, 2H), 5.05 (dq, J = 8.4, 6.3 Hz, 1H), 4.97 (ddd, J = 9.1, 8.1, 7.3 Hz, 1H), 4.22 (dd, J = 11.6, 7.4 Hz, 1H), 3.89 (s, 3H), 3.58 (dd, J = 11.2, 5.5 Hz, 1H), 3.29-3.09 (m, 2H), 2.95-2.63 (m, 4H), 2.55 (hept, J = 7.0 Hz, 1H), 2.20-2.04 (m, 1H), 1.82-1.70 (m, 1H), 1.43 (d, J = 6.4 Hz, 3H), 1.14 (d, J = 7.0 Hz, 6H) $^{19}$F NMR (376 MHz, CDCl$_3$) δ −62.30 |
| 58 | 158-161 | — | ESIMS m/z 695 [M + H]$^+$ | $^1$H NMR (400 MHz, CDCl$_3$) δ 8.36 (d, J = 8.1 Hz, 1H), 8.27 (d, J = 5.4 Hz, 1H), 7.25-7.13 (m, 6H), 6.98-6.92 (m, 3H), 5.76-5.71 (m, 2H), 5.11-4.99 (m, 1H), 5.02-4.95 (m, 1H), 4.21 (dd, J = 11.6, 7.5 Hz, 1H), 3.91 (s, 3H), 3.66 (dd, J = 11.0, 6.1 Hz, 1H), 3.31-3.19 (m, 2H), 2.85 (dd, J = 14.8, 6.9 Hz, 1H), 2.81-2.70 (m, 2H), 2.63 (dd, J = 13.7, 4.7 Hz, 1H), 2.13-2.02 (m, 4H), 1.78-1.68 (m, 1H), 1.39 (d, J = 6.5 Hz, 3H) $^{13}$C NMR (101 MHz, CDCl$_3$) δ 171.96, 170.25, 163.16, 160.21, 147.72 (q, J = 1.8 Hz), 145.74, 143.97, 142.12, 138.67, 138.37, 131.81, 130.37, 130.32, 121.09, 124.74-116.27 (m), 109.70, 89.38, 75.61, 71.24, 56.18, 51.32, 48.68, 45.27, 38.42, 36.88, 21.36, 20.85 $^{19}$F NMR (376 MHz, CDCl$_3$) δ −57.45−−58.63 (m) |
| 59 | 80-85 | — | ESIMS m/z 665 [M + H]$^+$ | $^1$H NMR (400 MHz, CDCl$_3$) δ 8.54 (d, J = 8.3 Hz, 1H), 8.33 (d, J = 5.4 Hz, 1H), 7.25-7.13 (m, 6H), 7.00 (d, J = 5.5 Hz, 1H), 6.94 (d, J = 8.4 Hz, 2H), 5.05 (p, J = 6.6 Hz, 1H), 4.96 (q, J = 8.4 Hz, 1H), 4.18 (dd, J = 11.7, 7.4 Hz, 1H), 3.90 (s, 3H), 3.65 (dd, J = 11.0, 6.1 Hz, 1H), 3.24 (dd, J = 11.6, 9.1 Hz, 2H), 2.85 (dd, J = 14.8, 7.0 Hz, 1H), 2.79-2.69 (m, 2H), 2.61 (dd, J = 13.6, 4.7 Hz, 1H), 2.40 (s, 3H), 2.06 (p, J = 6.7 Hz, 1H), 1.78-1.67 (m, 1H), 1.38 (d, J = 6.5 Hz, 3H) $^{13}$C NMR (101 MHz, CDCl$_3$) δ 171.86, 168.85, 162.66, 159.43, 147.84-147.60 (m), 146.72, 141.12, 138.67, 138.38, 137.52, 131.80, 130.37, 130.33, 128.35, 121.09, 124.96-116.24 (m), 109.91, 75.56, 71.24, 71.21, 56.28, 51.11, 48.72, 45.27, 38.47, 36.92, 21.37, 20.71 $^{19}$F NMR (376 MHz, CDCl$_3$) δ −57.91 |
| 60 | — | — | HRMS-FAB (m/z) [M + H]$^+$ calcd for C$_{31}$H$_{34}$FN$_2$O$_7$, 565.2350; found, 565.2350 | $^1$H NMR (400 MHz, CDCl$_3$) δ 8.54 (d, J = 8.4 Hz, 1H), 8.32 (d, J = 5.4 Hz, 1H), 7.32-6.91 (m, 10H), 5.14-4.92 (m, 2H), 4.17 (dd, J = 11.7, 7.6 Hz, 1H), 3.89 (s, 3H), 3.67 (dd, J = 10.8, 6.1 Hz, 1H), 3.33-3.15 (m, 2H), 2.86-2.69 (m, 4H), 2.39 (s, 3H), 2.12-2.00 (m, 1H), 1.84-1.74 (m, 1H), 1.37 (d, J = 6.4 Hz, 3H) $^{19}$F NMR (376 MHz, CDCl$_3$) δ −116.81 |
| 61 | — | — | HRMS-FAB (m/z) [M + H]$^+$ calcd for C$_{32}$H$_{36}$FN$_2$O$_8$, 595.2455; | $^1$H NMR (400 MHz, CDCl$_3$) δ 8.37 (d, J = 8.2 Hz, 1H), 8.27 (d, J = 5.4 Hz, 1H), 7.30-6.89 (m, 10H), 5.79-5.66 (m, 2H), 5.13-4.94 (m, 2H), 4.20 (dd, J = 11.6, 7.5 Hz, 1H), 3.90 (s, 3H), 3.68 (dd, J = 10.9, 6.1 Hz, 1H), 3.32-3.21 (m, 2H), 2.78 (dd, J = 23.0, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | found, 595.2453 | 6.9 Hz, 4H), 2.11-2.03 (m, 1H), 2.07 (s, 3H), 1.84-1.76 (m, 1H), 1.39 (d, J = 6.5 Hz, 3H) <br> $^{19}$F NMR (376 MHz, CDCl$_3$) δ −116.83 |
| 62 | — | — | HRMS-FAB (m/z) [M + H]$^+$ calcd for C$_{30}$H$_{41}$N$_2$O$_7$, 541.2914; found, 541.2910 | $^1$H NMR (400 MHz, CDCl$_3$) δ 8.57 (d, J = 8.0 Hz, 1H), 8.31 (d, J = 5.4 Hz, 1H), 7.32-7.14 (m, 5H), 6.99 (d, J = 5.5 Hz, 1H), 4.95 (q, J = 7.9 Hz, 1H), 4.83 (dq, J = 8.8, 6.4 Hz, 1H), 4.11 (dd, J = 11.7, 7.3 Hz, 1H), 3.88 (s, 3H), 3.75 (dd, J = 10.8, 5.7 Hz, 1H), 3.44-3.31 (m, 2H), 2.61 (t, J = 7.4 Hz, 2H), 2.38 (s, 3H), 1.86-1.76 (m, 1H), 1.58-1.40 (m, 4H), 1.36 (d, J = 6.4 Hz, 3H), 1.33-1.23 (m, 2H), 1.18 (dt, J = 14.7, 5.9 Hz, 1H), 1.02-0.98 (m, 1H), 0.85 (d, J = 6.7 Hz, 3H), 0.83 (d, J = 6.5 Hz, 3H) <br> $^{13}$C NMR (101 MHz, CDCl$_3$) δ 171.84, 168.87, 162.65, 159.42, 146.75, 142.28, 141.24, 137.50, 128.42, 128.28, 125.73, 109.90, 77.19, 74.33, 71.75, 56.29, 51.43, 45.85, 45.06, 41.70, 36.01, 30.63, 29.06, 26.95, 23.39, 22.53, 20.74, 20.69 |
| 63 | — | — | ESIMS m/z 495 [M + H]$^+$ | $^1$H NMR (400 MHz, CCCl3) d 8.40 (d, J = 8.0 Hz, 1H), 8.28 (d, J = 5.4 Hz, 1H), 6.95 (d, J = 5.5 Hz, 1H), 5.78-5.67 (m, 2H), 4.99 (q, J = 7.9 Hz, 1H), 4.86 (dq, J = 8.7, 6.4 Hz, 1H), 4.16 (dd, J = 11.6, 7.3 Hz, 1H), 3.91 (s, 3H), 3.77 (dd, J = 10.8, 5.6 Hz, 1H), 3.45-3.32 (m, 2H), 2.07 (s, 3H), 1.70-1.12 (m, 8H), 1.40 (d, J = 8.0 Hz, 3 H) 1.07 (ddd, J = 14.7, 8.2, 3.9 Hz, 1H), 0.91 (dd, J = 6.7, 4.7 Hz, 9H) <br> $^{13}$C NMR (101 MHz, CDCl$_3$) δ 171.98, 170.28, 163.15, 160.19, 145.76, 143.93, 142.29, 109.66, 89.42, 77.36, 74.30, 71.69, 56.19, 51.62, 45.79, 44.89, 41.71, 33.31, 27.00, 23.48, 22.59, 20.88, 20.70, 20.42, 14.32 |
| 64 | — | — | ESIMS m/z 465 [M + H]$^+$ | $^1$H NMR (400 MHz, CDCl$_3$) δ 8.57 (d, J = 7.5 Hz, 1H), 8.33 (d, J = 5.5 Hz, 1H), 7.00 (d, J = 5.5 Hz, 1H), 4.97 (q, J = 7.9 Hz, 1H), 4.85 (dq, J = 8.7, 6.5 Hz, 1H), 4.12 (dd, J = 11.7, 7.3 Hz, 1H), 3.90 (s, 3H), 3.76 (dd, J = 10.7, 5.7 Hz, 1H), 3.45-3.32 (m, 2H), 2.39 (s, 3H), 1.67-1.16 (m, 8H), 1.39 (d, J = 8.0 Hz, 3H), 1.07 (ddd, J = 14.7, 8.2, 3.9 Hz, 1H), 0.91 (dd, J = 6.8, 4.1 Hz, 9H) <br> $^{13}$C NMR (101 MHz, CDCl$_3$) δ 171.89, 168.88, 162.64, 159.41, 146.73, 141.28, 137.49, 109.85, 77.31, 74.33, 71.67, 56.29, 51.40, 45.81, 44.85, 41.72, 33.36, 26.99, 23.47, 22.61, 20.73, 20.40, 14.34 |
| 65 | — | — | ESIMS m/z 523 [M + H]$^+$ | $^1$H NMR (400 MHz, CDCl$_3$) δ 8.46 (d, J = 8.2 Hz, 1H), 8.27 (d, J = 5.4 Hz, 1H), 6.94 (d, J = 5.5 Hz, 1H), 5.90-5.54 (m, 2H), 4.99 (q, J = 8.0 Hz, 1H), 4.86 (dq, J = 8.8, 6.5 Hz, 1H), 4.15 (dd, J = 11.7, 7.3 Hz, 1H), 3.89 (s, 3H), 3.77 (dd, J = 10.9, 5.7 Hz, 1H), 3.39 (m, 2H), 2.54 (sep, J = 7.0 Hz, 1H), 1.70-1.16 (m, 8H), 1.40 (d, J = 8.0 Hz, 3H), 1.14 (d, J = 7.0 Hz, 6H), 1.07 (ddd, J = 14.7, 8.3, 3.9 Hz, 1H), 0.92 (m, 9H) <br> $^{13}$C NMR (101 MHz, CDCl$_3$) δ 176.24, 171.99, 163.12, 160.19, 145.61, 144.15, 141.95, 109.60, 89.78, 77.35, 74.26, 71.67, 56.14, 51.58, 45.78, 44.89, 41.72, 33.85, 33.29, 27.01, 23.49, 22.58, 20.70, 20.42, 18.67, 14.32 |
| 66 | 57-60 | — | ESIMS m/z 729 [M + H]$^+$ | $^1$H NMR (400 MHz, CDCl$_3$) δ 8.36 (d, J = 8.1 Hz, 1H), 8.27 (d, J = 5.3 Hz, 1H), 7.47 (d, J = 8.0 Hz, 2H), 7.24-7.19 (m, 2H), 7.18-7.09 (m, 4H), 6.95 (d, J = 5.4 Hz, 1H), 5.74 (dd, J = 6.2, 1.4 Hz, 2H), 5.12-5.01 (m, 1H), 5.02-4.94 (m, 1H), 4.22 (dd, J = 11.7, 7.4 Hz, 1H), 3.90 (s, 3H), 3.65 (dd, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | J = 11.1, 6.0 Hz, 1H), 3.30-3.19 (m, 2H), 2.91-2.81 (m, 2H), 2.75 (dd, J = 14.8, 6.2 Hz, 1H), 2.68 (dd, J = 13.7, 4.7 Hz, 1H), 2.13-2.04 (m, 4H), 1.84-1.71 (m, 1H), 1.41 (d, J = 6.5 Hz, 3H) ¹³C NMR (101 MHz, CDCl₃) δ 171.93, 170.23, 163.17, 160.21, 147.74 (q, J = 1.7 Hz), 145.74, 144.12 (q, J = 1.1 Hz), 143.96, 142.09, 138.55, 130.32, 129.33, 128.38 (q, J = 32.3 Hz), 125.13 (q, J = 3.8 Hz), 124.22 (q, J = 271.8 Hz), 121.10, 125.24-116.05 (m), 109.71, 89.34, 75.51, 71.26, 71.07, 56.16, 51.32, 48.75, 45.09, 38.48, 37.36, 21.34, 20.82 ¹⁹F NMR (376 MHz, CDCl₃) δ −57.94, −62.37 |
| 67 | 37-40 | — | ESIMS m/z 619 [M + H]⁺ | ¹H NMR (400 MHz, CDCl₃) δ 8.44 (d, J = 8.1 Hz, 1H), 8.28 (d, J = 5.4 Hz, 1H), 7.31-7.24 (m, 4H), 7.22-7.15 (m, 4H), 7.08-7.03 (m, 2H), 6.95 (d, J = 5.4 Hz, 1H), 5.78-5.69 (m, 2H), 5.10-4.94 (m, 2H), 4.11 (dd, J = 11.7, 7.4 Hz, 1H), 3.91 (s, 3H), 3.76 (dd, J = 10.4, 5.9 Hz, 1H), 3.54 (dd, J = 10.4, 1.4 Hz, 1H), 3.48 (dd, J = 11.7, 7.4 Hz, 1H), 2.70-2.39 (m, 4H), 2.07 (s, 3H), 1.86-1.37 (m, 11H) ¹³C NMR (101 MHz, CDCl₃) δ 171.88, 170.22, 163.15, 160.16, 145.74, 143.88, 142.21, 142.05, 141.99, 128.43, 128.34, 128.30, 128.10, 125.91, 125.75, 109.64, 89.38, 76.09, 75.25, 71.66, 56.15, 51.67, 46.84, 42.25, 36.02, 32.17, 31.47, 30.84, 28.25, 20.84, 20.31 |
| 68 | 41-45 | — | ESIMS m/z 541 [M + H]⁺ | ¹H NMR (400 MHz, CDCl₃) δ 8.37 (d, J = 8.1 Hz, 1H), 8.27 (d, J = 5.4 Hz, 1H), 7.31-7.23 (m, 2H), 7.21-7.15 (m, 3H), 6.94 (d, J = 5.4 Hz, 1H), 5.74-5.69 (m, 2H), 5.05-4.93 (m, 2H), 4.20 (dd, J = 11.6, 7.4 Hz, 1H), 3.99 (dd, J = 10.9, 5.3 Hz, 1H), 3.89 (s, 3H), 3.44 (d, J = 11.0 Hz, 1H), 3.34 (dd, J = 11.6, 8.7 Hz, 1H), 2.70 (d, J = 6.0 Hz, 2H), 2.05 (d, J = 2.4 Hz, 3H), 2.06-1.94 (m, 1H), 1.68-1.55 (m, 2H), 1.31 (d, J = 6.5 Hz, 3H), 1.12 (dd, J = 10.1, 7.6 Hz, 1H), 0.68 (qq, J = 7.6, 5.0 Hz, 1H), 0.43 (dddd, J = 9.2, 8.1, 5.3, 3.9 Hz, 1H), 0.35 (dddd, J = 9.2, 7.9, 5.3, 3.9 Hz, 1H), 0.07-0.00 (m, 1H), −0.12 (dtd, J = 9.3, 5.1, 3.9 Hz, 1H) ¹³C NMR (101 MHz, CDCl₃) δ 171.98, 170.19, 163.08, 160.13, 145.69, 143.87, 142.17, 140.19, 128.91, 128.35, 126.06, 109.63, 89.33, 76.14, 72.93, 71.18, 56.13, 51.30, 48.63, 44.37, 38.29, 36.34, 21.27, 20.81, 8.92, 5.38, 4.01 |
| 69 | 125-128 | — | ESIMS m/z 511 [M + H]⁺ | ¹H NMR (400 MHz, CDCl₃) δ 8.55 (d, J = 8.5 Hz, 1H), 8.33 (d, J = 5.4 Hz, 1H), 7.31-7.24 (m, 2H), 7.22-7.16 (m, 3H), 7.00 (d, J = 5.5 Hz, 1H), 5.05-4.92 (m, 2H), 4.17 (dd, J = 11.6, 7.5 Hz, 1H), 3.98 (dd, J = 10.8, 5.6 Hz, 1H), 3.89 (s, 3H), 3.45 (d, J = 11.5 Hz, 1H), 3.33 (dd, J = 11.6, 8.7 Hz, 1H), 2.70 (d, J = 6.0 Hz, 2H), 2.38 (s, 3H), 2.06-1.94 (m, 1H), 1.69-1.56 (m, 2H), 1.30 (d, J = 6.4 Hz, 3H), 1.12 (dd, J = 10.2, 7.6 Hz, 1H), 0.68 (qq, J = 7.6, 5.1 Hz, 1H), 0.49-0.30 (m, 2H), 0.07-−0.01 (m, 1H), −0.11 (dtd, J = 9.4, 5.2, 4.0 Hz, 1H) ¹³C NMR (101 MHz, CDCl₃) δ 171.92, 168.83, 162.59, 159.38, 146.69, 141.19, 140.23, 137.46, 128.95, 128.38, 126.09, 109.84, 76.15, 72.96, 71.21, 56.25, 51.12, 48.69, 44.39, 38.36, 36.41, 21.32, 20.69, 8.94, 5.40, 4.05 |
| 70 | 37-41 | — | ESIMS m/z 569 [M + H]⁺ | ¹H NMR (400 MHz, CDCl₃) δ 8.43 (d, J = 8.2 Hz, 1H), 8.26 (d, J = 5.3 Hz, 1H), 7.30-7.24 (m, 2H), 7.22-7.15 (m, 3H), 6.93 (d, J = 5.4 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1H), 5.78-5.72 (m, 2H), 5.06-4.93 (m, 2H), 4.20 (dd, J = 11.6, 7.5 Hz, 1H), 3.99 (dd, J = 10.8, 5.4 Hz, 1H), 3.88 (s, 3H), 3.44 (d, J = 11.6 Hz, 1H), 3.34 (dd, J = 11.6, 8.7 Hz, 1H), 2.70 (d, J = 6.0 Hz, 2H), 2.53 (hept, J = 7.0 Hz, 1H), 2.06-1.96 (m, 1H), 1.69-1.56 (m, 2H), 1.31 (d, J = 6.5 Hz, 3H), 1.15-1.11 (m, 7H), 0.75-0.62 (m, 1H), 0.43 (dddd, J = 9.2, 8.1, 5.4, 3.9 Hz, 1H), 0.35 (dddd, J = 9.2, 7.8, 5.3, 3.9 Hz, 1H), 0.08-0.00 (m, 1H), −0.11 (dtd, J = 9.3, 5.2, 4.0 Hz, 1H) $^{13}$C NMR (101 MHz, CDCl$_3$) δ 176.17, 172.00, 163.06, 160.13, 145.56, 144.11, 141.85, 140.21, 128.93, 128.37, 126.07, 109.58, 89.70, 76.14, 72.89, 71.18, 56.09, 51.28, 48.63, 44.39, 38.30, 36.34, 33.79, 21.28, 18.61, 8.94, 5.39, 4.02 |
| 71 | 54-59 | — | ESIMS m/z 611 [M + H]$^+$ | $^1$H NMR (400 MHz, CDCl$_3$) δ 8.32 (d, J = 8.1 Hz, 1H), 8.28-8.22 (m, 1H), 7.52 (d, J = 7.9 Hz, 2H), 7.32 (d, J = 8.1 Hz, 2H), 6.94 (d, J = 5.4 Hz, 1H), 5.71 (d, J = 1.0 Hz, 2H), 4.95 (dt, J = 8.9, 7.6 Hz, 1H), 4.87 (dq, J = 8.8, 6.4 Hz, 1H), 4.18 (dd, J = 11.6, 7.4 Hz, 1H), 3.89 (s, 3H), 3.53 (dd, J = 11.2, 5.1 Hz, 1H), 3.22-3.11 (m, 2H), 2.86 (dd, J = 13.7, 3.7 Hz, 1H), 2.75 (dd, J = 13.6, 11.2 Hz, 1H), 2.05 (s, 3H), 1.75-1.64 (m, 2H), 1.61-1.50 (m, 1H), 1.43 (d, J = 6.4 Hz, 3H), 1.41-1.34 (m, 1H), 1.16 (ddd, J = 14.6, 8.6, 3.5 Hz, 1H), 0.98-0.90 (m, 6H) $^{13}$C NMR (101 MHz, CDCl$_3$) δ 171.96, 170.20, 163.11, 160.15, 145.69, 144.84-144.60 (m), 143.88, 142.12, 129.40, 128.88-127.71 (m), 128.41-120.11 (m), 125.14 (q, J = 3.7 Hz), 109.65, 89.31, 76.78, 71.10, 70.82, 56.13, 51.17, 47.22, 45.54, 42.23, 36.74, 26.93, 23.47, 22.41, 20.80, 20.50 $^{19}$F NMR (376 MHz, CDCl$_3$) δ −62.30 |
| 72 | 75-79 | — | ESIMS m/z 581 [M + H]$^+$ | $^1$H NMR (400 MHz, CDCl$_3$) δ 8.50 (d, J = 8.4 Hz, 1H), 8.32 (d, J = 5.4 Hz, 1H), 7.53 (d, J = 7.8 Hz, 2H), 7.32 (d, J = 7.9 Hz, 2H), 6.99 (d, J = 5.5 Hz, 1H), 4.98-4.87 (m, 1H), 4.87 (dq, J = 8.6, 6.4 Hz, 1H), 4.15 (dd, J = 11.6, 7.5 Hz, 1H), 3.89 (s, 3H), 3.53 (dd, J = 11.2, 5.2 Hz, 1H), 3.20-3.11 (m, 2H), 2.86 (dd, J = 13.6, 3.7 Hz, 1H), 2.75 (dd, J = 13.6, 11.1 Hz, 1H), 2.39 (s, 3H), 1.77-1.63 (m, 2H), 1.63-1.49 (m, 1H), 1.43 (d, J = 6.5 Hz, 3H), 1.40-1.34 (m, 1H), 1.21-1.12 (m, 1H), 0.96 (d, J = 6.5 Hz, 3H), 0.93 (d, J = 6.6 Hz, 3H) $^{13}$C NMR (101 MHz, CDCl$_3$) δ 171.90, 168.84, 162.63, 159.41, 146.69, 144.76 (q, J = 1.1 Hz), 141.16, 137.48, 129.42, 128.33 (q, J = 32.3 Hz), 125.17 (q, J = 3.8 Hz), 128.46-120.07 (m), 109.87, 76.77, 71.15, 70.82, 56.26, 51.00, 47.22, 45.60, 42.30, 36.82, 26.92, 23.48, 22.47, 20.70, 20.57 $^{19}$F NMR (376 MHz, CDCl$_3$) δ −62.30 |
| 73 | — | (Neat) 3373, 2956, 1754, 1678, 1504, 1202 | HRMS-ESI (m/z) [M]$^+$ calcd for C$_{29}$H$_{37}$ClN$_2$O$_8$, 576.2238; found, 576.2242 | $^1$H NMR (400 MHz, CDCl$_3$) δ 8.33 (d, J = 8.1 Hz, 1H), 8.27 (d, J = 5.4 Hz, 1H), 7.26-7.21 (m, 2H), 7.17-7.12 (m, 2H), 6.95 (d, J = 5.6 Hz, 1H), 5.77-5.71 (m, 2H), 5.0-4.92 (m, 1H), 4.91-4.82 (m, 1H), 4.18 (dd, J = 11.6, 7.5 Hz, 1H), 3.91 (s, 3H), 3.55 (dd, J = 11.1, 5.1 Hz, 1H), 3.23-3.12 (m, 2H), 2.84-2.75 (m, 1H), 2.71-2.59 (m, 1H), 2.07 (s, 3H), 1.76-1.62 (m, 2H), 1.59-1.47 (m, 1H), 1.44 (d, J = 6.4 Hz, 3H), 1.42-1.34 (m, 1H), 1.21-1.12 (m, 1H), 0.96 (d, J = 6.5 Hz, 3H), 0.94 (d, J = 6.6 Hz, 3H) |
| 74 | — | (Neat) 3373, 2956, | HRMS-ESI (m/z) [M]$^+$ | $^1$H NMR (400 MHz, CDCl$_3$) δ 8.34 (d, J = 8.2 Hz, 1H), 8.27 (d, J = 5.4 Hz, 1H), 7.25-7.21 (m, 2H), 7.17-7.12 (m, 2H), 6.95 (d, J = 5.6 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | 1740, 1677, 1504, 1208 | calcd for C$_{31}$H$_{41}$ClN$_2$O$_9$, 620.2501; found, 620.2508 | 1H), 5.81 (s, 2H), 5.01-4.91 (m, 1H), 4.91-4.81 (m, 1H), 4.17 (dd, J = 11.9, 7.7 Hz, 1H), 4.10 (s, 2H), 3.90 (s, 3H), 3.59 (q, J = 7.0 Hz, 2H), 3.55 (dd, J = 12.0, 6.0 Hz, 1H), 3.22-3.11 (m, 2H), 2.84-2.75 (m, 1H), 2.70-2.59 (m, 1H), 1.77-1.62 (m, 2H), 1.57-1.44 (m, 1H), 1.44 (d, J = 6.4 Hz, 3H), 1.42-1.34 (m, 1H), 1.23 (t, J = 7.0 Hz, 3H), 1.20-1.12 (m, 1H), 0.97 (d, J = 6.5 Hz, 3H), 0.94 (d, J = 6.6 Hz, 3H) |
| 75 | — | (Neat) 3373, 2956, 1771, 1678, 1508, 1197 | HRMS-ESI (m/z) [M]$^+$ calcd for C$_{28}$H$_{35}$ClN$_2$O$_7$, 546.2133; found, 546.2141 | $^1$H NMR (400 MHz, CDCl$_3$) δ 8.50 (d, J = 8.8 Hz, 1H), 8.33 (d, J = 5.5 Hz, 1H), 7.26-7.21 (m, 2H), 7.16-7.11 (m, 2H), 7.00 (d, J = 5.4 Hz, 1H), 4.98-4.82 (m, 2H), 4.15 (dd, J = 11.6, 7.4 Hz, 1H), 3.91 (s, 3H), 3.54 (dd, J = 11.1, 5.2 Hz, 1H), 3.21-3.11 (m, 2H), 2.83-2.73 (m, 1H), 2.69-2.58 (m, 1H), 2.39 (s, 3H), 1.75-1.61 (m, 2H), 1.55-1.46 (m, 1H), 1.42 (d, J = 6.4 Hz, 3H), 1.42-1.34 (m, 1H), 1.20-1.12 (m, 1H), 0.96 (d, J = 6.5 Hz, 3H), 0.93 (d, J = 6.6 Hz, 3H) |
| 76 | — | (Neat) 3372, 2934, 1752, 1677, 1506, 1256, 1200 | HRMS-ESI m/z [M + H]$^+$ calcd for C$_{35}$H$_{40}$F$_3$N$_2$O$_9$, 689.2686; found, 689.2692 | $^1$H NMR (400 MHz, CDCl$_3$) δ 8.40 (d, J = 8.1 Hz, 1H), 8.28 (d, J = 5.3 Hz, 1H), 7.29-7.24 (m, 2H), 7.20-7.10 (m, 7H), 6.95 (d, J = 5.4 Hz, 1H), 5.75-5.71 (m, 2H), 5.06-4.96 (m, 2H), 4.17 (dd, J = 11.5, 7.2 Hz, 1H), 3.91 (s, 3H), 3.87-3.81 (m, 1H), 3.47-3.37 (m, 2H), 2.76-2.62 (m, 1H), 2.56-2.49 (m, 2H), 2.07 (s, 3H), 2.01-1.91 (m, 1H), 1.78-1.66 (m, 1H), 1.59-1.37 (m, 4H), 1.32 (d, J = 6.4 Hz, 3H) |
| 77 | — | (Neat) 3373, 2933, 1741, 1677, 1506, 1257, 1161 | HRMS-ESI (m/z) [M]$^+$ calcd for C$_{37}$H$_{43}$F$_3$N$_2$O$_{10}$, 732.2870; found, 732.2876 | $^1$H NMR (400 MHz, CDCl$_3$) δ 8.42 (d, J = 8.1 Hz, 1H), 8.28 (d, J = 5.4 Hz, 1H), 7.30-7.24 (m, 2H), 7.20-7.10 (m, 7H), 6.95 (d, J = 5.4 Hz, 1H), 5.83-5.79 (m, 2H), 5.06-4.95 (m, 2H), 4.19-4.13 (m, 1H), 4.10 (s, 2H), 3.91 (s, 3H), 3.84 (dd, J = 10.9, 5.5 Hz, 1H), 359 (q, J = 7.0 Hz, 2H), 3.46-3.36 (m, 2H), 2.77-2.61 (m, 2H), 2.56-2.49 (m, 2H), 2.01-1.91 (m, 1H), 1.79-1.64 (m, 1H), 1.59-1.37 (m, 4H), 1.32 (d, J = 6.5 Hz, 3H), 1.23 (t, J = 7.0 Hz, 3H) |
| 78 | — | — | ESIMS m/z 663 [M + H]$^+$ | $^1$H NMR (400 MHz, CDCl$_3$) δ 8.36 (d, J = 8.0 Hz, 1H), 8.28 (d, J = 5.3 Hz, 1H), 7.49 (d, J = 8.0 Hz, 2H), 7.17 (dd, J = 8.3, 4.8 Hz, 4H), 7.00 (t, J = 8.7 Hz, 2H), 6.96 (d, J = 5.4 Hz, 1H), 5.74 (m, 2H), 5.06 (m, 1H), 4.98 (q, J = 8.0 Hz, 1H), 4.23 (dd, J = 11.5, 7.4 Hz, 1H), 3.91 (s, 3H), 3.62 (dd, J = 11.2, 5.9 Hz, 1H), 3.23 (m, 2H), 2.91-2.80 (m, 2H), 2.72 (td, J = 13.8, 12.8, 5.1 Hz, 2H), 2.09 (m, 1H), 2.07 (s, 3H), 1.85-1.72 (m, 1H), 1.41 (d, J = 6.5 Hz, 3H) $^{13}$C NMR (101 MHz, CDCl$_3$) δ 171.99, 170.29, 163.21, 161.53 (d, J = 243 Hz), 160.25, 145.78, 144.28, 143.99 142.15, 135.40 (d, J = 3 Hz), 130.45 (d, J = 7 Hz), 129.40, 128.40 (q, J = 32 Hz), 125.18 (q, J = 4 Hz), 124.29 (q, J = 272 Hz), 115.45, (d, J = 21 Hz), 109.74, 89.40, 75.58, 71.23, 70.99, 56.21, 51.33, 48.93, 45.21, 38.19, 37.34, 21.36, 20.88 $^{19}$F NMR (376 MHz, CDCl$_3$) δ −62.33, −116.48 |
| 79 | — | — | ESIMS m/z 633 [M + H]$^+$ | $^1$H NMR (400 MHz, CDCl$_3$) δ 8.53 (d, J = 7.9 Hz, 1H), 8.33 (d, J = 5.4 Hz, 1H), 7.48 (d, J = 8.0 Hz, 2H), 7.16 (apparent (app) t, J = 7.1 Hz, 4H), 7.02 (d, J = 3.6 Hz, 1H), 7.00 (app t, J = 8.4 Hz, 2H), 5.05 (p, J = 6.5 Hz, 1H), 4.95 (m, 1H), 4.19 (dd, J = 11.5, 7.4 Hz, 1H), 3.91 (s, 3H), 3.61 (dd, J = 11.2, 5.9 Hz, 1H), 3.21 (app t, J = 10.5 Hz, 2H), 2.89-2.79 (m, 2H), 2.70 (td, J = 14.4, 13.3, 5.2 Hz, 2H), 2.40 (s, 3H), 2.06 (m, 1H), 1.78 (dd, J = 10.6, 5.8 Hz, 1H), 1.40 (d, J = 6.5 Hz, 3H) |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
|  |  |  |  | $^{13}$C NMR (101 MHz, CDCl$_3$) δ 171.89, 168.89, 162.7, 161.53 (d, J = 243 Hz), 159.46, 146.75, 144.28, 141.15 137.55, 135.39 (d, J = 3 Hz), 130.46 (d, J = 7 Hz), 129.40, 128.38 (q, J = 32 Hz), 125.17 (q, J = 4 Hz), 124.28 (q, J = 279 Hz), 115.45, (d, J = 21 Hz), 109.94, 75.52, 71.25, 70.94, 56.31, 51.13, 48.98, 45.21, 38.25, 37.39, 21.37, 20.74 $^{19}$F NMR (376 MHz, CDCl$_3$) δ −62.34, −116.49 |
| 80 | — | — | ESIMS m/z 691 [M + H]$^+$ | $^1$H NMR (400 MHz, CDCl$_3$) δ 8.41 (d, J = 8.2 Hz, 1H), 8.27 (d, J = 5.4 Hz, 1H), 7.49 (d, J = 8.0 Hz, 2H), 7.17 (app dd, J = 8.4, 4.9 Hz, 4H), 7.01 (app t, J = 8.7 Hz, 2H), 6.95 (d, J = 5.4 Hz, 1H), 5.77 (m, 2H), 5.06 (m, 1H), 4.98 (q, J = 8.0 Hz, 1H), 4.22 (dd, J = 11.7, 7.4 Hz, 1H), 3.89 (s, 3H), 3.62 (dd, J = 11.2, 5.8 Hz, 1H), 3.29-3.13 (m, 2H), 2.91-2.79 (m, 2H), 2.72 (td, J = 14.0, 12.9, 5.1 Hz, 2H), 2.55 (p, J = 7.0 Hz, 1H), 2.08 (m, 1H), 1.78 (m, 1H), 1.41 (d, J = 8 Hz, 3H), 1.14 (d, J = 7.0 Hz, 6H) $^{13}$C NMR (101 MHz, CDCl$_3$) δ 176.26, 171.99, 163.18, 161.53 (d, J = 243 Hz), 160.23, 145.64, 144.29, 144.22, 141.8, 135.40 (d, J = 4 Hz), 130.45 (d, J = 7 Hz), 129.40, 128.39 (q, J = 32 Hz), 125.18 (q, J = 3 Hz), 124.28 (q, J = 270 Hz), 115.45, (d, J = 21 Hz), 109.68, 89.76, 75.56, 71.22, 70.94, 56.16, 51.30, 48.93, 45.22, 38.20, 37.34, 33.86 21.36, 18.68 $^{19}$F NMR (376 MHz, CDCl$_3$) δ −62.33, −116.49 |
| 81 | — | (Neat) 3373, 2934, 1771, 1678, 1507, 1257 | HRMS-ESI (m/z) [M]$^+$ calcd for C$_{34}$H$_{37}$F$_3$N$_2$O$_8$, 658.2502; found, 658.2510 | $^1$H NMR (400 MHz, CDCl$_3$) δ 8.58 (d, J = 9.1 Hz, 1H), 8.34 (d, J = 5.4 Hz, 1H), 7.29-7.24 (m, 2H), 7.20-7.10 (m, 7H), 7.01 (d, J = 5.5 Hz, 1H), 5.07-4.93 (m, 2H), 4.18-4.09 (m, 1H), 3.91 (s, 3H), 3.83 (dd, J = 10.9, 5.5 Hz, 1H), 3.47-3.34 (m, 2H), 2.76-2.62 (m, 2H), 2.56-2.50 (m, 2H), 2.39 (s, 3H), 1.99-1.90 (m, 1H), 1.78-1.64 (m, 1H), 1.59-1.36 (m, 4H), 1.30 (d, J = 6.5 Hz, 3H) |
| 82 | — | — | HRMS-FAB (m/z) [M + H]$^+$ calcd for C$_{32}$H$_{45}$N$_2$O$_8$, 585.3176; found, 585.3180 | $^1$H NMR (400 MHz, CDCl$_3$) δ 8.39 (d, J = 8.2 Hz, 1H), 8.26 (d, J = 5.4 Hz, 1H), 7.33-7.17 (m, 5H), 6.93 (d, J = 5.4 Hz, 1H), 5.78-5.71 (m, 2H), 5.06-4.94 (m, 1H), 4.90 (dq, J = 9.0, 6.2 Hz, 1H), 4.13 (dd, J = 11.6, 7.6 Hz, 1H), 3.88 (s, 3H), 3.66-3.55 (m, 1H), 3.29-3.19 (m, 2H), 2.86-2.77 (m, 1H), 2.60-2.48 (m, 2H), 1.74-1.68 (m, 2H), 1.57-1.47 (m, 2H), 1.42 (d, J = 6.2 Hz, 3H), 1.30-1.24 (m, 2H), 1.14 (d, J = 7.0 Hz, 6H), 0.92 (d, J = 6.6 Hz, 6H), 0.86-0.82 (m, 1H) $^{13}$C NMR (101 MHz, CDCl$_3$) δ 176.22, 172.19, 163.13, 160.19, 145.62, 144.14, 141.90, 140.43, 129.13, 128.35, 126.03, 109.64, 89.75, 76.08, 72.08, 70.87, 56.14, 51.18, 47.18, 44.28, 37.15, 33.93, 33.86, 28.76, 27.59, 22.62, 22.49, 20.13, 18.68 |
| 83 | — | — | HRMS-FAB (m/z) [M + H]$^+$ calcd for C$_{32}$H$_{45}$N$_2$O$_9$, 601.3125; found, 601.3127 | $^1$H NMR (400 MHz, CDCl$_3$) δ 8.34 (d, J = 8.3 Hz, 1H), 8.26 (d, J = 5.3 Hz, 1H), 7.33-7.17 (m, 5H), 6.94 (d, J = 5.3 Hz, 1H), 5.80 (s, 2H), 4.98 (q, J = 8.2 Hz, 1H), 4.90 (dq, J = 8.9, 6.1 Hz, 1H), 4.19-4.10 (m, 1H), 4.09 (s, 2H), 3.90 (s, 3H), 3.65-3.55 (m, 3H), 3.23 (dd, J = 11.4, 8.9 Hz, 2H), 2.87-2.79 (m, 1H), 2.56 (dd, J = 14.6, 9.3 Hz, 1H), 1.75-1.68 (m, 2H), 1.59-1.47 (m, 2H), 1.42 (d, J = 6.2 Hz, 3H), 1.31-1.11 (m, 2H), 1.23 (t, J = 7.0 Hz, 3H), 0.92 (d, J = 6.6 Hz, 6H), 0.87-0.82 (m, 1H) $^{13}$C NMR (101 MHz, CDCl$_3$) δ 172.16, 170.06, 163.11, 160.11, 145.79, 143.89, 142.10, 140.42, 129.13, 128.35, 126.03, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 109.78, 89.41, 76.11, 72.09, 70.87, 67.80, 67.20, 56.23, 51.18, 47.18, 44.28, 37.15, 33.92, 28.76, 27.58, 22.61, 22.49, 20.13, 15.01 |
| 84 | — | — | HRMS-FAB (m/z) [M + H]$^+$ calcd for C$_{29}$H$_{39}$N$_2$O$_7$, 527.2757; found, 527.2756 | $^1$H NMR (400 MHz, CDCl$_3$) δ 8.50 (d, J = 8.4 Hz, 1H), 8.32 (d, J = 5.4 Hz, 1H), 7.34-7.16 (m, 5H), 6.99 (d, J = 5.4 Hz, 1H), 4.97 (td, J = 8.6, 7.6 Hz, 1H), 4.89 (dq, J = 9.1, 6.3 Hz, 1H), 4.09 (dd, J = 11.6, 7.6 Hz, 1H), 3.89 (s, 3H), 3.57 (dd, J = 10.5, 4.7 Hz, 1H), 3.30-3.17 (m, 2H), 2.83-2.76 (m, 1H), 2.60-2.49 (m, 1H), 2.39 (s, 3H), 1.70 (h, J = 3.7 Hz, 2H), 1.57-1.48 (m, 2H), 1.41 (d, J = 6.3 Hz, 3H), 1.30-1.13 (m, 2H), 0.92 (d, J = 6.6 Hz, 6H), 0.84 (dd, J = 6.6, 3.7 Hz, 3H) $^{13}$C NMR (101 MHz, CDCl$_3$) δ 172.10, 168.87, 162.65, 159.43, 146.73, 141.23, 140.42, 137.50, 129.14, 128.36, 126.04, 109.89, 76.12, 72.12, 70.87, 56.30, 51.00, 47.20, 44.26, 37.18, 33.93, 28.76, 27.60, 22.62, 22.50, 20.75, 20.14 |
| 85 | — | — | HRMS-FAB (m/z) [M + H]$^+$ calcd for C$_{30}$H$_{41}$N$_2$O$_8$, 557.2863; found, 557.2864 | $^1$H NMR (400 MHz, CDCl$_3$) δ 8.33 (d, J = 8.2 Hz, 1H), 8.27 (d, J = 5.2 Hz, 1H), 7.33-7.16 (m, 5H), 6.95 (d, J = 5.2 Hz, 1H), 5.76-5.72 (m, 2H), 5.07-4.94 (m, 1H), 4.90 (dq, J = 9.1, 6.1 Hz, 1H), 4.13 (dd, J = 11.6, 7.6 Hz, 1H), 3.90 (s, 3H), 3.59 (dd, J = 10.5, 4.5 Hz, 1H), 3.24 (dd, J = 11.6, 9.0 Hz, 2H), 2.86-2.80 (m, 1H), 2.55 (dd, J = 14.1, 9.7 Hz, 1H), 2.06 (s, 3H), 1.74-1.70 (m, 2H), 1.58-1.48 (m, 2H), 1.42 (d, J = 6.2 Hz, 3H), 1.35-1.22 (m, 2H), 0.92 (d, J = 6.6 Hz, 6H), 0.87-0.82 (m, 1H) $^{13}$C NMR (101 MHz, CDCl$_3$) δ 172.18, 170.27, 163.16, 160.19, 145.75, 143.91, 142.25, 140.42, 129.13, 128.35, 126.03, 109.71, 89.39, 76.11, 72.15, 70.88, 56.20, 51.22, 47.20, 44.27, 37.15, 33.92, 28.76, 27.58, 22.61, 22.49, 20.88, 20.14 |
| 86 | 85-89 | — | ESIMS m/z 559 [M + H]$^+$ | $^1$H NMR (400 MHz, CDCl$_3$) δ 8.52 (d, J = 8.4 Hz, 1H), 8.30 (d, J = 5.4 Hz, 1H), 7.25-7.17 (m, 4H), 6.99 (d, J = 5.4 Hz, 1H), 5.24 (qd, J = 6.7, 5.0 Hz, 1H), 4.88 (ddd, J = 9.7, 8.4, 7.0 Hz, 1H), 4.24 (dd, J = 11.6, 7.0 Hz, 1H), 3.89 (s, 3H), 3.78 (dd, J = 11.7, 6.5 Hz, 1H), 3.20-3.06 (m, 3H), 2.65 (dd, J = 13.3, 4.7 Hz, 1H), 2.39 (s, 3H), 2.07-1.89 (m, 3H), 1.70-1.46 (m, 6H), 1.42 (d, J = 6.7 Hz, 3H), 1.36-1.13 (m, 1H), 1.00-0.90 (m, 1H) $^{13}$C NMR (101 MHz, CDCl$_3$) δ 171.72, 168.80, 162.58, 159.37, 146.65, 141.12, 139.57, 137.43, 131.46, 130.52, 128.18, 109.84, 74.20, 71.91, 71.09, 56.23, 52.67, 51.52, 43.34, 37.61, 31.27, 29.82, 24.74, 24.67, 22.15, 20.68 |
| 87 | 73-77 | — | ESIMS m/z 587 [M + H]$^+$ | $^1$H NMR (400 MHz, CDCl$_3$) δ 8.48 (d, J = 8.4 Hz, 1H), 8.29 (d, J = 5.4 Hz, 1H), 7.25-7.17 (m, 4H), 6.97 (d, J = 5.4 Hz, 1H), 5.23 (qd, J = 6.6, 4.9 Hz, 1H), 4.89 (ddd, J = 9.7, 8.4, 7.0 Hz, 1H), 4.23 (dd, J = 11.6, 7.0 Hz, 1H), 3.86 (s, 3H), 3.78 (dd, J = 11.7, 6.5 Hz, 1H), 3.18-3.06 (m, 3H), 2.94 (dq, J = 14.0, 7.0 Hz, 1H), 2.65 (dd, J = 13.4, 4.8 Hz, 1H), 2.08-1.89 (m, 3H), 1.71-1.46 (m, 6H), 1.42 (d, J = 6.6 Hz, 3H), 1.36 (d, J = 7.0 Hz, 6H), 1.30-1.14 (m, 1H), 1.02-0.90 (m, 1H) $^{13}$C NMR (101 MHz, CDCl$_3$) δ 174.58, 171.78, 162.53, 159.34, 146.54, 141.47, 139.57, 137.59, 131.44, 130.51, 128.17, 109.68, 77.32, 74.13, 71.93, 71.04, 56.23, 52.62, 51.43, 43.32, 37.58, 33.89, 31.26, 29.79, 24.74, 24.66, 22.13, 18.74 |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| 88 | 56-60 | — | ESIMS m/z 589 [M + H]⁺ | ¹H NMR (400 MHz, CDCl₃) δ 8.34 (d, J = 8.1 Hz, 1H), 8.28-8.20 (m, 1H), 7.25-7.16 (m, 4H), 6.93 (d, J = 5.4 Hz, 1H), 5.76-5.68 (m, 2H), 5.23 (qd, J = 6.6, 5.0 Hz, 1H), 4.90 (ddd, J = 9.7, 8.2, 7.0 Hz, 1H), 4.26 (dd, J = 11.5, 7.0 Hz, 1H), 3.89 (s, 3H), 3.78 (dd, J = 11.7, 6.5 Hz, 1H), 3.20-3.07 (m, 3H), 2.66 (dd, J = 13.4, 4.8 Hz, 1H), 2.06 (s, 3H), 2.04-1.89 (m, 3H), 1.70-1.46 (m, 6H), 1.42 (d, J = 6.7 Hz, 3H), 1.32-1.14 (m, 1H), 1.00-0.89 (m, 1H) ¹³C NMR (101 MHz, CDCl₃) δ 171.78, 170.17, 163.06, 160.14, 145.66, 143.86, 142.09, 139.52, 131.43, 130.49, 128.16, 109.62, 89.31, 74.20, 71.84, 71.11, 56.11, 52.55, 51.68, 43.29, 37.58, 31.22, 29.77, 24.72, 24.63, 22.12, 20.79 |
| 89 | 54-58 | — | ESIMS m/z 617 [M + H]⁺ | ¹H NMR (400 MHz, CDCl₃) δ 8.40 (d, J = 8.1 Hz, 1H), 8.24 (d, J = 5.3 Hz, 1H), 7.25-7.17 (m, 4H), 6.93 (d, J = 5.4 Hz, 1H), 5.78-5.72 (m, 2H), 5.23 (qd, J = 6.6, 5.0 Hz, 1H), 4.90 (ddd, J = 9.7, 8.1, 7.0 Hz, 1H), 4.26 (dd, J = 11.6, 7.0 Hz, 1H), 3.87 (s, 3H), 3.78 (dd, J = 11.7, 6.5 Hz, 1H), 3.19-3.06 (m, 3H), 2.66 (dd, J = 13.4, 4.8 Hz, 1H), 2.53 (hept, J = 7.0 Hz, 1H), 2.09-1.90 (m, 3H), 1.72-1.46 (m, 6H), 1.43 (d, J = 6.7 Hz, 3H), 1.31-1.16 (m, 1H), 1.13 (d, J = 7.0 Hz, 6H), 1.02-0.89 (m, 1H) ¹³C NMR (101 MHz, CDCl₃) δ 176.15, 171.81, 163.05, 160.14, 145.55, 144.11, 141.77, 139.54, 131.45, 130.51, 128.17, 109.57, 89.71, 74.20, 71.86, 71.11, 56.07, 52.58, 51.69, 43.31, 37.59, 33.77, 31.24, 29.79, 24.74, 24.65, 22.14, 18.60 |
| 90 | 52-55 | — | ESIMS m/z 633 [M + H]⁺ | ¹H NMR (400 MHz, CDCl₃) δ 8.35 (d, J = 8.1 Hz, 1H), 8.24 (d, J = 5.4 Hz, 1H), 7.25-7.17 (m, 4H), 6.93 (d, J = 5.4 Hz, 1H), 5.83-5.77 (m, 2H), 5.23 (qd, J = 6.6, 5.0 Hz, 1H), 4.88 (ddd, J = 9.6, 8.1, 7.0 Hz, 1H), 4.25 (dd, J = 11.6, 7.0 Hz, 1H), 4.09 (s, 2H), 3.88 (s, 3H), 3.77 (dd, J = 11.7, 6.5 Hz, 1H), 3.58 (q, J = 7.0 Hz, 2H), 3.19-3.05 (m, 3H), 2.66 (dd, J = 13.4, 4.7 Hz, 1H), 2.09-1.88 (m, 3H), 1.72-1.45 (m, 6H), 1.43 (d, J = 6.7 Hz, 3H), 1.32-1.14 (m, 4H), 1.00-0.89 (m, 1H) ¹³C NMR (101 MHz, CDCl₃) δ 171.77, 169.97, 163.01, 160.06, 145.71, 143.84, 141.95, 139.52, 131.44, 130.50, 128.16, 109.72, 89.34, 74.21, 71.84, 71.11, 67.71, 67.10, 56.15, 52.56, 51.67, 43.30, 37.58, 31.23, 29.77, 24.73, 24.63, 22.13, 14.92 |
| 91 | 57-62 | — | ESIMS m/z 505 [M + H]⁺ | ¹H NMR (400 MHz, CDCl₃) δ 8.51 (d, J = 8.4 Hz, 1H), 8.29 (d, J = 5.4 Hz, 1H), 6.98 (d, J = 5.5 Hz, 1H), 5.24 (qd, J = 6.7, 4.4 Hz, 1H), 4.84 (td, J = 9.0, 7.0 Hz, 1H), 4.18 (dd, J = 11.6, 7.0 Hz, 1H), 4.00 (dd, J = 11.6, 6.8 Hz, 1H), 3.87 (s, 3H), 3.27-3.17 (m, 2H), 2.37 (s, 3H), 2.07-1.88 (m, 2H), 1.70-1.44 (m, 10H), 1.36 (dd, J = 13.2, 6.7 Hz, 4H), 1.12 (dddd, J = 17.8, 9.5, 4.4, 2.1 Hz, 2H), 0.91 (dd, J = 25.5, 6.6 Hz, 7H) ¹³C NMR (101 MHz, CDCl₃) δ 171.67, 168.80, 162.52, 159.34, 146.63, 141.19, 137.40, 109.79, 74.32, 72.66, 71.95, 56.21, 52.99, 51.56, 43.33, 41.70, 37.28, 31.29, 30.30, 30.05, 28.32, 24.80, 24.72, 22.70, 22.58, 22.38, 20.66 |
| 92 | 47-51 | — | ESIMS m/z 533 [M + H]⁺ | ¹H NMR (400 MHz, CDCl₃) δ 8.46 (d, J = 8.4 Hz, 1H), 8.28 (d, J = 5.4 Hz, 1H), 6.96 (d, J = 5.5 Hz, 1H), 5.24 (qd, J = 6.7, 4.5 Hz, 1H), 4.85 (td, J = 9.0, 7.0 Hz, 1H), 4.18 (dd, J = 11.6, 7.0 Hz, 1H), 4.00 (dd, J = 11.6, 6.8 Hz, 1H), 3.86 (s, 3H), |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | 3.26-3.13 (m, 2H), 2.91 (dp, J = 14.0, 7.0 Hz, 1H), 2.07-1.89 (m, 2H), 1.86-1.73 (m, 1H), 1.70-1.43 (m, 9H), 1.43-1.28 (m, 10H), 1.23-1.04 (m, 2H), 0.99-0.83 (m, 7H) ¹³C NMR (101 MHz, CDCl₃) δ 174.60, 171.75, 162.49, 159.32, 146.53, 141.57, 137.56, 109.63, 74.26, 72.61, 71.98, 56.22, 52.95, 51.49, 43.32, 41.71, 37.29, 33.88, 31.30, 30.27, 30.02, 28.32, 24.80, 24.72, 22.69, 22.60, 22.36, 18.73 |
| 93 | 47-53 | — | ESIMS m/z 535 [M + H]⁺ | ¹H NMR (400 MHz, CDCl₃) δ 8.33 (d, J = 8.1 Hz, 1H), 8.23 (d, J = 5.3 Hz, 1H), 6.92 (d, J = 5.4 Hz, 1H), 5.74-5.65 (m, 2H), 5.23 (qd, J = 6.7, 4.4 Hz, 1H), 4.86 (ddd, J = 9.1, 8.1, 7.0 Hz, 1H), 4.21 (dd, J = 11.5, 7.0 Hz, 1H), 3.99 (dd, J = 11.5, 6.7 Hz, 1H), 3.87 (s, 3H), 3.27-3.17 (m, 2H), 2.04 (s, 3H), 2.02-1.89 (m, 2H), 1.85-1.72 (m, 1H), 1.71-1.42 (m, 9H), 1.43-1.31 (m, 4H), 1.20-1.03 (m, 2H), 0.99-0.81 (m, 7H) ¹³C NMR (101 MHz, CDCl₃) δ 171.74, 170.16, 163.01, 160.11, 145.64, 143.83, 142.18, 109.58, 89.31, 74.32, 72.71, 71.90, 56.10, 52.87, 51.74, 43.28, 41.68, 37.25, 31.24, 30.23, 30.01, 28.28, 24.76, 24.70, 22.66, 22.57, 22.34, 20.78 |
| 94 | — | — | ESIMS m/z 563 [M + H]⁺ | ¹H NMR (400 MHz, CDCl₃) δ 8.40 (d, J = 8.1 Hz, 1H), 8.24 (d, J = 5.3 Hz, 1H), 6.92 (d, J = 5.4 Hz, 1H), 5.74 (d, J = 3.3 Hz, 2H), 5.28-5.21 (m, 1H), 4.87 (q, J = 8.1 Hz, 1H), 4.22 (dd, J = 11.5, 7.0 Hz, 1H), 4.01 (dd, J = 11.6, 6.7 Hz, 1H), 3.87 (s, 3H), 3.29-3.18 (m, 2H), 2.53 (hept, J = 7.0 Hz, 1H), 2.07-1.89 (m, 2H), 1.86-1.72 (m, 1H), 1.70-1.44 (m, 9H), 1.44-1.31 (m, 4H), 1.22-1.05 (m, 8H), 1.00-0.84 (m, 7H) ¹³C NMR (101 MHz, CDCl₃) δ 176.19, 171.81, 163.03, 160.15, 145.55, 144.12, 141.89, 109.54, 89.76, 74.36, 72.73, 71.95, 56.09, 52.94, 51.77, 43.34, 41.73, 37.31, 33.80, 31.30, 30.30, 30.05, 28.33, 24.81, 24.75, 22.71, 22.62, 22.39, 18.63 |
| 95 | 70-74 | — | ESIMS m/z 563 [M + H]⁺ | ¹H NMR (400 MHz, CDCl₃) δ 8.52 (d, J = 8.3 Hz, 1H), 8.34 (d, J = 5.4 Hz, 1H), 7.35-7.22 (m, 4H), 7.21-7.14 (m, 3H), 7.02-6.96 (m, 2H), 6.94-6.88 (m, 2H), 5.24 (dq, J = 9.1, 6.3 Hz, 1H), 4.97 (td, J = 8.8, 7.5 Hz, 1H), 4.20 (dd, J = 11.6, 7.5 Hz, 1H), 4.13 (dd, J = 10.0, 2.6 Hz, 1H), 4.08 (dd, J = 9.9, 3.0 Hz, 1H), 3.90 (s, 3H), 3.63 (dd, J = 10.9, 4.7 Hz, 1H), 3.26 (d, J = 10.8 Hz, 1H), 3.22 (dd, J = 11.6, 9.0 Hz, 1H), 2.83 (dd, J = 13.6, 4.0 Hz, 1H), 2.72 (dd, J = 13.6, 10.7 Hz, 1H), 2.41 (s, 3H), 2.16-2.07 (m, 1H), 2.00 (tt, J = 9.0, 2.8 Hz, 1H), 1.46 (d, J = 6.3 Hz, 3H) ¹³C NMR (101 MHz, CDCl₃) δ 172.19, 168.83, 162.62, 159.37, 158.68, 146.69, 141.13, 139.89, 137.45, 129.47, 129.11, 128.29, 126.04, 121.06, 114.38, 109.86, 74.84, 71.34, 70.86, 66.52, 56.24, 50.91, 47.96, 41.89, 36.94, 20.69, 19.60 |
| 96 | 56-61 | — | ESIMS m/z 593 [M + H]⁺ | ¹H NMR (400 MHz, CDCl₃) δ 8.34 (d, J = 8.3 Hz, 1H), 8.28 (d, J = 5.3 Hz, 1H), 7.35-7.21 (m, 4H), 7.20-7.13 (m, 3H), 7.02-6.93 (m, 2H), 6.94-6.88 (m, 2H), 5.77-5.71 (m, 2H), 5.24 (dq, J = 9.2, 6.3 Hz, 1H), 4.99 (dt, J = 8.9, 7.7 Hz, 1H), 4.23 (dd, J = 11.6, 7.5 Hz, 1H), 4.13 (dd, J = 9.9, 2.5 Hz, 1H), 4.09 (dd, J = 9.9, 2.9 Hz, 1H), 3.91 (s, 3H), 3.64 (dd, J = 11.0, 4.6 Hz, 1H), 3.30-3.18 (m, 2H), 2.84 (dd, J = 13.6, 4.0 Hz, 1H), 2.72 (dd, J = 13.6, 10.6 Hz, 1H), 2.16-2.05 (m, 4H), 2.01 (tt, J = 9.0, 2.7 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1.46 (d, J = 6.3 Hz, 3H)<br>$^{13}$C NMR (101 MHz, CDCl$_3$) δ 172.28, 170.21, 163.12, 160.14, 158.67, 145.71, 143.87, 142.14, 139.89, 129.47, 129.10, 128.28, 126.04, 121.06, 114.38, 109.65, 89.31, 74.83, 71.38, 70.86, 66.50, 56.14, 51.12, 47.96, 41.89, 36.91, 20.83, 19.60 |
| 97 | — | — | ESIMS<br>m/z 515<br>[M + H]$^+$ | $^1$H NMR (400 MHz, CDCl$_3$) δ 8.52 (d, J = 8.1 Hz, 1H), 8.30 (d, J = 5.4 Hz, 1H), 7.31 (app t, J = 7.3 Hz, 2H), 7.23 (m, 1H), 7.18-7.08 (m, 2H), 6.96 (d, J = 5.4 Hz, 1H), 5.75 (app q, J = 1.3 Hz, 2H), 5.18 (m, 2H), 4.14 (dd, J = 12.2, 7.3 Hz, 1H), 3.92 (s, 3H), 3.79 (m, 2H), 3.65 (dd, J = 11.7, 6.8 Hz, 1H), 2.65 (t, J = 10.4 Hz, 1H), 2.08 (s, 3H), 1.87 (m, 1H), 1.32 (m, 1H), 1.07-0.91 (m, 3H), 1.02 (d, J = 6.3 Hz, 3H), 0.66 (t, J = 7.0 Hz, 3H)<br>$^{13}$C NMR (101 MHz, CDCl$_3$) δ 171.84, 170.27, 163.25, 160.22, 145.82, 143.93, 142.25, 141.93, 128.71, 128.50, 126.85, 109.71, 89.44, 77.20, 76.26, 71.89, 57.09, 56.21, 51.95, 44.82, 33.58, 20.89, 20.83, 19.18, 14.12 |
| 98 | — | — | ESIMS<br>m/z 485<br>[M + H]$^+$ | $^1$H NMR (400 MHz, CDCl$_3$) δ 8.70 (d, J = 7.4 Hz, 1H), 8.35 (d, J = 5.4 Hz, 1H), 7.31 (app t, J = 7.8 Hz, 2H), 7.23 (app t, J = 7.3 Hz, 1H), 7.15-7.10 (m, 2H), 7.01 (d, J = 5.5 Hz, 1H), 5.27-5.06 (m, 2H), 4.10 (dd, J = 11.8, 7.6 Hz, 1H), 3.91 (s, 3H), 3.82-3.72 (m, 2H), 3.62 (dd, J = 11.7, 6.8 Hz, 1H), 2.63 (t, J = 10.4 Hz, 1H), 2.40 (s, 3H), 1.86 (m, 1H), 1.31 (m, 1H), 1.05-0.89 (m, 3H), 1.01 (d, J = 6.3 Hz, 3H), 0.66 (t, J = 7.0 Hz, 3H)<br>$^{13}$C NMR (101 MHz, CDCl$_3$) δ 171.75, 168.87, 162.73, 159.43, 146.78, 141.94, 141.20, 137.54, 128.71, 128.51, 126.85, 109.90, 77.22, 76.22, 71.83, 57.08, 56.30, 51.68, 44.80, 33.58, 20.82, 20.74, 19.16, 14.12 |
| 99 | — | — | ESIMS<br>m/z 543<br>[M + H]$^+$ | $^1$H NMR (400 MHz, CDCl$_3$) δ 8.58 (d, J = 8.1 Hz, 1H), 8.29 (d, J = 5.4 Hz, 1H), 7.31 (app t, J = 7.8 Hz, 2H), 7.23 (app t, J = 7.3 Hz, 1H), 7.15-7.10 (m, 2H), 6.95 (d, J = 5.4 Hz, 1H), 5.87-5.73 (m, 2H), 5.30-5.09 (m, 2H), 4.13 (dd, J = 11.7, 7.6 Hz, 1H), 3.90 (s, 3H), 3.83-3.73 (m, 2H), 3.64 (dd, J = 11.7, 6.9 Hz, 1H), 2.65 (t, J = 10.4 Hz, 1H), 2.55 (p, J = 7.0 Hz, 1H), 1.87 (m, 1H), 1.32 (m, 1H), 1.15 (d, J = 7.0 Hz, 6H), 1.07-0.91 (m, 3H), 1.02 (d, J = 6.3 Hz, 3H), 0.66 (t, J = 7.0 Hz, 3H)<br>$^{13}$C NMR (101 MHz, CDCl$_3$) δ 176.23, 171.85, 163.21, 160.22, 145.67, 144.17, 141.95, 141.90, 128.71, 128.50, 126.85, 109.65, 89.80, 77.18, 76.18, 71.86, 57.08, 56.15, 51.91, 44.82, 33.86, 33.57, 20.83, 19.19, 18.69, 14.12 |
| 100 | — | — | HRMS-FAB (m/z)<br>[M + H]$^+$<br>calcd for C$_{27}$H$_{33}$N$_2$O$_7$, 497.2288;<br>found, 497.2289 | $^1$H NMR (400 MHz, CDCl$_3$) δ 8.68 (d, J = 8.7 Hz, 1H), 8.35 (d, J = 5.4 Hz, 1H), 7.35-7.19 (m, 3H), 7.15-7.06 (m, 2H), 7.02 (d, J = 5.5 Hz, 1H), 5.25-5.09 (m, 2H), 4.20-4.08 (m, 1H), 3.99-3.81 (m, 2H), 3.91 (s, 3H), 3.59 (dd, J = 11.6, 7.3 Hz, 1H), 2.65 (t, J = 10.3 Hz, 1H), 2.40 (s, 3H), 2.04-1.95 (m, 1H), 1.16-1.06 (m, 1H), 1.00 (d, J = 6.3 Hz, 3H), 0.72 (ddd, J = 14.2, 7.9, 3.0 Hz, 1H), 0.56 (dtt, J = 10.6, 5.2, 2.6 Hz, 1H), 0.38 (dddd, J = 9.5, 8.0, 5.6, 4.0 Hz, 1H), 0.32-0.20 (m, 1H), −0.14 (dtd, J = 9.1, 5.3, 4.2 Hz, 1H), −0.36 (dtd, J = 9.3, 5.3, 4.2 Hz, 1H)<br>$^{13}$C NMR (101 MHz, CDCl$_3$) δ 171.93, 168.85, 162.72, 159.43, 146.78, 141.84, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 141.17, 137.53, 128.71, 128.53, 126.89, 109.93, 77.20, 75.33, 71.47, 57.02, 56.31, 51.47, 46.17, 36.09, 20.88, 20.74, 8.30, 5.60, 4.03 |
| 101 | — | — | HRMS-FAB (m/z) [M + H]$^+$ calcd for C$_{28}$H$_{35}$N$_2$O$_8$, 527.2393; found, 527.2389 | $^1$H NMR (400 MHz, CDCl$_3$) δ 8.50 (d, J = 8.0 Hz, 1H), 8.30 (d, J = 5.4 Hz, 1H), 7.35-7.19 (m, 3H), 7.15-7.08 (m, 2H), 6.97 (d, J = 5.4 Hz, 1H), 5.75 (d, J = 1.1 Hz, 2H), 5.27-5.11 (m, 2H), 4.18 (dd, J = 11.7, 7.7 Hz, 1H), 4.02-3.86 (m, 5H), 3.62 (dd, J = 11.7, 7.3 Hz, 1H), 2.66 (t, J = 10.4 Hz, 1H), 2.08 (s, 3H), 2.06-1.97 (m, 1H), 1.19-1.08 (m, 1H), 1.01 (d, J = 6.3 Hz, 3H), 0.80-0.66 (m, 1H), 0.65-0.50 (m, 1H), 0.45-0.32 (m, 1H), 0.31-0.21 (m, 1H), −0.14 (dtd, J = 9.1, 5.4, 4.2 Hz, 1H), −0.36 (dtd, J = 9.3, 5.3, 4.2 Hz, 1H) $^{13}$C NMR (101 MHz, CDCl$_3$) δ 172.03, 170.26, 163.25, 160.23, 145.81, 143.94, 142.24, 141.84, 128.71, 128.54, 126.89, 109.72, 89.43, 77.18, 75.37, 71.53, 57.04, 56.21, 51.73, 46.20, 36.08, 20.88, 8.32, 5.61, 4.02 |
| 102 | — | — | HRMS-FAB (m/z) [M + H]$^+$ calcd for C$_{30}$H$_{39}$N$_2$O$_8$, 555.2706; found, 555.2713 | $^1$H NMR (400 MHz, CDCl$_3$) δ 8.56 (d, J = 8.3 Hz, 1H), 8.29 (d, J = 5.3 Hz, 1H), 7.37-7.17 (m, 3H), 7.16-7.06 (m, 2H), 6.96 (d, J = 5.4 Hz, 1H), 5.85-5.69 (m, 2H), 5.26-5.09 (m, 2H), 4.17 (dd, J = 11.7, 7.7 Hz, 1H), 4.00-3.85 (m, 2H), 3.90 (s, 3H), 3.61 (dd, J = 11.6, 7.4 Hz, 1H), 2.66 (t, J = 10.4 Hz, 1H), 2.56 (h, J = 7.0 Hz, 1H), 2.07-1.94 (m, 1H), 1.15 (d, J = 7.0 Hz, 6H), 1.13-1.07 (m, 1H), 1.01 (d, J = 6.3 Hz, 3H), 0.73 (ddd, J = 14.2, 7.7, 3.0 Hz, 1H), 0.65-0.50 (m, 1H), 0.44-0.32 (m, 1H), 0.31-0.22 (m, 1H), −0.14 (dtd, J = 9.2, 5.2, 4.2 Hz, 1H), −0.36 (dtd, J = 9.3, 5.3, 4.2 Hz, 1H) $^{13}$C NMR (101 MHz, CDCl$_3$) δ 176.22, 172.03, 163.21, 160.22, 145.67, 144.17, 141.89, 141.85, 128.70, 128.55, 126.89, 109.67, 89.78, 77.16, 75.30, 71.52, 57.03, 56.15, 51.69, 46.20, 36.07, 33.86, 20.88, 18.68, 8.33, 5.60, 4.01 |
| 103 | — | — | HRMS-FAB (m/z) [M + H]$^+$ calcd for C$_{30}$H$_{39}$N$_2$O$_9$, 571.2655; found, 571.2654 | $^1$H NMR (400 MHz, CDCl$_3$) δ 8.51 (d, J = 8.1 Hz, 1H), 8.29 (d, J = 5.4 Hz, 1H), 7.35-7.20 (m, 3H), 7.16-7.08 (m, 2H), 6.97 (d, J = 5.4 Hz, 1H), 5.83 (s, 2H), 5.25-5.11 (m, 2H), 4.17 (dd, J = 11.7, 7.7 Hz, 1H), 4.11 (s, 2H), 3.99-3.83 (m, 2H), 3.91 (s, 3H), 3.67-3.54 (m, 3H), 2.66 (t, J = 10.4 Hz, 1H), 2.10-1.94 (m, 1H), 1.24 (t, J = 7.0 Hz, 3H), 1.18-1.08 (m, 1H), 1.02 (d, J = 6.3 Hz, 3H), 0.73 (ddd, J = 14.2, 7.7, 3.0 Hz, 1H), 0.65-0.50 (m, 1H), 0.45-0.32 (m, 1H), 0.33-0.22 (m, 1H), −0.08--0.19 (m, 1H), −0.36 (dtd, J = 9.2, 5.3, 4.2 Hz, 1H) $^{13}$C NMR (101 MHz, CDCl$_3$) δ 172.00, 170.04, 163.20, 160.15, 145.86, 143.90, 142.09, 141.84, 128.71, 128.54, 126.90, 109.82, 89.44, 77.18, 75.36, 71.53, 67.80, 67.19, 57.05, 56.24, 51.70, 46.20, 36.08, 20.87, 15.01, 8.33, 5.60, 4.01 |
| 104 | — | — | ESIMS m/z 559 [M + H]$^+$ | $^1$H NMR (400 MHz, CDCl$_3$) δ 8.38 (d, J = 8.1 Hz, 1H), 8.29 (d, J = 5.4 Hz, 1H), 7.15 (dd, J = 8.6, 5.4 Hz, 2H), 7.03-6.91 (m, 3H), 5.74 (m, 2H), 5.07-4.93 (m, 2H), 4.21 (dd, J = 11.6, 7.5 Hz, 1H), 4.00 (dd, J = 10.8, 5.7 Hz, 1H), 3.91 (s, 3H), 3.47 (d, J = 10.8 Hz, 1H), 3.37 (dd, J = 11.6, 8.6 Hz, 1H), 2.69 (m, 2H), 2.07 (s, 3H), 1.97 (m, 1H), 1.63 (d, J = 10.4 Hz, 2H), 1.31 (d, J = 6.5 Hz, 3H), 1.15 (m, 1H), 0.68 (m, 1H), 0.49-0.35 (m, 2H), 0.06 (app dq, J = 8.9, 5.0 Hz, 1H), −0.09 (app dq, J = 9.4, 5.1 Hz, 1H) $^{13}$C NMR (101 MHz, CDCl$_3$) δ 172.05, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | 170.30, 163.17, 161.38 (d, J = 245.4 Hz), 160.22, 145.76, 143.98, 142.24, 135.95 (d, J = 3.2 Hz), 130.33 (d, J = 7.8 Hz), 115.33, 115.22 (d, J = 21.1), 109.69, 89.43, 75.90, 73.05, 71.32, 56.20, 51.40, 48.96, 44.37, 37.76, 36.52, 21.43, 20.89, 9.04, 5.45, 4.15 $^{19}$F NMR (376 MHz, CDCl$_3$) δ −117.09 |
| 105 | — | — | ESIMS m/z 529 [M + H]⁺ | $^1$H NMR (400 MHz, CDCl$_3$) δ 8.56 (d, J = 7.9 Hz, 1H), 8.34 (d, J = 5.4 Hz, 1H), 7.15 (app dd, J = 8.6, 5.4 Hz, 2H), 7.06-6.90 (m, 3H), 4.99 (m, 2H), 4.17 (dd, J = 11.6, 7.5 Hz, 1H), 3.99 (dd, J = 10.8, 5.9 Hz, 1H), 3.90 (s, 3H), 3.47 (d, J = 10.7 Hz, 1H), 3.35 (dd, J = 11.6, 8.6 Hz, 1H), 2.69 (app t, J = 5.8 Hz, 2H), 2.39 (s, 3H), 1.95 (m, 1H), 1.59 (m, 2H), 1.30 (d, J = 6.5 Hz, 3H), 1.13 (m, 1H), 0.67 (m, 1H), 0.48-0.34 (m, 2H), 0.04 (app dt, J = 8.9, 4.6 Hz, 1H), −0.10 (app dq, J = 9.3, 5.0 Hz, 1H) $^{13}$C NMR (101 MHz, CDCl$_3$) δ 171.95, 168.89, 162.66, 161.36 (d, J = 244.3 Hz), 159.44, 146.74, 141.21, 137.52, 135.96 (d, J = 3.3 Hz), 130.34 (d, J = 7.7 Hz), 115.21 (d, J = 21.3 Hz), 109.91, 75.86, 73.04, 71.31, 56.30, 51.19, 48.99, 44.35, 37.80, 36.54, 21.44, 20.73, 9.03, 5.43, 4.15 $^{19}$F NMR (376 MHz, CDCl$_3$) δ −117.09 |
| 106 | 55-60 | — | ESIMS m/z 603 [M + H]⁺ | $^1$NMR (400 MHz, CDCl$_3$) δ 8.51 (d, J = 8.7 Hz, 1H), 8.32 (d, J = 5.4 Hz, 1H), 7.26-7.18 (m, 4H), 6.99 (d, J = 5.4 Hz, 1H), 5.24 (qd, J = 6.6, 5.0 Hz, 1H), 4.88 (ddd, J = 9.7, 8.3, 7.0 Hz, 1H), 4.23 (dd, J = 11.6, 7.0 Hz, 1H), 3.90 (s, 3H), 3.82 (t, J = 6.6 Hz, 2H), 3.78 (dd, J = 11.7, 6.5 Hz, 1H), 3.42 (s, 3H), 3.18-3.07 (m, 3H), 2.99 (t, J = 6.6 Hz, 2H), 2.66 (dd, J = 13.4, 4.7 Hz, 1H), 2.09-1.89 (m, 3H), 1.72-1.46 (m, 6H), 1.43 (d, J = 6.6 Hz, 3H), 1.34-1.14 (m, 2H) $^{13}$C NMR (101 MHz, CDCl$_3$) δ 171.80, 169.40, 162.57, 159.43, 146.75, 141.24, 139.61, 137.35, 131.52, 130.57, 128.24, 109.86, 74.24, 71.96, 71.13, 67.55, 58.79, 56.31, 52.68, 51.53, 43.39, 37.65, 34.62, 31.32, 29.86, 24.79, 24.71, 22.20 |
| 107 | 57-62 | — | ESIMS m/z 517 [M + H]⁺ | $^1$H NMR (400 MHz, CDCl$_3$) δ 8.56 (d, J = 7.8 Hz, 1H), 8.31 (d, J = 5.4 Hz, 1H), 7.18-7.11 (m, 2H), 7.01-6.93 (m, 3H), 5.04-4.93 (m, 2H), 4.13 (dd, J = 11.6, 7.4 Hz, 1H), 3.88 (s, 3H), 3.82 (dd, J = 10.8, 5.9 Hz, 1H), 3.44-3.33 (m, 2H), 2.68 (d, J = 6.1 Hz, 2H), 2.37 (s, 3H), 1.92 (p, J = 6.9 Hz, 1H), 1.57-1.11 (m, 8H), 0.83 (t, J = 7.0 Hz, 3H) $^{13}$C NMR (101 MHz, CDCl$_3$) δ 171.74, 168.78, 162.57, 161.25 (d, J = 244.2 Hz), 159.34, 146.66, 141.09, 137.42, 136.00 (d, J = 3.3 Hz), 130.22 (d, J = 7.7 Hz), 115.12 (d, J = 21.1 Hz), 109.84, 75.80, 73.52, 71.40, 56.21, 51.20, 49.11, 43.32, 37.68, 33.74, 29.63, 21.39, 20.64, 20.28, 14.16 $^{19}$F NMR (376 MHz, CDCl$_3$) δ −117.12 |
| 108 | 38-43 | — | ESIMS m/z 547 [M + H]⁺ | $^1$H NMR (400 MHz, CDCl$_3$) δ 8.39 (d, J = 8.1 Hz, 1H), 8.26 (d, J = 5.4 Hz, 1H), 7.19-7.10 (m, 2H), 7.01-6.91 (m, 3H), 5.76-5.67 (m, 2H), 5.05-4.94 (m, 2H), 4.16 (dd, J = 11.6, 7.4 Hz, 1H), 3.89 (s, 3H), 3.86-3.80 (m, 1H), 3.45-3.34 (m, 2H), 2.69 (d, J = 6.0 Hz, 2H), 2.05 (s, 3H), 1.94 (p, J = 6.8, 6.2 Hz, 1H), 1.59-1.09 (m, 8H), 0.84 (t, J = 7.0 Hz, 3H) $^{13}$C NMR (101 MHz, CDCl$_3$) δ 171.86, 170.20, 163.09, 161.28 (d, J = 244.3 Hz), 160.14, 145.70, 143.89, 142.13, 136.01 (d, J = 3.3 Hz), 130.23 (d, J = 7.7 Hz), 115.14 (d, J = 21.1 Hz), 109.64, 89.33, 75.85, 73.52, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 109 | — | — | ESIMS m/z 471 [M + H]$^+$ | 71.43, 56.13, 51.44, 49.11, 37.66, 33.73, 29.63, 21.40, 20.81, 20.31, 14.18 $^{19}$F NMR (376 MHz, CDCl$_3$) δ −117.15 $^1$H NMR (400 MHz, CDCl$_3$) δ 12.00 (s, 1H), 8.50 (d, J = 8.4 Hz, 1H), 7.97 (d, J = 5.2 Hz, 1H), 7.33-7.24 (m, 2H), 7.20 (tt, J = 6.3, 1.1 Hz, 3H), 6.85 (d, J = 5.2 Hz, 1H), 5.03-4.87 (m, 2H), 4.13 (dd, J = 11.6, 7.6 Hz, 1H), 3.92 (s, 3H), 3.58 (dd, J = 10.7, 4.5 Hz, 1H), 3.33-3.19 (m, 2H), 2.89-2.75 (m, 1H), 2.56 (dd, J = 14.0, 10.1 Hz, 1H), 1.76-1.66 (m, 2H), 1.66-1.45 (m, 2H), 1.43 (d, J = 6.3 Hz, 3H), 1.41-1.21 (m, 4H), 0.94 (t, J = 7.0 Hz, 3H) $^{13}$C NMR (101 MHz, CDCl$_3$) δ 171.54, 168.93, 155.32, 148.71, 140.59, 140.35, 130.23, 129.12, 128.37, 126.07, 109.56, 76.43, 72.22, 70.70, 56.07, 50.87, 47.23, 44.45, 37.10, 29.78, 27.28, 23.43, 20.17, 14.01. |
| 110 | — | — | ESIMS m/z 471 [M + H]$^+$ | $^1$H NMR (400 MHz, CDCl$_3$) δ 11.99 (s, 1H), 8.49 (d, J = 8.3 Hz, 1H), 7.99 (d, J = 5.2 Hz, 1H), 7.33-7.27 (m, 2H), 7.23-7.16 (m, 3H), 6.86 (d, J = 5.2 Hz, 1H), 5.02-4.88 (m, 2H), 4.14 (dd, J = 11.6, 7.6 Hz, 1H), 3.94 (s, 3H), 3.58 (dd, J = 10.6, 4.6 Hz, 1H), 3.33-3.19 (m, 2H), 2.83 (d, J = 13.8 Hz, 1H), 2.57 (dd, J = 13.7, 10.6 Hz, 1H), 1.71 (d, J = 4.9 Hz, 2H), 1.63-1.48 (m, 2H), 1.43 (d, J = 6.3 Hz, 3H), 1.38-1.28 (m, 2H), 1.24 (dt, J = 9.2, 4.6 Hz, 1H), 1.16 (dd, J = 12.9, 5.8 Hz, 1H), 0.94 (t, J = 7.0 Hz, 3H) $^{13}$C NMR (101 MHz, CDCl$_3$) δ 171.95, 169.33, 155.77, 149.16, 140.98, 140.77, 130.7, 129.53 (2), 128.72 (2), 126.48, 109.95, 76.85, 72.65, 71.16, 56.48, 51.29, 47.67, 44.87, 37.53, 30.21, 27.71, 23.83, 20.56, 14.38 |
| 111 | 201-204 | — | ESIMS m/z 503 [M − H]$^−$ | $^1$H NMR (400 MHz, CDCl$_3$) δ 12.01 (s, 1H), 8.91 (s, 1H), 7.99 (d, J = 5.0 Hz, 1H), 7.35-7.11 (m, 6H), 7.02 (d, J = 7.0 Hz, 2H), 6.92-6.82 (m, 3H), 5.35 (q, J = 6.7 Hz, 1H), 4.81 (ddd, J = 8.0, 4.7, 2.5 Hz, 1H), 4.06 (dd, J = 12.2, 4.6 Hz, 1H), 3.94 (s, 3H), 3.86 (dd, J = 10.7, 2.6 Hz, 1H), 3.78 (d, J = 11.2 Hz, 1H), 3.44 (dd, J = 10.7, 8.0 Hz, 1H), 3.13 (d, J = 13.0 Hz, 1H), 2.92 (dd, J = 14.2, 10.6 Hz, 1H), 2.64-2.54 (m, 1H), 2.43 (t, J = 11.1 Hz, 1H), 2.03-1.82 (m, 2H), 1.46 (d, J = 6.6 Hz, 3H) $^{13}$C NMR (101 MHz, CDCl$_3$) δ 169.24, 168.40, 155.48, 148.83, 140.72, 140.31, 139.62, 130.42, 129.09, 128.88, 128.45, 128.32, 126.03, 126.00, 109.59, 73.99, 72.64, 71.94, 56.13, 54.87, 39.96, 36.44, 34.06, 19.31 |
| 112 | 69-72 | — | ESIMS m/z 505 [M + H]$^+$ | $^1$H NMR (400 MHz, CDCl$_3$) δ 12.01 (d, J = 1.7 Hz, 1H), 8.53 (d, J = 8.3 Hz, 1H), 7.99 (d, J = 5.2 Hz, 1H), 7.36-7.29 (m, 2H), 7.29-7.21 (m, 5H), 7.21-7.15 (m, 1H), 7.12-7.06 (m, 2H), 6.86 (d, J = 5.2 Hz, 1H), 5.12-5.03 (m, 1H), 4.98 (q, J = 8.3 Hz, 1H), 4.22 (dd, J = 11.6, 7.5 Hz, 1H), 3.93 (s, 3H), 3.66 (dd, J = 11.0, 5.6 Hz, 1H), 3.34-3.18 (m, 2H), 2.92-2.69 (m, 4H), 2.21-2.10 (m, 1H), 1.85-1.73 (m, 1H), 1.41 (d, J = 6.4 Hz, 3H) $^{13}$C NMR (101 MHz, CDCl$_3$) δ 171.35, 168.85, 155.25, 148.64, 140.52, 140.03, 139.82, 130.14, 129.05, 129.00, 128.51, 128.18, 126.28, 125.94, 109.49, 76.31, 71.32, 70.74, 55.99, 50.82, 48.59, 45.48, 38.45, 37.28, 21.20 |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| 113 | 52-56 | — | ESIMS m/z 533 [M + H]⁺ | $^1$H NMR (400 MHz, CDCl$_3$) δ 12.01 (s, 1H), 8.59 (d, J = 8.3 Hz, 1H), 8.00 (d, J = 5.1 Hz, 1H), 7.33-7.23 (m, 4H), 7.23-7.15 (m, 4H), 7.07-7.01 (m, 2H), 6.86 (d, J = 5.1 Hz, 1H), 5.08-4.94 (m, 2H), 4.18 (dd, J = 11.7, 7.4 Hz, 1H), 3.97-3.85 (m, 4H), 3.58-3.44 (m, 2H), 2.80 (ddd, J = 14.0, 9.1, 5.1 Hz, 1H), 2.53 (dt, J = 13.8, 8.4 Hz, 1H), 2.47-2.34 (m, 2H), 1.87-1.51 (m, 6H), 1.47 (d, J = 6.3 Hz, 3H) $^{13}$C NMR (101 MHz, CDCl$_3$) δ 171.39, 168.97, 155.37, 148.77, 142.03, 141.96, 140.65, 130.29, 128.49, 128.46, 128.18, 126.01, 125.97, 109.60, 76.15, 74.42, 71.34, 56.11, 51.26, 46.97, 41.33, 33.08, 32.98, 32.30, 31.35, 20.36 |
| 114 | — | — | ESIMS m/z 379 [M + H]⁺ | $^1$H NMR (400 MHz, CDCl$_3$) δ 12.04 (s, 1H), 8.89 (d, J = 7.5 Hz, 1H), 8.02 (d, J = 5.3 Hz, 1H), 6.87 (d, J = 5.1 Hz, 1H), 5.00 (m, 2H), 4.05 (s, 1H), 4.04 (d, J = 1.8 Hz, 1H), 3.94 (s, 3H), 3.92 (d, J = 3.4 Hz, 1H), 3.75 (d, J = 9.7 Hz, 1H), 2.29 (ddt, J = 13.1, 6.1, 3.1 Hz, 1H), 1.73 (m, 2H), 1.57 (m, 2H), 1.49-1.40 (m, 2H), 1.31 (d, J = 6.9 Hz, 3H), 1.29-1.14 (m, 2H), 1.01 (td, J = 12.5, 3.4 Hz, 1H) $^{13}$C NMR (101 MHz, CDCl$_3$) δ 169.95, 168.85, 155.29, 148.69, 140.64, 130.44, 109.47, 79.43, 78.23, 74.65, 56.06, 53.02, 39.55, 39.38, 32.12, 29.49, 26.57, 26.07, 13.65 |
| 115 | — | — | ESIMS m/z 379 [M + H]⁺ | $^1$H NMR (400 MHz, CDCl$_3$) δ 12.00 (s, 1H), 8.69 (d, J = 8.2 Hz, 1H), 8.00 (d, J = 5.1 Hz, 1H), 6.87 (d, J = 5.3 Hz, 1H), 5.11 (td, J = 7.7, 5.5 Hz, 1H), 4.79 (dq, J = 9.3, 6.4 Hz, 1H), 4.02 (dd, J = 11.9, 7.5 Hz, 1H), 3.94 (s, 3H), 3.73 (dd, J = 11.8, 5.5 Hz, 1H), 3.65-3.55 (m, 2H), 1.81-1.69 (m, 3H), 1.63 (d, J = 13.3 Hz, 1H), 1.42-1.14 (m, 4H), 1.36 (d, J = 6.3 Hz, 3H), 0.95 (m, 2H) $^{13}$C NMR (101 MHz, CDCl$_3$) δ 170.75, 168.92, 155.31, 148.70, 140.63, 130.31, 109.52, 80.88, 78.24, 72.18, 56.08, 52.05, 49.55, 44.21, 32.00, 29.13, 26.32, 25.88, 19.85 |
| 116 | 64-72 | — | ESIMS m/z 477 [M + H]⁺ | $^1$H NMR (400 MHz, CDCl$_3$) δ 11.99 (s, 1H), 8.71 (d, J = 8.3 Hz, 1H), 8.02 (d, J = 5.2 Hz, 1H), 7.21-6.75 (m, 11H), 5.44-5.34 (m, 1H), 5.34-5.24 (m, 1H), 4.21-4.10 (m, 2H), 4.00-3.91 (m, 4H), 3.74 (dd, J = 11.7, 6.9 Hz, 1H), 3.17-3.05 (m, 2H), 1.11 (d, J = 6.3 Hz, 3H) $^{13}$C NMR (101 MHz, CDCl$_3$) δ 171.36, 169.02, 155.36, 148.76, 142.55, 140.87, 140.69, 130.23, 128.30, 128.17, 127.62, 126.52, 126.17, 109.62, 77.47, 77.46, 71.47, 58.64, 56.09, 53.26, 51.55, 20.81 |
| 117 | — | — | ESIMS m/z 465 [M + H]⁺ | $^1$H NMR (400 MHz, CDCl$_3$) δ 12.01 (s, 1H), 8.58 (d, J = 7.9 Hz, 1H), 8.00 (d, J = 5.0 Hz, 1H), 6.87 (d, J = 5.1 Hz, 1H), 5.01 (q, J = 7.5 Hz, 1H), 4.93 (dq, J = 12.4, 6.2 Hz, 1H), 4.10 (dd, J = 11.7, 7.3 Hz, 1H), 3.94 (s, 3H), 3.73 (dd, J = 10.4, 5.8 Hz, 1H), 3.54-3.48 (m, 2H), 1.63-1.02 (m, 12H), 1.40 (d, J = 6.3 Hz, 3H), 0.94-0.80 (m, 12H) $^{13}$C NMR (101 MHz, CDCl$_3$) δ 171.30, 168.89, 155.34, 148.71, 140.60, 130.30, 109.52, 76.07, 71.48, 56.09, 51.41, 47.03, 42.17, 35.77, 33.60, 29.70, 29.08, 28.75, 28.37, 27.23, 22.82, 22.53, 22.47, 22.38, 20.22 |
| 118 | 57-63 | — | ESIMS m/z 441 [M + H]⁺ | $^1$H NMR (400 MHz, CDCl$_3$) δ 11.98 (d, J = 0.6 Hz, 1H), 8.55 (d, J = 8.4 Hz, 1H), 7.98 (d, J = 5.2 Hz, 1H), 7.31-7.23 (m, 2H), 7.23-7.16 (m, 1H), 7.16-7.11 (m, 2H), 6.85 (d, J = 5.2 Hz, 1H), 5.54 (dt, J = 17.0, |

TABLE 2-continued

Analytical Data

| Cmpd. No. | MP (°C.) | IR (cm⁻¹) | MASS | NMR (¹H, ¹³C or ¹⁹F) |
|---|---|---|---|---|
| | | | | 10.1 Hz, 1H), 5.27 (dd, J = 10.2, 1.7 Hz, 1H), 5.20 (dd, J = 16.9, 1.7 Hz, 1H), 5.04 (q, J = 7.7 Hz, 1H), 4.95 (dq, J = 10.0, 6.3 Hz, 1H), 4.06 (dd, J = 11.7, 7.6 Hz, 1H), 3.92 (s, 3H), 3.57 (dd, J = 10.4, 5.9 Hz, 1H), 3.50 (dd, J = 10.4, 1.8 Hz, 1H), 3.41 (dd, J = 11.7, 7.7 Hz, 1H), 2.93 (dd, J = 14.0, 3.3 Hz, 1H), 2.31-2.21 (m, 2H), 1.79-1.65 (m, 1H), 1.36 (d, J = 6.3 Hz, 3H) ¹³C NMR (101 MHz, CDCl₃) δ 171.42, 168.92, 155.33, 148.72, 140.62, 140.14, 137.88, 130.21, 129.10, 128.37, 126.08, 119.17, 109.57, 75.65, 73.10, 71.11, 56.08, 55.70, 51.19, 45.01, 36.87, 20.92 |
| 119 | 69-75 | — | ESIMS m/z 517 [M + H]⁺ | ¹H NMR (400 MHz, CDCl₃) δ 12.01 (s, 0H), 8.54 (d, J = 8.3 Hz, 1H), 7.99 (d, J = 5.2 Hz, 1H), 6.87 (d, J = 5.2 Hz, 1H), 4.96 (q, J = 8.0 Hz, 1H), 4.84 (dq, J = 8.9, 6.4 Hz, 1H), 4.16 (dd, J = 11.6, 7.5 Hz, 1H), 3.94 (s, 2H), 3.75 (dd, J = 10.8, 5.5 Hz, 1H), 3.44-3.31 (m, 2H), 1.88-1.58 (m, 12H), 1.50 (tq, J = 6.9, 3.8, 3.2 Hz, 1H), 1.45-0.72 (m, 20H) ¹³C NMR (101 MHz, CDCl₃) δ 171.44, 168.88, 155.32, 148.71, 140.57, 130.29, 109.52, 77.86, 73.97, 71.14, 56.07, 51.06, 45.49, 42.03, 40.28, 38.61, 36.86, 34.92, 34.84, 34.40, 33.44, 32.53, 26.65, 26.50, 26.48, 26.43, 26.21, 20.64 |
| 120 | — | — | ESIMS m/z 499 [M + H]⁺ | ¹H NMR (400 MHz, CDCl₃) δ 12.00 (d, J = 0.5 Hz, 1H), 8.48 (d, J = 8.4 Hz, 1H), 7.98 (d, J = 5.2 Hz, 1H), 7.32-7.25 (m, 2H), 7.24-7.17 (m, 3H), 6.86 (d, J = 5.2 Hz, 1H), 5.11 (dq, J = 9.3, 6.3 Hz, 1H), 4.99-4.86 (m, 3H), 4.20 (dd, J = 11.6, 7.5 Hz, 1H), 3.93 (s, 3H), 3.90-3.79 (m, 2H), 3.63-3.50 (m, 3H), 3.26-3.13 (m, 2H), 2.82 (dd, J = 13.5, 3.9 Hz, 1H), 2.69 (dd, J = 13.6, 11.0 Hz, 1H), 2.06-1.94 (m, 1H), 1.84-1.73 (m, 4H), 1.47 (d, J = 6.3 Hz, 3H) ¹³C NMR (101 MHz, CDCl₃) δ 171.64, 168.93, 155.33, 148.72, 141.84, 140.59, 140.30, 130.24, 129.17, 128.33, 126.05, 112.62, 109.55, 75.58, 75.55, 71.48, 70.66, 68.86, 56.07, 50.78, 48.54, 42.08, 36.98, 19.64 |
| 121 | — | — | ESIMS m/z 501 [M + H]⁺ | ¹H NMR (400 MHz, CDCl₃) δ 12.01 (s, 1H), 8.48 (d, J = 8.3 Hz, 1H), 7.98 (d, J = 5.2 Hz, 1H), 7.32-7.24 (m, 2H), 7.24-7.16 (m, 3H), 6.86 (d, J = 5.2 Hz, 1H), 5.09 (dq, J = 9.3, 6.3 Hz, 1H), 4.91 (q, J = 8.4 Hz, 1H), 4.19 (dd, J = 11.6, 7.5 Hz, 1H), 3.93 (s, 3H), 3.61-3.50 (m, 3H), 3.26-3.08 (m, 4H), 2.83 (dd, J = 13.6, 3.7 Hz, 1H), 2.66 (dd, J = 13.7, 11.1 Hz, 1H), 2.05-1.95 (m, 1H), 1.86 (dp, J = 13.3, 6.7 Hz, 1H), 1.77 (tt, J = 9.1, 2.7 Hz, 1H), 1.46 (d, J = 6.3 Hz, 3H), 0.91 (d, J = 6.7 Hz, 6H) ¹³C NMR (101 MHz, CDCl₃) δ 171.68, 168.92, 155.33, 148.72, 140.58, 140.43, 130.25, 129.15, 128.33, 126.02, 109.55, 78.46, 75.79, 71.70, 70.73, 69.40, 56.07, 50.83, 48.66, 42.09, 36.87, 28.39, 19.58, 19.41 |
| 122 | — | — | ESIMS m/z 501 [M + H]⁺ | ¹H NMR (400 MHz, CDCl₃) δ 12.00 (s, 1H), 8.47 (d, J = 8.3 Hz, 1H), 7.98 (d, J = 5.2 Hz, 1H), 7.32-7.24 (m, 2H), 7.24-7.15 (m, 3H), 6.85 (d, J = 5.2 Hz, 1H), 5.09 (dq, J = 9.4, 6.3 Hz, 1H), 4.91 (td, J = 8.8, 7.5 Hz, 1H), 4.19 (dd, J = 11.6, 7.5 Hz, 1H), 3.92 (s, 3H), 3.61-3.52 (m, 3H), 3.25-3.08 (m, 4H), 2.82 (dd, J = 13.6, 3.8 Hz, 1H), 2.66 (dd, J = 13.7, 11.1 Hz, 1H), 2.06-1.70 (m, 3H), 1.46 (d, J = 6.3 Hz, 3H), 0.91 (d, J = 6.7 Hz, 6H) |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | ¹³C NMR (101 MHz, CDCl₃) δ 171.62, 168.86, 155.27, 148.65, 140.52, 140.37, 130.19, 129.09, 128.27, 125.96, 109.48, 78.40, 75.73, 71.63, 70.67, 69.34, 56.01, 50.77, 48.59, 42.02, 36.81, 28.33, 19.52, 19.37, 19.35 |
| 123 | — | — | HRMS-FAB (m/z) [M + H]⁺ calcd for C₂₇H₃₄F₃N₂O₆, 539.2369; found, 539.2392 | ¹H NMR (400 MHz, CDCl₃) δ 11.98 (d, J = 0.5 Hz, 1H), 8.50 (d, J = 8.4 Hz, 1H), 7.99 (d, J = 5.2 Hz, 1H), 7.65-7.46 (m, 2H), 7.32 (d, J = 8.0 Hz, 2H), 6.87 (d, J = 5.2 Hz, 1H), 4.94 (tdd, J = 9.0, 6.9, 3.4 Hz, 2H), 4.16 (dd, J = 11.6, 7.5 Hz, 1H), 3.94 (s, 3H), 3.54 (dd, J = 10.8, 4.3 Hz, 1H), 3.36-3.11 (m, 2H), 2.93-2.78 (m, 1H), 2.69 (dd, J = 13.7, 10.4 Hz, 1H), 1.77-1.67 (m, 2H), 1.64-1.48 (m, 2H), 1.44 (d, J = 6.3 Hz, 3H), 1.40-1.27 (m, 4H), 0.94 (t, J = 7.0 Hz, 3H) ¹⁹F NMR (376 MHz, DMSO-d₆) δ −62.32 |
| 124 | 62-65 | — | ESIMS m/z 565 [M + H]⁺ | ¹H NMR (400 MHz, CDCl₃) δ 11.98 (d, J = 0.5 Hz, 1H), 8.51 (d, J = 8.3 Hz, 1H), 7.98 (d, J = 5.2 Hz, 1H), 7.25-7.20 (m, 1H), 7.18-7.12 (m, 1H), 6.87-6.61 (m, 7H), 5.07 (dq, J = 8.3, 6.4 Hz, 1H), 4.96 (td, J = 8.7, 7.5 Hz, 1H), 4.21 (dd, J = 11.6, 7.5 Hz, 1H), 3.92 (s, 3H), 3.79 (s, 3H), 3.75 (s, 3H), 3.67 (dd, J = 11.0, 5.7 Hz, 1H), 3.31-3.21 (m, 2H), 2.86-2.68 (m, 4H), 2.18-2.09 (m, 1H), 1.84-1.74 (m, 1H), 1.42 (d, J = 6.4 Hz, 3H) ¹³C NMR (101 MHz, CDCl₃) δ 171.34, 168.89, 159.72, 159.49, 155.31, 148.71, 141.70, 141.45, 140.52, 130.22, 129.47, 129.10, 121.48, 121.39, 115.08, 114.68, 111.48, 111.37, 109.53, 76.31, 71.49, 70.83, 56.00, 55.09, 55.03, 50.89, 48.53, 45.40, 38.60, 37.42, 21.19 |
| 125 | — | — | HRMS-FAB (m/z) [M + H]⁺ calcd for C₂₆H₃₅N₂O₆, 471.2495; found, 471.2489 | ¹H NMR (400 MHz, CDCl₃) δ 11.99 (d, J = 0.6 Hz, 1H), 8.49 (d, J = 8.3 Hz, 1H), 7.99 (d, J = 5.2 Hz, 1H), 7.37-7.18 (m, 5H), 6.86 (dd, J = 5.3, 0.6 Hz, 1H), 5.02-4.81 (m, 2H), 4.18 (dd, J = 11.6, 7.5 Hz, 1H), 3.94 (s, 3H), 3.60 (dd, J = 11.0, 5.1 Hz, 1H), 3.32-3.11 (m, 2H), 2.86 (dd, J = 13.7, 3.5 Hz, 1H), 2.64 (dd, J = 13.6, 11.1 Hz, 1H), 1.79-1.64 (m, 2H), 1.61-1.54 (m, 1H), 1.46 (d, J = 6.4 Hz, 3H), 1.40 (ddd, J = 14.7, 6.8, 5.0 Hz, 1H), 1.21 (ddd, J = 14.7, 8.7, 3.3 Hz, 1H), 0.97 (d, J = 6.5 Hz, 3H), 0.94 (d, J = 6.6 Hz, 3H) ¹³C NMR (101 MHz, CDCl₃) δ 171.49, 168.93, 155.33, 148.71, 140.59, 140.47, 130.23, 129.12, 128.33, 126.05, 109.56, 77.43, 71.43, 70.85, 56.07, 50.88, 47.37, 45.55, 42.12, 36.86, 27.10, 23.64, 22.46, 20.56 |
| 126 | — | — | HRMS-FAB (m/z) [M + H]⁺ calcd for C₂₅H₃₃N₂O₆, 457.2338; found, 457.2335 | ¹H NMR (400 MHz, CDCl₃) δ 11.99 (d, J = 0.6 Hz, 1H), 8.55 (d, J = 8.3 Hz, 1H), 8.00 (d, J = 5.2 Hz, 1H), 7.36-7.16 (m, 5H), 6.87 (dd, J = 5.2, 0.7 Hz, 1H), 5.04 (dq, J = 8.1, 6.4 Hz, 1H), 4.97 (td, J = 8.3, 7.4 Hz, 1H), 4.19 (dd, J = 11.7, 7.4 Hz, 1H), 3.94 (s, 3H), 3.86 (dd, J = 10.9, 5.1 Hz, 1H), 3.42 (ddd, J = 11.7, 5.3, 3.7 Hz, 2H), 2.83-2.64 (m, 2H), 2.08-1.96 (m, 1H), 1.57-1.34 (m, 4H), 1.32 (d, J = 6.5 Hz, 3H), 1.24-1.15 (m, 1H), 0.85 (t, J = 7.0 Hz, 3H) ¹³C NMR (101 MHz, CDCl₃) δ 171.30, 168.92, 155.30, 148.69, 140.60, 140.32, 130.21, 128.93, 128.44, 126.14, 109.57, 76.42, 73.66, 71.21, 56.04, 51.16, 48.98, 43.50, 38.37, 33.68, 21.39, 20.34, 14.23 |
| 127 | — | — | ESIMS m/z 489 [M + H]⁺ | ¹H NMR (400 MHz, CDCl₃) δ 11.98 (s, 1H), 8.52 (d, J = 8.3 Hz, 1H), 7.96 (d, J = 5.2 Hz, 1H), 6.84 (d, J = 5.2 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 4.99-4.86 (m, 2H), 4.15 (dd, J = 11.7, 7.3 Hz, 1H), 3.91 (s, 3H), 3.79 (dd, J = 11.0, 5.4 Hz, 1H), 3.43-3.30 (m, 2H), 1.96-1.33 (m, 21H), 1.32-1.21 (m, 2H), 1.05 (tdd, J = 16.4, 8.4, 5.2 Hz, 4H) $^{13}$C NMR (101 MHz, CDCl$_3$) δ 171.31, 168.82, 155.23, 148.62, 140.49, 130.21, 109.44, 77.07, 73.77, 71.24, 55.99, 51.10, 47.31, 43.29, 38.71, 37.90, 37.48, 37.32, 33.66, 33.58, 33.17, 32.07, 25.00, 24.90, 24.77, 24.73, 20.73 |
| 128 | — | — | HRMS-FAB (m/z) [M + H]$^+$ calcd for C$_{30}$H$_{35}$N$_2$O$_6$, 519.2495; found, 519.2491 | $^1$H NMR (400 MHz, CDCl$_3$) δ 11.99 (d, J = 0.6 Hz, 1H), 8.51 (d, J = 8.4 Hz, 1H), 7.99 (d, J = 5.2 Hz, 1H), 7.39-7.13 (m, 10H), 6.87 (d, J = 5.2 Hz, 1H), 5.10-4.94 (m, 2H), 4.15 (dd, J = 11.6, 7.6 Hz, 1H), 3.94 (s, 3H), 3.69-3.60 (m, 1H), 3.30 (dd, J = 11.4, 8.5 Hz, 2H), 2.91-2.81 (m, 1H), 2.71 (ddd, J = 13.7, 11.6, 5.0 Hz, 1H), 2.64-2.52 (m, 2H), 2.01-1.76 (m, 4H), 1.53 (d, J = 6.3 Hz, 3H) $^{13}$C NMR (101 MHz, CDCl$_3$) δ 171.56, 168.94, 155.37, 148.76, 141.87, 140.61, 140.18, 130.25, 129.12, 128.61, 128.45, 128.20, 126.18, 126.13, 109.57, 76.16, 72.18, 70.76, 56.09, 50.87, 47.11, 44.63, 37.14, 32.62, 31.83, 20.30 |
| 129 | — | — | HRMS-FAB (m/z) [M + H]$^+$ calcd for C$_{28}$H$_{39}$N$_2$O$_6$, 499.2808; found, 499.2800 | $^1$H NMR (400 MHz, CDCl$_3$) δ 12.00 (s, 1H), 8.60 (d, J = 8.3 Hz, 1H), 8.00 (d, J = 5.2 Hz, 1H), 7.36-7.13 (m, 5H), 6.87 (d, J = 5.2 Hz, 1H), 5.04 (qd, J = 7.7, 7.0, 4.9 Hz, 2H), 4.12 (dd, J = 11.8, 7.4 Hz, 1H), 3.94 (s, 3H), 3.76 (dd, J = 10.4, 5.9 Hz, 1H), 3.58-3.49 (m, 2H), 2.57 (dddd, J = 34.6, 13.7, 11.3, 5.3 Hz, 2H), 1.86-1.64 (m, 3H), 1.57-1.26 (m, 5H), 1.49 (d, J = 6.3 Hz, 3H), 1.17-1.03 (m, 1H), 0.91 (d, J = 4.9 Hz, 3H), 0.89 (d, J = 4.8 Hz, 3H) $^{13}$C NMR (101 MHz, CDCl$_3$) δ 171.33, 168.93, 155.35, 148.74, 142.11, 140.62, 130.29, 128.54, 128.15, 126.02, 109.55, 76.45, 75.86, 71.49, 56.09, 51.40, 46.95, 42.57, 35.85, 32.28, 31.54, 29.14, 28.40, 22.83, 22.41, 20.39 |
| 130 | — | — | HRMS-FAB (m/z) [M + H]$^+$ calcd for C$_{27}$H$_{35}$N$_2$O$_6$, 483.2495; found, 483.2490 | $^1$H NMR (400 MHz, CDCl$_3$) δ 12.02 (d, J = 0.7 Hz, 1H), 8.52 (d, J = 8.3 Hz, 1H), 7.99 (d, J = 5.2 Hz, 1H), 7.32-7.15 (m, 5H), 6.87 (d, J = 5.2 Hz, 1H), 5.35-5.22 (m, 1H), 4.92 (ddd, J = 9.4, 8.3, 7.0 Hz, 1H), 4.29 (dd, J = 11.6, 7.0 Hz, 1H), 3.94 (s, 3H), 3.85 (dd, J = 11.6, 6.5 Hz, 1H), 3.29-3.07 (m, 3H), 2.74 (dd, J = 13.4, 4.9 Hz, 1H), 2.09-1.95 (m, 3H), 1.74-1.52 (m, 6H), 1.47 (d, J = 6.6 Hz, 3H), 1.30-1.15 (m, 1H), 1.05-0.93 (m, 1H) $^{13}$C NMR (101 MHz, CDCl$_3$) δ 171.33, 168.92, 155.36, 148.74, 141.04, 140.59, 130.31, 129.18, 128.22, 125.93, 109.54, 74.78, 71.74, 71.71, 56.09, 52.57, 51.46, 43.46, 43.35, 38.34, 31.30, 29.94, 24.86, 24.75, 22.22 |
| 131 | 63-69 | — | ESIMS m/z 589 [M + H]$^+$ | $^1$H NMR (400 MHz, CDCl$_3$) δ 11.99 (s, 1H), 8.54 (d, J = 8.3 Hz, 1H), 7.98 (d, J = 5.2 Hz, 1H), 7.28-7.13 (m, 7H), 7.08-7.03 (m, 2H), 6.86 (d, J = 5.2 Hz, 1H), 5.14-5.05 (m, 1H), 4.99 (q, J = 8.3 Hz, 1H), 4.22 (dd, J = 11.7, 7.5 Hz, 1H), 3.93 (s, 3H), 3.71 (dd, J = 10.9, 6.2 Hz, 1H), 3.39-3.27 (m, 2H), 2.91-2.69 (m, 4H), 2.11 (p, J = 6.7 Hz, 1H), 1.81 (ddq, J = 11.9, 6.5, 3.1, 2.0 Hz, 1H), 1.41 (d, J = 6.5 Hz, 3H) $^{13}$C NMR (101 MHz, CDCl$_3$) δ 171.33, 168.88, 155.29, 148.67, 147.63 (q, J = 1.6 Hz), 140.56, 139.78, 138.76, 130.26, 130.13, 128.96, 128.27, 126.07, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 124.68-116.24 (m), 121.02, 109.52, 76.04, 71.75, 70.97, 56.00, 50.94, 48.59, 45.25, 38.32, 37.45, 21.35<br>$^{19}$F NMR (376 MHz, CDCl$_3$) δ −57.87 |
| 132 | 185-190 | — | ESIMS<br>m/z 491<br>[M + H]$^+$ | $^1$H NMR (400 MHz, CDCl$_3$) δ 11.99 (s, 1H), 8.60 (d, J = 8.4 Hz, 1H), 7.99 (d, J = 5.2 Hz, 1H), 7.40-7.34 (m, 2H), 7.31-7.11 (m, 6H), 6.97-6.92 (m, 2H), 6.86 (d, J = 5.2 Hz, 1H), 5.24 (dq, J = 10.2, 6.3 Hz, 1H), 5.15 (q, J = 7.7 Hz, 1H), 4.09 (dd, J = 11.7, 7.7 Hz, 1H), 3.92 (s, 3H), 3.73-3.65 (m, 2H), 3.51 (dd, J = 11.7, 7.5 Hz, 1H), 2.75 (t, J = 10.0 Hz, 1H), 2.50 (d, J = 11.5 Hz, 1H), 2.24-2.09 (m, 2H), 1.07 (d, J = 6.3 Hz, 3H)<br>$^{13}$C NMR (101 MHz, CDCl$_3$) δ 171.33, 168.86, 155.24, 148.64, 141.60, 140.55, 139.83, 130.12, 128.94, 128.81, 128.53, 128.20, 127.15, 125.97, 109.50, 77.05, 73.41, 70.96, 57.47, 56.00, 51.12, 47.23, 37.04, 20.85 |
| 133 | — | (Neat) 3364, 2952, 1736, 1649, 1528, 1453, 1263 | HRMS-ESI (m/z) [M]$^+$ calcd for C$_{27}$H$_{36}$N$_2$O$_6$, 484.2573; found, 484.2570 | $^1$H NMR (400 MHz, CDCl$_3$) δ 12.00 (s, 1H), 8.56 (d, J = 8.3 Hz, 1H), 8.00 (d, J = 5.2 Hz, 1H), 7.32-7.26 (m, 2H), 7.23-7.17 (m, 3H), 6.87 (d, J = 5.3 Hz, 1H), 5.10-5.00 (m, 1H), 5.01-4.93 (m, 1H), 4.18 (dd, J = 11.7, 7.3 Hz, 1H), 3.94 (s, 3H), 3.84 (dd, J = 10.8, 4.9 Hz, 1H), 3.48-3.39 (m, 2H), 2.75-2.70 (m, 2H), 2.08-1.98 (m, 2H), 1.53-1.36 (m, 4H), 1.34 (d, J = 6.4 Hz, 3H), 1.32-1.21 (m, 1H), 1.12-0.97 (m, 1H), 0.84 (d, J = 6.6 Hz, 6H) |
| 134 | — | — | HRMS-FAB (m/z) [M + H]$^+$ calcd for C$_{31}$H$_{37}$N$_2$O$_6$, 533.2651; found, 533.2641 | $^1$H NMR (400 MHz, CDCl$_3$) δ 12.03 (s, 1H), 8.58 (d, J = 8.3 Hz, 1H), 7.95 (d, J = 5.2 Hz, 1H), 7.32-7.08 (m, 10H), 6.81 (d, J = 5.3 Hz, 1H), 5.13-4.99 (m, 1H), 4.95 (q, J = 7.9 Hz, 1H), 4.15 (dd, J = 11.7, 7.3 Hz, 1H), 3.87 (s, 3H), 3.82 (dd, J = 10.9, 5.2 Hz, 1H), 3.50-3.32 (m, 2H), 2.81-2.60 (m, 2H), 2.50 (t, J = 7.3 Hz, 2H), 2.02-1.95 (m, 1H), 1.77-1.66 (m, 1H), 1.57-1.37 (m, 3H), 1.32 (d, J = 6.4 Hz, 3H), 1.29-1.21 (m, 1H)<br>$^{13}$C NMR (101 MHz, CDCl$_3$) δ 171.28, 168.97, 155.32, 148.73, 142.30, 140.64, 140.22, 130.23, 128.99, 128.50, 128.38, 128.31, 126.20, 125.76, 109.63, 76.30, 73.84, 71.32, 56.06, 51.27, 49.04, 43.62, 38.37, 36.04, 31.18, 30.90, 29.12, 21.39 |
| 135 | — | (Neat) 3365, 2925, 1736, 1650, 1529, 1482, 1280 | HRMS-ESI (m/z) [M]$^+$ calcd for C$_{29}$H$_{31}$ClN$_2$O$_6$, 538.1871; found, 538.1870 | $^1$H NMR (400 MHz, CDCl$_3$) δ 11.97 (s, 1H), 8.50 (d, J = 8.3 Hz, 1H), 8.00 (d, J = 5.2 Hz, 1H), 7.37-7.25 (m, 2H), 7.29-7.14 (m, 5H), 7.0-6.95 (m, 2H), 6.87 (d, J = 5.2 Hz, 1H), 5.11-5.0 (m, 1H), 4.98-4.90 (m, 1H), 4.22 (dd, J = 11.7, 7.4 Hz, 1H), 3.94 (s, 3H), 3.60 (dd, J = 11.2, 5.4 Hz, 1H), 3.24 (dd, J = 11.7, 9.1 Hz, 1H), 3.18 (d, J = 11.1 Hz, 1H), 2.91-2.60 (m, 4H), 2.18-2.08 (m, 1H), 1.77-1.67 (m, 1H), 1.42 (d, J = 6.4 Hz, 3H) |
| 136 | — | — | HRMS-FAB (m/z) [M + H]$^+$ calcd for C$_{30}$H$_{32}$F$_3$N$_2$O$_6$, 573.2212; found, 573.2207 | $^1$H NMR (400 MHz, CDCl$_3$) δ 11.97 (d, J = 0.6 Hz, 1H), 8.51 (d, J = 8.3 Hz, 1H), 7.99 (d, J = 5.2 Hz, 1H), 7.52-7.07 (m, 9H), 6.87 (dd, J = 5.3, 0.7 Hz, 1H), 5.07 (dq, J = 8.4, 6.4 Hz, 1H), 4.94 (ddd, J = 9.0, 8.3, 7.4 Hz, 1H), 4.23 (dd, J = 11.6, 7.4 Hz, 1H), 3.94 (s, 3H), 3.59 (dd, J = 11.2, 5.4 Hz, 1H), 3.30-3.12 (m, 2H), 2.95-2.63 (m, 4H), 2.21-2.07 (m, 1H), 1.84-1.70 (m, 1H), 1.44 (d, J = 6.4 Hz, 3H)<br>$^{13}$C NMR (101 MHz, CDCl$_3$) δ 171.39, 168.96, 155.38, 148.76, 144.32, 140.63, 139.55, 130.22, 129.45, 129.14, 128.68, 128.49, 128.17, 126.54, 125.65, 125.19, 125.15, 125.11, 125.07, 122.95, 109.59, 76.14, 70.90, 56.10, 50.91, 48.75, 45.28, 38.74, 37.27, 21.22 |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 137 | 64-68 | — | ESIMS m/z 623 [M + H]$^+$ | $^1$H NMR (400 MHz, CDCl$_3$) δ 11.96 (s, 1H), 8.52 (d, J = 8.3 Hz, 1H), 7.99 (d, J = 5.2 Hz, 1H), 7.25-7.14 (m, 6H), 6.98-6.93 (m, 2H), 6.87 (d, J = 5.3 Hz, 1H), 5.13-5.02 (m, 1H), 4.96 (td, J = 8.6, 7.4 Hz, 1H), 4.22 (dd, J = 11.7, 7.5 Hz, 1H), 3.93 (s, 3H), 3.66 (dd, J = 11.1, 5.9 Hz, 1H), 3.30 (dd, J = 11.7, 8.8 Hz, 1H), 3.24 (dd, J = 11.1, 1.9 Hz, 1H), 2.85 (dd, J = 14.8, 7.0 Hz, 1H), 2.81-2.71 (m, 2H), 2.63 (dd, J = 13.6, 4.7 Hz, 1H), 2.09 (p, J = 6.8 Hz, 1H), 1.73 (dtd, J = 11.3, 6.4, 1.8 Hz, 1H), 1.40 (d, J = 6.5 Hz, 3H) $^{13}$C NMR (101 MHz, CDCl$_3$) δ 171.32, 168.92, 155.34, 148.72, 147.74 (q, J = 1.6 Hz), 140.60, 138.58, 138.28, 131.85, 130.35, 130.31, 130.15, 128.38, 121.11, 120.44 (q, J = 257.0 Hz), 109.56, 75.84, 71.32, 71.03, 56.05, 50.94, 48.67, 45.29, 38.38, 36.84, 21.32 $^{19}$F NMR (376 MHz, CDCl$_3$) δ −57.90 |
| 138 | — | — | ESIMS m/z 657 [M + H]$^+$ | $^1$H NMR (400 MHz, CDCl$_3$) δ 11.96 (d, J = 0.6 Hz, 1H), 8.52 (d, J = 8.3 Hz, 1H), 7.98 (d, J = 5.1 Hz, 1H), 7.47 (d, J = 8.0 Hz, 2H), 7.25-7.20 (m, 2H), 7.19-7.10 (m, 4H), 6.86 (d, J = 5.2 Hz, 1H), 5.13-5.04 (m, 1H), 4.96 (td, J = 8.7, 7.5 Hz, 1H), 4.23 (dd, J = 11.7, 7.4 Hz, 1H), 3.93 (s, 3H), 3.65 (dd, J = 11.2, 5.9 Hz, 1H), 3.36-3.19 (m, 2H), 2.94-2.64 (m, 4H), 2.10 (p, J = 6.7 Hz, 1H), 1.78 (ddd, J = 10.9, 7.7, 4.7 Hz, 1H), 1.42 (d, J = 6.5 Hz, 3H) $^{13}$C NMR (101 MHz, CDCl$_3$) δ 171.31, 168.93, 155.34, 148.72, 147.77 (q, J = 2.0 Hz), 144.03 (q, J = 1.2 Hz), 140.61, 138.46, 130.32, 129.31, 128.42 (q, J = 32.4 Hz), 125.15 (q, J = 3.8 Hz), 124.21 (q, J = 271.8 Hz), 121.13, 120.43 (q, J = 256.9 Hz), 109.56, 75.75, 71.16, 71.05, 56.03, 50.95, 48.73, 45.11, 38.44, 37.32, 21.30 $^{19}$F NMR (376 MHz, CDCl$_3$) δ −57.94, −62.37 |
| 139 | 48-52 | — | ESIMS m/z 547 [M + H]$^+$ | $^1$H NMR (400 MHz, CDCl$_3$) δ 12.02 (d, J = 0.5 Hz, 1H), 8.61 (d, J = 8.3 Hz, 1H), 8.00 (d, J = 5.1 Hz, 1H), 7.32-7.26 (m, 4H), 7.23-7.17 (m, 4H), 7.09-7.05 (m, 2H), 6.87 (d, J = 5.2 Hz, 1H), 5.09-4.99 (m, 2H), 4.13 (dd, J = 11.7, 7.4 Hz, 1H), 3.94 (s, 3H), 3.77 (dd, J = 10.5, 5.7 Hz, 1H), 3.59-3.49 (m, 2H), 2.71-2.42 (m, 4H), 1.90-1.39 (m, 11H) $^{13}$C NMR (101 MHz, CDCl$_3$) δ 171.21, 168.85, 155.24, 148.64, 141.99, 141.88, 140.54, 130.17, 128.41, 128.31, 128.27, 128.07, 125.91, 125.74, 109.48, 76.26, 75.55, 71.40, 56.00, 51.29, 46.84, 42.22, 35.97, 32.15, 31.44, 30.78, 28.25, 20.27 |
| 140 | 56-61 | — | ESIMS m/z 469 [M + H]$^+$ | $^1$H NMR (400 MHz, CDCl$_3$) δ 11.99 (s, 1H), 8.54 (d, J = 8.3 Hz, 1H), 7.98 (d, J = 5.2 Hz, 1H), 7.32-7.24 (m, 2H), 7.22-7.15 (m, 3H), 6.86 (d, J = 5.1 Hz, 1H), 5.03 (dq, J = 8.2, 6.4 Hz, 1H), 4.94 (td, J = 8.5, 7.4 Hz, 1H), 4.21 (dd, J = 11.6, 7.4 Hz, 1H), 4.01 (dd, J = 10.9, 5.2 Hz, 1H), 3.92 (s, 3H), 3.50-3.33 (m, 2H), 2.70 (d, J = 6.1 Hz, 2H), 2.01 (dt, J = 13.3, 6.5 Hz, 1H), 1.69-1.57 (m, 2H), 1.32 (d, J = 6.5 Hz, 3H), 1.13 (dd, J = 10.1, 7.6 Hz, 1H), 0.69 (dddd, J = 13.0, 7.9, 5.3, 2.9 Hz, 1H), 0.48-0.40 (m, 1H), 0.36 (dddd, J = 9.2, 7.8, 5.3, 4.0 Hz, 1H), 0.09-0.01 (m, 1H), −0.08--0.14 (m, 1H) $^{13}$C NMR (101 MHz, CDCl$_3$) δ 171.34, 168.83, 155.25, 148.63, 140.52, 140.09, 130.17, 128.91, 128.37, 126.10, 109.47, 76.33, 72.98, 70.97, 56.00, 50.94, 48.63, 44.35, 38.28, 36.30, 21.26, 8.92, 5.39, 3.98 |

TABLE 2-continued

Analytical Data

| Cmpd. No. | MP (° C.) | IR (cm$^{-1}$) | MASS | NMR ($^{1}$H, $^{13}$C or $^{19}$F) |
|---|---|---|---|---|
| 141 | 66-71 | — | ESIMS m/z 539 [M + H]$^{+}$ | $^{1}$H NMR (400 MHz, CDCl$_3$) δ 11.97 (d, J = 0.6 Hz, 1H), 8.49 (d, J = 8.3 Hz, 1H), 7.96 (d, J = 5.1 Hz, 1H), 7.53 (d, J = 8.0 Hz, 2H), 7.32 (d, J = 8.0 Hz, 2H), 6.85 (d, J = 5.2 Hz, 1H), 4.98-4.85 (m, 2H), 4.19 (dd, J = 11.6, 7.4 Hz, 1H), 3.92 (s, 3H), 3.53 (dd, J = 11.2, 5.0 Hz, 1H), 3.22 (dd, J = 11.7, 9.0 Hz, 1H), 3.15 (d, J = 11.0 Hz, 1H), 2.87 (dd, J = 13.7, 3.7 Hz, 1H), 2.76 (dd, J = 13.7, 11.2 Hz, 1H), 1.76-1.65 (m, 2H), 1.62-1.50 (m, 1H), 1.48-1.35 (m, 4H), 1.17 (ddd, J = 14.6, 8.7, 3.5 Hz, 1H), 0.96 (d, J = 6.6 Hz, 3H), 0.93 (d, J = 6.5 Hz, 3H) $^{13}$C NMR (101 MHz, CDCl$_3$) δ 171.33, 168.88, 155.28, 148.65, 144.62, 140.54, 130.13, 129.39, 128.33 (q, J = 32.3 Hz), 125.16 (q, J = 3.7 Hz), 124.25 (q, J = 271.8 Hz), 109.50, 77.04, 70.86, 55.99, 50.79, 47.23, 45.50, 42.20, 36.69, 26.94, 25.20, 23.47, 22.38, 20.46 $^{19}$F NMR (376 MHz, CDCl$_3$) δ -62.28 |
| 142 | — | — | ESIMS m/z 423 [M + H]$^{+}$ | $^{1}$H NMR (400 MHz, CDCl$_3$) for the major diastereomer δ 12.00 (d, J = 0.5 Hz, 1H), 8.56 (d, J = 8.2 Hz, 1H), 8.00 (d, J = 5.3 Hz, 1H), 6.87 (d, J = 5.3 Hz, 1H), 4.96 (q, J = 8.0 Hz, 1H), 4.92-4.83 (m, 1H), 4.16 (dd, J = 11.7, 7.3 Hz, 1H), 3.94 (s, 3H), 3.78 (dd, J = 10.8, 5.5 Hz, 1H), 3.47-3.37 (m, 2H), 1.71-1.44 (m, 4H), 1.41 (d, J = 6.5 Hz, 3H), 1.34-1.18 (m, 3H), 1.08 (ddd, J = 14.7, 8.2, 4.0 Hz, 2H), 0.96-0.88 (m, 9H) $^{13}$C NMR (101 MHz, CDCl$_3$) for the major diastereomer δ 171.33, 168.89, 155.32, 148.70, 140.58, 130.29, 109.52, 77.52, 74.37, 71.48, 56.07, 51.27, 45.80, 44.87, 41.74, 33.27, 26.99, 23.46, 22.57, 20.69, 20.44, 14.31 |
| 143 | — | — | HRMS-FAB (m/z) [M + H]$^{+}$ calcd for C$_{29}$H$_{32}$FN$_{2}$O$_{6}$, 523.2244; found, 523.2246 | $^{1}$H NMR (400 MHz, CDCl$_3$) δ 11.99 (d, J = 0.6 Hz, 1H), 8.53 (d, J = 8.3 Hz, 1H), 7.97 (d, J = 5.2 Hz, 1H), 7.32-6.92 (m, 9H), 6.85 (dd, J = 5.3, 0.7 Hz, 1H), 5.07 (dq, J = 8.1, 6.5 Hz, 1H), 4.98 (td, J = 8.6, 7.5 Hz, 1H), 4.21 (dd, J = 11.7, 7.5 Hz, 1H), 3.92 (s, 3H), 3.68 (dd, J = 11.0, 6.0 Hz, 1H), 3.36-3.20 (m, 2H), 2.78 (dd, J = 21.0, 6.9 Hz, 4H), 2.14-2.05 (m, 1H), 1.85-1.73 (m, 1H), 1.39 (d, J = 6.4 Hz, 3H) $^{19}$F NMR (376 MHz, CDCl$_3$) δ -116.68 |
| 144 | — | — | HRMS-FAB (m/z) [M + H]$^{+}$ calcd for C$_{28}$H$_{39}$N$_{2}$O$_{6}$, 499.2808; found, 499.2805 | $^{1}$H NMR (400 MHz, CDCl$_3$) δ 12.01 (d, J = 0.6 Hz, 1H), 8.56 (d, J = 8.3 Hz, 1H), 7.97 (d, J = 5.2 Hz, 1H), 7.34-7.13 (m, 5H), 6.85 (d, J = 5.2 Hz, 1H), 4.94 (q, J = 7.9 Hz, 1H), 4.86 (dq, J = 8.8, 6.4 Hz, 1H), 4.15 (dd, J = 11.7, 7.2 Hz, 1H), 3.92 (s, 3H), 3.77 (dd, J = 10.9, 5.4 Hz, 1H), 3.48-3.36 (m, 2H), 2.62 (t, J = 7.4 Hz, 2H), 1.85-1.77 (m, 1H), 1.59-1.41 (m, 4H), 1.39 (d, J = 6.4 Hz, 3H), 1.32-1.24 (m, 2H), 1.25-1.14 (m, 1H), 1.03-0.97 (m, 1H), 0.86 (d, J = 6.7 Hz, 3H), 0.84 (d, J = 6.6 Hz, 3H) $^{13}$C NMR (101 MHz, CDCl$_3$) δ 171.30, 168.91, 155.31, 148.71, 142.24, 140.59, 130.27, 128.42, 128.29, 125.75, 109.55, 77.43, 74.37, 71.51, 56.06, 51.30, 45.84, 45.10, 41.71, 35.99, 30.55, 29.08, 26.97, 23.39, 22.49, 20.64 |
| 145 | — | (Neat) 3367, 2955, 1749, 1649, 1526, 1261 | HRMS-ESI (m/z) [M]$^{+}$ calcd for, C$_{26}$H$_{33}$ClN$_{2}$O$_{6}$, 504.2027; found, 504.2032 | $^{1}$H NMR (400 MHz, CDCl$_3$) δ 11.98 (s, 1H), 8.49 (d, J = 8.3 Hz, 1H), 7.99 (d, J = 5.2 Hz, 1H), 7.28-7.23 (m, 2H), 7.18-7.11 (m, 2H), 6.87 (d, J = 5.3 Hz, 1H), 4.99-4.83 (m, 2H), 4.19 (dd, J = 11.7, 7.5 Hz, 1H), 3.94 (s, 3H), 3.55 (dd, J = 11.1, 5.0 Hz, 1H), 3.28-3.11 (m, 2H), 2.81 (dd, J = 13.8, 3.7 Hz, 1H), 2.65 (dd, J = 13.7, 11.3 Hz, 1H), 1.77-1.64 (m, 2H), 1.55-1.46 (m, 1H), |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | 1.45 (d, J = 6.4 Hz, 3H), 1.42-1.34 (m, 1H), 1.17 (ddd, J = 14.6, 8.7, 3.4 Hz, 1H), 0.97 (d, J = 6.5 Hz, 3H), 0.94 (d, J = 6.5 Hz, 3H) |
| 146 | — | (Neat) 3367, 2930, 1749, 1650, 1509, 1259 | HRMS-ESI (m/z) [M]⁺ calcd for $C_{32}H_{35}F_3N_2O_7$, 616.2396; found, 616.2404 | ¹H NMR (400 MHz, CDCl₃) δ 11.98 (s, 1H), 8.56 (d, J = 8.3 Hz, 1H), 7.99 (d, J = 5.2 Hz, 1H), 7.29-7.24 (m, 2H), 7.20-7.10 (m, 7H), 6.86 (d, J = 5.3 Hz, 1H), 5.09-5.01 (m, 1H), 5.01-4.92 (m, 1H), 4.17 (dd, J = 11.7, 7.3 Hz, 1H), 3.93 (s, 3H), 3.85 (dd, J = 11.0, 5.3 Hz, 1H), 3.48-3.39 (m, 2H), 2.77-2.62 (m, 2H), 2.56-2.50 (m, 2H), 2.02-1.93 (m, 1H), 1.79-1.67 (m, 1H), 1.59-1.37 (m, 4H), 1.32 (d, J = 6.5 Hz, 3H) |
| 147 | — | — | ESIMS m/z 591 [M + H]⁺ | ¹H NMR (400 MHz, CDCl₃) δ 11.96 (s, 1H), 8.51 (d, J = 8.3 Hz, 1H), 8.00 (d, J = 5.3 Hz, 1H), 7.49 (d, J = 8.0 Hz, 2H), 7.17 (dd, J = 8.3, 5.6 Hz, 4H), 7.01 (t, J = 8.7 Hz, 2H), 6.87 (d, J = 5.1 Hz, 1H), 5.07 (m, 1H), 4.95 (m, 1H), 4.23 (dd, J = 11.7, 7.4 Hz, 1H), 3.94 (s, 3H), 3.63 (dd, J = 11.3, 5.8 Hz, 1H), 3.30-3.12 (m, 2H), 2.91-2.79 (m, 2H), 2.73 (td, J = 13.7, 12.9, 5.1 Hz, 2H), 2.08 (m, 1H), 1.79 (m, 1H), 1.42 (d, J = 6.4 Hz, 3H) ¹³C NMR (101 MHz, CDCl₃) δ 171.36, 168.96, 161.55 (d, J = 244 Hz), 155.39, 148.77, 144.17, 140.64, 135.30 (d, J = 3 Hz), 130.44 (d, J = 8 Hz), 130.19, 129.39, 128.45 (q, J = 33 Hz), 125.21 (q, J = 4 Hz), 124.27 (q, J = 270 Hz), 115.48, (d, J = 21 Hz), 109.6, 75.83, 71.04, 56.1, 50.96, 48.93, 45.24, 38.17, 37.31, 21.34 ¹⁹F NMR (376 MHz, CDCl₃) δ −62.34, −116.38 |
| 148 | — | — | HRMS-FAB (m/z) [M + H]⁺ calcd for $C_{27}H_{37}N_2O_6$, 485.2651; found, 485.2647 | ¹H NMR (400 MHz, CDCl₃) δ 12.00 (d, J = 0.6 Hz, 1H), 8.49 (d, J = 8.4 Hz, 1H), 7.99 (d, J = 5.2 Hz, 1H), 7.36-7.14 (m, 5H), 6.86 (dd, J = 5.3, 0.7 Hz, 1H), 5.05-4.85 (m, 2H), 4.14 (dd, J = 11.6, 7.6 Hz, 1H), 3.94 (s, 3H), 3.59 (dd, J = 10.6, 4.5 Hz, 1H), 3.33-3.22 (m, 2H), 2.88-2.80 (m, 2H), 2.57 (dd, J = 13.5, 10.4 Hz, 1H), 1.76-1.49 (m, 3H), 1.43 (d, J = 6.2 Hz, 3H), 1.32-1.12 (m, 3H), 0.92 (d, J = 6.6 Hz, 6H), 0.88-0.83 (m, 1H) ¹³C NMR (101 MHz, CDCl₃) δ 171.55, 168.91, 155.35, 148.73, 140.59, 140.35, 130.26, 129.13, 128.38, 126.08, 109.54, 76.35, 72.21, 70.68, 56.08, 50.85, 47.19, 44.27, 37.13, 33.91, 28.76, 27.58, 22.61, 22.49, 20.12 |
| 149 | 80-84 | — | ESIMS m/z 517 [M + H]⁺ | ¹H NMR (400 MHz, CDCl₃) δ 11.99 (d, J = 0.6 Hz, 1H), 8.51 (d, J = 8.3 Hz, 1H), 7.96 (d, J = 5.2 Hz, 1H), 7.25-7.18 (m, 4H), 6.85 (d, J = 5.2 Hz, 1H), 5.25 (qd, J = 6.6, 5.1 Hz, 1H), 4.88 (ddd, J = 9.6, 8.3, 7.0 Hz, 1H), 4.27 (dd, J = 11.6, 7.0 Hz, 1H), 3.92 (s, 3H), 3.79 (dd, J = 11.7, 6.4 Hz, 1H), 3.19 (dd, J = 11.6, 9.7 Hz, 1H), 3.16-3.08 (m, 2H), 2.67 (dd, J = 13.4, 4.8 Hz, 1H), 2.10-1.89 (m, 3H), 1.73-1.47 (m, 6H), 1.45 (d, J = 6.7 Hz, 3H), 1.31-1.13 (m, 1H), 0.95 (ddt, J = 9.9, 7.3, 2.3 Hz, 1H) ¹³C NMR (101 MHz, CDCl₃) δ 171.20, 168.84, 155.26, 148.63, 140.52, 139.42, 131.50, 130.48, 130.15, 128.21, 109.48, 74.50, 71.65, 71.26, 56.00, 52.52, 51.32, 43.29, 37.57, 31.23, 29.76, 24.74, 24.64, 22.11 |
| 150 | 38-43 | — | ESIMS m/z 463 [M + H]⁺ | ¹H NMR (400 MHz, CDCl₃) δ 12.00 (d, J = 0.5 Hz, 2H), 8.51 (d, J = 8.3 Hz, 1H), 7.96 (d, J = 5.2 Hz, 1H), 6.84 (d, J = 5.1 Hz, 1H), 5.27 (qd, J = 6.7, 3.6 Hz, 1H), 4.85 (ddd, J = 9.1, 8.4, 7.0 Hz, 1H), 4.23 (dd, J = 11.6, 7.0 Hz, 1H), 4.02 (dd, J = 11.6, 6.6 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 3.92 (s, 3H), 3.31-3.20 (m, 2H), 2.08-1.89 (m, 2H), 1.86-1.74 (m, 1H), 1.70-1.45 (m, 9H), 1.45-1.33 (m, 4H), 1.21-1.07 (m, 2H), 0.90-0.88 (m, 6H) $^{13}$C NMR (101 MHz, CDCl$_3$) δ 171.18, 168.81, 155.26, 148.64, 140.50, 130.25, 109.45, 74.64, 72.89, 71.76, 56.01, 52.88, 51.43, 43.29, 41.72, 37.27, 31.26, 30.25, 30.02, 28.31, 24.80, 24.74, 22.70, 22.60, 22.35 |
| 151 | 68-73 | — | ESIMS m/z 521 [M + H]$^+$ | $^1$H NMR (400 MHz, CDCl$_3$) δ 12.00 (d, J = 0.5 Hz, 1H), 8.50 (d, J = 8.4 Hz, 1H), 7.99 (d, J = 5.1 Hz, 1H), 7.34-7.27 (m, 2H), 7.27-7.21 (m, 2H), 7.20-7.13 (m, 3H), 7.01-6.95 (m, 1H), 6.94-6.88 (m, 2H), 6.86 (d, J = 5.2 Hz, 1H), 5.32-5.20 (m, 1H), 4.96 (td, J = 8.8, 7.6 Hz, 1H), 4.23 (dd, J = 11.6, 7.5 Hz, 1H), 4.13 (dd, J = 9.9, 2.5 Hz, 1H), 4.09 (dd, J = 9.9, 3.0 Hz, 1H), 3.93 (s, 3H), 3.64 (dd, J = 11.0, 4.4 Hz, 1H), 3.30-3.21 (m, 2H), 2.84 (dd, J = 13.6, 4.0 Hz, 1H), 2.73 (dd, J = 13.6, 10.7 Hz, 1H), 2.16-2.07 (m, 1H), 2.02 (tt, J = 9.0, 2.7 Hz, 1H), 1.47 (d, J = 6.3 Hz, 3H) $^{13}$C NMR (101 MHz, CDCl$_3$) δ 171.63, 168.88, 158.63, 155.27, 148.66, 140.54, 139.80, 130.14, 129.48, 129.08, 128.30, 126.08, 121.10, 114.37, 109.51, 75.09, 71.45, 70.65, 66.45, 56.01, 50.74, 47.96, 41.87, 36.88, 19.57 |
| 152 | — | — | ESIMS m/z 443 [M + H]$^+$ | $^1$H NMR (400 MHz, CDCl$_3$) δ 12.00 (s, 1H), 8.67 (d, J = 8.3 Hz, 1H), 8.01 (d, J = 5.2 Hz, 1H), 7.31 (app t, J = 7.3 Hz, 2H), 7.24 (app t, J = 7.3 Hz, 1H), 7.13 (app d, J = 6.9 Hz, 2H), 6.88 (d, J = 5.1 Hz, 1H), 5.26-5.10 (m, 2H), 4.14 (dd, J = 11.8, 7.5 Hz, 1H), 3.95 (s, 3H), 3.85-3.74 (m, 2H), 3.69 (dd, J = 11.8, 6.7 Hz, 1H), 2.66 (t, J = 10.4 Hz, 1H), 2.00-1.79 (m, 1H), 1.33 (m, 1H), 1.08-0.92 (m, 3H), 1.03 (d, J = 6.3 Hz, 3H), 0.67 (t, J = 7.0 Hz, 3H) $^{13}$C NMR (101 MHz, CDCl$_3$) δ 171.20, 168.95, 155.34, 148.73, 141.82, 140.65, 130.27, 128.74, 128.50, 126.91, 109.56, 77.42, 76.46, 71.70, 57.14, 56.09, 51.64, 44.80, 33.57, 20.81, 19.21, 14.11 |
| 153 | — | — | ESIMS m/z 487 [M + H]$^+$ | $^1$H NMR (400 MHz, CDCl$_3$) δ 11.99 (s, 1H), 8.55 (d, J = 8.3 Hz, 1H), 8.00 (d, J = 6.2 Hz, 1H), 7.15 (app dd, J = 8.6, 5.4 Hz, 2H), 6.98 (app t, J = 8.7 Hz, 2H), 6.88 (d, J = 5.2 Hz, 1H), 5.04 (p, J = 6.5 Hz, 1H), 5.00-4.90 (m, 1H), 4.22 (dd, J = 11.6, 7.4 Hz, 1H), 4.02 (dd, J = 10.9, 5.4 Hz, 1H), 3.94 (s, 3H), 3.48 (s, 1H), 3.40 (dd, J = 11.6, 8.6 Hz, 1H), 2.69 (m, 2H), 1.98 (p, J = 7.0 Hz, 1H), 1.64 (m, 2H), 1.32 (d, J = 6.5 Hz, 3H), 1.21-1.09 (m, 1H), 0.69 (m, 1H), 0.51-0.35 (m, 2H), 0.06 (app dq, J = 9.0, 5.0 Hz, 1H), −0.08 (app dq, J = 9.3, 5.1 Hz, 1H) $^{13}$C NMR (101 MHz, CDCl$_3$) δ 171.41, 168.92, 161.39 (d, J = 244.3 Hz), 155.36, 148.73, 140.61, 135.85 (d, J = 3.3 Hz), 130.33 (d, J = 7.8 Hz), 130.24, 115.24 (d, J = 21.1 Hz), 109.56, 76.09, 73.11, 71.11, 56.08, 51.05, 48.96, 44.37, 37.76, 36.47, 21.40, 9.03, 5.45, 4.11 |
| 154 | — | — | HRMS-FAB (m/z) [M + H]$^+$ calcd for C$_{25}$H$_{31}$N$_2$O$_6$, 455.2182; found, 455.2180 | $^1$H NMR (400 MHz, CDCl$_3$) δ 12.00 (d, J = 0.6 Hz, 1H), 8.65 (d, J = 8.2 Hz, 1H), 8.01 (d, J = 5.2 Hz, 1H), 7.34-7.20 (m, 3H), 7.14-7.08 (m, 2H), 6.88 (dd, J = 5.2, 0.7 Hz, 1H), 5.27-5.10 (m, 2H), 4.18 (dd, J = 11.7, 7.7 Hz, 1H), 4.00-3.88 (m, 2H), 3.95 (s, 3H), 3.65 (dd, J = 11.7, 7.2 Hz, 1H), 2.67 (t, J = 10.4 Hz, 1H), 2.07-1.96 (m, 1H), 1.13 (ddd, J = 14.7, 9.6, 5.7 Hz, 1H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1.03 (d, J = 6.3 Hz, 3H), 0.80-0.70 (m, 1H), 0.65-0.50 (m, 1H), 0.44-0.33 (m, 1H), 0.32-0.23 (m, 1H), −0.13 (dtd, J = 9.2, 5.2, 4.2 Hz, 1H), −0.35 (dtd, J = 9.3, 5.3, 4.2 Hz, 1H) $^{13}$C NMR (101 MHz, CDCl$_3$) δ 171.38, 168.96, 155.35, 148.75, 141.73, 140.65, 130.26, 128.75, 128.55, 126.96, 109.57, 77.40, 75.52, 71.35, 57.07, 56.09, 51.40, 46.19, 36.07, 20.87, 8.34, 5.63, 4.00 |
| 155 | 43-48 | — | ESIMS m/z 475 [M + H]$^+$ | $^1$H NMR (400 MHz, CDCl$_3$) δ 11.97 (s, 1H), 8.54 (d, J = 8.3 Hz, 1H), 7.97 (d, J = 5.2 Hz, 1H), 7.19-7.10 (m, 2H), 7.01-6.93 (m, 2H), 6.85 (d, J = 5.2 Hz, 1H), 5.07-4.91 (m, 2H), 4.17 (dd, J = 11.7, 7.4 Hz, 1H), 3.91 (s, 3H), 3.84 (dd, J = 11.0, 5.6 Hz, 1H), 3.47-3.38 (m, 2H), 2.69 (d, J = 6.1 Hz, 2H), 1.95 (h, J = 6.7, 6.1 Hz, 1H), 1.56-1.13 (m, 8H), 0.84 (t, J = 7.0 Hz, 3H) $^{13}$C NMR (101 MHz, CDCl$_3$) δ 171.20, 168.82, 161.28 (d, J = 244.3 Hz), 155.25, 148.63, 140.52, 135.91 (d, J = 3.3 Hz), 130.21 (d, J = 7.8 Hz), 130.14, 115.15 (d, J = 21.1 Hz), 109.47, 76.02, 73.59, 71.21, 55.98, 51.09, 49.11, 43.34, 37.66, 33.67, 21.37, 20.30, 14.14 $^{19}$F NMR (376 MHz, CDCl$_3$) δ −117.03 |
| 156 | 206-211 | — | ESIMS m/z 354 [M − H]$^-$ | — |
| 157 | 184 (dec) | — | ESIMS m/z 382 [M + H]$^+$ | $^1$H NMR (400 MHz, CDCl$_3$) δ 8.81 (s, 3H), 7.29-7.08 (m, 8H), 6.97 (d, J = 7.3 Hz, 2H), 8.84-4.93 (m, 4H), 4.53 (s, 1H), 4.36 (t, J = 9.3 Hz, 1H), 4.08 (t, J = 9.7 Hz, 1H), 3.91-3.79 (m, 1H), 3.56 (d, J = 9.3 Hz, 1H), 2.79-2.65 (m, 1H), 2.53-2.41 (m, 1H), 2.34 (t, J = 8.4 Hz, 2H), 1.79-1.49 (m, 7H), 1.45 (d, J = 5.7 Hz, 3H) $^{13}$C NMR (101 MHz, CDCl$_3$) δ 169.64, 142.03, 141.87, 128.46, 128.44, 128.16, 125.97, 125.91, 74.97, 68.77, 52.23, 46.77, 41.14, 33.17, 32.81, 32.20, 31.28, 20.25 |
| 158 | — | — | ESIMS m/z 326 [M + H]$^+$ | $^1$H NMR (400 MHz, CD$_3$OD) δ 7.05-6.69 (m, 10H), 5.35 (dq, J = 10.2, 6.3 Hz, 1H), 4.52 (dd, J = 6.9, 4.2 Hz, 1H), 4.11-3.98 (m, 2H), 3.95 (dd, J = 10.5, 1.5 Hz, 1H), 3.87 (dd, J = 12.6, 4.2 Hz, 1H), 3.16 (t, J = 10.5 Hz, 1H), 3.02 (ddd, J = 10.7, 7.3, 1.4 Hz, 1H), 1.00 (d, J = 6.3 Hz, 3H) $^{13}$C NMR (101 MHz, CD$_3$OD) δ 170.20, 144.56, 142.41, 129.38, 129.22, 128.90, 127.59, 127.05, 82.21, 79.26, 71.23, 68.16, 59.90, 54.33, 20.88 |
| 159 | 208 (dec) | — | ESIMS m/z 290 [M + H]$^+$ | $^1$H NMR (300 MHz, CD$_3$OD) δ 7.33-7.09 (m, 5H), 5.63 (dt, J = 16.9, 10.1 Hz, 1H), 5.32-5.20 (m, 2H), 5.27-5.14 (m, 1H), 4.44-4.34 (m, 1H), 4.01 (dd, J = 12.6, 6.9 Hz, 1H), 3.77-3.64 (m, 2H), 3.50 (dd, J = 10.8, 5.8 Hz, 1H), 2.91 (dd, J = 14.1, 3.4 Hz, 1H), 2.30 (q, J = 9.9 Hz, 1H), 2.12 (dd, J = 13.9, 12.2 Hz, 1H), 1.78 (tt, J = 10.0, 4.2 Hz, 1H), 1.37 (d, J = 6.0 Hz, 3H) |
| 160 | 191-197 (dec) | — | ESIMS m/z 366 [M + H]$^+$ | $^1$H NMR (400 MHz, CDCl$_3$) δ 8.68 (s, 3H), 4.88-4.74 (m, 1H), 4.32 (dt, J = 37.4, 7.6 Hz, 2H), 3.86 (t, J = 9.7 Hz, 1H), 3.74-3.64 (m, 1H), 3.31 (d, J = 10.5 Hz, 1H), 1.87-0.68 (m, 31H) $^{13}$C NMR (101 MHz, CDCl$_3$) δ 169.64, 78.71, 73.78, 68.40, 51.71, 45.32, 41.78, 40.31, 38.59, 36.81, 34.86, 34.82, 34.36, 33.44, 32.53, 26.66, 26.50, 26.47, 26.43, 26.22, 20.57 |
| 161 | 184-187 (dec) | — | ESIMS m/z 348 [M + H]$^+$ | $^1$H NMR (400 MHz, CD$_3$OD) δ 7.20-7.12 (m, 2H), 7.11-7.04 (m, 3H), 5.17-5.07 (m, 1H), 4.87 (s, 1H), 4.80 (s, 1H), 4.16 (t, J = 6.4 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1H), 4.00 (dd, J = 12.1, 6.8 Hz, 1H), 3.76 (d, J = 3.1 Hz, 1H), 3.68-3.30 (m, 6H), 3.21 (p, J = 1.6 Hz, 1H), 2.79 (dd, J = 13.4, 3.8 Hz, 1H), 2.37 (dd, J = 13.6, 11.2 Hz, 1H), 1.95-1.80 (m, 1H), 1.74-1.61 (m, 3H), 1.37 (d, J = 6.3 Hz, 3H) $^{13}$C NMR (101 MHz, CD$_3$OD) δ 170.26, 143.33, 141.54, 130.21, 129.34, 127.07, 112.88, 77.36, 76.30, 70.48, 69.51, 68.05, 53.31, 50.59, 43.88, 37.80, 20.01, 19.87 |
| 162 | 196-199 | — | ESIMS m/z 350 [M + H]$^+$ | $^1$H NMR (400 MHz, CD$_3$OD) δ 7.21-7.12 (m, 2H), 7.08 (d, J = 7.2 Hz, 3H), 5.12 (dq, J = 9.6, 6.3 Hz, 1H), 4.15 (t, J = 6.6 Hz, 1H), 3.99 (dd, J = 12.3, 6.8 Hz, 1H), 3.60-3.33 (m, 5H), 3.13-3.01 (m, 2H), 2.81 (dd, J = 13.6, 3.8 Hz, 1H), 2.36 (dd, J = 13.6, 11.5 Hz, 1H), 1.88 (ddtd, J = 10.2, 8.2, 4.2, 1.8 Hz, 1H), 1.76 (hept, J = 6.6 Hz, 1H), 1.66 (tt, J = 9.2, 2.6 Hz, 1H), 1.37 (d, J = 6.3 Hz, 3H), 0.83 (d, J = 6.6 Hz, 6H) $^{13}$C NMR (101 MHz, CD$_3$OD) δ 170.30, 141.66, 130.21, 129.35, 127.07, 79.26, 77.58, 70.60, 70.07, 68.08, 53.39, 50.81, 43.98, 37.75, 29.64, 19.96, 19.80, 19.77 |
| 163 | — | — | ESIMS m/z 350 [M + H]+ | $^{13}$C NMR (101 MHz, CD$_3$OD) δ 169.50, 140.93, 130.12, 129.01, 126.66, 79.14, 76.92, 71.24, 70.40, 68.00, 54.09, 50.66, 43.36, 37.88, 29.08, 20.68, 19.58, 19.56 |
| 164 | — | — | ESIMS m/z 320 [M + H]$^+$ | $^{13}$C NMR (101 MHz, CDCl$_3$) δ 175.85, 140.50, 129.11, 128.33, 126.01, 75.55, 72.77, 71.20, 52.96, 47.12, 44.50, 37.08, 29.78, 27.32, 23.45, 20.15, 14.00 |
| 165 | 181-186 (dec) | — | ESIMS m/z 414 [M + H]$^+$ | $^1$H NMR (300 MHz, CDCl$_3$) δ 8.77 (s, 3H), 7.18 (t, J = 7.7 Hz, 1H), 7.10 (t, J = 7.8 Hz, 1H), 6.81-6.50 (m, 6H), 5.01 (s, 1H), 4.32 (s, 2H), 3.76 (s, 3H), 3.72 (s, 3H), 3.58 (s, 1H), 3.18 (d, J = 11.1 Hz, 1H), 2.72 (d, J = 6.1 Hz, 2H), 2.61 (d, J = 7.1 Hz, 2H), 2.14-1.95 (m, 1H), 1.84 (s, 1H), 1.71 (s, 1H), 1.36 (d, J = 5.9 Hz, 3H) |
| 166 | — | — | ESIMS m/z 388 [M + H]$^+$ | $^1$H NMR (400 MHz, CD$_3$OD) δ 7.65-7.53 (m, 2H), 7.39 (d, J = 8.0 Hz, 2H), 4.99 (dq, J = 9.2, 6.3 Hz, 1H), 4.00 (ddd, J = 18.7, 12.7, 7.0 Hz, 2H), 3.52 (dd, J = 11.0, 4.8 Hz, 1H), 3.36 (dd, J = 11.5, 6.9 Hz, 2H), 2.99-2.87 (m, 1H), 2.60 (dd, J = 13.7, 10.8 Hz, 1H), 1.84-1.48 (m, 4H), 1.43 (d, J = 6.3 Hz, 3H), 1.42-1.24 (m, 4H), 0.95 (t, J = 6.9 Hz, 2H) $^{19}$F NMR (376 MHz, CD$_3$OD) δ −63.86 |
| 167 | — | (Thin Film) 3367, 2953, 2926, 1740. | ESIMS m/z 320 [M + H]$^+$ | $^1$H NMR (400 MHz, CD$_3$OD) δ 7.31-7.14 (m, 5H), 3.98-3.86 (m, 2H), 3.75 (s, 1H), 3.56 (dd, J = 11.2, 5.3 Hz, 1H), 3.29-3.18 (m, 2H), 2.85 (dd, J = 13.6, 4.0 Hz, 1H), 2.55 (dd, J = 13.6, 10.8 Hz, 1H), 1.76-1.50 (m, 3H), 1.44 (d, J = 6.4 Hz, 3H), 1.30-1.11 (m, 3H), 0.96 (d, J = 6.5 Hz, 3H), 0.93 (d, J = 6.6 Hz, 3H), 0.89-0.83 (m, 1H) |
| 168 | — | (Thin Film) 3396, 2955, 2928, 2871, 1745. | ESIMS m/z 306 [M + H]$^+$ | $^1$H NMR (400 MHz, CD$_3$OD) δ 7.32-7.14 (m, 5H), 5.10 (dq, J = 7.8, 6.5 Hz, 1H), 4.19 (t, J = 6.6 Hz, 1H), 4.09 (dd, J = 12.2, 6.8 Hz, 1H), 3.80 (dd, J = 11.2, 5.9 Hz, 1H), 3.62 (dd, J = 12.2, 6.4 Hz, 1H), 3.56 (dd, J = 11.2, 2.1 Hz, 1H), 2.75 (dd, J = 6.2, 4.5 Hz, 2H), 2.01 (tt, J = 7.7, 6.1 Hz, 1H), 1.56 (tdd, J = 7.7, 5.6, 2.1 Hz, 1H), 1.46-1.35 (m, 3H), 1.33 (d, J = 6.5 Hz, 3H), 1.30-1.07 (m, 3H), 0.84-0.78 (m, 3H) |
| 169 | 196-202 | — | ESIMS m/z 354 [M + H]$^+$ | $^1$H NMR (400 MHz, CD$_3$OD) δ 7.34-7.07 (m, 8H), 7.06-6.98 (m, 2H), 5.16 (dt, J = 7.8, 6.4 Hz, 1H), 4.29 (t, J = 7.1 Hz, 1H), 4.15 (dd, J = 12.2, 7.1 Hz, 1H), 3.58 (dd, J = 12.2, 7.0 Hz, 1H), 3.42 (dd, J = 11.0, 2.3 Hz, 1H), 3.31 (dt, J = 3.4, 1.6 Hz, 1H), 2.93-2.68 (m, 3H), 2.57 (dd, J = 13.7, 10.7 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1H), 2.11 (p, J = 6.5 Hz, 1H), 1.92-1.82 (m, 1H), 1.42 (d, J = 6.5 Hz, 3H) $^{13}$C NMR (101 MHz, CD$_3$OD) δ 170.26, 141.42, 141.34, 130.24, 130.11, 129.54, 129.26, 127.29, 127.03, 78.50, 74.98, 69.98, 53.01, 50.32, 46.30, 39.63, 38.70, 21.60. |
| 170 | 164-167 | — | ESIMS m/z 338 [M + H]$^+$ | $^1$H NMR (400 MHz, CDCl$_3$) δ 8.70 (s, 3H), 4.87 (dq, J = 8.3, 6.3 Hz, 1H), 4.38-4.21 (m, 2H), 3.88-3.80 (m, 1H), 3.78-3.71 (m, 1H), 3.38-3.28 (m, 1H), 1.94-1.43 (m, 18H), 1.39 (d, J = 6.5 Hz, 3H), 1.31-1.17 (m, 2H), 1.13-0.91 (m, 4H) $^{13}$C NMR (101 MHz, CDCl$_3$) δ 169.47, 77.95, 73.75, 68.63, 51.76, 47.27, 43.15, 38.70, 37.99, 37.47, 37.37, 33.67, 33.56, 33.19, 32.12, 25.04, 24.94, 24.81, 24.77, 20.71. |
| 171 | — | — | ESIMS m/z 368 [M + H]$^+$ | $^1$H NMR (400 MHz, CD$_3$OD) δ 7.36-7.08 (m, 10H), 5.17 (dq, J = 9.1, 6.3 Hz, 1H), 4.29 (dd, J = 7.0, 6.2 Hz, 1H), 4.05 (dd, J = 12.3, 7.0 Hz, 1H), 3.62-3.50 (m, 3H), 2.90 (dd, J = 13.9, 3.8 Hz, 1H), 2.77-2.54 (m, 2H), 2.45 (dd, J = 13.8, 10.9 Hz, 1H), 2.00-1.75 (m, 4H), 1.52 (d, J = 6.3 Hz, 3H) $^{13}$C NMR (101 MHz, CD$_3$OD) δ 170.24, 143.37, 141.54, 130.24, 129.59, 129.47, 129.35, 127.21, 127.07, 78.19, 76.77, 70.37, 53.42, 49.08, 45.93, 38.24, 33.90, 32.69, 20.66. |
| 172 | — | — | ESIMS m/z 348 [M + H]$^+$ | $^1$H NMR (400 MHz, CD$_3$OD) δ 7.37-7.08 (m, 5H), 5.17 (dq, J = 9.6, 6.3 Hz, 1H), 4.34 (dd, J = 6.6, 4.9 Hz, 1H), 4.07 (dd, J = 12.7, 6.6 Hz, 1H), 3.79 (dd, J = 12.6, 4.9 Hz, 1H), 3.77-3.73 (m, 1H), 3.70-3.66 (m, 1H), 2.57 (dd, J = 9.2, 7.3 Hz, 2H), 1.84-1.64 (m, 3H), 1.57-1.49 (m, 3H), 1.48 (d, J = 6.4 Hz, 3H), 1.37-1.25 (m, 2H), 1.19-1.06 (m, 1H), 0.90 (t, J = 6.8 Hz, 6H) $^{13}$C NMR (101 MHz, CD$_3$OD) δ 170.02, 143.46, 129.56, 129.26, 127.05, 80.61, 78.16, 71.23, 54.20, 44.11, 36.96, 33.60, 32.40, 30.55, 29.61, 23.23, 22.82, 20.65. |
| 173 | — | — | ESIMS m/z 332 [M + H]$^+$ | $^1$H NMR (400 MHz, CD$_3$OD) δ 7.41-7.10 (m, 5H), 5.39 (qd, J = 6.8, 4.1 Hz, 1H), 4.30-4.15 (m, 2H), 3.86 (dd, J = 11.5, 7.1 Hz, 1H), 3.60-3.50 (m, 1H), 3.40 (dd, J = 11.5, 2.5 Hz, 1H), 3.00 (dd, J = 13.4, 9.8 Hz, 1H), 2.79 (dd, J = 13.5, 5.7 Hz, 1H), 2.23-1.96 (m, 3H), 1.72-1.44 (m, 6H), δ 1.51 (d, J = 6.8 Hz, 3H), 1.20 (qd, J = 10.3, 8.0 Hz, 1H), 0.96 (tt, J = 10.3, 7.5 Hz, 1H) $^{13}$C NMR (101 MHz, CD$_3$OD) δ 170.15, 142.14, 130.20, 129.34, 127.10, 76.97, 74.59, 70.57, 54.33, 53.26, 44.98, 44.93, 39.69, 32.38, 31.63, 25.86, 25.83, 22.74. |
| 174 | — | (Neat) 3376, 2952, 2927, 1729, 1454, 1382, 1181 | ESIMS m/z 334.3 [M + H]$^+$ | $^1$H NMR (400 MHz, CDCl$_3$) δ 7.34-7.15 (m, 5H), 5.03-4.85 (m, 1H), 4.07-3.87 (m, 1H), 3.85-3.70 (m, 2H), 3.34-3.23 (m, 1H), 3.23-3.09 (m, 1H), 2.77-2.63 (m, 2H), 2.18 (bs, 2H), 2.03-1.93 (m, 1H), 1.52-1.34 (m, 4H), 1.30 (d, J = 6.3 Hz, 3H), 1.30-1.22 (m, 1H), 1.09-0.95 (m, 1H), 0.83 (d, J = 6.6 Hz, 6H) |
| 175 | — | (Neat) 2927, 1730, 1492, 1454, 1197 | ESIMS m/z 388.3 [M + H]$^+$ | — |
| 176 | 144-148 | — | ESIMS m/z 472 [M + H]$^+$ | $^1$H NMR (400 MHz, CD$_3$OD) δ 7.34-7.26 (m, 2H), 7.23-7.13 (m, 4H), 7.02-6.94 (m, 2H), 4.31 (t, J = 6.8 Hz, 1H), 4.17 (dd, J = 12.3, 7.0 Hz, 2H), 3.75-3.59 (m, 2H), 3.54-3.46 (m, 1H), 2.87 (qd, J = 14.8, 6.6 Hz, 2H), 2.73-2.56 (m, 2H), 2.11 (h, J = 6.5 Hz, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 1H), 1.89 (tq, J = 11.6, 5.5, 3.9 Hz, 1H), 1.46 (d, J = 6.5 Hz, 3H) $^{13}$C NMR (101 MHz, CD$_3$OD) δ 170.26, 148.93 (q, J = 1.8 Hz), 140.97, 140.08, 132.82, 131.86, 131.70, 129.28, 122.09, 121.93 (q, J = 255.2 Hz), 78.47, 75.42, 70.35, 53.27, 50.23, 45.96, 39.65, 38.16, 21.63 $^{19}$F NMR (376 MHz, CD$_3$OD) δ 116.77 |
| 177 | — | — | ESIMS m/z 438 [M + H]$^+$ | $^1$H NMR (400 MHz, CD$_3$OD) δ 7.32-7.25 (m, 2H), 7.24-7.07 (m, 5H), 7.02-6.95 (m, 2H), 5.20 (p, J = 7.7, 7.1 Hz, 1H), 4.31 (t, J = 6.8 Hz, 1H), 4.15 (ddd, J = 12.5, 7.2, 1.9 Hz, 1H), 3.71 (dd, J = 10.9, 6.9 Hz, 1H), 3.66-3.61 (m, 1H), 3.51 (dd, J = 10.9, 2.6 Hz, 1H), 2.93-2.80 (m, 2H), 2.72 (dd, J = 13.7, 5.3 Hz, 1H), 2.60 (dd, J = 13.7, 10.0 Hz, 1H), 2.16-2.05 (m, 1H), 1.96-1.84 (m, 1H), 1.44 (d, J = 6.6 Hz, 3H) $^{13}$C NMR (101 MHz, CD$_3$OD) δ 170.29, 148.87 (q, J = 1.7 Hz), 141.25, 141.03, 131.83, 130.08, 129.44-128.89 (m), 127.09, 122.06, 125.76-117.87 (m), 78.54, 75.60, 70.24, 53.27, 50.24, 46.01, 39.61, 38.86, 21.68 $^{19}$F NMR (376 MHz, CD$_3$OD) δ −55.48 |
| 178 | — | — | ESIMS m/z 340 [M + H]$^+$ | $^1$H NMR (400 MHz, CD$_3$OD) δ 7.46-7.05 (m, 8H), 6.94 (dd, J = 7.3, 2.1 Hz, 2H), 5.34 (dtd, J = 12.5, 6.3, 3.1 Hz, 1H), 4.47 (ddd, J = 7.1, 4.7, 2.4 Hz, 1H), 4.05 (ddd, J = 12.5, 7.1, 2.4 Hz, 1H), 3.85 (d, J = 10.5 Hz, 1H), 3.75 (ddd, J = 12.7, 4.9, 2.3 Hz, 1H), 3.70-3.57 (m, 1H), 2.81 (td, J = 10.3, 2.2 Hz, 1H), 2.33 (dt, J = 13.9, 2.6 Hz, 1H), 2.17 (qq, J = 8.7, 5.8, 4.4 Hz, 1H), 1.98 (ddd, J = 13.9, 11.6, 2.2 Hz, 1H), 1.07 (d, J = 6.3 Hz, 3H) $^{13}$C NMR (101 MHz, CD$_3$OD) δ 170.12, 143.00, 141.31, 130.19, 129.93, 129.75, 129.29, 128.41, 127.06, 78.93, 78.04, 70.61, 59.29, 54.04, 48.31, 38.37, 20.93 |
| 179 | 172-175 | — | ESIMS m/z 506 [M + H]$^+$ | $^1$H NMR (400 MHz, CD$_3$OD) δ 7.47-7.40 (m, 2H), 7.31-7.22 (m, 2H), 7.18-7.11 (m, 4H), 5.20 (p, J = 6.6 Hz, 1H), 4.29 (t, J = 6.8 Hz, 1H), 4.14 (dd, J = 12.4, 7.0 Hz, 1H), 3.69 (dd, J = 11.0, 6.6 Hz, 1H), 3.65-3.57 (m, 1H), 3.49 (dd, J = 11.1, 2.4 Hz, 1H), 2.85 (qd, J = 14.6, 6.6 Hz, 2H), 2.78-2.63 (m, 2H), 2.09 (p, J = 6.5 Hz, 1H), 1.98-1.88 (m, 1H), 1.45 (d, J = 6.5 Hz, 3H) $^{13}$C NMR (101 MHz, CD$_3$OD) δ 170.27, 148.96 (q, J = 1.8 Hz), 146.18-145.95 (m), 140.94, 131.88, 130.76, 129.36 (q, J = 32.2 Hz), 126.08 (q, J = 3.9 Hz), 125.80 (q, J = 270.9 Hz), 122.11, 121.94 (q, J = 255.2 Hz), 78.49, 75.44, 70.43, 53.30, 50.27, 45.75, 39.74, 38.63, 21.63 $^{19}$F NMR (376 MHz, CD$_3$OD) δ 116.72, 112.36 |
| 180 | 147-151 | — | ESIMS m/z 396 [M + H]$^+$ | $^1$H NMR (400 MHz, CD$_3$OD) δ 7.28-7.10 (m, 8H), 7.00 (d, J = 7.5 Hz, 2H), 5.14 (dt, J = 13.0, 6.4 Hz, 1H), 4.34 (t, J = 5.7 Hz, 1H), 4.07 (dd, J = 12.7, 6.5 Hz, 1H), 3.86-3.70 (m, 2H), 3.70-3.60 (m, 1H), 2.61 (hept, J = 6.9 Hz, 2H), 2.43 (tt, J = 13.3, 6.1 Hz, 2H), 1.77 (qt, J = 12.6, 6.3 Hz, 1H), 1.71-1.39 (m, 9H), 1.30 (ddt, J = 18.5, 13.7, 7.0 Hz, 1H) $^{13}$C NMR (101 MHz, CD$_3$OD) δ 169.95, 143.34, 143.30, 129.51, 129.46, 129.38, 129.25, 126.93, 126.85, 80.65, 78.07, 71.26, 54.21, 43.73, 36.83, 33.47, 32.29, 31.94, 29.23, 20.58 |
| 181 | — | — | EIMS m/z 272 [M + H]$^+$ | — |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 182 | 189-195 | — | ESIMS m/z 318 [M + H]$^+$ | $^1$H NMR (400 MHz, CD$_3$OD) δ 7.32-7.14 (m, 5H), 5.19-5.07 (m, 1H), 4.26 (t, J = 6.8 Hz, 1H), 4.16 (dd, J = 12.2, 6.9 Hz, 1H), 3.96 (dd, J = 11.1, 6.0 Hz, 1H), 3.72-3.60 (m, 2H), 2.75 (qd, J = 14.7, 6.3 Hz, 2H), 2.03 (p, J = 6.8 Hz, 1H), 1.72 (tdd, J = 11.5, 6.5, 3.5 Hz, 1H), 1.56-1.43 (m, 1H), 1.36 (d, J = 6.5 Hz, 3H), 1.12 (ddd, J = 13.9, 7.5, 4.2 Hz, 1H), 0.66 (qq, J = 7.9, 5.2 Hz, 1H), 0.44-0.30 (m, 2H), 0.02--0.07 (m, 1H), -0.08--0.17 (m, 1H) $^{13}$C NMR (101 MHz, CD$_3$OD) δ 170.27, 141.60, 130.20, 129.45, 127.21, 78.49, 76.59, 70.31, 53.26, 50.57, 45.36, 39.54, 38.01, 21.61, 9.81, 5.87, 4.64. |
| 183 | 163-168 | — | ESIMS m/z 388 [M + H]$^+$ | $^1$H NMR (400 MHz, CD$_3$OD) δ 7.58 (d, J = 8.0 Hz, 2H), 7.42 (d, J = 8.1 Hz, 2H), 5.03 (dq, J = 8.0, 6.3 Hz, 1H), 4.27 (t, J = 6.7 Hz, 1H), 4.11 (dd, J = 12.3, 6.9 Hz, 1H), 3.61-3.53 (m, 2H), 3.45 (d, J = 11.2 Hz, 1H), 2.96 (dd, J = 13.3, 3.4 Hz, 1H), 2.66 (dd, J = 13.7, 10.5 Hz, 1H), 1.79-1.61 (m, 3H), 1.49 (d, J = 6.5 Hz, 3H), 1.44-1.25 (m, 2H), 0.96 (d, J = 6.6 Hz, 3H), 0.93 (d, J = 6.6 Hz, 3H) $^{13}$C NMR (101 MHz, CD$_3$OD) δ 170.13, 146.51, 130.93, 129.43 (d, J = 32.0 Hz), 126.21 (q, J = 3.8 Hz), 125.84 (d, J = 270.8 Hz), 79.04, 75.76, 70.55, 53.32, 48.21, 47.46, 43.09, 38.22, 28.21, 23.39, 23.06, 20.96 $^{19}$F NMR (376 MHz, CD$_3$OD) δ 112.40 |
| 184 | — | — | ESIMS m/z 372 [M + H]$^+$ | $^1$H NMR (400 MHz, CD$_3$OD) δ 7.37-6.91 (m, 9H), 5.19 (p, J = 6.7 Hz, 1H), 4.30 (t, J = 6.8 Hz, 1H), 4.13 (dd, J = 12.3, 7.0 Hz, 1H), 3.69 (dd, J = 11.0, 6.5 Hz, 1H), 3.59 (dd, J = 12.3, 6.6 Hz, 1H), 3.49 (dd, J = 11.0, 2.4 Hz, 1H), 2.95-2.73 (m, 3H), 2.60 (dd, J = 13.7, 10.3 Hz, 1H), 2.10 (p, J = 6.6 Hz, 1H), 1.98-1.85 (m, 1H), 1.44 (d, J = 6.5 Hz, 3H) $^{19}$F NMR (376 MHz, CD$_3$OD) δ -119.17 |
| 185 | — | — | ESIMS m/z 348 [M + H]$^+$ | $^1$H NMR (400 MHz, CD$_3$OD) δ 7.29-7.11 (m, 5H), 4.95 (dq, J = 8.9, 6.4 Hz, 1H), 4.25 (dd, J = 6.4, 5.3 Hz, 1H), 4.08 (dd, J = 12.6, 6.4 Hz, 1H), 3.78-3.58 (m, 3H), 2.61 (t, J = 7.2 Hz, 2H), 1.85-1.74 (m, 1H), 1.61-1.44 (m, 4H), 1.39 (d, J = 6.4 Hz, 3H), 1.37-1.20 (m, 2H), 1.16-1.01 (m, 2H), 0.85 (d, J = 6.5 Hz, 3H), 0.81 (d, J = 6.5 Hz, 3H) |
| 186 | — | — | ESIMS m/z 440 [M + H]$^+$ | $^1$H NMR (400 MHz, DMSO-d$_6$) δ 8.43 (bs, 3H), 7.60 (d, J = 8.0 Hz, 2H), 7.28 (dd, J = 7.6, 4.2 Hz, 4H), 7.13 (t, J = 8.8 Hz, 2H), 5.0 (m, 1H), 4.28 (bt, J = 8.0 Hz, 1H), 4.01 (dd, J = 12.0, 7.5 Hz, 1H), 3.56 (dd, J = 12.0, 8 Hz, 1H), 3.44 (dd, J = 12.1, 7.7 Hz, 1H), 3.23 (d, J = 10.7 Hz, 1H), 2.89-2.72 (m, 3H), 2.71-2.59 (m, 1H), 2.01 (m, 1H), 1.81 (bs, 1H), 1.37 (d, J = 6.4 Hz, 3H) $^{19}$F NMR (376 MHz, DMSO-d$_6$) δ -60.74, -117.07 |
| 187 | — | — | ESIMS m/z 354.2 [M + H]$^+$ | $^1$H NMR (400 MHz, CDCl$_3$) δ 8.73 (bs, 3H), 7.25-7.20 (m, 2H), 7.12-7.07 (m, 2H), 4.89-4.76 (m, 1H), 4.34-4.22 (m, 2H), 3.45 (dd, J = 11.3, 4.6 Hz, 1H), 3.15-3.05 (m, 1H), 2.79-2.67 (m, 1H), 2.64-2.51 (m, 1H), 1.87-1.56 (m, 3H), 1.52-1.38 (m, 1H), 1.38 (d, J = 6.3 Hz, 3H), 1.32-1.23 (m, 1H), 1.18-1.08 (m, 1H), 0.93 (d, J = 6.7 Hz, 3H), 0.91 (d, J = 6.7 Hz, 3H) |
| 188 | — | — | ESIMS m/z 466.3 [M + H]$^+$ | $^1$H NMR (400 MHz, CDCl$_3$) δ 8.79 (bs, 3H), 7.27-7.21 (m, 2H), 7.19-7.04 (m, 7H), 5.08-4.98 (m, 1H), 4.41-4.32 (m, 1H), 4.24 (dd, J = 12.3, 7.1 Hz, 1H), 3.96 (dd, J = 12.4, 7.1 Hz, 1H), 3.76-3.68 (m, 1H), 3.47-3.39 (m, 1H), 2.68-2.57 (m, 2H), |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 189 | — | (Thin Film) 3389, 2952, 2870, 1749 | ESIMS m/z 334 [M + H]$^+$ | 2.50-2.41 (m, 2H), 1.94-1.82 (m, 1H), 1.66-1.29 (m, 5H), 1.26 (d, J = 6.4 Hz, 3H) $^1$H NMR (400 MHz, CD$_3$OD) δ 7.37-7.09 (m, 5H), 5.05 (dt, J = 12.7, 6.1 Hz, 1H), 4.26 (t, J = 6.5 Hz, 1H), 4.02 (dd, J = 12.4, 6.9 Hz, 1H), 3.66 (d, J = 1.8 Hz, 3H), 3.60-3.47 (m, 3H), 2.87 (dd, J = 13.9, 3.4 Hz, 1H), 2.41 (dd, J = 13.8, 10.4 Hz, 1H), 1.78-1.48 (m, 4H), 1.45 (d, J = 6.2 Hz, 3H), 1.31-1.16 (m, 2H), 0.94 (dd, J = 6.5, 1.6 Hz, 6H), 0.78 (dd, J = 6.6, 4.9 Hz, 1H) |
| 190 | 200-203 | — | ESIMS m/z 366 [M + H]$^+$ | $^1$H NMR (400 MHz, CD$_3$OD) δ 7.30-7.20 (m, 4H), 5.37 (qd, J = 6.6, 4.1 Hz, 1H), 4.29-4.15 (m, 2H), 3.83 (dd, J = 11.6, 6.9 Hz, 1H), 3.60-3.48 (m, 1H), 3.34 (dd, J = 11.7, 2.1 Hz, 1H), 3.02 (dd, J = 13.4, 10.1 Hz, 1H), 2.76 (dd, J = 13.5, 5.4 Hz, 1H), 2.18-1.94 (m, 3H), 1.73-1.44 (m, 9H), 1.27-1.13 (m, 1H), 0.97 (ddd, J = 15.9, 11.4, 7.9 Hz, 1H) $^{13}$C NMR (101 MHz, CD$_3$OD) δ 170.10, 140.94, 132.73, 131.82, 129.29, 76.71, 74.04, 70.57, 54.26, 53.07, 44.85, 44.77, 38.86, 32.31, 31.44, 25.81, 25.77, 22.69 |
| 191 | 149-153 | — | ESIMS m/z 312 [M + H]$^+$ | $^1$H NMR (400 MHz, CD$_3$OD) δ 5.33 (dq, J = 8.9, 5.4, 4.9 Hz, 1H), 4.26-4.11 (m, 2H), 4.02 (dd, J = 11.8, 5.2 Hz, 1H), 3.63-3.53 (m, 1H), 3.41 (d, J = 11.4 Hz, 1H), 2.14-1.89 (m, 2H), 1.83-1.28 (m, 14H), 1.28-1.12 (m, 2H), 1.01 (h, J = 7.8 Hz, 1H), 0.95-0.85 (m, 6H) $^{13}$C NMR (101 MHz, CD$_3$OD) δ 169.99, 76.64, 75.42, 70.64, 54.43, 53.24, 44.50, 43.18, 38.35, 32.08, 31.63, 31.53, 29.55, 25.91, 25.72, 23.14, 22.99, 22.83 |
| 192 | 209-214 | — | ESIMS m/z 370 [M + H]$^+$ | $^1$H NMR (400 MHz, CD$_3$OD) δ d 7.33-7.25 (m, 2H), 7.25-7.18 (m, 2H), 7.17-7.10 (m, 3H), 6.99-6.91 (m, 3H), 5.36 (dq, J = 9.3, 6.3 Hz, 1H), 4.30 (t, J = 6.6 Hz, 1H), 4.20 (dd, J = 10.4, 2.7 Hz, 1H), 4.12 (dd, J = 12.2, 6.8 Hz, 1H), 4.09 (dd, J = 10.4, 2.8 Hz, 1H), 3.66-3.48 (m, 3H), 2.88 (dd, J = 13.6, 3.9 Hz, 1H), 2.51 (dd, J = 13.6, 11.0 Hz, 1H), 2.15-1.96 (m, 2H), 1.48 (d, J = 6.4 Hz, 3H) $^{13}$C NMR (101 MHz, CD$_3$OD) δ 170.35, 160.18, 141.34, 130.60, 130.21, 129.38, 127.13, 122.21, 115.51, 77.14, 76.57, 70.59, 67.64, 53.39, 50.08, 43.91, 37.76, 19.98 |
| 193 | — | — | ESIMS m/z 292 [M + H]$^+$ | $^1$H NMR (400 MHz, DMSO-d$_6$) δ 8.42 (bs, 3H), 7.35 (app t, J = 7.4 Hz, 2H), 7.26 (app t, J = 7.3 Hz, 1H), 7.21 (app d, J = 6.9 Hz, 2H), 5.09 (m, 1H), 4.47 (t, J = 6.7 Hz, 1H), 3.99 (dd, J = 12.3, 7.5 Hz, 1H), 3.78-3.63 (m, 3H), 2.71 (app t, J = 10.4 Hz, 1H), 1.78 (s, 1H), 1.25 (m, 1H), 1.02-0.82 (m, 3H), 0.94 (d, J = 6.3 Hz, 3H), 0.59 (t, J = 7.2 Hz, 3H) |
| 194 | — | — | EIMS m/z 336 [M + H]$^+$ | $^1$H NMR (400 MHz, DMSO-d$_6$) δ 8.41 (bd, J = 11.2 Hz, 3H), 7.24 (dd, J = 8.6, 5.6 Hz, 2H), 7.16-7.08 (m, 2H), 4.93 (m, 1H), 4.26 (t, J = 7.4 Hz, 1H), 4.02 (dd, J = 12.1, 7.1 Hz, 1H), 3.88 (dd, J = 10.9, 6.1 Hz, 1H), 3.50 (dd, J = 11.8, 7.8 Hz, 1H), 3.42 (d, J = 11.3 Hz, 1H), 2.73 (dd, J = 14.8, 6.8 Hz, 1H), 2.64 (m, 1H), 1.91 (m, 1H), 1.55 (m, 1H), 1.46 (m, 1H), 1.30 (d, J = 6.5 Hz, 3H), 1.01 (m, 1H), 0.63 (m, 1H), 0.34 (m, 2H), −0.04 (m, 1H), −0.14 (m, 1H) $^{19}$F NMR (376 MHz, DMSO-d$_6$) δ −117.21 |
| 195 | — | — | ESIMS m/z 304 [M + H]$^+$ | $^1$H NMR (400 MHz, CDCl$_3$) δ 8.81 (s, 3H), 7.34-7.18 (m, 3H), 7.13-6.99 (m, 2H), 5.25-5.13 (m, 1H), 4.71-4.60 (m, 1H), 4.35-4.24 (m, 1H), 4.23-4.12 (m, 1H), 4.02-3.94 (m, 1H), 3.87-3.78 (m, 1H), |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | 2.63 (t, J = 10.2 Hz, 1H), 2.12-1.90 (m, 1H), 1.16-0.96 (m, 4H), 0.79-0.65 (m, 1H), 0.58-0.43 (m, 1H), 0.41-0.27 (m, 1H), 0.28-0.17 (m, 1H), −0.11--0.25 (m, 1H), −0.32--0.48 (m, 1H) |
| 196 | 184-187 | — | ESIMS m/z 324 [M + H]⁺ | ¹H NMR (400 MHz, CD₃OD) δ 7.24 (dd, J = 8.4, 5.2 Hz, 2H), 7.01 (t, J = 8.5 Hz, 2H), 5.12 (p, J = 6.5 Hz, 1H), 4.30 (t, J = 6.3 Hz, 1H), 4.15 (dd, J = 12.4, 6.6 Hz, 1H), 3.81 (dd, J = 11.1, 5.9 Hz, 1H), 3.73 (dd, J = 12.3, 5.8 Hz, 1H), 3.60 (d, J = 10.8 Hz, 1H), 2.83-2.67 (m, 2H), 1.99 (p, J = 6.6 Hz, 1H), 1.64-1.52 (m, 1H), 1.44-1.14 (m, 7H), 0.81 (t, J = 6.6 Hz, 3H) ¹³C NMR (101 MHz, CD₃OD) δ 170.10, 162.79 (d, J = 243.0 Hz), 137.62 (d, J = 3.2 Hz), 131.73 (d, J = 7.7 Hz), 116.01 (d, J = 21.3 Hz), 78.23, 77.59, 70.63, 53.60, 50.80, 44.41, 38.70, 35.40, 21.64, 21.21, 14.50 ¹⁹F NMR (376 MHz, CD₃OD) δ 57.05 |
| 197 | — | — | ESIMS m/z 382 [M + H]⁺ | — |
| 198 | — | — | — | |
| 199 | — | — | — | — |
| 200 | — | — | ESIMS m/z 476 [M + Na]⁺ | ¹H NMR (400 MHz, CDCl₃) δ 7.40-7.24 (m, 7H), 7.24-7.15 (m, 3H), 5.34 (d, J = 8.3 Hz, 1H), 5.09 (s, 2H), 4.86 (dq, J = 9.3, 6.3 Hz, 1H), 4.63 (q, J = 8.1 Hz, 1H), 4.04 (dd, J = 11.7, 7.6 Hz, 1H), 3.52 (dd, J = 10.7, 4.2 Hz, 1H), 3.28-3.02 (m, 2H), 2.90-2.72 (m, 1H), 2.53 (dd, J = 14.8, 8.7 Hz, 1H), 1.74-1.61 (m, 2H), 1.64-1.43 (m, 2H), 1.40 (d, J = 6.3 Hz, 3H), 1.37-1.14 (m, 4H), 0.92 (t, J = 6.9 Hz, 3H) ¹³C NMR (101 MHz, CDCl₃) δ 172.25, 155.51, 140.37, 136.10, 129.11, 128.55, 128.36, 128.23, 128.11, 126.06, 76.27, 72.19, 71.36, 67.08, 52.63, 47.21, 44.41, 37.09, 29.74, 27.24, 23.43, 20.12, 13.99 |
| 201 | — | — | ESIMS m/z 476 [M + Na]⁺ | ¹H NMR (400 MHz, CDCl₃) δ 7.36-7.08 (m, 6H), 7.01 (d, J = 7.1 Hz, 2H), 6.91-6.72 (m, 2H), 5.21 (s, 1H), 4.38 (s, 1H), 3.92 (dd, J = 12.1, 4.8 Hz, 1H), 3.74 (d, J = 8.4 Hz, 1H), 3.67-3.53 (m, 1H), 3.36 (t, J = 9.6 Hz, 1H), 3.02 (d, J = 11.4 Hz, 1H), 2.78 (dd, J = 14.0, 10.5 Hz, 1H), 2.51 (dd, J = 14.0, 7.2 Hz, 1H), 2.44-2.31 (m, 1H), 2.07-1.79 (m, 2H), 1.46 (s, 9H), 1.43 (d, J = 6.8 Hz, 3H), 1.35-1.20 (m, 1H) ¹³C NMR (101 MHz, CDCl₃) δ 170.26, 154.81, 140.21, 139.59, 129.10, 128.81, 128.42, 128.31, 125.98, 80.35, 73.43, 73.09, 72.58, 55.95, 39.64, 36.60, 34.40, 28.34, 19.06 |
| 202 | — | — | ESIMS m/z 504 [M + Na]⁺ | ¹H NMR (400 MHz, CDCl₃) δ 7.32-7.22 (m, 4H), 7.22-7.14 (m, 4H), 7.03 (d, J = 7.4 Hz, 2H), 5.18 (d, J = 8.4 Hz, 1H), 4.94 (dq, J = 9.0, 6.2 Hz, 1H), 4.62 (q, J = 8.0 Hz, 1H), 4.05 (dd, J = 11.7, 7.3 Hz, 1H), 3.81 (dd, J = 10.6, 5.7 Hz, 1H), 3.48 (d, J = 10.5 Hz, 1H), 3.32 (dd, J = 11.8, 7.7 Hz, 1H), 2.85-2.71 (m, 1H), 2.50 (dt, J = 13.7, 8.3 Hz, 1H), 2.45-2.32 (m, 2H), 1.82-1.57 (m, 5H), 1.57-1.48 (m, 1H), 1.48-1.42 (m, 12H) ¹³C NMR (101 MHz, CDCl₃) δ 172.52, 155.01, 142.05, 142.00, 128.47, 128.44, 128.17, 125.98, 125.95, 80.08, 75.82, 74.37, 72.01, 52.61, 46.94, 41.30, 33.07, 32.97, 32.25, 31.32, 28.33, 20.35 |
| 203 | 41-45 | — | ESIMS m/z 476 [M + Na]⁺ | ¹H NMR (400 MHz, CDCl₃) δ 7.35-7.28 (m, 2H), 7.24 (tdd, J = 7.1, 3.2, 1.5 Hz, 5H), 7.20-7.15 (m, 1H), 7.11-7.04 (m, 2H), 5.10 (d, J = 8.4 Hz, 1H), 5.00 (dq, J = 8.6, |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| | | | | 6.4 Hz, 1H), 4.58 (q, J = 8.3 Hz, 1H), 4.08 (dd, J = 11.6, 7.5 Hz, 1H), 3.58 (dd, J = 11.0, 5.7 Hz, 1H), 3.15 (d, J = 11.1 Hz, 1H), 3.08 (dd, J = 11.6, 8.9 Hz, 1H), 2.87-2.65 (m, 4H), 2.13 (td, J = 8.0, 4.0 Hz, 1H), 1.81-1.66 (m, 1H), 1.44 (s, 9H), 1.39 (d, J = 6.4 Hz, 3H) $^{13}$C NMR (101 MHz, CDCl$_3$) δ 172.49, 154.83, 140.11, 139.87, 129.07, 129.01, 128.52, 128.18, 126.28, 125.93, 79.98, 76.05, 71.46, 71.19, 52.16, 48.55, 45.41, 38.37, 37.29, 28.24, 21.19 |
| 204 | 63-71 | — | ESIMS m/z 448 [M + Na]$^+$ | $^1$H NMR (400 MHz, CDCl$_3$) δ 7.17-6.72 (m, 10H), 5.38-5.26 (m, 2H), 4.90 (q, J = 7.7 Hz, 1H), 4.13-4.05 (m, 1H), 4.02 (dd, J = 11.6, 7.7 Hz, 1H), 3.89 (d, J = 9.6 Hz, 1H), 3.55 (dd, J = 11.7, 7.0 Hz, 1H), 3.12-3.01 (m, 2H), 1.46 (s, 9H), 1.08 (d, J = 6.3 Hz, 3H) $^{13}$C NMR (101 MHz, CDCl$_3$) δ 172.54, 155.10, 142.62, 140.96, 128.27, 128.15, 127.61, 126.47, 126.13, 80.16, 77.38, 77.17, 77.11, 72.02, 58.66, 53.28, 52.94, 28.33, 20.83 |
| 205 | 134-138 | — | ESIMS m/z 412 [M + Na]$^+$ | $^1$H NMR (400 MHz, CDCl$_3$) δ 7.31-7.24 (m, 2H), 7.22-7.12 (m, 3H), 5.54 (dt, J = 17.0, 9.9 Hz, 1H), 5.36-5.22 (m, 1H), 5.15 (dd, J = 10.2, 1.8 Hz, 1H), 5.04 (dd, J = 17.0, 1.8 Hz, 1H), 4.69 (q, J = 7.5 Hz, 1H), 4.52-4.38 (m, 1H), 4.19-4.06 (m, 1H), 4.01 (dd, J = 11.9, 7.4 Hz, 1H), 3.75 (p, J = 6.3 Hz, 1H), 3.50 (dd, J = 11.8, 6.5 Hz, 1H), 3.03 (dd, J = 14.0, 3.6 Hz, 1H), 2.37-2.26 (m, 1H), 2.11-1.98 (m, 2H), 1.43 (s, 9H), 1.06 (d, J = 6.1 Hz, 3H) $^{13}$C NMR (101 MHz, CDCl$_3$) δ 173.26, 154.97, 140.20, 138.55, 128.89, 128.38, 126.11, 117.49, 80.06, 78.63, 69.71, 68.41, 55.41, 53.07, 45.26, 37.96, 28.22, 19.83 |
| 206 | 44-50 | — | ESIMS m/z 488 [M + Na]$^+$ | $^1$H NMR (400 MHz, CDCl$_3$) δ 5.14 (d, J = 8.5 Hz, 1H), 4.84-4.71 (m, 1H), 4.57 (q, J = 8.0 Hz, 1H), 4.01 (dd, J = 11.6, 7.4 Hz, 1H), 3.66 (dd, J = 10.6, 5.7 Hz, 1H), 3.30 (d, J = 10.8 Hz, 1H), 3.22 (dd, J = 11.6, 8.2 Hz, 1H), 1.86-1.57 (m, 15H), 1.43 (s, 9H), 1.37 (d, J = 6.4 Hz, 3H), 1.34-0.71 (m, 13H) $^{13}$C NMR (101 MHz, CDCl$_3$) δ 172.55, 154.95, 79.95, 77.54, 74.09, 71.88, 52.44, 45.57, 42.01, 40.18, 38.62, 36.88, 34.94, 34.83, 34.39, 33.45, 32.51, 28.29, 26.64, 26.49, 26.48, 26.42, 26.20, 20.61 |
| 207 | — | — | ESIMS m/z 472 [M + Na]$^+$ | $^1$H NMR (400 MHz, CDCl$_3$) δ 7.31-7.24 (m, 2H), 7.23-7.14 (m, 3H), 5.15-4.96 (m, 2H), 4.51 (q, J = 8.3 Hz, 1H), 4.06 (dd, J = 11.6, 7.5 Hz, 1H), 3.58-3.45 (m, 3H), 3.19-2.94 (m, 4H), 2.80 (dd, J = 13.6, 3.8 Hz, 1H), 2.64 (q, J = 13.1 Hz, 1H), 1.94 (td, J = 9.6, 9.2, 4.5 Hz, 1H), 1.84 (dp, J = 13.3, 6.7 Hz, 1H), 1.73 (tt, J = 9.1, 2.8 Hz, 1H), 1.52-1.36 (m, 12H), 0.90 (d, J = 6.7 Hz, 6H) $^{13}$C NMR (101 MHz, CDCl$_3$) δ 172.78, 154.88, 140.50, 129.14, 128.30, 125.98, 79.95, 78.43, 75.41, 71.60, 71.46, 69.39, 52.14, 48.63, 42.04, 36.83, 28.40, 28.29, 19.57, 19.41 |
| 208 | 84-88 | — | ESIMS m/z 470 [M + Na]$^+$ | $^1$H NMR (400 MHz, CDCl$_3$) δ 7.31-7.24 (m, 2H), 7.18 (d, J = 7.7 Hz, 3H), 5.12-5.00 (m, 2H), 4.95 (s, 1H), 4.91 (s, 1H), 4.51 (q, J = 8.4 Hz, 1H), 4.06 (dd, J = 11.7, 7.5 Hz, 1H), 3.88-3.76 (m, 2H), 3.58-3.47 (m, 3H), 3.08 (d, J = 11.0 Hz, 1H), 3.02 (t, J = 10.4 Hz, 1H), 2.79 (dd, J = 13.6, 3.9 Hz, 1H), 2.65 (t, J = 12.4 Hz, 1H), 1.94 (td, J = 9.7, 9.2, 4.5 Hz, 1H), 1.74 (s, 3H), |

TABLE 2-continued

Analytical Data

| Cmpd. No. | MP (° C.) | IR (cm⁻¹) | MASS | NMR ($^1$H, $^{13}$C or $^{19}$F) |
|---|---|---|---|---|
| | | | | 1.50-1.37 (m, 12H) $^{13}$C NMR (101 MHz, CDCl$_3$) δ 172.75, 154.89, 141.85, 140.37, 129.16, 128.30, 126.01, 112.58, 79.96, 75.55, 75.17, 71.40, 68.86, 52.09, 48.53, 42.03, 36.94, 28.29, 19.64, 19.63 |
| 209 | — | — | ESIMS m/z 472 [M + Na]$^+$ | — |
| 210 | — | — | ESIMS m/z 536 [M + Na]$^+$ | $^1$H NMR (400 MHz, CDCl$_3$) δ 7.25-7.11 (m, 2H), 6.85-6.60 (m, 6H), 5.14-5.06 (m, 1H), 4.99 (dq, J = 8.5, 6.4 Hz, 1H), 4.57 (q, J = 8.3 Hz, 1H), 4.08 (dd, J = 11.6, 7.5 Hz, 1H), 3.82-3.74 (m, 7H), 3.59 (dd, J = 11.1, 5.6 Hz, 1H), 3.18-3.01 (m, 2H), 2.85-2.61 (m, 4H), 1.80-1.66 (m, 1H), 1.44 (s, 9H), 1.40 (d, J = 6.4 Hz, 3H) $^{13}$C NMR (101 MHz, CDCl$_3$) δ 172.46, 159.68, 159.44, 154.84, 141.76, 141.47, 129.47, 129.09, 121.48, 121.39, 115.06, 114.65, 111.44, 111.31, 79.98, 76.02, 71.45, 71.24, 55.08, 55.03, 52.16, 48.43, 45.33, 38.46, 37.37, 28.24, 21.16 |
| 211 | — | — | ESIMS m/z 522 [M + H]$^+$ | $^1$H NMR (400 MHz, CDCl$_3$) δ 7.59-7.49 (m, 2H), 7.41-7.26 (m, 7H), 5.33 (d, J = 8.3 Hz, 1H), 5.09 (s, 2H), 4.87 (dq, J = 9.2, 6.2 Hz, 1H), 4.61 (q, J = 8.2 Hz, 1H), 4.06 (dd, J = 11.7, 7.5 Hz, 1H), 3.47 (dd, J = 10.8, 4.3 Hz, 1H), 3.09 (dd, J = 12.2, 9.2 Hz, 2H), 2.90-2.77 (m, 1H), 2.65 (dd, J = 13.6, 10.4 Hz, 1H), 1.69 (tt, J = 9.3, 5.1 Hz, 2H), 1.60-1.45 (m, 2H), 1.41 (d, J = 6.3 Hz, 3H), 1.38-1.15 (m, 4H), 0.93 (t, J = 7.0 Hz, 3H) $^{19}$F NMR (376 MHz, CDCl$_3$) δ −62.33 |
| 212 | — | — | ESIMS m/z 454 [M + H]$^+$ | $^1$H NMR (400 MHz, CDCl$_3$) δ 7.40-7.15 (m, 10H), 5.32 (d, J = 15.8 Hz, 1H), 5.09 (s, 2H), 4.82 (dq, J = 9.1, 6.4 Hz, 1H), 4.66-4.56 (m, 1H), 4.08 (dd, J = 11.7, 7.5 Hz, 1H), 3.53 (dd, J = 11.0, 5.1 Hz, 1H), 3.19-3.03 (m, 2H), 2.85-2.79 (m, 1H), 2.60 (t, J = 12.5 Hz, 1H), 1.76-1.61 (m, 2H), 1.56-1.47 (m, 1H), 1.42 (d, J = 6.4 Hz, 3H), 1.36 (ddd, J = 14.7, 6.8, 5.0 Hz, 1H), 1.18 (ddd, J = 14.8, 8.7, 3.4 Hz, 1H), 0.95 (d, J = 6.5 Hz, 3H), 0.92 (d, J = 6.6 Hz, 3H) |
| 213 | — | — | ESIMS m/z 440 [M + H]$^+$ | $^1$H NMR (400 MHz, CDCl$_3$) δ 7.40-7.09 (m, 10H), 5.40 (d, J = 8.3 Hz, 1H), 5.10 (s, 2H), 4.97 (dq, J = 8.5, 6.5 Hz, 1H), 4.63 (q, J = 7.9 Hz, 1H), 4.08 (dd, J = 11.7, 7.3 Hz, 1H), 3.78 (dd, J = 11.0, 4.9 Hz, 1H), 3.40-3.20 (m, 2H), 2.79-2.61 (m, 2H), 2.02-1.93 (m, 1H), 1.54-1.34 (m, 4H), 1.29 (d, J = 6.4 Hz, 3H), 1.22-1.07 (m, 1H), 0.84 (t, J = 7.0 Hz, 3H) $^{13}$C NMR (101 MHz, CDCl$_3$) δ 172.11, 155.65, 140.35, 136.22, 128.96, 128.55, 128.49, 128.21, 128.12, 126.18, 81.67, 76.36, 73.63, 71.73, 67.05, 53.00, 48.95, 43.47, 38.27, 21.37, 20.36, 14.28 |
| 214 | — | — | ESIMS m/z 490 [M + Na]$^+$ | $^1$H NMR (400 MHz, CDCl$_3$) δ 7.34-7.13 (m, 10H), 5.10 (d, J = 8.5 Hz, 1H), 4.96 (dq, J = 9.0, 6.1 Hz, 1H), 4.60 (q, J = 8.3 Hz, 1H), 4.01 (dd, J = 11.6, 7.6 Hz, 1H), 3.56 (dd, J = 10.6, 4.4 Hz, 1H), 3.24 (d, J = 10.6 Hz, 1H), 3.11 (dd, J = 11.7, 8.6 Hz, 1H), 2.89-2.76 (m, 1H), 2.68 (ddd, J = 13.8, 11.7, 5.1 Hz, 1H), 2.61-2.47 (m, 2H), 1.96-1.70 (m, 4H), 1.50 (d, J = 6.3 Hz, 3H), 1.43 (s, 9H) $^{13}$C NMR (101 MHz, CDCl$_3$) δ 172.71, 154.94, 141.92, 140.25, 129.12, 128.60, 128.43, 128.19, 126.15, 126.12, 80.08, 75.81, 72.10, 71.45, 52.23, 47.11, 44.57, 37.13, 32.60, 31.80, 28.31, 20.30 |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 215 | — | — | ESIMS m/z 460 [M + Na]$^+$ | $^1$H NMR (400 MHz, CDCl$_3$) δ 5.15 (d, J = 8.2 Hz, 1H), 4.86 (dq, J = 8.7, 6.4 Hz, 1H), 4.55 (q, J = 7.9 Hz, 1H), 4.03 (dd, J = 11.7, 7.3 Hz, 1H), 3.73 (dd, J = 10.9, 5.5 Hz, 1H), 3.33 (d, J = 10.8 Hz, 1H), 3.23 (dd, J = 11.7, 8.2 Hz, 1H), 1.96-1.83 (m, 1H), 1.83-1.68 (m, 7H), 1.66-1.32 (m, 22H), 1.27 (ddd, J = 13.1, 9.9, 3.2 Hz, 2H), 1.15-0.98 (m, 4H) $^{13}$C NMR (101 MHz, CDCl$_3$) δ 172.43, 154.89, 79.88, 76.79, 73.99, 72.05, 52.53, 47.40, 43.28, 38.77, 37.79, 37.52, 37.35, 33.67, 33.61, 33.20, 32.08, 28.24, 25.01, 24.92, 24.78, 24.74, 20.72 |
| 216 | — | — | ESIMS m/z 470 [M + Na]$^+$ | $^1$H NMR (400 MHz, CDCl$_3$) δ 7.33-7.11 (m, 5H), 5.19 (d, J = 8.5 Hz, 1H), 4.97 (dq, J = 9.6, 6.3 Hz, 1H), 4.64 (q, J = 7.6 Hz, 1H), 3.98 (dd, J = 11.7, 7.4 Hz, 1H), 3.68 (dd, J = 10.3, 6.0 Hz, 1H), 3.50 (d, J = 10.2 Hz, 1H), 3.37 (dd, J = 11.7, 7.3 Hz, 1H), 2.65-2.44 (m, 2H), 1.83-1.62 (m, 3H), 1.56-1.45 (m, 2H), 1.44 (s, 9H), 1.40-1.21 (m, 3H), 1.12-1.05 (m, 1H), 0.89 (d, J = 5.1 Hz, 3H), 0.88 (d, J = 5.1 Hz, 3H) $^{13}$C NMR (101 MHz, CDCl$_3$) δ 172.45, 155.04, 142.15, 128.52, 128.13, 126.00, 80.04, 76.09, 75.95, 72.23, 52.82, 46.97, 42.54, 35.84, 32.24, 31.50, 29.13, 28.38, 28.30, 22.82, 22.40, 20.37 |
| 217 | — | — | ESIMS m/z 454 [M + Na]$^+$ | $^1$H NMR (400 MHz, CDCl$_3$) δ 7.32-7.16 (m, 5H), 5.18 (p, J = 6.4 Hz, 1H), 5.07 (d, J = 8.8 Hz, 1H), 4.59-4.47 (m, 1H), 4.14 (dd, J = 11.6, 7.0 Hz, 1H), 3.78 (dd, J = 11.5, 6.4 Hz, 1H), 3.07 (ddd, J = 17.1, 12.6, 10.1 Hz, 3H), 2.70 (dd, J = 13.4, 4.9 Hz, 1H), 2.05-1.90 (m, 3H), 1.72-1.50 (m, 6H), 1.44 (s, 9H), 1.31-1.16 (m, 1H), 1.03-0.91 (m, 1H) $^{13}$C NMR (101 MHz, CDCl$_3$) δ 172.39, 154.92, 141.11, 129.18, 128.18, 125.88, 80.03, 74.50, 72.41, 71.50, 52.78, 52.34, 43.40, 43.22, 38.43, 31.22, 29.77, 28.30, 24.87, 24.68, 22.17 |
| 218 | — | (Neat) 3337, 2953, 1720, 1517, 1324, 1202 | ESIMS m/z 468.4 [M + H]$^+$ | $^1$H NMR (400 MHz, CDCl$_3$) δ 7.37-7.22 (m, 7H), 7.21-7.14 (m, 3H), 5.55 (d, J = 8.2 Hz, 1H), 5.12-5.05 (m, 2H), 5.01-4.90 (m, 1H), 4.69-4.57 (m, 1H), 4.05 (dd, J = 11.7, 7.3 Hz, 1H), 3.76 (dd, J = 10.9, 4.7 Hz, 1H), 3.39-3.22 (m, 2H), 2.72-2.64 (m, 2H), 2.03-1.93 (m, 1H), 1.48-1.32 (m, 4H), 1.29 (d, J = 6.4 Hz, 3H), 1.28-1.20 (m, 1H), 1.08-0.94 (m, 1H), 0.82 (d, J = 6.5 Hz, 6H) |
| 219 | — | (Neat) 3338, 2933, 1718, 1492, 1207 | ESIMS m/z 522.3 [M + H]$^+$ | $^1$H NMR (400 MHz, CDCl$_3$) δ 7.36-7.26 (m, 7H), 7.25-7.14 (m, 5H), 6.97-6.91 (m, 2H), 5.46 (d, J = 8.1 Hz, 1H), 5.08 (s, 2H), 5.02-4.92 (m, 1H), 4.65-4.54 (m, 1H), 4.13-4.03 (m, 1H), 3.52 (dd, J = 11.1, 5.4 Hz, 1H), 3.13-3.0 (m, 2H), 2.86-2.56 (m, 4H), 2.12-2.03 (m, 1H), 1.71-1.58 (m, 1H), 1.37 (d, J = 6.4 Hz, 3H) |
| 220 | — | — | ESIMS m/z 504 [M + Na]$^+$ | $^1$H NMR (400 MHz, CDCl$_3$) δ 7.30-7.07 (m, 10H), 5.19 (d, J = 8.4 Hz, 1H), 4.96 (dq, J = 8.4, 6.4 Hz, 1H), 4.57 (q, J = 7.9 Hz, 1H), 4.01 (dd, J = 11.7, 7.3 Hz, 1H), 3.79-3.71 (m, 1H), 3.34 (d, J = 10.8 Hz, 1H), 3.28-3.21 (m, 1H), 2.65 (d, J = 5.9 Hz, 2H), 2.49 (t, J = 7.2 Hz, 2H), 2.00-1.91 (m, 1H), 1.77-1.65 (m, 1H), 1.54-1.45 (m, 1H), 1.43 (s, 9H), 1.29 (d, J = 6.4 Hz, 3H), 1.27-1.22 (m, 1H) $^{13}$C NMR (101 MHz, CDCl$_3$) δ 172.39, 155.01, 142.32, 140.25, 128.98, 128.50, 128.38, 128.31, 126.19, 125.77, 81.59, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| 221 | — | — | ESIMS m/z 594 [M + Na]⁺ | 80.00, 76.05, 73.94, 72.08, 52.67, 49.00, 43.60, 38.25, 36.07, 29.12, 28.34, 21.36 $^{1}$H NMR (400 MHz, CDCl$_3$) δ 7.24-7.13 (m, 6H), 6.93 (d, J = 8.3 Hz, 2H), 5.11 (d, J = 8.4 Hz, 1H), 5.00 (p, J = 6.5 Hz, 1H), 4.57 (q, J = 8.3 Hz, 1H), 4.08 (dd, J = 11.7, 7.4 Hz, 1H), 3.59 (dd, J = 11.0, 5.9 Hz, 1H), 3.23-3.02 (m, 2H), 2.82 (dd, J = 14.9, 6.9 Hz, 1H), 2.78-2.66 (m, 2H), 2.61 (dd, J = 13.6, 4.7 Hz, 1H), 2.05 (p, J = 6.8 Hz, 1H), 1.76-1.61 (m, 1H), 1.43 (s, 9H), 1.37 (d, J = 6.5 Hz, 3H) $^{13}$C NMR (101 MHz, CDCl$_3$) δ 172.41, 154.85, 147.71 (q, J = 1.9 Hz), 138.60, 138.33, 131.80, 130.34, 130.28, 128.34, 121.08, 120.43 (q, J = 257.0 Hz), 80.10, 75.56, 71.67, 71.14, 52.27, 48.58, 45.17, 38.25, 36.81, 28.23, 21.27 $^{19}$F NMR (376 MHz, CDCl$_3$) δ −57.91 |
| 222 | — | — | ESIMS m/z 544 [M + Na]⁺ | $^{1}$H NMR (400 MHz, CDCl$_3$) δ 7.51-7.08 (m, 9H), 5.07 (d, J = 8.4 Hz, 1H), 4.99 (dq, J = 8.6, 6.4 Hz, 1H), 4.54 (q, J = 8.3 Hz, 1H), 4.09 (dd, J = 11.7, 7.4 Hz, 1H), 3.51 (dd, J = 11.2, 5.5 Hz, 1H), 3.14-2.98 (m, 2H), 2.93-2.61 (m, 4H), 2.16-2.04 (m, 1H), 1.76-1.66 (m, 1H), 1.44 (s, 9H), 1.41 (d, J = 6.4 Hz, 3H) $^{19}$F NMR (376 MHz, CDCl$_3$) δ −62.34 |
| 223 | 47-51 | — | ESIMS m/z 560 [M + Na]⁺ | $^{1}$H NMR (400 MHz, CDCl$_3$) δ 7.28-7.11 (m, 7H), 7.04 (d, J = 7.5 Hz, 2H), 5.14 (d, J = 8.4 Hz, 1H), 5.02 (p, J = 6.6 Hz, 1H), 4.61 (q, J = 8.2 Hz, 1H), 4.08 (dd, J = 11.7, 7.5 Hz, 1H), 3.64 (dd, J = 10.8, 6.2 Hz, 1H), 3.23 (d, J = 10.8 Hz, 1H), 3.15 (dd, J = 11.7, 8.7 Hz, 1H), 2.82 (d, J = 6.2 Hz, 2H), 2.72 (d, J = 7.5 Hz, 2H), 2.08 (p, J = 6.7 Hz, 1H), 1.84-1.69 (m, 1H), 1.44 (s, 9H), 1.38 (d, J = 6.5 Hz, 3H) $^{13}$C NMR (101 MHz, CDCl$_3$) δ 172.46, 154.87, 147.63 (q, J = 1.7 Hz), 139.85, 138.79, 130.24, 128.97, 128.26, 126.05, 121.01, 120.43 (q, J = 257.0 Hz), 80.04, 75.75, 71.63, 52.29, 48.53, 45.15, 38.22, 37.44, 28.22, 21.32 $^{19}$F NMR (376 MHz, CDCl$_3$) δ −57.89 |
| 224 | 66-71 | — | ESIMS m/z 462 [M + Na]⁺ | $^{1}$H NMR (400 MHz, CDCl$_3$) δ 7.36 (t, J = 7.5 Hz, 2H), 7.30-7.09 (m, 6H), 6.96-6.90 (m, 2H), 5.25-5.11 (m, 2H), 4.75 (q, J = 8.0 Hz, 1H), 3.96 (dd, J = 11.7, 7.8 Hz, 1H), 3.62 (d, J = 3.4 Hz, 2H), 3.32 (dd, J = 11.7, 7.6 Hz, 1H), 2.71 (t, J = 9.9 Hz, 1H), 2.54-2.42 (m, 1H), 2.21-2.05 (m, 2H), 1.44 (s, 9H), 1.04 (d, J = 6.3 Hz, 3H) $^{13}$C NMR (101 MHz, CDCl$_3$) δ 172.53, 154.95, 141.73, 139.92, 128.93, 128.83, 128.54, 128.20, 127.13, 125.96, 80.04, 76.72, 73.29, 71.63, 57.52, 52.55, 47.24, 37.07, 28.25, 20.87 |
| 225 | 50-56 | — | ESIMS m/z 606 [M + H]⁺ | $^{1}$H NMR (400 MHz, CDCl$_3$) δ 7.47 (d, J = 8.1 Hz, 2H), 7.24-7.07 (m, 6H), 5.09 (d, J = 8.3 Hz, 1H), 5.07-4.95 (m, 1H), 4.57 (q, J = 8.3 Hz, 1H), 4.10 (dd, J = 11.7, 7.4 Hz, 1H), 3.58 (dd, J = 11.2, 6.1 Hz, 1H), 3.24-3.01 (m, 2H), 2.91-2.59 (m, 4H), 2.07 (p, J = 6.7 Hz, 1H), 1.81-1.68 (m, 1H), 1.44 (s, 9H), 1.40 (d, J = 6.5 Hz, 3H) $^{13}$C NMR (101 MHz, CDCl$_3$) δ 172.42, 154.87, 147.79 (q, J = 1.9 Hz), 144.09 (q, J = 1.4, 1.0 Hz), 130.31, 129.33, 128.44 (q, J = 32.2 Hz), 125.16 (q, J = 3.8 Hz), 124.23 (q, J = 271.8 Hz), 124.48-116.31 (m), 80.17, 75.50, 71.75, 70.99, 52.29, 48.68, 45.04, 38.35, 37.33, 28.26, 21.30 $^{19}$F NMR (376 MHz, CDCl$_3$) δ −57.95, −62.39 |

TABLE 2-continued

Analytical Data

| Cmpd. No. | MP (° C.) | IR (cm$^{-1}$) | MASS | NMR ($^1$H, $^{13}$C or $^{19}$F) |
|---|---|---|---|---|
| 226 | — | — | ESIMS m/z 518 [M + Na]$^+$ | $^1$H NMR (400 MHz, CDCl$_3$) δ 7.32-7.24 (m, 4H), 7.23-7.15 (m, 4H), 7.08-7.02 (m, 2H), 5.19 (d, J = 8.4 Hz, 1H), 4.96 (dq, J = 9.1, 6.2 Hz, 1H), 4.63 (q, J = 7.6 Hz, 1H), 3.98 (dd, J = 11.7, 7.4 Hz, 1H), 3.69 (dd, J = 10.4, 5.8 Hz, 1H), 3.49 (d, J = 10.4 Hz, 1H), 3.35 (dd, J = 11.7, 7.3 Hz, 1H), 2.69-2.39 (m, 4H), 1.86-1.24 (m, 20H) $^{13}$C NMR (101 MHz, CDCl$_3$) δ 172.36, 154.97, 142.06, 141.98, 128.45, 128.36, 128.32, 128.11, 125.95, 125.78, 80.02, 75.97, 75.68, 72.20, 52.75, 46.91, 42.26, 36.03, 32.16, 31.46, 30.83, 28.28, 20.31 |
| 227 | — | — | ESIMS m/z 372 [M + H]$^+$ | $^1$H NMR (400 MHz, CDCl$_3$) δ 5.18 (d, J = 7.9 Hz, 1H), 4.81 (dq, J = 8.8, 6.4 Hz, 1H), 4.57 (q, J = 7.7 Hz, 1H), 4.01 (dd, J = 11.5, 7.3 Hz, 1H), 3.70 (dd, J = 10.6, 5.3 Hz, 1H), 3.36 (d, J = 10.5 Hz, 1H), 3.28 (dd, J = 11.3, 8.0 Hz, 1H), 1.66-1.58 (m, 1H), 1.56-1.31 (m, 4H), 1.43 (s, 9H), 1.38 (d, J = 8.0 Hz, 3H), 1.31-1.15 (m, 3H), 1.10-1.01 (m, 1H), 0.90 (t, J = 8.0 Hz, 3H), 0.90 (dd, J = 8.0, 4.0 Hz, 6H) $^{13}$C NMR (101 MHz, CDCl$_3$) δ 172.41, 154.97, 79.91, 74.54, 72.23, 52.68, 45.84, 44.83, 41.64, 33.28, 28.27, 26.99, 23.43, 22.58, 20.63, 20.40, 14.27 |
| 228 | — | — | ESIMS m/z 440 [M + Na]$^+$ | $^1$H NMR (400 MHz, CDCl$_3$) δ 7.31-7.23 (m, 2H), 7.22-7.13 (m, 3H), 5.13 (d, J = 8.4 Hz, 1H), 4.96 (dq, J = 8.4, 6.4 Hz, 1H), 4.56 (q, J = 8.2 Hz, 1H), 4.07 (dd, J = 11.6, 7.5 Hz, 1H), 3.93 (dd, J = 11.0, 4.7 Hz, 1H), 3.39 (d, J = 10.8 Hz, 1H), 3.20 (dd, J = 11.7, 8.6 Hz, 1H), 2.76-2.61 (m, 2H), 2.05-1.92 (m, 1H), 1.69-1.50 (m, 2H), 1.43 (s, 9H), 1.30 (d, J = 6.4 Hz, 3H), 1.12 (dd, J = 10.2, 7.5 Hz, 1H), 0.66 (dtt, J = 10.3, 5.1, 3.1 Hz, 1H), 0.49-0.37 (m, 1H), 0.41-0.29 (m, 1H), 0.04 (dq, J = 9.4, 4.9 Hz, 1H), −0.12 (dq, J = 9.4, 4.9 Hz, 1H) $^{13}$C NMR (101 MHz, CDCl$_3$) δ 172.48, 154.87, 140.15, 128.92, 128.38, 126.10, 79.94, 76.09, 73.00, 71.70, 52.32, 48.60, 44.32, 38.19, 36.31, 28.25, 21.25, 8.93, 5.41, 4.00 |
| 229 | 115-118 | — | ESIMS m/z 510 [M + Na]$^+$ | $^1$H NMR (400 MHz, CDCl$_3$) δ 7.52 (d, J = 8.0 Hz, 2H), 7.30 (d, J = 8.0 Hz, 2H), 5.08 (d, J = 8.4 Hz, 1H), 4.83 (dq, J = 8.9, 6.4 Hz, 1H), 4.53 (q, J = 8.3 Hz, 1H), 4.05 (dd, J = 11.7, 7.4 Hz, 1H), 3.47 (dd, J = 11.2, 5.0 Hz, 1H), 3.13-2.96 (m, 2H), 2.92-2.67 (m, 2H), 1.74-1.62 (m, 2H), 1.57-1.32 (m, 14H), 1.15 (ddd, J = 14.7, 8.7, 3.6 Hz, 1H), 0.95 (d, J = 6.5 Hz, 3H), 0.92 (d, J = 6.6 Hz, 3H) $^{13}$C NMR (101 MHz, CDCl$_3$) δ 172.44, 154.85, 144.73, 128.38 (q, J = 32.1 Hz), 125.17 (q, J = 3.7 Hz), 124.28 (q, J = 271.8 Hz), 80.01, 76.73, 71.66, 70.86, 52.20, 47.20, 45.58, 42.21, 36.76, 28.24, 26.96, 23.49, 22.43, 20.49 $^{19}$F NMR (376 MHz, CDCl$_3$) δ −62.33 |
| 230 | — | — | ESIMS m/z 494 [M + Na]$^+$ | $^1$H NMR (400 MHz, CDCl$_3$) δ 7.29-6.93 (m, 9H), 5.07 (d, J = 8.4 Hz, 1H), 4.99 (dq, J = 8.1, 6.5 Hz, 1H), 4.58 (q, J = 8.2 Hz, 1H), 4.07 (dd, J = 11.7, 7.5 Hz, 1H), 3.60 (dd, J = 10.9, 6.0 Hz, 1H), 3.18 (d, J = 11.0 Hz, 1H), 3.10 (t, J = 10.3 Hz, 1H), 2.79-2.67 (m, 4H), 2.11-2.00 (m, 1H), 1.81-1.69 (m, 1H), 1.43 (s, 9H), 1.37 (d, J = 6.4 Hz, 3H) $^{19}$F NMR (376 MHz, CDCl$_3$) δ −116.81 |
| 231 | — | — | ESIMS m/z 470 [M + Na]$^+$ | $^1$H NMR (400 MHz, CDCl$_3$) δ 7.33-7.12 (m, 5H), 5.19 (d, J = 8.4 Hz, 1H), 4.79 (dq, J = 9.0, 6.4 Hz, 1H), 4.55 (q, J = 7.8 Hz, 1H), 4.00 (dd, J = 11.7, 7.2 Hz, 1H), 3.69 (dd, J = 11.2, |

TABLE 2-continued

Analytical Data

| Cmpd. No. | MP (° C.) | IR (cm$^{-1}$) | MASS | NMR ($^{1}$H, $^{13}$C or $^{19}$F) |
|---|---|---|---|---|
| | | | | 5.1 Hz, 1H), 3.43-3.19 (m, 2H), 2.60 (t, J = 7.4 Hz, 2H), 1.84-1.74 (m, 1H), 1.62-1.46 (m, 4H), 1.43 (s, 9H), 1.35 (d, J = 6.4 Hz, 3H), 1.28-1.12 (m, 3H), 1.02-0.93 (m, 1H), 0.84 (d, J = 6.6 Hz, 3H), 0.82 (d, J = 6.6 Hz, 3H) |
| 232 | — | (Neat) 3353, 2957, 1712, 1491, 1386, 1163 | HRMS-ESI (m/z) [M]$^{+}$ calcd for C$_{24}$H$_{36}$ClNO$_{5}$, 453.2282; found, 453.2281 | $^{1}$H NMR (400 MHz, CDCl$_{3}$) δ 7.26-7.22 (m, 2H), 7.14-7.10 (m, 2H), 5.05 (d, J = 8.5 Hz, 1H), 4.87-4.76 (m, 1H), 4.59-4.47 (m, 1H), 4.05 (dd, J = 11.6, 7.5 Hz, 1H), 3.48 (dd, J = 11.1, 5.0 Hz, 1H), 3.12-2.97 (m, 2H), 2.78 (dd, J = 13.8, 3.8 Hz, 1H), 2.67-2.53 (m, 1H), 1.75-1.59 (m, 2H), 1.54-1.43 (m, 1H), 1.44 (d, J = 6.5 Hz, 3H), 1.43 (s, 9H), 1.42-1.34 (m, 1H), 1.18-1.10 (m, 1H), 0.95 (d, J = 6.6 Hz, 3H), 0.93 (d, J = 6.6 Hz, 3H) |
| 233 | — | (Neat) 3355, 2931, 1712, 1508, 1257, 1160 | HRMS-ESI (m/z) [M]$^{+}$ calcd for C$_{30}$H$_{38}$F$_{3}$NO$_{6}$, 565.2651; found, 565.2652 | $^{1}$H NMR (400 MHz, CDCl$_{3}$) δ 7.30-7.22 (m, 2H), 7.20-7.09 (m, 7H), 5.12 (d, J = 8.4 Hz, 1H), 5.01-4.91 (m, 1H), 4.63-4.52 (m, 1H), 4.03 (dd, J = 11.7, 7.3 Hz, 1H), 3.81-3.72 (m, 1H), 3.42-3.33 (m, 1H), 3.32-3.21 (m, 1H), 2.74-2.60 (m, 2H), 2.56-2.46 (m, 2H), 2.00-1.87 (m, 1H), 1.79-1.63 (m, 1H), 1.52-1.35 (m, 4H), 1.43 (s, 9H), 1.30 (d, J = 6.5 Hz, 3H) |
| 234 | — | — | ESIMS m/z 562 [M + Na]$^{+}$ | $^{1}$H NMR (400 MHz, CDCl$_{3}$) δ 7.48 (d, J = 8.0 Hz, 2H), 7.22-7.10 (m, 4H), 7.00 (t, J = 8.6 Hz, 2H), 5.07 (d, J = 8.2 Hz, 1H), 4.99 (m, 1H), 4.56 (q, J = 8.2 Hz, 1H), 4.09 (dd, J = 11.1, 7.1 Hz, 1H), 3.55 (dd, J = 11.0, 5.6 Hz, 1H), 3.15-3.05 (m, 2H), 2.88-2.59 (m, 4H), 2.05 (m, 1H), 1.83-1.67 (bs, 1H), 1.44 (s, 9H), 1.39 (d, J = 6.4 Hz, 3H) $^{13}$C NMR (101 MHz, CDCl$_{3}$) δ 172.45, 161.53 (d, J = 244 Hz), 154.88, 144.23, 135.32 (d, J = 3 Hz), 130.41 (d, J = 8 Hz), 129.38, 128.41 (q, J = 32 Hz), 125.17 (q, J = 4 Hz), 124.27 (q, J = 270 Hz), 115.46, (d, J = 21 Hz), 80.17, 75.55, 71.71, 70.87, 52.27, 48.83, 45.12, 38.04, 37.29, 28.28, 21.3 $^{19}$F NMR (376 MHz, CDCl$_{3}$) δ −62.35, −116.44 |
| 235 | — | (Thin Film) 3436, 3354, 2954, 2931, 1712 | ESIMS m/z 434 [M + H]$^{+}$ | $^{1}$H NMR (400 MHz, CDCl$_{3}$) δ 7.32-7.15 (m, 5H), 5.07 (d, J = 8.5 Hz, 1H), 4.85 (dq, J = 9.5, 6.1 Hz, 1H), 4.57 (q, J = 8.3 Hz, 1H), 4.00 (dd, J = 11.6, 7.6 Hz, 1H), 3.57-3.46 (m, 1H), 3.26-3.02 (m, 2H), 2.80 (dd, J = 14.0, 2.5 Hz, 1H), 2.52 (t, J = 11.5 Hz, 1H), 1.73-1.62 (m, 1H), 1.57-1.48 (m, 1H), 1.43 (s, 9H), 1.40 (d, J = 6.3 Hz, 3H), 1.32-1.02 (m, 3H), 0.91 (d, J = 6.6 Hz, 6H), 0.83 (dd, J = 6.5, 2.3 Hz, 1H) |
| 236 | — | — | ESIMS m/z 412 [M + H]$^{+}$ | $^{1}$H NMR (400 MHz, CDCl$_{3}$) δ 5.17 (qd, J = 6.6, 4.6 Hz, 1H), 5.07 (d, J = 8.3 Hz, 1H), 4.45 (q, J = 8.1 Hz, 1H), 4.07 (dd, J = 11.6, 7.0 Hz, 1H), 3.95 (dd, J = 11.5, 6.6 Hz, 1H), 3.23-3.03 (m, 2H), 2.02-1.84 (m, 2H), 1.67-1.21 (m, 23H), 1.20-1.02 (m, 2H), 1.01-0.80 (m, 7H) $^{13}$C NMR (101 MHz, CDCl$_{3}$) δ 172.29, 154.92, 79.91, 74.37, 72.84, 72.50, 52.85, 52.79, 43.29, 41.67, 37.29, 31.22, 30.19, 28.35, 28.28, 24.79, 22.74, 22.63, 22.37 |
| 237 | 113-115 | — | ESIMS m/z 466 [M + H]$^{+}$ | $^{1}$H NMR (400 MHz, CDCl$_{3}$) δ 7.22 (d, J = 8.5 Hz, 2H), 7.17 (d, J = 8.5 Hz, 2H), 5.16 (p, J = 6.5 Hz, 1H), 5.08 (d, J = 8.2 Hz, 1H), 4.48 (q, J = 8.3 Hz, 1H), 4.12 (dd, J = 11.6, 7.0 Hz, 1H), 3.73 (dd, J = 11.6, 6.3 Hz, 1H), 3.08 (dd, J = 13.5, 10.8 Hz, 1H), 3.05-2.96 (m, 2H), 2.64 (dd, J = 13.4, 4.8 Hz, 1H), 2.04-1.84 (m, 3H), 1.73-1.37 (m, 18H), 1.30-1.14 (m, 1H), 1.01-0.88 (m, 1H) $^{13}$C NMR (101 MHz, CDCl$_{3}$) δ 172.28, 154.84, 139.51, 131.50, 130.50, 128.20, 79.99, 74.23, 72.36, 71.06, 52.68, 52.34, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| 238 | — | — | ESIMS m/z 470 [M + H]⁺ | 43.27, 43.18, 37.69, 31.18, 29.61, 28.23, 24.78, 24.60, 22.08 <br> ¹H NMR (400 MHz, CDCl₃) δ 7.32-7.25 (m, 2H), 7.18-7.09 (m, 3H), 6.99-6.94 (m, 1H), 6.89-6.85 (m, 3H), 6.85-6.82 (m, 1H), 5.24-5.09 (m, 2H), 4.56 (q, J = 8.3 Hz, 1H), 4.16-3.99 (m, 3H), 3.55 (dd, J = 11.0, 4.6 Hz, 1H), 3.18 (d, J = 10.9 Hz, 1H), 3.07 (dd, J = 11.7, 8.8 Hz, 1H), 2.80 (dd, J = 13.6, 3.9 Hz, 1H), 2.66 (dd, J = 13.7, 10.7 Hz, 1H), 2.12-2.00 (m, 1H), 2.01-1.88 (m, 1H), 1.48-1.38 (m, 12H) <br> ¹³C NMR (101 MHz, CDCl₃) δ 172.79, 158.64, 155.99, 139.85, 129.48, 129.08, 128.29, 126.06, 120.23, 114.36, 80.25, 74.85, 71.50, 71.33, 66.42, 52.14, 47.95, 41.82, 36.84, 28.23, 19.55 |
| 239 | — | — | ESIMS m/z 414 [M + Na]⁺ | ¹H NMR (400 MHz, CDCl₃) δ 7.32-7.21 (m, 3H), 7.10 (m, 2H), 5.24 (d, J = 8.8 Hz, 1H), 5.13 (m, 1H), 4.76 (q, J = 7.2 Hz, 1H), 4.00 (dd, J = 11.8, 7.5 Hz, 1H), 3.73 (m, 2H), 3.51 (dd, J = 11.6, 6.6 Hz, 1H), 2.61 (t, J = 10.4 Hz, 1H), 1.82 (q, J = 8.6 Hz, 1H), 1.45 (s, 9H), 1.29 (m, 1H), 1.06-0.83 (m, 3H) 1.00 (d, J = 6.3 Hz, 3H), 0.65 (t, J = 7.0 Hz, 3H) <br> ¹³C NMR (101 MHz, CDCl₃) δ 172.35, 155.08, 141.90, 128.70, 128.48, 126.85, 80.05, 76.33, 72.32, 57.16, 53.03, 44.78, 33.55, 28.30, 20.81, 19.20, 14.08 |
| 240 | — | — | ESIMS m/z 458 [M + Na]⁺ | ¹H NMR (400 MHz, CDCl₃) δ 7.13 (app dd, J = 8.7, 5.4 Hz, 2H), 6.97 (app t, J = 8.7, 2H), 5.11 (d, J = 8.2 Hz, 1H), 5.00-4.90 (m, 1H), 4.57 (q, J = 7.8 Hz, 1H), 4.07 (dd, J = 11.6, 7.5 Hz, 1H), 3.94 (bd, J = 10.5 Hz, 1H), 3.40 (bd, J = 10.9 Hz, 1H), 3.22 (m, 1H), 2.67 (app d, J = 6.1 Hz, 2H), 1.94 (p, J = 6.8 Hz, 1H), 1.61 (m, 2H), 1.43 (s, 9H), 1.30 (d, J = 6.5 Hz, 3H), 1.13 (m, 1H), 0.66 (m, 1H), 0.50-0.32 (m, 2H), 0.04 (m, 1H), −0.10 (m, 1H) <br> ¹³C NMR (101 MHz, CDCl₃) δ 172.53, 161.38 (d, J = 244.7 Hz), 154.91, 135.86, 130.30 (d, J = 7.7 Hz), 115.23 (d, J = 20.9 Hz), 80.06, 75.83, 73.07, 71.82, 52.39, 48.89, 44.30, 37.61, 36.45, 28.29, 21.37, 9.01, 5.44, 4.10 <br> ¹⁹F NMR (376 MHz, CDCl₃) δ −117.06 |
| 241 | — | — | ESIMS m/z 404 [M + H]⁺ | ¹H NMR (400 MHz, CDCl₃) δ 7.32-7.19 (m, 3H), 7.12-7.03 (m, 2H), 5.26 (d, J = 8.4 Hz, 1H), 5.11 (dq, J = 10.2, 6.3 Hz, 1H), 4.78 (q, J = 7.7 Hz, 1H), 4.04 (dd, J = 11.7, 7.7 Hz, 1H), 3.94-3.76 (m, 2H), 3.52-3.44 (m, 1H), 2.62 (t, J = 10.4 Hz, 1H), 2.03-1.89 (m, 1H), 1.45 (s, 9H), 1.16-1.05 (m, 1H), 1.00 (d, J = 6.3 Hz, 3H), 0.76-0.65 (m, 1H), 0.62-0.48 (m, 1H), 0.43-0.31 (m, 1H), 0.31-0.19 (m, 1H), −0.15 (tt, J = 9.4, 3.9 Hz, 1H), −0.38 (dtd, J = 9.3, 5.3, 4.2 Hz, 1H) <br> ¹³C NMR (101 MHz, CDCl₃) δ 172.55, 155.06, 141.82, 128.70, 128.53, 126.90, 80.08, 75.37, 71.96, 57.09, 52.78, 46.18, 36.05, 28.30, 20.86, 8.35, 5.60, 3.97 |
| 242 | — | — | ESIMS m/z 424 [M + H]⁺ | ¹H NMR (400 MHz, CDCl₃) δ 7.18-7.09 (m, 2H), 7.02-6.92 (m, 2H), 5.13 (d, J = 8.4 Hz, 1H), 4.95 (dq, J = 8.1, 6.5 Hz, 1H), 4.58 (q, J = 7.9 Hz, 1H), 4.03 (dd, J = 11.7, 7.4 Hz, 1H), 3.77 (dd, J = 11.1, 4.9 Hz, 1H), 3.36 (d, J = 10.8 Hz, 1H), 3.26 (dd, J = 11.8, 8.1 Hz, 1H), 2.67 (d, J = 6.0 Hz, 2H), 1.92 (p, J = 6.8 Hz, 1H), 1.52-1.11 (m, 17H), 0.83 (t, J = 7.0 Hz, 3H) <br> ¹³C NMR (101 MHz, CDCl₃) δ 172.37, 161.33 (d, J = 244.4 Hz), 154.91, 135.97 (d, |

TABLE 2-continued

Analytical Data

| Cmpd. No. | MP (° C.) | IR (cm⁻¹) | MASS | NMR (¹H, ¹³C or ¹⁹F) |
|---|---|---|---|---|
| | | | | J = 3.3 Hz), 130.23 (d, J = 7.7 Hz), 115.19 (d, J = 21.1 Hz), 80.00, 75.84, 73.71, 71.97, 52.53, 49.10, 43.34, 37.56, 33.74, 28.25, 21.38, 20.33, 14.18<br>¹⁹F NMR (376 MHz, CDCl₃) δ −117.11 |
| 243 | — | — | ESIMS m/z 328 [M + H]⁺ | — |
| 244 | — | — | — | — |

Cmpd. No.—Compound Number
¹H NMR were run at 400 MHz unless noted otherwise.
¹³C NMR were run at 101 MHz unless noted otherwise.
¹⁹F NMR were run at 376 MHz unless noted otherwise.

TABLE 3

Biological Testing Rating Scale
Rating Table for Fungal Pathogens

| % Control | Rating |
|---|---|
| >70 | A |
| ≤70 | B |
| Not Tested | C |

TABLE 4

Biological Activity-PUCCRT and SEPTTR Disease Control in High and Low Volume Applications

| | Low Volume (121.5 g/H*) | | | | High Volume (100 ppm*) | | | |
|---|---|---|---|---|---|---|---|---|
| | PUCCRT* | | SEPTTR* | | PUCCRT* | | SEPTTR* | |
| *Cmpd. No. | 1 DP* | 3 DC* | 1 DP* | 3 DC* | 1 DP* | 3 DC* | 1 DP* | 3 DC* |
| 1 | A | B | A | A | A | A | A | A |
| 2 | C | C | C | C | B | B | B | B |
| 3 | A | A | A | A | A | B | A | A |
| 4 | A | B | A | A | A | A | A | A |
| 5 | C | C | C | C | B | C | B | B |
| 6 | C | C | C | C | A | C | B | B |
| 7 | A | A | A | A | A | A | A | A |
| 8 | C | C | C | C | A | A | A | A |
| 9 | C | C | C | C | A | A | A | A |
| 10 | C | C | C | C | A | A | A | B |
| 12 | A | B | A | A | A | A | A | A |
| 13 | A | A | A | A | A | A | A | A |
| 14 | C | C | C | C | B | B | B | B |
| 15 | A | A | A | A | A | A | A | A |
| 16 | A | A | A | A | C | C | C | C |
| 17 | A | B | A | A | C | C | C | C |
| 18 | A | B | A | A | C | C | C | C |
| 19 | A | A | A | A | C | C | C | C |
| 20 | A | A | A | A | C | C | C | C |
| 21 | A | A | A | A | C | C | C | C |
| 22 | A | A | A | A | C | C | C | C |
| 23 | A | A | A | A | C | C | C | C |
| 24 | A | A | A | A | C | C | C | C |
| 25 | A | A | A | A | C | C | C | C |
| 26 | A | A | A | A | C | C | C | C |
| 27 | A | A | A | A | C | C | C | C |
| 28 | A | A | A | A | C | C | C | C |
| 29 | A | A | A | A | C | C | C | C |
| 30 | A | A | A | A | C | C | C | C |
| 31 | A | A | A | A | C | C | C | C |
| 32 | A | A | A | A | C | C | C | C |
| 33 | A | A | A | A | C | C | C | C |
| 34 | A | A | A | A | C | C | C | C |
| 35 | A | A | A | A | C | C | C | C |
| 36 | A | B | A | A | C | C | C | C |
| 37 | A | A | A | A | C | C | C | C |
| 38 | A | A | A | A | C | C | C | C |
| 39 | A | A | A | A | C | C | C | C |
| 40 | A | A | A | A | C | C | C | C |
| 41 | A | A | A | A | C | C | C | C |
| 42 | A | B | A | A | C | C | C | C |
| 43 | A | B | A | A | C | C | C | C |
| 44 | A | B | A | A | C | C | C | C |
| 45 | A | A | A | A | C | C | C | C |
| 46 | A | A | A | A | C | C | C | C |
| 47 | A | A | A | A | C | C | C | C |
| 48 | A | B | A | A | C | C | C | C |
| 49 | A | B | A | B | C | C | C | C |
| 50 | A | B | A | B | C | C | C | C |
| 51 | A | B | A | B | C | C | C | C |
| 52 | C | C | C | C | C | C | C | C |
| 53 | A | A | A | A | C | C | C | C |
| 54 | A | A | A | A | C | C | C | C |
| 55 | A | A | A | A | C | C | C | C |
| 56 | A | B | A | B | C | C | C | C |
| 57 | A | B | A | A | C | C | C | C |
| 58 | A | B | A | A | C | C | C | C |
| 59 | B | B | B | B | C | C | C | C |
| 60 | B | B | A | B | C | C | C | C |
| 61 | A | A | A | A | C | C | C | C |
| 62 | A | A | A | A | C | C | C | C |
| 63 | A | B | B | B | C | C | C | C |
| 64 | A | A | A | A | C | C | C | C |
| 65 | A | A | A | A | C | C | C | C |
| 66 | A | A | A | A | C | C | C | C |
| 67 | B | B | B | B | C | C | C | C |
| 68 | A | B | A | B | C | C | C | C |
| 69 | A | A | A | A | C | C | C | C |
| 70 | A | A | A | A | C | C | C | C |
| 71 | A | A | A | A | C | C | C | C |
| 72 | A | A | A | A | C | C | C | C |
| 73 | A | B | A | A | C | C | C | C |
| 74 | A | B | A | A | C | C | C | C |
| 75 | A | A | A | A | C | C | C | C |
| 76 | A | B | A | A | C | C | C | C |
| 77 | B | B | B | B | C | C | C | C |
| 78 | B | B | B | B | C | C | C | C |
| 79 | A | B | A | B | C | C | C | C |
| 80 | A | B | B | B | C | C | C | C |

TABLE 4-continued

Biological Activity-PUCCRT and SEPTTR Disease Control in High and Low Volume Applications

| *Cmpd. No. | Low Volume (121.5 g/H*) PUCCRT* 1 DP* | Low Volume PUCCRT* 3 DC* | Low Volume SEPTTR* 1 DP* | Low Volume SEPTTR* 3 DC* | High Volume (100 ppm*) PUCCRT* 1 DP* | High Volume PUCCRT* 3 DC* | High Volume SEPTTR* 1 DP* | High Volume SEPTTR* 3 DC* |
|---|---|---|---|---|---|---|---|---|
| 81 | B | B | B | B | C | C | C | C |
| 82 | B | B | B | B | C | C | C | C |
| 83 | A | A | A | A | C | C | C | C |
| 84 | A | A | A | A | C | C | C | C |
| 85 | A | A | A | A | C | C | C | C |
| 86 | A | A | A | A | C | C | C | C |
| 87 | A | B | A | A | C | C | C | C |
| 88 | A | B | A | B | C | C | C | C |
| 89 | A | B | A | A | C | C | C | C |
| 90 | A | B | A | A | C | C | C | C |
| 91 | A | B | A | A | C | C | C | C |
| 92 | A | A | A | A | C | C | C | C |
| 93 | A | B | A | B | C | C | C | C |
| 94 | A | B | A | A | C | C | C | C |
| 95 | A | A | A | A | C | C | C | C |
| 96 | A | B | A | A | C | C | C | C |
| 97 | A | A | A | A | C | C | C | C |
| 98 | A | A | A | A | C | C | C | C |
| 99 | A | A | A | A | C | C | C | C |
| 100 | A | A | A | A | C | C | C | C |
| 101 | A | A | A | A | C | C | C | C |
| 102 | A | A | A | A | C | C | C | C |
| 103 | A | A | A | A | C | C | C | C |
| 104 | A | A | A | A | C | C | C | C |
| 105 | C | C | C | C | C | C | C | C |
| 106 | A | A | A | A | C | C | C | C |
| 107 | A | A | A | A | C | C | C | C |
| 108 | A | A | A | A | C | C | C | C |
| 109 | C | C | C | C | C | C | C | C |
| 110 | C | C | C | C | B | B | A | A |
| 111 | C | C | C | C | A | A | A | B |
| 112 | C | C | C | C | B | B | B | B |
| 113 | C | C | C | C | A | B | A | A |
| 114 | C | C | C | C | A | A | A | B |
| 115 | C | C | C | C | C | C | C | C |
| 116 | C | C | C | C | A | A | A | B |
| 117 | C | C | C | C | A | A | A | B |
| 118 | C | C | C | C | C | C | C | C |
| 119 | C | C | C | C | A | A | A | B |
| 120 | C | C | C | C | B | B | B | B |
| 121 | C | C | C | C | B | B | B | A |
| 122 | C | C | C | C | B | B | B | B |
| 123 | C | C | C | C | B | B | B | B |
| 124 | C | C | C | C | A | B | B | B |
| 125 | C | C | C | C | A | B | B | B |
| 126 | C | C | C | C | A | A | A | A |
| 127 | C | C | C | C | A | A | A | A |
| 128 | C | C | C | C | A | B | A | A |
| 129 | C | C | C | C | A | A | A | A |
| 130 | C | C | C | C | C | C | C | C |
| 131 | C | C | C | C | A | A | A | A |
| 132 | C | C | C | C | A | A | A | A |
| 133 | C | C | C | C | A | A | A | A |
| 134 | C | C | C | C | C | C | C | C |
| 135 | C | C | C | C | A | B | A | B |
| 136 | C | C | C | C | A | A | A | B |
| 137 | C | C | C | C | A | B | B | A |
| 138 | C | C | C | C | B | B | B | B |
| 139 | C | C | C | C | A | B | B | B |
| 140 | C | C | C | C | A | B | A | B |
| 141 | C | C | C | C | A | A | A | A |
| 142 | C | C | C | C | B | B | B | B |
| 143 | C | C | C | C | A | B | A | B |
| 144 | C | C | C | C | A | A | A | A |
| 145 | C | C | C | C | A | A | A | A |
| 146 | C | C | C | C | B | B | B | B |
| 147 | C | C | C | C | A | B | A | B |
| 148 | C | C | C | C | B | B | A | A |
| 149 | C | C | C | C | A | A | A | A |
| 150 | C | C | C | C | A | A | A | A |
| 151 | C | C | C | C | A | B | A | A |
| 152 | C | C | C | C | A | A | A | A |
| 153 | C | C | C | C | A | A | A | A |
| 154 | C | C | C | C | A | A | A | A |
| 155 | C | C | C | C | A | B | A | A |

*Cmpd. No.—Compound Number
*PUCCRT—Wheat Brown Rust (*Puccinia triticina*)
*SEPTTR—Wheat Leaf Blotch (*Septoria tritici*)
*1 DP—1 Day Protectant
*3 DC—3 Day Curative
*g/H—Grams Per Hectare
*ppm—Parts Per Million

TABLE 5

Biological Activity-Disease Control at 100 ppm

| *Cmpd. No. | ALTESO* | CERCBE* | COLLLA* | ERYSCI* 1 DP* | ERYSGH* | ERYSGT |
|---|---|---|---|---|---|---|
| 1 | A | A | A | A | A | C |
| 3 | A | C | A | C | A | C |
| 7 | A | A | A | A | A | A |
| 16 | A | A | A | A | A | C |
| 27 | A | A | A | B | B | C |
| 100 | A | A | A | A | A | C |

*Cmpd. No.—Compound Number
*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*ERYSCI—Powdery Mildew of Cucumber (*Erysiphe cichoracearum*)
*ERYSGH—Barley Powdery Mildew (*Blumeria graminis* f. sp. *hordei*; Synonym: *Erysiphe graminis* f. sp. *hordei*)
ERYSGT—Wheat Powdery Mildew (*Blumeria graminis* f. sp. *tritici*)
*1 DP—1 Day Protectant

TABLE 6

| Biological Activity-Disease Control at 100 ppm | | | | | |
|---|---|---|---|---|---|
| *Cmpd. No. | LEPTNO* | PYRIOR | RHYNSE* 1 DP | UNCINE* | VENTIN* |
| 1 | A | A | A | A | B |
| 3 | A | A | C | C | C |
| 7 | C | A | C | A | C |
| 16 | A | C | A | A | A |
| 27 | A | A | A | C | C |
| 100 | A | A | B | C | C |

Cmpd. No.—Compound Number
*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*VENTIN—Apple Scab (*Venturia inaequalis*)
*1 DP—1 Day Protectant

TABLE 7

| Biological Activity - Disease Control at 25 ppm | |
|---|---|
| *Cmpd. No. | PHAKPA* 1DP* |
| 3 | A |

*Cmpd. No. - Compound Number
*PHAKPA - Asian Soybean Rust (*Phakopsora pachyrhizi*)
*1DP - 1 Day Protectant

What is claimed is:

1. A compound of Formula I

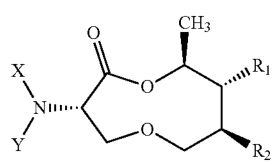

I wherein:

X is hydrogen or $C(O)R_3$;

Y is Q;

Q is 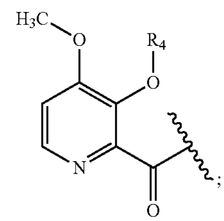 $R_1$ and $R_2$ are independently selected from the group consisting of alkyl, alkenyl, and aryl, each optionally substituted with 0, 1 or multiple $R_6$;

$R_3$ is alkoxy or benzyloxy, each optionally substituted with 0, 1, or multiple $R_6$;

$R_4$ is hydrogen, —$C(O)R_5$, or —$CH_2OC(O)R_5$;

$R_5$ is alkyl, alkoxy, or aryl, each optionally substituted with 0, 1, or multiple $R_6$;

$R_6$ is hydrogen, alkyl, aryl, halo, alkenyl, alkoxy, or thioalkyl, each optionally substituted with 0, 1, or multiple $R_7$; and $R_7$ is hydrogen, alkyl, haloalkyl, alkoxy, haloalkoxy, aryl, or halo.

2. The compound according to claim 1, wherein X is hydrogen and Y is Q.

3. The compound according to claim 2, wherein $R_4$ is hydrogen.

4. The compound according to claim 2, wherein $R_4$ is —$C(O)R_5$ or —$CH_2OC(O)R_5$.

5. The compound according to claim 4, wherein $R_5$ is alkyl or alkoxy, each optionally substituted with 0, 1, or multiple $R_6$.

6. The compound according to claim 5, wherein $R_5$ is chosen from—$CH_3$, —$CH(CH_3)_2$, —$CH_2OCH_2CH_3$, or —$CH_2CH_2OCH_3$.

7. A method for the control of fungal attack on a plant, the method including the step of:

applying a fungicidally effective amount of at least one compounds of claim 1 to at least one portion of a plant, an area adjacent to the plant, a portion of soil adapted to support growth of the plant, a root of the plant, and foliage of the plant.

* * * * *